US009090947B2

(12) United States Patent
Iadonato et al.

(10) Patent No.: US 9,090,947 B2
(45) Date of Patent: Jul. 28, 2015

(54) DETECTION OF MUTATIONS IN A GENE ASSOCIATED WITH RESISTANCE TO VIRAL INFECTION, OAS1

(71) Applicant: Kineta Two, LLC, Seattle, WA (US)

(72) Inventors: Shawn P. Iadonato, Seattle, WA (US); Charles L. Magness, Seattle, WA (US); Gary Rosenberg, Danbury, CT (US); Christina A. Scherer, Seattle, WA (US); Thierry Guillaudeux, Rennes (FR)

(73) Assignee: Kineta Two, LLC, Seattle, WA (US)

( * ) Notice: Subject to any disclaimer, the term of this patent is extended or adjusted under 35 U.S.C. 154(b) by 22 days.

(21) Appl. No.: 13/903,926

(22) Filed: May 28, 2013

(65) Prior Publication Data

US 2014/0010800 A1  Jan. 9, 2014

Related U.S. Application Data

(60) Continuation of application No. 13/468,937, filed on May 10, 2012, now abandoned, which is a continuation of application No. 11/592,711, filed on Nov. 2, 2006, now Pat. No. 8,192,973, which is a division of application No. 10/972,135, filed on Oct. 22, 2004, now abandoned.

(60) Provisional application No. 60/605,243, filed on Aug. 26, 2004, provisional application No. 60/578,323, filed on Jun. 9, 2004, provisional application No. 60/560,524, filed on Apr. 8, 2004, provisional application No. 60/554,758, filed on Mar. 19, 2004, provisional application No. 60/542,373, filed on Feb. 6, 2004, provisional application No. 60/513,888, filed on Oct. 23, 2003.

(51) Int. Cl.
C12N 9/12 (2006.01)
C12Q 1/70 (2006.01)
A61K 38/45 (2006.01)
C12Q 1/68 (2006.01)
C07K 16/40 (2006.01)
C12N 15/113 (2010.01)

(52) U.S. Cl.
CPC ............ C12Q 1/707 (2013.01); A61K 38/45 (2013.01); C07K 16/40 (2013.01); C12N 9/1241 (2013.01); C12N 15/1137 (2013.01); C12Q 1/6876 (2013.01); C12Q 1/6883 (2013.01); C12Q 1/6888 (2013.01); C12Q 1/70 (2013.01); C12Q 2600/156 (2013.01)

(58) Field of Classification Search
CPC ....... C12N 9/10; C12N 9/1241; C12N 9/1258
USPC .................. 435/183, 194; 530/350
See application file for complete search history.

(56) References Cited

U.S. PATENT DOCUMENTS

| 4,863,873 | A | 9/1989 | Matson |
| 5,266,459 | A | 11/1993 | Beutler |
| 5,480,640 | A | 1/1996 | Morales |
| 5,866,781 | A | 2/1999 | Silverman |
| 6,558,955 | B1 | 5/2003 | Kristal |
| 6,566,328 | B1 | 5/2003 | Rosen |
| 7,354,908 | B2 | 4/2008 | Mohapatra |
| 8,030,046 | B2 | 10/2011 | Iadonato ............ 435/194 |
| 8,088,907 | B2 | 1/2012 | Iadonato et al. |
| 8,192,973 | B2 | 6/2012 | Iadonato et al. |
| 8,551,772 | B2 | 10/2013 | Iadonato et al. |
| 2001/0001290 | A1 | 5/2001 | Lau |
| 2001/0001709 | A1 | 5/2001 | Lau |
| 2001/0034023 | A1 | 10/2001 | Stanton |
| 2003/0044783 | A1 | 3/2003 | Williams |
| 2003/0165920 | A1 | 9/2003 | Chou |
| 2003/0165921 | A1 | 9/2003 | Tang |
| 2003/0235575 | A1 | 12/2003 | Matzuk |
| 2004/0009152 | A1 | 1/2004 | Mohapatra |
| 2005/0191649 | A1 | 9/2005 | Iadonato |
| 2006/0275802 | A1 | 12/2006 | Iadonato et al. |
| 2009/0291074 | A1 | 11/2009 | Iadonato et al. |
| 2013/0142773 | A1 | 6/2013 | Iadonato et al. |

FOREIGN PATENT DOCUMENTS

| DE | 10122206.8 | 11/2002 |
| RU | 02108386 | 4/1998 |
| WO | WO91/11520 | 8/1991 |
| WO | WO93/07283 | 4/1993 |
| WO | WO95/22245 | 8/1995 |
| WO | WO99/13075 | 3/1999 |
| WO | WO01/66689 | 9/2001 |

(Continued)

OTHER PUBLICATIONS

Rebouillat and Hovanessian, J Inter. Cyto. Res., vol. 19, pp. 295-308, 1999.*
Sigma Catalog, 1993 (p. 1089, Catalog No. G5149).
Accession No. NP_002525.1—Pruitt, K., et. al., Reference Sequence (RefSeq) Database (http://www.ncbi.nlm.nih.gov/books/NBK21091/), Release 16 dated Mar. 17, 2006. (Also cited as Accession No. NP_002525, Aug. 20, 2004, Brand, et al.).
Accession No. NP_058132.1—Pruitt, K., et. al., Reference Sequence (RefSeq) Database (http://www.ncbi.nlm.nih.gov/books/NBK21091/), Release 16 dated Mar. 17, 2006. (Also cited as Accession No. NP_058132, Aug. 20, 2004, Tan, et al.).

(Continued)

Primary Examiner — Richard Hutson

(57) ABSTRACT

A method for detecting a mutation related to the gene encoding OAS1. This and other disclosed mutations correlate with resistance of humans to viral infection including hepatitis C. Also provided is a therapeutic agent consisting of a protein or polypeptide encoded by the mutated gene, or a polynucleotide encoding the protein or polypeptide. Inhibitors of human OAS1, including antisense oligonucleotides, methods, and compositions specific for human OAS1, are also provided.

7 Claims, 33 Drawing Sheets

(56) References Cited

FOREIGN PATENT DOCUMENTS

Figure 7:
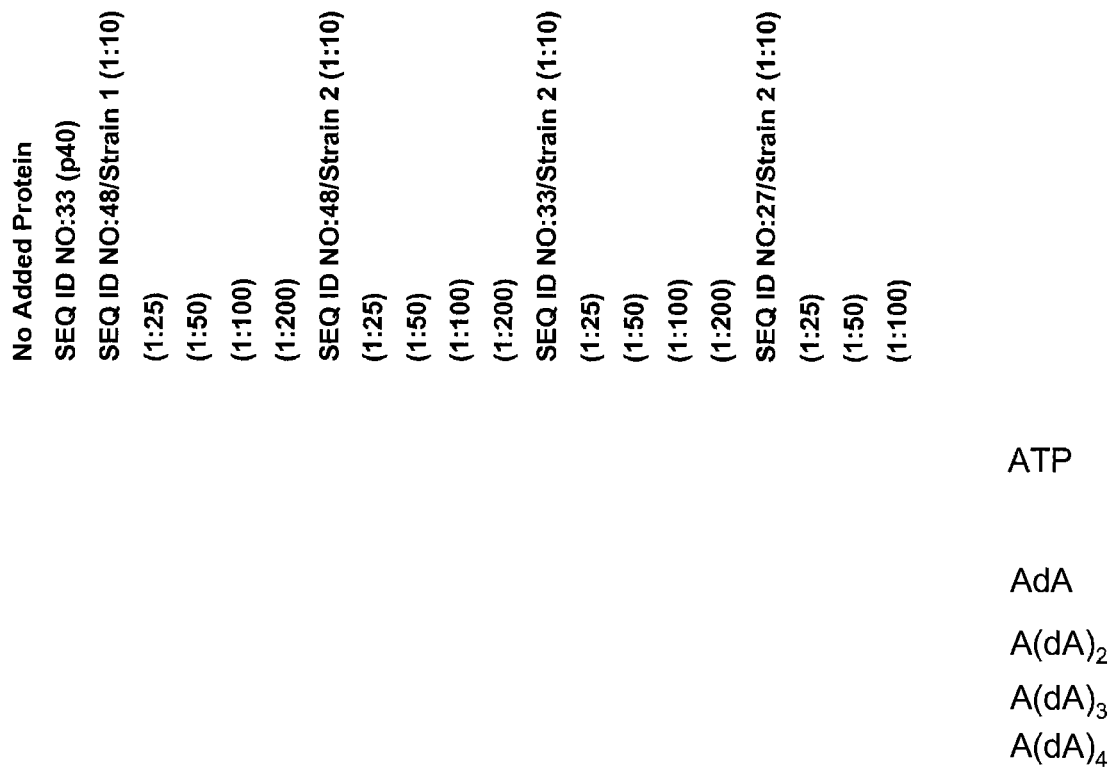

| WO | WO01/79556 | 10/2001 |
|---|---|---|
| WO | WO02/081741 | 10/2002 |
| WO | WO02/090552 | 11/2002 |
| WO | WO03/089003 | 10/2003 |
| WO | WO2004/000998 | 12/2003 |
| WO | WO2005/040428 | 5/2005 |
| WO | WO2006/119363 | 11/2006 |

OTHER PUBLICATIONS

Accession No. P00973—Ota,T., et al., "Complete sequencing and characterization of 21,243 full-length human cDNAs," Nat. Genet. 36:40-45 (2004) (Also cited as Accession No. P00973, Mar. 15, 2004, Knapp, et al.).
Accession No. AC004551, PRI Jul. 11, 1998, Submitted (Apr. 11, 1998).
Accession No. NP_001027581.1—Pruitt, K., et. al., Reference Sequence (RefSeq) Database (http://www.ncbi.nlm.nih.gov/books/NBK21091/), Release 16 dated Mar. 17, 2006.
GenBank: BAA00047.1 Shiojiri,S., Fukunaga,R., Ichii,Y. and Sokawa,Y. "Structure and expression of a cloned cDNA for human" (2'-5')oligoadenylate synthetase J. Biochem. 99 (5), 1455-1464 (1986).
Accession No. AAP36147.1, May 13, 2003, Kalnine,N., Chen,X., Rolfs,A., Halleck,A., Hines,L., Eisenstein,S., Koundinya,M., Raphael,J., Moreira,D., Kelley,T., LaBaer,J., Lin,Y., Phelan,M. and Farmer,A. Cloning of human full-length CDSs in BD Creator(TM) System Donor vector.
GenBank: CAA26633.1 PRI=Sep. 9, 2004? Benech,P., Mory,Y., Revel,M. and Chebath,J. "Structure of two forms of the interferon-induced (2'-5') oligo A synthetase of human cells based on cDNAs and gene sequences"EMBO J. 4 (9), 2249-2256 (1985).
GenBank: AAB59553.1 PRI=Dec. 14, 2000 Benech,P., Mory,Y., Revel,M. and Chebath,J. "Structure of two forms of the interferon-induced (2'-5') oligo A synthetase of human cells based on cDNAs and gene sequences"EMBO J. 4 (9), 2249-2256 (1985).
Genbank Accession No. NM 002534, PRI= Jan. 10, 2014, Saunders,M.E., Gewert,D.R., Tugwell,M.E., McMahon,M. and Williams,B.R., Human 2-5A synthetase: characterization of a novel cDNA andcorresponding gene structure, EMBO J. 4 (7), 1761-1768 (1985).
Alter, et al, "The importance of preventing hepatitis C virus infection among injection drug users in the United States,"Journal of Acquired Immune Deficiency Syndrome and Human Retrovirology, 18(Suppl 1):S6-S10, 1998.
Australian Examiners Report, Nov. 23, 2010 for Serial No. 2004283294.
Bae, et al., "Arginine-rich anti-vascular endothelial growth factor peptides inhibit tumor growth and metastasis by blocking angiogenesis," Journal of Biological Chemistry, 275, No. 18, pp. 13588-13596, 2000.
Bonnevie-Neilsen, et al, "The antiviral 2',5'-oligoadenylate synthetase is persistently activated in type 1 diabetes," Clinical Immunology, 96(1):11-18, 2000.
Buckwold, et al, "Bovine viral diarrhea virus as a surrogate model of hepatitis C virus for the evaluation of antiviral agents," Antiviral Research, 60:1-15, 2003.
Chousterman, et al, "2',5'-Oligoadenylate synthetase expression is induced in response to heat shock." The Journal of Biological Chemistry, 262(10):4806-4811, 1987.
Crance, et al., "Interferon, ribavirin, 6-azauridine and glycyrrhizin: antiviral compounds active against pathogenic flaviviruses"Antiviral Research, 58(1):73-79, 2003.
Dansako, et al., "Differential activation of interferon-inducible genes by hepatitis C virus core protein mediated by the interferon stimulated response element" Virus Research, 97:17-30, 2003.
Database DBSNP [Online] http://www.ncbi.nlm.nih.gov/snp/?term=7955146 NCKI; retrieved from NCBI SNP Database accession No. 7955146, originally accessed for European Search Report on Jun. 12, 2009, original date of publication unknown.
Eskildsen, et al., "Characterization of the 2'-5'-oligoadenylate synthetase ubiquitin-like family" Nucleic Acids Research, 31(12):3166-3173, 2003.
Field, L. Leigh et al "OAS1 splice site polymorphism controlling antiviral enzyme activity influences susceptibility to type 1 diabetes" Diabetes, 54:1588-1591, 2005.
Fowke, et al, Resistance to HIV-1 infection among persistently seronegative prostitutes in Nairobi, Kenya the Lancet, England, 348(9038):1347-1351, 1996.
Ghosh, et al, "A specific isozyme of 2'-5' oligoadenylate synthetase is a dual function proapoptotic protein of the Bcl-2 family" Journal of Biological Chemistry, 276(27):25447-25455, 2001.
Ghosh, et al, "Cloning, sequencing, and expression of two murine 2'-5'-oligoadenylate synthetases. Structure-function relationships" Journal of Biological Chemistry, 266(23):15293-15299, 1991.
Hamano, E., et al., "Polymorphisms of interferon-inducible genes OAS-1 and MxA associated with SARS in the Vietnamese population" Biochemical and Biophysical Research Communications, 329(4):1234-1239, 2005.
Hassel, BA "A proliferation-related constraint on endogenous and interferon-induced 2-5A synthetase activity in normal and neoplastic Syrian hamster cells" Molecular Carcinogenesis, 5:41-51, 1992.
Hitman, G. A. et al., "2'-5' oligoadenylate synthetase and its relationship to HLA and genetic markers of insulin-dependent diabetes mellitus" Immunogenetics, 30(6):427-431, 1989.
Hovanessian, et al, "Identification of 69-kd and 100-kd forms of 2-5A synthetase in interferon-treated human cells by specific monoclonal antibodies" The EMBO Journal, 6(5):1273-1280, 1987.
Hovnanian, et al, "The human 2',5'-oligoadenylate synthetase locus is composed of three distinct genes clustered on chromosome 12q24.2 encoding the 100-, 69-, and 40-kDa forms" Genomics, 52:267-277, 1998.
Justesen, et al, "2'5' oligoadenylate synthetase, an interferon induced enzyme: direct assay methods for the products, 2'5' oligoadenylates and 2'5' co-oligonucleotides" Nucleic Acids Research, 8(14):3073-3085, 1980.
Justesen, et al, Gene Structure and Function of the 2'-5'-Oligoadenylate Synthetase Family, CMLS Cellular and Molecular Life Sciences, Birkhauser Verlag, Basel, CH, vol. 57, No. 11, Oct. 2000, p. 1593-1612.
Kakuta, et al, "Genomic structure of the mouse 2',5'-oligoadenylate synthetase gene family" Journal of Interferon & Cytokine Research, 22:981-993, 2002.
Kimchi, et al, "Anti-mitogenic function of interferon-induced (2'-5')oligo(adenylate) and growth-related variations in enzymes that synthesize and degrade this oligonucleotide" Eur. J. Biochem, 114:5-10, 1981.
Knapp, et al, "Polymorphisms in interferon-induced genes and the outcome of hepatitis C virus infection: roles of MxA, OAS-1 and PKR" Genes Immun., 4(6):411-419, 2003.
Knobler, et al, "Tumor necrosis factor-alpha-induced insulin resistance may mediate the hepatitis C virus-diabetes association" The American Journal of Gastroenterology, 98(12):2751-2756, 2003.
Marie, et al, "Preparation and characterization of polyclonal antibodies specific for the 69 and 100 k-dalton forms of human 2-5A synthetase" Biochemical and Biophysical Research Communications, 160(2):580-587, 1989.
Marie, et al, "The expression of both domains of the 69/71 kDa 2',5' oligoadenylate synthetase generates a catalytically active enzyme and mediates an anti-viral response" Eur J Biochem, 262(1):155-165, 1999.
Marie, et al, "The 69-kDa 2-5A synthetase is composed of two homologous and adjacent functional domains" The Journal of Biological Chemistry, 267(14):9933-9939, 1992.
Mashimo, et al, "Structural and functional genomics and evolutionary relationships in the cluster of genes encoding murine 2',5'-oligoadenylate synthetases" Genomics, 82:537-552, 2003.
Mashimo, et al, "A nonsense mutation in the gene encoding 2'-5'-oligoadenylate synthetase/L1 isoform is associated with West Nile virus susceptibility in laboratory mice" PNAS, 99(17):11311-11316, 2002.

(56) References Cited

OTHER PUBLICATIONS

McKusick, et al, 164350, Online Mendelian Inheritance in Man, 1986.

Muller, et al, "Functional characterization of Tat protein from human immunodeficiency virus. Evidence that Tat links viral RNAs to nuclear matrix" The Journal of Biological Chemistry, 265(7):3803-3808, 1990.

Ngo et al, Computational Complexity, Protein Structure Prediction, and the Levinthal Paradox, in the Protein Folding Problem and Tertiary Structure Prediction, 1994, Merz, et al (ed.), Birkhauser, Boston MA, p. 433 and 492-495.

Olson, "When less is more: gene loss as an engine of evolutionary change" Am. J. Hum. Genet., 64:18-23, 1999.

Perelygin, et al, "Functional characterization of Tat protein from human immunodeficiency virus. Evidence that Tat links viral RNAs to nuclear matrix" PNAS 99(14):9322-9327, 2002.

Player, et al, "The 2-5A system: modulation of viral and cellular processes through acceleration of RNA degradation" Pharmacol. Ther., 78(2):55-113, 1998.

Qiagen Product Guide, 1997, p. 106-110.

Rasooly, 603350, Online Mendelian Inheritance in Man, 1998.

Rebouillat and Hovanessian, "The human 2',5'-oligoadenylate synthetase family: interferon-induced proteins with unique enzymatic properties" Journal of Interferon and Cytokine Research, vol. 19, 295-308, 1999.

Replicated Natural Resistance, http://www.illumigen.com/technology/html, 2003.

Richard, J.P. "Cell-penetrating peptides. A reevaluation of the mechanism of cellular uptake" Journal of Biological Chemistry, 278(1): 585-590, 2003; Epub Oct. 30, 2002.

Rysiecki, et al, "Constitutive expression of a 2',5'-oligoadenylate synthetase cDNA results in increased antiviral activity and growth suppression" Journal of Interferon Research, 9:649-657, 1989.

Salzberg, et al, "Interferon-independent activation of (2'-5') oligoadenylate synthetase in Friend erythroleukemia cellvariants exposed to HMBA," Journal of Cell Science, 109:1517-1526, 1996.

Samuel, "Host genetic variability and West Nile virus susceptibility," PNAS, 99(18):11555-11557, 2002.

Schattner, A et al:, "No evidence for autoimmunity in schizophrenia," Journal of Autoimmunity: 9(5): 661-666 1996.

Schwartz, et al, "Activation of 2',5'-oligoadenylate synthetase activity on induction of HL-60 leukemia cell differentiation," Molecular and Cellular Biology, 9(9):3897-3903, 1989.

Taguchi, et al., "Hepatitis C virus NS5A protein interacts with 2',5'-oligoadenylate synthetase and inhibits antiviral activity of IFN in an IFN sensitivity-determining region-independent manner," Journal of General Virology, 85:959-969, 2004.

Urosevic, "Is flavivirus resistance interferon type I-independent?" Immunology and Cell Biology, 81(3):224, 2003.

Wathelet, et al., "Full-length sequence and expression of the 42 kDa 2-5A synthetase induced by human interferon," FEBS Letters, vol. 196, 113-120, Feb. 1986.

Wells, et al., "Expression of the 2-5A system during the cell cycle," Experimental Cell Research, 159:27-36, 1985.

Xiang, et al., "Effects of RNase L mutations associated with prostate cancer on apoptosis induced by 2',5'-oligoadenylates," Cancer Research, 63:6795-6801, 2003.

Zarghami, M et al: "Studies on the Association Between 2'5'-Oligoadenylate Synthetase and Type 1 Diabetes," Tissue Antigens, 59(2 SUPPL):53 2002.

Zubriski, M A, et al, "Molecular Evolution and Diversity of Human Interferon Stimulated Genes," FASEB Journal (Federation of American Societies for Experimental Biology), Bethesda, US vol. 16, No. 4, Mar. 20, 2002, p. A152.

Zullo, et al, "Platelet-derived growth factor and double-stranded ribonucleic acids stimulate expression of the same genes in 3T3 cells" Cell, 43(3 Part 2):793-800, 1985.

Accession No. A22842. PRI=Jul. 21, 2000, Benech,P., Mory,Y., Revel,M. and Chebath,J. "Structure of two forms of the interferon-induced (2'-5') oligo A synthetase of human cells based on cDNAs and gene sequences," EMBO J. 4 (9), 2249-2256, 1985.

Office Action for Russian application 2007144986 citing WO91/11520 (RU2108386) (Apr. 10, 1998).

Office Action for Japanese application 2006536883 citing WO93/07283 (JP10-506001) mailed Nov. 15, 2011 from Japanese Patent Office.

Office Action mailed Jun. 24, 2014 in Korean Application No. 10-2007-7028236.

Office Action dated Apr. 1, 2010 in Russian Application No. 2007144986.

Office Action dated Apr. 10, 2013 in Israel Application No. 187079.

Office Action dated Feb. 10, 2011 in Russian Application No. 2007144986.

Office Action dated Jan. 31, 2014 in Canadian Applicaiton No. 2607575.

Office Action dated Jul. 21, 2011 in Russian Application No. 2007144986.

Office Action mailed Jun. 19, 2014 in New Zealand Application No. 603105.

Office Action dated Mar. 9, 2014 in Israel Application No. 187079.

Office Action dated May 26, 2009 in Australian Application No. 2004283294.

Office Action mailed on Apr. 3, 2014 in U.S. Appl. No. 13/676,928.

Office Action mailed Aug. 3, 2010 in Japanese Application No. 2006-536883.

Office Action mailed on Feb. 21, 2014 in U.S. Appl. No. 13/180,132.

Office Action mailed Jan. 8, 2013 in Japanese Application No. 2006-536883.

Office Action mailed Jan. 7, 2014 in Japanese Application No. 2012-111782.

Perelygin, et al., "Positional cloning of the murine flavivirus resistance gene," PNAS, vol. 99, No. 14, Jul. 2002, pp. 9322-9327.

Re-Examination Report mailed Jun. 17, 2014 in Japanese Application No. 2006-536883.

Sarkar, et al., "The Nature of the Catalytic Domain of 2'-5'-Oligoadenylate Synthetases," Journal of Biological Chemistry, vol. 274, No. 36, Sep. 1999, pp. 25535-25542.

Strausberg et al., "Generation and Initial Analysis of More than 15,000 Full-Length Human and Mouse cDNA Sequence", PNAS, vol. 99 (26), pp. 16899-16903, Dec. 24, 2002.

Yakub, et al., "Single Nucleotide Polymorphisms in Genes for 2'-5'-Oligoadenylate Synthetase and RNase L in Patients Hospitalized with West Nile Virus Infection," Journal of Infectious Diseases, vol. 192, No. 10, Nov. 2005, pp. 1741-1748.

Lucas, et al., "Infection of mouse neurones by West Nile virus is modulated by the interferon-inducible 2'-5' oligoadenylate synthetase 1b protein," Immunology and Cell Biology, vol. 81, No. 3, Jun. 2003, pp. 230-236.

Marie, I. et al., "The 69-kDa 2-5A Synthetase is Composed of Two Homologous and Adjacent Functional Domains," J. Biol. Chem. 267:9933-9939, 1992.

Ghosh, A. et al., "Cell Growth Regulatory and Antiviral Effects of the P69 Isozyme of 225 (A) Synthetase," Virology 266:319-328, 2000.

Accession No. AC004551, Apr. 11, 1998.

Genbank Accession No. NM 002534, PRI= Jan 10, 2014, Saunders,M.E., Gewert,D.R., Tugwell,M.E., McMahon,M. and Williams,B.R., Human 2-5A synthetase: characterization of a novel cDNA andcorresponding gene structure, EMBO J. 4 (7), 1761-1768 (1985).

Alter, et al, Journal of Acquired Immune Deficiency Syndrome and Human Retrovirology, 18(Suppl 1):S6-S10, 1998.

Australian Examiner's Report, Nov. 23, 2010 for Serial No. 2004283294.

Bae, et al., Journal of Biological Chemistry, 275, No. 18, pp. 13588-13596, 2000.

Bonnevie-Neilsen, et al, Clinical Immunology, 96(1):11-18, 2000.

Buckwold, et al, Antiviral Research, 60:1-15, 2003.

Chousterman, et al, The Journal of Biological Chemistry, 262(10):4806-4811, 1987.

Crance, et al., Antiviral Research, 58(1):73-79, 2003.

Dansako, et al., Virus Research, 97:17-30, 2003.

(56) References Cited

OTHER PUBLICATIONS

Database DBSNP [Online] http://www.ncbi.nlm.nih.gov/snp/?term=7955146 NCKI; retrieved from NCBI SNP Database accession No. 7955146.
Eskildsen, et al., Nucleic Acids Research, 31(12):3166-3173, 2003.
Field, L. Leigh et al Diabetes, 54:1588-1591, 2005.
Fowke, et al, The Lancet, England, 348(9038):1347-1351, 1996.
Ghosh, et al, Journal of Biological Chemistry, 276(27):25447-25455, 2001.
Ghosh, et al, Journal of Biological Chemistry, 266(23):15293-15299, 1991 (incorrectly cited as 286(23):15293-15299, 1991).
Hamano, E., et al., Biochemical and Biophysical Research Communications, 329(4):1234-1239, 2005.
Hassel, Molecular Carcinogenesis, 5:41-51, 1992.
Hitman, G. A. et al., Immunogenetics, 30(6):427-431, 1989.
Hovanessian, et al, The EMBO Journal, 6(5):1273-1280, 1987.
Hovnanian, et al, Genomics, 52:267-277, 1998.
Justesen, et al, Nucleic Acids Research, 8(14):3073-3085, 1980.
Kakuta, et al, Journal of Interferon & Cytokine Research, 22:981-993, 2002.
Kimchi, et al, Eur. J. Biochem, 114:5-10, 1981.
Knapp, et al, Genes Immun., 4(6):411-419, 2003.
Knobler, et al, The American Journal of Gastroenterology, 98(12):2751-2756, 2003.
Marie, et al, Biochemical and Biophysical Research Communications, 160(2):580-587, 1989.
Marie, et al, Eur J Biochem, 262(1):155-165, 1999.
Marie, et al, The Journal of Biological Chemistry, 267(14):9933-9939, 1992.
Mashimo, et al, Genomics, 82:537-552, 2003.
Mashimo, et al, PNAS, 99(17):11311-11316, 2002.
Muller, et al, The Journal of Biological Chemistry, 265(7):3803-3808, 1990.
Olson, Am. J. Hum. Genet., 64:18-23, 1999.
Perelygin, et al, PNAS 99(14):9322-9327, 2002.
Player, et al, Pharmacol., Ther., 78(2):55-113, 1998.
Rebouillat and Hovanessian, Journal of Interferon and Cytokine Research, vol. 19, 295-308, 1999.
Richard, J.P. Journal of Biological Chemistry, 278(1): 585-590, 2003.
Rysiecki, et al, Journal of Interferon Research, 9:649-657, 1989.
Salzberg, et al, Journal of Cell Science, 109:1517-1526, 1996.
Samuel, PNAS, 99(18):11555-11557, 2002.
Schattner, A et al:, "No evidence for autoimmunity in schizophrenia", Journal of Autoimmunity: 9(5): 661-666 1996.
Schwartz, et al, Molecular and Cellular Biology, 9(9):3897-3903, 1989.
Taguchi, et al., Journal of General Virology, 85:959-969, 2004.
Urosevic, Immunology and Cell Biology, 81(3):224, 2003.
Wathelet, et al., FEBS Letters, vol. 196, 113-120, Feb. 1986.
Wells, et al., Experimental Cell Research, 159:27-36, 1985.
Xiang, et al., Cancer Research, 63:6795-6801, 2003.
Zarghami, M et al: "Studies on the Association Between 2'5'-Oligoadenylate Synthetase and Type 1 Diabetes" Tissue Antigens, 59(2 SUPPL):53 2002.
Zubriski, M A, et al, Molecular Evolution and Diversity of Human Interferon Stimulated Genes, FASEB Journal (Federation of American Societies for Experimental Biology), Bethesda, US vol. 16, No. 4, Mar. 20, 2002, p. A152.
Zullo, et al, Cell, 43(Part 2):793-800, 1985.
Accession No. A22842. PRI=Jul. 21, 2000, Benech,P., Mory,Y., Revel,M. and Chebath,J. "Structure of two forms of the interferon-induced (2'-5') oligo A synthetase of human cells based on cDNAs and gene sequences"EMBO J. 4 (9), 2249-2256 (1985).
Office Action for Japanese application 2006536883 citing WO93/07283 (JP10-506001).

\* cited by examiner

FIGURE 1

SEQ ID NO:1
AllelicVariants:C/T
Genbank Genomic Sequence ID: NT_009775.13
Coordinates of Mutation on Genomic Sequence (start-stop): 2135728-2135728
NCBI dbSNP ID (if any): 7955146

CCCTCAGAGTGACTGAAGGAAATTCAGAGAAGAGCTGACACCTAAGTTGTAG
ATTTTGCCYGAACAGGTCAGTTGACTGGCRGCTATAAACCTAACCCCCAAAT
CTATGTCAAGCTCATCG

SEQ ID NO:2
AllelicVariants: G/A
Genbank Genomic Sequence ID: NT_009775.13
Coordinates of Mutation on Genomic Sequence (start-stop) :2135749-2135749
NCBI dbSNP ID (if any): 3741981

ATTCAGAGAAGAGCTGACACCTAAGTTGTAGATTTTGCCYGAACAGGTCAGT
TGACTGGCRGCTATAAACCTAACCCCCAAATCTATGTCAAGCTCATCGAGGA
GTGCACCGACCTGCAGA

SEQ ID NO:3
AllelicVariants: G/A
Genbank Genomic Sequence ID: NT_009775.13
Coordinates of Mutation on Genomic Sequence (start-stop): 2135978-2135978
NCBI dbSNP ID (if any): NONE ATGTATGGCCCTCCCACCAGGCCTGGTGGGTCCTGTCTCGACTGGGAGCAGA
GGAGGGGTRGGGGGAGGAGAGAAAGAAGGGAGTGAAGGGAAGAGGAGGGG
GAGTGGTGGAGGGAAATAG

SEQ ID NO:4
AllelicVariants: G/A
Genbank Genomic Sequence ID: NT_009775.13
Coordinates of Mutation on Genomic Sequence (start-stop): 2144072-2144072
NCBI dbSNP ID (if any): NONE ACTGAATCCAGCTGCAATGCAGGAAGACTCCCTGATGTGATCATGTGTCTCA
CCCTTTCARGCTGAAAGCAACAGTRCAGACGATGAGACCGACGATCCCAGGA
SGTATCAGAAATATGGT FIGURE 1 cont.

| SEQ ID NO:5 |
| --- |
| AllelicVariants: G/A<br>Genbank Genomic Sequence ID: NT_009775.13<br>Coordinates of Mutation on Genomic Sequence (start-stop): 2144088-2144088<br>NCBI dbSNP ID (if any): 2177979<br><br>ATGCAGGAAGACTCCCTGATGTGATCATGTGTCTCACCCTTTCARGCTGAAAG<br>CAACAGTRCAGACGATGAGACCGACGATCCCAGGASGTATCAGAAATATGGT<br>TACATTGGAACACATG |

| SEQ ID NO:6 |
| --- |
| AllelicVariants: G/C<br>Genbank Genomic Sequence ID: NT_009775.13<br>Coordinates of Mutation on Genomic Sequence (start-stop): 2144116-2144116<br>NCBI dbSNP ID (if any): 1051042<br><br>GTGTCTCACCCTTTCARGCTGAAAGCAACAGTRCAGACGATGAGACCGACGA<br>TCCCAGGASGTATCAGAAATATGGTTACATTGGAACACATGAGTACCCTCATT<br>TCTCTCATAGACCCAG |

| SEQ ID NO:7 |
| --- |
| AllelicVariants: G/A<br>Genbank Genomic Sequence ID: NT_009775.13<br>Coordinates of Mutation on Genomic Sequence (start-stop): 2144321-2144321<br>NCBI dbSNP ID (if any): 2660<br><br>GGGCTCCAGTGTTATCTGGACCAGTTCCTTCATKTTCAGGTGGGACTCTTGAT<br>CCAGAGARGACAAAGCTCCTCAGTGAGCTGGTGTATAATCCAGGACAGAACC<br>CAGGTCTCCTGACTCC |

| SEQ ID NO:57 |
| --- |
| AllelicVariants: C/G<br>Genbank Genomic Sequence ID: NT_009775.13<br>Coordinates of Mutation on Genomic Sequence (start-stop): 2131025-2131025<br>NCBI dbSNP ID (if any): 1015542<br><br>TAACGCATGCCTGTAGTCCCAGGTATTCAGGAGGCTGGGGCAGGAGGATC<br>SCTTGAACCCAGGAAGTTGAGGTTGCACGAGTCATGATCATGCCCCTGCAC |

FIGURE 1 cont.

SEQ ID NO:58
AllelicVariants: G/A
Genbank Genomic Sequence ID: NT_009775.13
Coordinates of Mutation on Genomic Sequence (start-stop): 2133961-2133961
NCBI dbSNP ID (if any): 757398

GACAGGAAGTGTAACCTCTCAGAGGCTCCCTTGCCACATCAGGAGAATTG<u>R</u>
TAAAACCACACTACCTGTATCATATCATTATTTTAAGTGATAAATGATCA

SEQ ID NO:59
AllelicVariants: C/A
Genbank Genomic Sequence ID: NT_009775.13
Coordinates of Mutation on Genomic Sequence (start-stop): 2139587-2139587
NCBI dbSNP ID (if any): (unknown)

TAGCATTAGGTATATCTCCTAATGCTATCCCTCCCCAATTCCCCCCACCC<u>M</u>GC
TTGTTGGTATTTGTATATCTTCATTTGAGAATTCTCTGTTCATGTCCT

SEQ ID NO:60
AllelicVariants: T/G
Genbank Genomic Sequence ID: NT_009775.13
Coordinates of Mutation on Genomic Sequence (start-stop): 2144294-2144294
NCBI dbSNP ID (if any): (unknown)

GTGCATCTTGGGGGAAAGGGCTCCAGTGTTATCTGGACCAGTTCCTTCAT<u>K</u>
TTCAGGTGGGACTCTTGATCCAGAGA<u>R</u>GACAAAGCTCCTCAGTGAGCTGG

SEQ ID NO:61
AllelicVariants: A/G
Genbank Genomic Sequence ID: NT_009775.13
Coordinates of Mutation on Genomic Sequence (start-stop): 2144985-2144985
NCBI dbSNP ID (if any): 7135577

GAAAAATTATAGAACCTCCCTGTGTGACACAGCAGCCACTAGCCACATGT<u>R</u>
TCAAATGCTTAAAATGTAGCTAGTCTAAATCTACATGTGCTGTGAGTGCA

SEQ ID NO:62
AllelicVariants: C/T
Genbank Genomic Sequence ID: NT_009775.13
Coordinates of Mutation on Genomic Sequence (start-stop): 2156523-2156523
NCBI dbSNP ID (if any): 7968145

ATGCTTCTATAGGCTTTTCTCACTGATGCTCTCTGGGCAGACAGGCTCCT<u>Y</u>
AATATGAGAGTGACACACACTCCTTTCTTCATTTTCAGGTAAACCTCACA

FIGURE 1 cont.

| |
|---|
| SEQ ID NO:63<br>AllelicVariants: A/- (A or deletion of A)<br>Genbank Genomic Sequence ID: NT_009775.13<br>Coordinates of Mutation on Genomic Sequence (start-stop): 2156595-2156595<br>NCBI dbSNP ID (if any): (unknown)<br><br>CCTTTCTTCATTTTCAGGTAAACCTCACACTGGTTGGCAGAAGGAACTAT**(A-)**<br>CCAATAATTAGTGAACATGCGGTGAATTTGCAACAGACAAGASGAGCCTC |
| SEQ ID NO:64<br>AllelicVariants: G/C<br>Genbank Genomic Sequence ID: NT_009775.13<br>Coordinates of Mutation on Genomic Sequence (start-stop): 2156638-2156638<br>NCBI dbSNP ID (if any): 7967461<br><br>GAACTAT(A-)CCAATAATTAGTGAACATGCGGTGAATTTGCAACAGACAAGAS<br>GAGCCTCATTATCCTATAGTTTCCAGGTTGCTTAGGGAGGCAGAAATCAC |

Bold, singly underlined bases represent the particular allelic variant identified by each SEQ ID NO. Doubly underlined bases within SEQ ID NO: 1, 2, 4, 5, 6, 60, 63 and 64 represent overlapping mutations within the defining sequence that are identified by another of the provided SEQ ID NOs. As an example, the defining sequences provided for SEQ ID NO:1 and SEQ ID NO:2 overlap within the genomic sequence and thus their sequences each contain both mutations identified by SEQ ID NO:1 and SEQ ID NO:2.

In SEQ ID NO:63, the mutation is states are alternately an A or a deletion of the A at the position indicated as denoted by (A-).

Degenerate nucleic acid codes:

R=A/G
Y=C/T
S=C/G
K=G/T
M=A/C
W=A/T

FIGURE 2

```
SEQUENCE FRAGMENT OF NCBI Accession NT_009775.13 FROM 2,130,000 - 2,157,999
2130000    GGCTGCAGTGAGCTAAGATTGTGCCACTGCACCCCAGCCTGGGCAACAGAGTGAGACCCT
2130060    GTCTCAACAAAATAAATAAATATATTTTGAATTAAATTAAAATGAAAAAACAGCCTATCA
2130120    AAAAGTGTGGGATGTAGTGAAAGTAGTGTTTAGAGGGAAAGTTATAGCATTGAATGCATA
2130180    TATTAGGAGAAGAAAGATCTAACTCAGAGAGGGATGAACAGGTGAGGCATAGGGGATTTT
2130240    AAGGTAGTGAAACTCTTGCAGGGCAGGGGAGCCCCAAAACTGGGACACCGTCCGGGAAGG
2130300    CTCTTGGCTTCGTCCAGGAAGGAATTCAAGGGTGAGCTAGAGGAGGAAGAAAAAGGTTTA
2130360    TTGAGGCAGCAGGGTTACAGTTCTGTGACTGTCCCTGCAGAGCAGGGCCACCCCATAGGC
2130420    AGTGCCTGGAGAGCAGCAGCTCAGGGCACTTCTATAGTCACATTCATACCCACTTTTAAA
2130480    TACGTGCAAATTAAGGGCAGGTTATTCAGAAATTTCTAGAAGAAGGGTGGTAACTGGGTC
2130540    ATTGCCAGGGAATGAGTAAACTGTTCATGGTGCTGGTGCTCATGCCAGCCAGTCTTCAAT
2130600    CTGGCCCTGAGTCAAGCCCCACCTCCTATCTCAAAACTATTCTGCATGGTGCTGTAATGG
2130660    TGGATACATGACATGTTATGTTTGGCAAAATCCATAGAACTGTAGGACACAAGAGTGAAC
2130720    CTTAATGTAAACCTTAATGTAAATGGACTTTTGTTAATTATGATGTATTAATATCAATTC
2130780    ATCAATTGTAACAAATGTATCACAGTACTGTTAATAATAGAGGAACTTATTGGCAGGAGA
2130840    GAGAGCTTATGGAACTCTCTGCACATTCAGCTCAATATTTCTGTAAGCCTAAAACTGCTG
2130900    TGAGAAATAAAATCCAACCTGGGCAACATAGCAAGACCTTGTCTCTACAAAAAATAAAAA
2130960    ATGAGCTGGGTGCAGTAACGCATGCCTGTAGTCCCAGGTATTCAGGAGGCTGGGCAGGA
2131020    GGATCCCTTGAACCCAGGAAGTTGAGGTTGCACGAGTCATGATCATGCCCCTGCACTCCA
2131080    GCCTGGATAACAAAGCAAGATCCTGTCTCCAAAAAATAATAAAATAAAATAAAAATCTAC
2131140    TAATTGAAAGGGAAAAAAGCATAGTATAATACCATTCTTAACAAAAAGAAAAGAGACCTG
2131200    TGTTTGTGTGTGTGTTAACATTTGAAAAAAATCTGGAAAGCTCTATATCAAAACGTTTAT
2131260    AGAGGCAATTTTGTAGTGTTAGAATCATAGATGATCTTTCCACTTCCTGGTTTTTCTGAC
2131320    TTTTTTTCTTTTTGCAGTGGGCATGTATTGCTGGAAAATACCACAGACAACTGTGAAGG
2131380    ATTTCATCAACAACAAAAAAAGATAAAGAAGGAAACACAAAATCTGTTAAATAAGATTT
2131440    ATGTTGGCTGGAGGTTAAAATGCATTTCCAGAGCAGAGTTCAGAGAAAGGCTGGGCTGCT
2131500    TGTTGCTGGCTAAAGGACAAAGGGTAAGTTTCAGGAAGCAGAAGAGTGAGCAGATGAAAT
2131560    TCAGCACTGGGATCAGGGGAGTGTCTGATTTGCAAAAGGAAAGTGCAAAGACAGCTCCTC
2131620    CCTTCTGAGGAAACGAAACCAACAGCAGTCCAAGCTCAGTCAGCAGAAGAGATAAAAGCA
2131680    AACAGGTCTGGGAGGCAGTTCTGTTGCCACTCTCTCTCCTGTCAATGATGGATCTCAGAA
2131740    ATACCCCAGCCAAATCTCTGGACAAGTTCATTGAAGACTATCTCTTGCCAGACACGTGTT
2131800    TCCGCATGCAAATCAACCATGCCATTGACATCATCTGTGGGTTCCTGAAGGAAAGGTGCT
2131860    TCCGAGGTAGCTCCTACCCTGTGTGTGTCCAAGGTGGTAAAGGTGAGTCCAGGCCTGC
2131920    CTGGCCAGGGGAGGGTGGCTGAATGTGCAAGAGTTGAGATTGAGAATGAGAGAGAGAGA
2131980    GAGAGAGAAGCAAAAACCTAGAACCCAGGGTGCAAATGTGAGTACAGAGAGCTGAGATCT
2132040    TCTGGGATGGTGGTTTCTTATTTATCCACACAGCATGTTAAAATAGATTCTGGGGTGAAA
2132100    TCCTACATCCCTATTATTAACAAGTGACCCTCCCCCCTACTTCCCGCTGAAGTTTATGAA
2132160    CCACTGTCCTGGGCGATGCCCATTTCAGAAATAGGGAACTGAATCCCAGCTCTGGTAAAC
2132220    AGTTTGCTAATTCGTGGCCAGGCTAGGGGCTCACCATTTCTGCAGTGAAGAATCATATGT
2132280    TTTGAAAGCAAATAGCACCTGCTGCTGCAAGACCTTGAGCAAGTCACTTAACTACTCTG
2132340    TGTTCCAATTTCCTCAGCCATAATCCCCAATACTGTTGCAGTCTTGCCAGTGCACCTTAA
2132400    TGTAGCAGCTTCTCACTGAATTAGTACCCAAGGTTCTTTGTCCTGCATCCAAGAAAATTA
2132460    AGGAACATGGACACAAACGTGAGCTTGGAGCAAAAGTTCAGTAAGCAAAAGAAGAAAGCT
2132520    GTCTCCACTGTGGAGAGGGAAGTCTGAGTGGATTGCCAGATTGCAGCTGAATGCAAAAAA
2132580    CTTTTATAAGAAACCACTCTCCTCCCTGTAACTGTTTGAGAAACTTTTTATCAGTAAAGC
2132640    TGTGCAACTTCCCTTACCTTATGCAGCTGTGGGTATATCTAGGCAAGCATAAAGCGCT
2132700    GCTTCTCTTGTATGTATAACTGTGGATTTGTTTTAGGTAAGTCCCACTCCCTGCGCCAGT
2132760    TTCAGGCAGGCCGCTCCTCCAGGGCCCAGCCTTGACCATTTACCTAACTGATTTTTCCTC
2132820    TACTTTCCCTCAATACCTCATAGGGCCGTGTAGATTAAGTAAAATAGTAAGTGTGAACCA
2132880    CCCAGCATAAGCTAGTCCTGGGCATCGTAAAGGACAATGGGAAAAGAACACAGATCCTGG
2132940    AAGAAGGCCCCAGGTTTGAATTGTATTTGCCACCTACTAGCTGGGTGATGGGCTGATA
2133000    TATTATCTCACTGAGCATCCATTTTCCCATCTGTAAAATGGAACTAATGATAATGGCAT
2133060    CCAAATCATAGCATCATTGTGAGCATTATAGGAGTTTAAGACATGCAATGCCTTCAGAAC
2133120    AGTGGCTAGTGCTCCATAATGTTAGTGATTGCTCCTGTCATTTTATTTAGGGAGGTTTGC
```

FIGURE 2 cont.

| | |
|---|---|
| 2133180 | CTCACTAAGCATCAATTATTATTTTTGTCGTCTTTTTCAGGGTGGCTCCTCAGGCAAGGG |
| 2133240 | CACCACCCTCAGAGGCCGATCTGACGCTGACCTGGTTGTCTTCCTCAGTCCTCTCACCAC |
| 2133300 | TTTTCAGGATCAGTTAAATCGCCGGGGAGAGTTCATCCAGGAAATTAGGAGACAGCTGGA |
| 2133360 | AGCCTGTCAAAGAGAGAGAGCATTTTCCGTGAAGTTTGAGGTCCAGGCTCCACGCTGGGG |
| 2133420 | CAACCCCCGTGCGCTCAGCTTCGTACTGAGTTCGCTCCAGCTCGGGGAGGGGTGGAGTT |
| 2133480 | CGATGTGCTGCCTGCCTTTGATGCCCTGGGTGAGAGCTCCCAGCTTCTTTTTCTCCCTCT |
| 2133540 | TCCCATTTCTGAGCAGAAATCTCCCACAGTTTGAGAGCTTTTTGCCCCAACAGGGCATCT |
| 2133600 | CTCTAAAGCAGGGTGGGAGGAGATCTTAGGATCTGTCCCGGGGCAAGAATGAATACGGTC |
| 2133660 | ATGATCTATCACAGGAGAGACATTAAACAGCAAATTGGCATAATGTGGGGACAAAGACAT |
| 2133720 | TTCTTACAGAACATCTGCAAGGCTTACTGGTTCTGTTTAAGGCAAATGTGTGAATTTTA |
| 2133780 | TCTTTCTAAAATCAGGCAGCAAAGATGTGGCTTAAAGTTCATGTTACTCTCATCTTTGTC |
| 2133840 | CCAACATGAGATCTCATCAAACGTATGCAGCACGTTGGGAGATAGATATTTATAATTTGC |
| 2133900 | AGGAACATTTGGACAGGAAGTGTAACCTCTCAGAGGCTCCCTTGCCACATCAGGAGAATT |
| 2133960 | GGTAAAACCACACTACCTGTATCATATCATTATTTTAAGTGATAAATGATCATCTACATT |
| 2134020 | CAGCTCTGATGAGTAATAGGTGTTCAAAAATAGGAACTTCCAGCCAAGTGTGGTGGCTCA |
| 2134080 | TGCTTGTAATTCCAACACTTTTGGAGGCTGAGGCAGGAGGGTCGCTTGAGCCCAGGAGTT |
| 2134140 | CAAGACCAGCCTGGGCAGCAAAGTGAAACCTCATCTCTACTAAAAATTTTAAAACATTAG |
| 2134200 | CCAAGTGTGGTGGTACATGCCTGTGGTCGCAGTTATTCAGGACGCTGAGACTGAACGATC |
| 2134260 | ACATGAGGCCAGCCAAGGATTCGAGGTGTCAGTGAGCCACGAATGTACCACTGCACTCCA |
| 2134320 | TCCTAGGCACAGAGCAAGAGCAAGACCCTGTCTCAATCAATCAGTCAATCAGTCAAAACT |
| 2134380 | ATGAATTTCCCAGCTGTATATGAAGGCACCTCAAAACACCACAGTGAACTCACAGAGGGA |
| 2134440 | CACGGAATAGTTTAGATTTTAATTTTTTGAGGGAAATGCGATGACATCTGTCACACACCG |
| 2134500 | CACAAACGGCTACTATTAAACTGAACTTACTGATTAGTGGCTACTAATTAATAGTTGGTC |
| 2134560 | ATTAAGCAGTAATTAGTGATTAATTATCAAGTAATTAGGACTTAATTAAAGGAACTGTCA |
| 2134620 | CAGTTTCCTTTAGTCCTAGGGCAGCCATGAAAAAAAAAATGCTGACTCTCCAAAGACACC |
| 2134680 | AGGGTATGAGAAAGTTTTGGATTCTCTCCTTTGTGCCATCTCCTGTGTTGGGGGCTGAAG |
| 2134740 | TACAATGGTTGTAAAAGACAAGAGGGAGAAGGCTGGTCACAGTGGCTCACGCCTGTAATC |
| 2134800 | TCAGCACTTTGGGAGGCCAAAGTGGGGGGATCACTTGAAGTCAGGAATTCAAGACCAGCC |
| 2134860 | TGGCCAACATGGTGAAATCTCACATCTACTAAAAATACAAAAATTAGCTGGGCGTGGTGG |
| 2134920 | TGTGTGCCTGTAATCACAGCTACTCGGGAGGCTGAGGCAGGAGAATTGCTTGAACCCAGG |
| 2134980 | AGATGGAGGTTGCAATGAGCCAAGATCATGCCATTGCACTCCAGCCTGGGCAACAGAGTG |
| 2135040 | AGACTCCATCTCGAAAAAAGAAAAAGAAAAGAATATAAGGAGTGATTAAAAAAGAAAA |
| 2135100 | GAAAAGAAAACTAAGTAGGGTGAAACAATAGATAGCCATGGGGGTTAGGGAGCTTTTTA |
| 2135160 | GACAGGGTCGTGAGGGAGGGTCCCTGAGCCTGAGTGGCGAGAAGGAGTGAGCCTTGGGGA |
| 2135220 | GATCTGGAGGTTCTGGGAAGAGGAATGGCAAGTGCAGAGGCCCTGAAGCAGCAATGACCA |
| 2135280 | TGGCACATTTGAGGAAGAGAGAAAAAGTCAGAGAAGTAGAAAGTGGGCAAAGGAAGCAAG |
| 2135340 | ACAGGAGGTGAGGTGGGAGAGGTTCCAGAGACCAGATCACACCAGACATCATTGGCCACC |
| 2135400 | ATAAGATCTTTGGGTTTTAAAATTCCAGATGTTATGGGATGCAGGAAGCAGCATGATCAG |
| 2135460 | CAGCATTCTCTAGGTGCCAGGTTGAGAACAGGCTGTGGGGGAACCTGTAAAGAGGTTGCT |
| 2135520 | GCCATAGTTCCGGCGAGTGACGGTGGTGGCTTGGATGGGTGATGGCAGTGGAGAGGGCA |
| 2135580 | GGAGGGAGGATCAGGAATGGACCTCAAGACTTCCCAGCCCTGGGTCTGCTGCACTTTTCA |
| 2135640 | ATCAAACCCCATGGCCAGGGAGATTGTCCCCTCAGAGTGACTGAAGGAAATTCAGAGAAG |
| 2135700 | AGCTGACACCTAAGTTGTAGATTTTGCCCGAACAGGTCAGTTGACTGGCGGCTATAAACC |
| 2135760 | TAACCCCCAAATCTATGTCAAGCTCATCGAGGAGTGCACCGACCTGCAGAAAGAGGGCGA |
| 2135820 | GTTCTCCACCTGCTTCACAGAACTACAGAGAGACTTCCTGAAGCAGCGCCCCACCAAGCT |
| 2135880 | CAAGAGCCTCATCCGCCTAGTCAAGCACTGGTACCAAAATGTATGGCCCTCCCACCAGGC |
| 2135940 | CTGGTGGGTCCTGTCTCGACTGGGAGCAGAGGAGGGTGGGGGAGGAGAGAAAGAAGGG |
| 2136000 | AGTGAAGGGAAGAGGAGGGGGAGTGGTGGAGGGAAATAGAGGGATGGAAAAAGGAGAGAA |
| 2136060 | AGGAAAAAGAGGTGGAGAGAGGAGCCTGCAACAGAAGGGAGAATGAAAGGGAAGGAAGAG |
| 2136120 | AGAAAGGAAGGGATTTTGGTGTTCTGTTCACTGCTGTATCCCCAGAACTTAAAACAGAGC |
| 2136180 | CTGGTGCATAATAGGTGTAAATAACTGTTGAATAAATGAATCAATGCTACATACACACAC |
| 2136240 | GCACGCACACACACAGAGAGAGAGTCAACCACACTCTTCAGAAGGTGGATAAGTTAAA |
| 2136300 | ACAAGAGTTTCAAACAAATATATGTTCAGATGCCCTTTCCTCCCACTTACTGGCTGGCTG |
| 2136360 | GCCTTAAGTAAGCAACTTAACCTTTCTGTTCTTTCTGCTTTCTTATCTGCAACGAGTAGC |
| 2136420 | ATGCCATAGCTAGAGTAACACGGCATATAGTTGGTCCTGATAAATGTAGCATATTTTAGC |

FIGURE 2 cont.

```
2136480  CACCATAGGAGTACACATAATAAAAGCTAACATGTAGTATGTGCTTAGCTTATCTATGTT
2136540  TTGTGGATGTGATACAATTTTCTGTTCACTTTTAAATGCCCTGCATCTTAGTCAATTTTA
2136600  ACAGTGATTCTGTAAGTTAGATAAGGTTAGGCATTATTATTAAATCCATTTTACACCAAG
2136660  AGAAACTTGGGTCAAAAAGAGAAACTCCTGGGTCACATGGCTCATTCGGCCAATAAGTAG
2136720  CAGAAGTAAAATTTGAATTTGGCTGGGCGCGGTAGCTCACACCAGTAATCCCAGCACTTT
2136780  GGGAAGCCAAGGCAGGTAGATTGCTTGAGCCCAGGAGTTCAAGACTAGCCTGAGCAACAT
2136840  GGCAAAACCTCGTCTCTACAAAATAAACTAAAAATTTAGCCAGGTGTGATGGTGAGCACC
2136900  TGTAGCCCCAGCTACTGGGTAGGCTGAGGTGGGAGGATCGCTTGAGCCTGGGAGGAGGAG
2136960  GTTGCAGTAAGTCAGGATTGCACTACTGCCCTCCAGCCTGTGAGACAGAGCAAGATCTTC
2137020  TCTCAAACAAACAAACAAACAAACAAAAACTCGAATTTGGGTCTATTGACTTAAGA
2137080  GTTTGCCTGATAATAATAGGCATTCAATGTATATTTCTTGAATGAACGAATGAATGAAAA
2137140  TAATCAGGAATAAACTTTCCAATTTAAAAGTAACACCTCTAGGTAAAAAAAGACAATCA
2137200  TTTAGTTGCCAGACTTCTAAGTGTTTGCTGTTCTATGAATTGTAATCATGGAGCCTGAGC
2137260  ATTGTAGAATTTACAAAAGCAGTTCCTGACAAAAGCAGCACTGCCCCCAGGGACATATTG
2137320  AAAATTAATGAGGGTGTTTTTGGTAACCATGGTGATGGGAGGACATGGGTGCTACTTATA
2137380  TTTAGTGGAAAGAAGACAAGAATGCTAGTTATTGTACAATGATCAAGAGAGTCCTGCACA
2137440  GCCAAGAATTGTCTTTTTCTTTCTTTCTTGATGCTGTTCTCCTTTAAAACAAGACAAGAT
2137500  TAACAATAATTTAACTCCACTAACCACCATCATCACCACCTCCAACTTATATGCTACATT
2137560  TCTTGTATATTTCAAGTCTGTTTATATTTTCAAGTGCCTCGAAGTATTATTGTTTTATAG
2137620  CCAAATGTTTAGTTAATCTGCTCACAGATTTACCACTTTCTTCACTATTCATTCTGTCTT
2137680  ACACCTCTAACATTCCATCTGGGGTAATTTTCCTAAATGATCATGCATCCTTTGGGATTT
2137740  CTTTTGATGATGGTCTATTGGTAGTAAACTCTCTCAGTTATTGTTTGTCTGAAAATGTCA
2137800  TGCTTTTGCCTTCATTGTTGAAGGGTGCTTTTGCTGGGTGGTCATTTCAGTATATTGAAT
2137860  ATATCATTCCATCTTCCAGTGTCATCATTAAAAAGTCAGTTGCCAGTCTAACTGCAGCTC
2137920  TTTTATAAGTAACCTGTCTTATTCTTCTGGCTGCATGTAAAAGTTTTCTCTTTGTCTTTG
2137980  ATTTTGTTTAGCTTCAATCTGCTGTGTCTTAATGATGGGTTCCTATTGTTTGTCCTGATT
2138040  GGGATTCCGTTAAGATTCCTGAATCTGTGGGTAGATATCTTTAATCAGTTTTGAAACTTC
2138100  TCAGCCATTCTTCTAAAATATTGATTCTCCTTCATTCTCTCCTCACCTTCTAGAATTCCA
2138160  ATTAAATGTATGTTAGACCCTGCTCTATCTTTCATATCTCTATACTCTCTTCTGTGTTTT
2138220  TCATCCTTTTGTCTATTTTTCCATGCTTTATTCTGAATAGTTCCTTCTAATCTACCTTCC
2138280  AATTAACTAATTTTCTCTTTAGCTATATCTAATTTGCTGTAATTAATTACAGTTGCCATT
2138340  TTTATCCTAAAATTTCTATTTCATATTTTTGTATCTGCCATGGTACTTCTTATGGCTTTT
2138400  AATTCCCTGCTAACTATTTAAAGTTCTTATTTTATCCTGTGAATATGATATTCCTAGTTA
2138460  TTTTATTTTTAATTTTTATTATTTGTTAATCTTATGTTTTATTTACACTTCTTTTCTGTG
2138520  ACATGAGCACACACAGATTCATGTGTATACATATATGGCTCTGATACCTCTCCTTTCCTG
2138580  TCCTCATTCAAACCACTGATCACAGAGAGAGGACTATTTTTTTTATTTTTAATTTTTCT
2138640  ATTTCAATAGGTTTTTGGGGGAACAGGTGGTGTTTGGTTACATGAATAAGTTCTTTAGTG
2138700  GTGATTTTGGTGCACCCATCACCCAAACAGTGTACATTGTACCCAATGTGTAATCTTTTA
2138760  ACCCTTGCCACACCCCACCCTTTCCCCGCAGTCCGCAAAGTCCCATGTATCATTCTTATG
2138820  CCTTTGCTTCCTCATAGCTTAGCTCCCACATATGAGTGAGAACATACAATGTTTGGTTTT
2138880  CCATTCCTGAGTTATTTAATTAAAATAATAGTATCCAATTCCATCCAGGTTGCTGTGAAT
2138940  GCCATTATTTTGTTCCTTTTTATGGTTGAGTAGTATTCCATGGTGTGTTTGTGTGTGTAT
2139000  AACATTTTTCTTTATCCACTCATTGATTGATGGGCATTTGGGCTGGTTCCATATTTTTGC
2139060  AATTGCAAATTGTGCTGTTATAAACATGTGTGTGCAAGTATCTTTTTTGTATAATGACTT
2139120  CTTTTCCTCTGGGTAGATACCTAGTAGTGGGATTGCTGGATCAAATGGTAGATCTACTTT
2139180  TAGTTCTATAAGGAATCTCCACACTGTTTTCCATAGTGGTTGTATGAGTTTACATTCCCA
2139240  CCAATGGTGTAAAAGTGTTCCCTTTTCACCACATCCACACCAACATCTATTATTGTTTGA
2139300  TTTTTTATTATGACCATTCTTGCAGGAGTGAGGTGGTATCACATTGTGGTTTTGATTTGC
2139360  ATTTCCCTGATAATTAGGGATGTTGAGCATTTTTCCATATGCTTGTTGGTATTTGTTTTT
2139420  TTTTTTTTTTTTCATTATTATACTTTAAGTTTTAGGGTACATGTGCACAATGTGCAGGT
2139480  TAGTTACATATGTATACATGTGCCATGCTGGTGTGCTGCACCCATTAACCCGTCATTTAG
2139540  CATTAGGTATATCTCCTAATGCTATCCCTCCCCAATTCCCCCCACCCCGCTTGTTGGTAT
2139600  TTGTATATCTTCATTTGAGAATTCTCTGTTCATGTCCTTAGCCCACTTTTTGATGAGATT
2139660  TTTTTTTTCTTGCTGATTCGTTTGAGTTCTTTGTAGATTCTGGATATTAGTTGGATGTAT
2139720  AGATTGTGAAGATTTTCTCCCATTCTGTGGGTTGTCTGTTAACTCTGCTAATTATTTCTT
```

FIGURE 2 cont.

| | |
|---|---|
| 2139780 | TTGCTTTGCAGAAGCTTTTTAGTTTAATTAAGTCCCATCTATTTATCTTTGTTTTTGTTG |
| 2139840 | CATTTGCTTTTGGGTTCTTGGTCATGAAGTCTTTGCCTAAGCCAATGTGTAGGAGGGTTT |
| 2139900 | TTCCAATATTATCTTCTAGAATCTTTATGGTTTCAGGTCTTAGATTTAAGTATTTGATCG |
| 2139960 | ATTTTGAGTTGAATTTGTATAAGGGGAGAGAGAAGGATTCAGTTTCATTCTTCTACATG |
| 2140020 | CAACTTGCCAATTATCCTAGGACCATTTGTTGAATAGGGTGTCCTTTCCCCATTTTATGT |
| 2140080 | TTTTGTTTGGTTTGTCAAAGATCAGTTGGCTGTAAGTGTTTGGCTTTATTTCTGGGTTAT |
| 2140140 | CTATTCTGTTCCATTTGTCTACGTGACTATTTTTATACCAGTACCATGTTGTTTTGGTGA |
| 2140200 | CTATGGCCTTACAGTATAGTTTGAAGTCTGATAATGTAATGCCTCCAGATTTGTTCTTTT |
| 2140260 | TACTTAGTCTTGCTTTGGCTATGTGAGCTCTTTTTTGGTGCCATATGAATTTTAGGATTG |
| 2140320 | TTTTTTCTAGTTCTGTGAAGAATGATGGTGGTATTTTGATGGGAATTGCATTGAATTTGT |
| 2140380 | AGATTGTTTTTGGGAGTATGGTCATTTTCACAATATTGATTCTACCCATTCATGAGCATG |
| 2140440 | GGATGTGTTTCCATTTGTTTGTGTCATCTATGATTTTCTTTCAGCAATGTTTTGTAGTTT |
| 2140500 | TCCTTGTAGAGTTCCTAGTTATTTAAAGTCTGTGTTCGGTCTTTCAGCATTTAAAGTTT |
| 2140560 | GTAGGTTTATTACTATTTCTCTTCTTTCTGTTGGTCATAACTCTTAGTGTTTTGTTTCCT |
| 2140620 | TGTGTGCCTGGTTACATATGTGCTGGTCATTGTATTTGAAAATTATGTGTGAAATAATTT |
| 2140680 | GAGGTTTTGGATTATGTATATTCCTCCAGAAAGAATTTCATTTGCTTCTGTGCATTTCTT |
| 2140740 | AGGAACATTACAAGTCCTTCTTCTCAGTTAATTTCGTAGTATCTTTATCAGATAGGTGC |
| 2140800 | TATTACAACCACTCACTTAGCAGATGAAAATCATGAGGCTCTGAGAGTCTAAGTCATCTA |
| 2140860 | CTTAGAATTGGACAATGGTGAAGCCAGGATTCAAACCCACATCAATAAGAATCCAGCGCT |
| 2140920 | CTTAACAAGGGGCCAGTACACTTTTTTAAAAAATAAAAGGCTAGATAGTAAATATTTTAG |
| 2140980 | ACTTTGTGGACTGCACAGCCTCTGTTGCAACTACTCAACCCTGCCTTTGTAGCATGAATG |
| 2141040 | CAGTCATAAACTATACATAAATGAATGAGCCTGGATTCGTTCCAAGGAAACTTTATAAAA |
| 2141100 | ACAGGTGGCAGGCTGGATTTGGCCCATGAGAAGTGTAGTTTACACAAAAGTTGAGCAAAC |
| 2141160 | CAATTTTTTTCTGATTGTTTTTCCTCTTCTCAGTGTAAGAAGAAGCTTGGGAAGCTGCCA |
| 2141220 | CCTCAGTATGCCCTGGAGCTCCTGACGGTCTATGCTTGGGAGCGAGGGAGCATGAAAACA |
| 2141280 | CATTTCAACACAGCCCAGGGATTTCGGACGGTCTTGGAATTAGTCATAAACTACCAGCAA |
| 2141340 | CTCTGCATCTACTGGACAAAGTATTATGACTTTAAAAACCCCATTATTGAAAAGTACCTG |
| 2141400 | AGAAGGCAGCTCACGAAACCCAGGTATGCTATCCCCACATGGCTTAGCTCCCCTATGTAA |
| 2141460 | ATGAACACCTGGATACAGGTACAGTGCCTTGGAAATGGAGGAGGTGGGAGGGCTCCCCAC |
| 2141520 | TTAGTGAGAATCTCCTGTTGCCCATCATTGTACTGGGCATTTTACTACTGCCATCTGTTT |
| 2141580 | TAAACACCTACCTCCAACCCTGTGAGGCAGGCACTATGCCAATTATTTTACAGGTGAGTA |
| 2141640 | AACTGAGGTTCTGAGAGGTAAGGAGCTTGTCCAACCCTTAACAGAAAATGAGTAAAATAG |
| 2141700 | CTGCAGTTTGAACTGAAATAAGAACAGCAGCAACAACAATGATAGTAATTGCTCCCAGGT |
| 2141760 | ATTGAAAGCTTGTTGTAAGACTAACACATGCTAATATAATAGTAAAAATTATTAGCAATA |
| 2141820 | TTACTGATATGTATGTTATGTTCTAGTCGCTGTGCTGAGCATTTCATATAACTGGGCTTT |
| 2141880 | TTCTATCCTCACAGCATAGCCTTTGAGATAGGTATGTGGAACTATTCCCATTTTACAGAT |
| 2141940 | AAGAATCCTGAGGCTTAGAGAGTTCAAGTGACCTACCCAAGGGCACATCACTGATAAAGG |
| 2142000 | GCAGAGGTGGGATTCAAACCCACATCTGTCAGGTGCAAGTGCAAGGCTCCTTCTCCTCAT |
| 2142060 | GCTCACTGCCTGCTGGGGAATAGGGCACTGGGGACATACCCCAGGGAGCCCTTCCTCATG |
| 2142120 | TTCTGAGTCCCAGTTCATCCCATGCTGCTATTTTGCTCTCCCAGGAGCATCTGGACTCCC |
| 2142180 | TAGACAGAGCCCCAGCTTCTCACCTGTCCCTCTCTAAATGCTGCTCTGCAGGCCTGTGAT |
| 2142240 | CCTGGACCCGGCGGACCCTACAGGAAACTTGGGTGGTGGAGACCCAAAGGGTTGGAGGCA |
| 2142300 | GCTGGCACAAGAGGCTGAGGCCTGGCTGAATTACCCATGCTTTAAGAATTGGGATGGGTC |
| 2142360 | CCCAGTGAGCTCCTGGATTCTGCTGGTGAGACCTCCTGCTTCCTCCCTGCCATTCATCCC |
| 2142420 | TGCCCCTCTCCATGAAGCTTGAGACATATAGCTGGAGACCATTCTTTCCAAAGAACTTAC |
| 2142480 | CTCTTGCCAAAGGCCATTTATATTCATATAGTGACAGGCTGTGCTCCATATTTTACAGTC |
| 2142540 | ATTTTGGTCACAATCGAGGGTTTCTGGAATTTTCACATCCCTTGTCCAGAATTCATTCCC |
| 2142600 | CTAAGAGTAATAATAAATAATCTCTAACACCATTTATTGACTGTCTGCTTCGGGCTCAGG |
| 2142660 | TTCTGTCCTAAGCCCTTTAATATGCACTCTCTCATTAAATAGTCACAACAATCCCATGAG |
| 2142720 | GCATTTTAAAAATTTTTTATTATTTTAGATTCAGAGGGCACATGTGCCATTTGTTACAC |
| 2142780 | AGCTATATTGTGTAATGGTGGGGTTTGGGCCTCTATTGATCCTGTCGCCCAAATAGTGAA |
| 2142840 | CAGAGTACCCAAAAAGAATTTTTTCAACCTTTGCCTTTCTCCCTTCCTCCTCCCTGTTGG |
| 2142900 | AGTCCCTAGTGTCTATTGTTCCCATCTTTAGCAGATGTTAAGTATTTGATTTCTGTTTC |
| 2142960 | TGGGTTAATTCACTTCGGATAATGGCCTCCAGCTGCAACCATGATTTCATTCTTTCTTAT |
| 2143020 | GGCTGCATAATACTCCATGGTGTAGATATACCACACTTTCTTTATCCAGTTCACACTGAT |

FIGURE 2 cont.

```
2143080   GGGCACTTAAGTTGATTCCATGACTTTGCTATTGTGAATCGTACTGCGATAAACATACGA
2143140   GTGCCGGTGTCTTTTGATAGAATGATTTCTTTACCTTTGGGTAGATACCGAGTAGTGGGA
2143200   TTGCTGGGTTGAATGGACATTCTACTTTTAGTTATTTGAAAAGTCCCATGAGGCATGTTT
2143260   TCTATCATTCCCATCTTACAGATGAGACAAAGGCTCAGAGAGGTGAGGTCACTTGCTCAA
2143320   GGACATCAGCTAACAAGTGGTGGAAATGGAATTCAAGCTCAGTGGACTCTAAAGCCAGTG
2143380   CTCATGTCACTGTGCTAAACAGCCTGCCTTGTCACATCCCCACCTCTCATCTGACCAATG
2143440   GGAGACTCTGAGCAGCTGAGTGACTTGGGTTGTCACACAGCTAAACAGGGGCAAAGGACC
2143500   CAGTCTTGGATCTTTCCACCTCCAAGCAGGAATCTGTCTGATTCCAGGGGATTGATGATG
2143560   TTGCAGATGGCTAGGAAGCAGACTCCAGGATGGAATTTAGTATGCAGGATGTTCTGGGGG
2143620   AGAGCCACTGGAACCAGCACTCAGGGAAAGGGGGGAAGAAAGGATAGGAAGGAAGCATGA
2143680   AAGAGAATAGGGAGAAGTGAACAGGGATGCAGAGCGAATGCCAGTTTCAGCCAACTCCAA
2143740   GGACAGCCCTGGAGCTGGAATGGCCTTTAGAGCTGCCCCATGGTGACAGAGGTGGCCAGG
2143800   CTTCTATACCCCTACGTGGATCACTCACTGTGCTTGGGCACCTTGGGAAAGGGCATGGCT
2143860   TTGAGCAAAAGGCTCTCTGCAGCTGAGGCAACCCCTAAAAGGGCTGACGGCTGAAGTCTG
2143920   TCTGCTGACCACTGTCCCAGCAGCTGGGGCTTGTTAGTCCTTCCTCAAAGGGGGATCCAG
2143980   ATGGCATGTCACAGTGTCTACCGTAAATGCTCACTGAATCCAGCTGCAATGCAGGAAGAC
2144040   TCCCTGATGTGATCATGTGTCTCACCCTTTCAGGCTGAAAGCAACAGTGCAGACGATGAG
2144100   ACCGACGATCCCAGGAGGTATCAGAAATATGGTTACATTGGAACACATGAGTACCCTCAT
2144160   TTCTCTCATAGACCCAGCACACTCCAGGCAGCATCCACCCCACAGGCAGAAGAGGACTGG
2144220   ACCTGCACCATCCTCTGAATGCCAGTGCATCTTGGGGGAAAGGGCTCCAGTGTTATCTGG
2144280   ACCAGTTCCTTCATTTTCAGGTGGGACTCTTGATCCAGAGAGGACAAAGCTCCTCAGTGA
2144340   GCTGGTGTATAATCCAGGACAGAACCCAGGTCTCCTGACTCCTGGCCTTCTATGCCCTCT
2144400   ATCCTATCATAGATAACATTCTCCACAGCCTCACTTCATTCCACCTATTCTCTGAAAATA
2144460   TTCCCTGAGAGAGAACAGAGAGATTTAGATAAGAGAATGAAATTCCAGCCTTGACTTTCT
2144520   TCTGTGCACCTGATGGGAGGGTAATGTCTAATGTATTATCAATAACAATAAAAATAAAGC
2144580   AAATACCATTTATTGGGTGTTTATTAACTTCAAGGCACAGAGCCAAGAAGTACAGATGCA
2144640   TATCTAGGGGTATTGTGTGTGTATATACATTGATTCAACAAGAAATATTTATTGAGCACT
2144700   TACTATGTGCCAAGCATAGCTCTGGGCACTGGGAATATAGCAATGCACAAAAGCAGACAG
2144760   AAATCCCTGTCCTCATGACCCTGCAGAGCCAAGACTTCCAGAATTTTTAAATAAAAAAA
2144820   TCCCTGTCCTCATGGAGTTGACATTTGTGCAAAACATCTTAATGTTAGATGGTTTTCCTA
2144880   TTACTAATAATTCTGAAATAAGCATCCTTGATTTATCCTTTCTCCATATCTCTGAGAAAA
2144940   ATTATAGAACCTCCCTGTGTGACACAGCAGCCACTAGCCACATGTATCAAATGCTTAAAA
2145000   TGTAGCTAGTCTAAATCTACATGTGCTGTGAGTGCAAGGTATATACTTGGTTTCAAAGAC
2145060   TTAGTACAAATGAAAAGAATGCCAAGTTCTTGCCAACTGATAATTTTTTTAATTGTGTGC
2145120   TGAAATGACAATTTTTAAATATATTTGAGTTAAATCAAATGAACTTCATCTCTTTCTTTT
2145180   CCCTTTTTAATTGTGGCTACTAGAAAATGTGAAATCATACATGTGGCTTGTGTTATATTA
2145240   TGTATTTCTATTGGACAGCTCTGTCCTCCAAGGTAAATCACTGGATTAAAGATTCGACTA
2145300   TACTGACTTACATTGCCACATTGTCACACTGTCCTTGGGACCAAGAATCAACATATCATT
2145360   CATAAGACTCTAAAATATAAAACTCTCATAAATACTCACAAAAGAACCTAGCATGCTCTG
2145420   ATCACCTGAGTTGCTGGTCACTTTTGGTGGCTGGTAAGCAGCCTTTGGTCCGTCCAGATT
2145480   ATATTCTTCCATTTAGTCCCCCCACATCCCTGTGAGATGGGTTTTGTTGTTATTCTCATA
2145540   ATATTAAGTGGAATAACTTGAGGTTCTAAGAGGTTACAGTGCTTGCCCAGGGTCACCCAG
2145600   CTGGTCAGGGCAGAGTCTGAACTTGAACCCTAATCCTTCTCTCTCTAAAGCTCATGTTC
2145660   TTAATCACTGTAGCATGGTCTTAATGTGTCCTCATTCATTGAAAGCTTATGTTTTCCTAC
2145720   TCTGGCGCCATGAGAACCAGAAGCATCAATGTCCAGGGGCAGGGAAAGATGAATGTCCCA
2145780   GCTCAACCTGAGCACAGATTCACCCTTCCTCGGTCTTTTTGTCCTATTTGTAGACTGGAT
2145840   TAGATGATGCCAGTCTACTGATTCAAATGTGAATCTCTTTCAGAAAAACCCTCACAGATA
2145900   CACCTAGAAATGATGTTTCACCAGCTATCTTGGCACCCTTAGCCCAGTCAACTTGTCACA
2145960   TAAAATCAATCATCACACACTCCATGCTGATAGGCAAGTGTGGACATCCCAATGTAATGG
2146020   CTTCATTGTATTTTACTGTGTGGAAAATGCACTTGTGTTGCCTTTTGAGAGTGTTTCATT
2146080   TTATAGCAATGCCACAACCAACAGTAGATTAATGGAATCAGTAATTAGTTGCTTGATCGA
2146140   AGAGCCACATGGCCACGTGATCAGCCTTCCATCTACAACAGGACCCAGGAGTATACCGGG
2146200   ATTGTTTTCAAAGGGCATAGACATTTTTGCTGCAAATGACATGGGCTTACTCCAGAGTC
2146260   CTGGAGGGGTCTGTGTTATAATTCTCTAAATAGATATTGCCATAATCTCTGAATGACACC
2146320   TTTTCCCATGACTAACACTTTGAACACCATGGGGTCTGCCAGGCTGGTGTGGGCCAAGTA
```

FIGURE 2 cont.

```
2146380    GAGGGGCGACTTGCACCACAGCCTATACCAGCTGCAGAGCCCTTTAGGACTTAATAAAAG
2146440    GGTGCTAATTTCTGTACTTCCCTGGCTCTGAGATGTAATAGTGGTTTTAATTTACTATCC
2146500    TGGCCAGGGAGGTGGCAGTTTCAAAGGTATCCCCATGACCTTCCTCACTGTGATAGCCCT
2146560    CACTTAACCCTCAGGCCAATGTCGGGTAGTGTCTTTTACCAAGCATGTCCTTTTTGAATA
2146620    TACATTCAGGGGACAGGGAAATGATCACCAGGTCGGTCCATAGACACAGTGGGCAAATGA
2146680    CAAGCCTGACTTGGCCAGGGCTCCATTTTTCACTCTTGGCTCCTATATGCCCCTACTCTG
2146740    ATGGGGACAGAATCTGATGACGCTTTTCGTTATCAGTGTTGATCCTCTGCCCAACAGTCT
2146800    TAGAAATGTTGAGTGACTCCCCTTTTCCAGTGTATCATCCTCTGAATAAATGGCCATAGG
2146860    TCCTTTGGGGGAAACCATTACTATATATGCTATGGTGTCACAGCATCCTTTCCCAAGGGG
2146920    ACTCTGCCTCCTCTTTGTTAATGGGGTCTAGTCTGAAAACTGGGTTGGTCAGTTCCAAAA
2146980    ATCAGGAAGGGATGATGACTTTTTATTGGAATGGCTCCCCTTAACCCCCTGGTCGTCCGG
2147040    CCTTGATTTCTTCTAATGGTATAAATTGAGTAGTGCCCTTTCAAGATACTCATCCACTAA
2147100    GTCACTAAGAGGCCACATTGTGTTAACCAGGTCCCTAACCCTGTATCAGTCACGACCCCT
2147160    GGCTGCCCCTCCAACCTCACCATTCATTATAGTCATTGCACCCACCTGGCTTCTATTGCT
2147220    CTGGGAGTCCTGCCTGCCCTATTGCCCTTATCAATCCAAGCTCTGTAACAGCCCTCTTC
2147280    CCAGGAGGCCACCACCAGAACACCTCATGATGCAGGTGTCCCTCTCTCCACACATTCCTT
2147340    ATGGCCTCGGGGAATGTTTTGTCCCCTGGGACTCTATTTCCAGACTTACATAGTAAACAT
2147400    ATCCACTCCTCTTCACTGTGCCCATTTCCCTTGGCCTCTTAATACCTTCTTCCATCAGCT
2147460    CCACAGCAATTCTGGAATTTCATACTTTTCTGCATTTCTAGGAGCCATCCTAGGAGTCAG
2147520    GGAAAACCTCGGCTTCACAAGTAAATGGGACTTCAGTTGTGTGCCAACATGCCTGGCTAA
2147580    TTTTTAAATTTTTTTGTAGAGATGGGGTCTTGCTGTGTTGTCCAGGCTGGTCTTGAACTC
2147640    CTGGCCTCAAACAATCTTTCCTCCTTGGCCACTCAAAGTGCTGGGATCACAGCTACCATT
2147700    CCCACACACATTTTCTTATTTTTAAAGGCTGTATGTGCACTGTATACATTAAATGTGTGC
2147760    ACTGTATACATTAACTGTGTGCACTGTATACATTAATTTTCTTTAACGAATTTATCCATT
2147820    TATAGTTGCTTTGGTTGTTTCCACTTGATTATTGTGAATAGTGCTGCAGTAAACATGGGA
2147880    ATGCAGTTATCTCTTTGATATCCTGATTTCAATTCTTTTGGATACTCAGAAGTGGGATTG
2147940    CTGGAACATATCGTAGTTCCATTTTTAATTTTTTGAGGAACCTCCATACTGTTTTTCACA
2148000    GTGGCTCACCAACAGTGTGCAAGAGTTCCCATCCCTCCACATCCTCACACTTGTTATCTT
2148060    TTGTTCATTCTTTAAAAAATGATAGCCATCCTACCAGGAGTAAGGTGATATTGCATCGTG
2148120    ATTTGATTTGCACTTCTCTGATAATTAGTGATATTGAGTATATTTTCATAGACCTGTTA
2148180    TCCATTTGTGTGTCTTCTTTGGAGAAAGATCTATTCCTATCCTTAGCCCATTTTTAAATC
2148240    AAGTTATTAATTTTTTTGCTAGTGAGTGGTAGGAGTTCCTTACATATTGTGGAGATTAAC
2148300    CCTTATTAGATGTATGGTTTGTGAATGTTTTCTTCATTCCATAGATTGTCTTTTCAGCCC
2148360    GTTGATTGTTTCCTTTGCTATGCAGAAGCTTTTTAGTCTGATGTAGTCCAAGTTGCCTAT
2148420    TTTTGCTTTTGTTGCCTGTGCTTTGCATACGTGGCCACCTGATCTTTGACAAGATTGCCA
2148480    AGAATACACAATGGGGAAAGGACAGTGTCTTCAACAAATGGTGTTTGGAAAGCTGAATGT
2148540    CCACATGCAAAAGAATAAAATTGGACCCTTACCTTACAGCATACACAAAAATCAACTCAA
2148600    AATGGATTAAAGACTTAAACGTAAGACCTGAAACTGAAACTACTAGAAGAAAACTTAGGG
2148660    GAAAACTTCATGACATTGGTCTTTCCAGTGATTTCAGGGATGTGACACCAAAAGCACAGA
2148720    CAACAAAAGGCATTTATTTTTATATGGCATGTGAGGAAGGGGTTCAGTTCCAGTTCTTCC
2148780    AATGTGGATGCTCAATTATCCCAGCAGCATTTATTGAACGGATCATGTTCTCTCCACTTC
2148840    TTTGCAAAGCCACCTCTTAAATATTCCCAGAGCCCATCTATGTGGGAGTCTGTTTCTGGA
2148900    CTCTGCTCTTTTCCATTGGTCTATTTTTTGTGTCCTTGAGTTAACACAACCTTGTCTTAA
2148960    TTACTATAACCTTATAATTCTTAGTATCTTTGGGAGAACTCTGTTCTCTTTTATCAAGT
2149020    CATTGGTTCCTCTTGGCCCTTTTATTTCTACATTAATTTATACTCAATTTGTGAAGCT
2149080    CCTCCCAAAATATGGGGAGGCATTTGATTAGAATTACACATATTAGCTTGGGAAGAATAA
2149140    CATCTATATTTTATATATATATCTATATAGAATTTGATGATTCTGATCCATGAACTTGGA
2149200    GTTTCTTTTCATTAATTTTTGTCCTCTTTAGTGACAGTGACAATGTTTTATCATTTTCCC
2149260    TGCAGAGGTCTTTCATGGTTTTTGTCATATGTATTCCCAAGTATTTGTTTCAGTACTATC
2149320    GTACTTGGCATGCTTTCTTTAATTTCATTTGCAATGGTTGCTTCATGGGAGACTTAAAC
2149380    ATTTTCAGTGGTGATATTTGGCTATAGCATTATAGGTGATCTTTATACTTTTCTAAATTT
2149440    TCTGTGGCCACGGGAAATAATAAAGACACTTTTCTTGCACAGAAAAAAAAAACTTTTGGG
2149500    AAGTATTTCTCACAGCTAAGATCTGATAGTTTACGCAAAGTTGGCAGGCACAGGCTACAG
2149560    AAAGCTCTGGGGTGCTGTTGTTTGGAGCTGCTGGTTCAAGGACAAATTCACAAGATTTGG
2149620    AAACAGAGGACCAAGTGTGTAAGGACGAGGGAAACTATGGTATAACATTGAAGCACCTGA
```

FIGURE 2 cont.

| | |
|---|---|
| 2149680 | GCTGGAAATTTCTGAGCCCTCAGAGATAAATTTCCTCAGCTCCTCCCTGCCGAGAAAACA |
| 2149740 | AAACTAAAAGAGTTAATGTTTAGCCAACAGAAATGAGAGTGAAGTTCACAGAAGAAATT |
| 2149800 | AGGGCACAGCTGGAAGTGTTCAAAATGAGGAAACGTTCAATGTCAAGTTTGAGATCCAGG |
| 2149860 | GTTGATGGGTGAACTCTGCACGCTCAGCTTCATGTTAGGTCTCCCAGCTCAACGAGGGGG |
| 2149920 | TGAATTTTGGTGTACTGCTGTCTTTGAGGCCCTGCGTGAACTCTCCCACACCCTCCCCCT |
| 2149980 | TTTCCTCATACAAATCCCCTCCTTGCACACCCCTCACGCCTGTCTGTGAGGTGCCAGGGC |
| 2150040 | CCCTCTCCCAGCCAACCGCAGGCCAGTATTGCCCCTCCCCAAACTTCCCTTCAGGCAGAT |
| 2150100 | CAAACCCAGGGCTCTGGAGTCACACTGCCTGGGCTCAAATCCTGCTTCTGAATCTTATGA |
| 2150160 | GACATCAAGTCACTTACCTAACTCCTTGGTGAAACAGGCTCTCCTCTGTCAAATAGGTGT |
| 2150220 | GCATGCTTTGGGAGGCCAAGGCAGGAGGATTGCTTGAGCCCAGGAGTTCAAGACCAGCCT |
| 2150280 | GGGTAACATAGTGAGACCCTGTCTCTATAAAAATAAAAAAATTAGCCAGGTGTGGTGGCT |
| 2150340 | CATGCCTGTAGTCCCAGCTACTCAGGAGGCTGAGGAGGAAGAATTCCTTGAGCCCACGAA |
| 2150400 | GTCAAGGCTGCAGTGAGCCATGATCAAGCCGCTGCACTCCAGCCTGGGCAACAGAATGCG |
| 2150460 | ACCCTGTCTCAGAAATAAGTAAATAAATAAATACATAAATAAATTTGGGTGCAATTGTGG |
| 2150520 | CTCTTAGTGTTACAGAGAGGACTGAAGGAGCTAATGGATGATGGATTTATGGCAGTACCT |
| 2150580 | CACATATAGCTTATCCTAAAGGAAGTTAGAGCTTATTATGATGATTATTCAAAAATATTT |
| 2150640 | ATCAAAGGTCTGCCCTGGGCCATGTTCTGAGCTAAGTGCTGGGGATGCAAAGATGAGCAA |
| 2150700 | GAGACTCCTCAGGGACAATTGTCTGATGAGATAACAGGCACTATTTATGAGAGGTCCAAT |
| 2150760 | CAATACAGTTCTATTTATCTTATAATTATCCAATAAATGATATAATAATTTATTAGAGGG |
| 2150820 | CCAATAAATCTGATGGCAGGAGCCTGTGGGGGTAATGGCCAGGTCTCACTATTGTGCCC |
| 2150880 | AGGCTGGTCTTGAACTCCTGGCCTCAAGCATTCCTTCTGCCTCCACCTCCCAGCATGCTG |
| 2150940 | CAATTACAGAGGCATGAACAACTGCACCTGGCCTAAAATTTTATGTTAATAAAAAAATGC |
| 2151000 | ATGTATTTGAGGAGTACGACATGATGCTTGAATATCATACTGTATCGGGGGAAACCAGCC |
| 2151060 | CCCGATATTTCAATGTAGGTTCTTTTCTATTTTCCCCAAGTGTCGGCTGGTCTGAGAAAT |
| 2151120 | AAAGGGAAAGAGTACAAAAGAGATAAATTTTAAAGCTGGGTGTCCAGGGCAGACATCACA |
| 2151180 | TGTCGGCAGGTTCTGTGGTGCCCCCTGAGCCATAAAACCAGCAAGTTTTTATTAGCAATC |
| 2151240 | TTCAAAGGGAGGAAATGTACATATAGGGTGTGGGTCACAGAGAACACATGATTCAAGGGC |
| 2151300 | GACAAAAGATCACAAGGCAGAAGGTCAGGGTGAGATCACAAGGTCAGGGCAAAACTAGAA |
| 2151360 | TTACTAAGGAAGTTTCATGTTCCACTGTGCATGCATTGTCATTGATAAACATCTTAACAG |
| 2151420 | TGTTCAAGAGCAGAGAACCAGTCTGACTAGAATTCGCCAGGCTGGAATTTCCTAATCCTA |
| 2151480 | GCAAGCCTGGGGGTGCTGCAGGAGACCAGGGCGTGTTTCATCCCTTATCTGCAACTGGAT |
| 2151540 | AAGGCAGACACCCCCAGAGCGGCCATTTTAGAGGCCCCCGGGAATGCATTCTTTTCCCA |
| 2151600 | GGGCTGTTAATTATTAATATTCCTTACTGGGGAAAGAATTCAGGGATATTTCTCTTACCT |
| 2151660 | GTTTTTGGTAATAAGAGAAATATGGCTCTGTCTTGCCTGGCTCCCAGGCAGTCAGACCTA |
| 2151720 | ATGGTTATCTCCCTTGTTCCCTGAACATCGCTATTATCCTGTTCTTCTTTCAAGGTGCCC |
| 2151780 | AGATTTCATATTGTTCAAACACACATGCTTTACGAACAATTTGTGCAGTTAACGCAATCA |
| 2151840 | TCACAGGGTCCTGAGGCAACATACATCCTCAGCTTATGAAGATGACAGGATTAAGAGATT |
| 2151900 | AAAGACAGACATAGGAAATTATGAGAGTATTGATTGAGGAAGTGATAAATGTCCATGAAA |
| 2151960 | TCTTCACAATTTATGTTCTTCTGTCATGGCTTCAGTAGGTCCCTCCGTTCGGGGTCCCTG |
| 2152020 | ACTTCCCACAACATCACTGTATACCTGAAATTAGCATTGATTCTAATTCTCTGGTCACAC |
| 2152080 | GTCATTCAGAGCATAGGATCTTCGGTGGATTTAAGAAGTGCCTCCCTCCCTATTCTCAGC |
| 2152140 | CATGTGACTCCCAGAATCCTATGAAATTAAAGATCTTGTGTTTGGCCATAGGAGACTTCT |
| 2152200 | ATTCACCATCTTTGTTCTCTCCCACAAATGGCGAGGCCTCCAGTCTCCCACATGACAGCT |
| 2152260 | TTGTACTAAAATCAACCTTACTCTATAGAACATGCATGATTGCAGCAGGACTACTATGAT |
| 2152320 | CTTGGTTTGATGAATTAGTTAGGATAACATTAGCTGCTGTAACAAACAGACCCCCAAGCT |
| 2152380 | GCAGCATGACTCAGATGCAATATAAGTGTCTTTTCACTTATATCAAGCAAGAATGACCA |
| 2152440 | GATTTTCTGATTTTTTTTCCGCTGTGCTAATGTAGGGAGAAGTTGTTGGAGGTCACGTC |
| 2152500 | ACAGTTCACAGCAACCATCTATGTTTGGGAGCAAGGATGCTGGAAATAGAATCCAGCATA |
| 2152560 | CTTGTAGCTTGTCCATAATTACAGACACCTTTGCATTTACTGAACTGAATCCTATGACTT |
| 2152620 | GAAGACCAAAGACTGTAGCATGCCTGAAGGGACAGCCTCAGAACTGTGGATGCCTGTCCC |
| 2152680 | TCTCCTGGTTTGGGTTTGTGCTGACCACAGGCAAACCCACTGAACTCAGGATCACTGCAT |
| 2152740 | AAAGTGACGTATTAAGCCTAGTGCCAGGATCTTTAGTGTTTGCAGGAAGGTCTCATGATT |
| 2152800 | TTTCTGCTAACTCAGCTAATAGGTAGTCCTCTGTCCCTTCAAGTTACAAACACATCCTTC |
| 2152860 | ATTCAGGAATTTGAATGTTCAGTCCTTGATATTTTATCAACCCTTCATTCTGTGGTCAAA |
| 2152920 | GGGCAGACGTCTCTCCCAGTTAAGACTGGAAGTTAGCAGCCTGCCTCCAGGGATGGGGTT |

FIGURE 2 cont.

| | |
|---|---|
| 2152980 | GTGGTTGCCTTCTGCTCTCTCTGTTCCTCTGGGAAGCAGCAGAATCATTCCATGGGAGGA |
| 2153040 | CTAGAGCAGTTCTTTCTTGAGAGAAGAGATTTACTCCTTCCAAGTGTATTGGTTAGTGAT |
| 2153100 | TGCTACATAACAAACTACCCCAAAACTCTCAGTAGCTTAAAACAACTGTGAAGTGATTGA |
| 2153160 | TGCTCATGTGAGCATGGGTTGGTTGATCCAGGCTGGGCTCAGCTGGGCACCTCTGTATAT |
| 2153220 | GCTGTGGGTTCTCCTGAGCTCAACTCCTTCCTGCCAGTTGCATTTAAGGCTGTTCTGTGC |
| 2153280 | GTGTCTTCTGGAGCCCAGGCTGAATGGGCTTTGGAGATGGCAGAAGCACAAGCGAGTAAA |
| 2153340 | CAGAGACACATGAAGCCATTTAAGGCCTCAGCCCAGCACTGACGTGCCGTCACTTCTCAC |
| 2153400 | ATTCCACTGGCCATGCAAGTCACATGGCTGAGCAAACTCAAGGACTTGGGAAGTAACCAT |
| 2153460 | CGTCTTTAGTGGGAGGAACTACAACATCCCATGGCAAAGCATGGATCCAGGAAGCAGTGA |
| 2153520 | AATGGGGGCCAGTGACTCAGTTTACCACACTGAGGTCTGGCAGATGGCTAGAAGTGGCGC |
| 2153580 | TTTCTCTTGAGGATTGGGGGAGAGGGTGTGTTTATGGATTCTACAGCAATCCCAGGCCTG |
| 2153640 | GGAACCTCTGTAAGTCCCTTTCCCAGGGCCTCTACATCTCTCCTCTACATGGTCCCGTCT |
| 2153700 | AACTCCTGCCTCATCTAGATTTCTGTACCACACCCAGCTTCTTGTGAGCATCTCTTTGCT |
| 2153760 | GCCAGAGGGCCCTGTGAGACAAGCCCCAAGATGACCCCATGCCAGAATTGTCACCCATG |
| 2153820 | TGATTCACATCTGGACCAGAGGAAATGCCTCCCAAATGAAGCCCATCCTGCCCCCATCAG |
| 2153880 | GCAACTACAGGCCACTTCAGCTTTCTTGGGTGTAAGGCAGACCTCAGAATCTCTGTGTCT |
| 2153940 | CCCAGCTAGATGGAAAGCTTTCCAAGGGGTCCTTGGGAAGCCAGCTGGATTGAGGCAAGG |
| 2154000 | AATATCACACCCCCATCCATCTCCCAAAGGGAAGCAACACATCACCTGACAACAGTTCTC |
| 2154060 | TCCAGGGCAATCTCTTTGCCAAACATTGCTCCTCTCCACACTCCAACCCCTTTATGTATT |
| 2154120 | CTTAACATGACTGAGGAGCCCCTTTATAAATTCTGCATTTGGGAGTTTGTTGCATATTCT |
| 2154180 | GTTTGGTTCCTGGAGTTACCTACACAAGAGCCTCAGGCAATGAGATTTTATTTATCAAAC |
| 2154240 | CATTACCAGATGTCAGGTGCTGTCCCAAACACTTTGTAAATGTTAACCCATTTAATCCTC |
| 2154300 | ATATAAATCCTATGAGGTAGGTGCTATTAACATCTTTATTTTAGAGATAGGGAAGCTGAG |
| 2154360 | GCACAGAGAGGTTAAGTAATTAGCCCAAAGTCACACAGAAGGCAACTGTCTTCTCACCCA |
| 2154420 | GGCAAGAAGAGTCCTTTTTTATGATAATAAGGTGGAAGAAGGCAAGGGGGAGATAAGCAA |
| 2154480 | GAAGATGATAATGATGATGGTGGCCTTCCCTGAGTTACTGTGCTTAGCACTTAGTGTGCG |
| 2154540 | TGGCCTTGCCTTGCCTGTCCTTTGAGACAGGTATGTCAGACTCTCCCCATTTCGCAGATG |
| 2154600 | AATAAACTGAGGCTGATATAGTTTGAATGTATGTCTCCACCCAAATCTCATGTTGAAATG |
| 2154660 | TAATCCCCAGTGTTGGAGGTGGGGCCTGTTGGGAGGTGATTGGATCATGGGGGTGGATTT |
| 2154720 | CTCATGGGTAGTTTAACACCATCGCCTTGGTGCTATCCTTATGATAGTGAGTACATTCTC |
| 2154780 | ATGAGACCTGGTTGTTTAAAACTGGGTGGCACCTCCTCCCCACTTTCTCTCACTCCTGCT |
| 2154840 | TTCGCCACATGATATGCCTGCTCCCCCTTTGCCTTCTGCTATGATTGTAAGCCTCCTGAG |
| 2154900 | GCCTCCCCAGAAGCCAAGCAGACGTCAGTACCATGCTTCCTGTAAAGCCTGCAGAACCAT |
| 2154960 | GAGCCGATTAAACCTCTTTTTCTTTATAAATTACCCAGTCTCAGATATCCCTTAATAGCA |
| 2155020 | ATGCAAGAATGGCCTGATACAGAGGCTTTGAGAGGTCAAGTGACCTGCCCAAGGGCACAC |
| 2155080 | CACTGATAAAGGACAGATGTGGGATTTGAACCCACCTTTGTTAGGCCCCAGTGCAAGGCC |
| 2155140 | CCTTCTCCTCATGCTCACTGCCCACTGCGGAGCTGGGCACTTGGGACACACCCTAGGGAG |
| 2155200 | CTGTGCTCTGCTGGGGCCTTCCTCATGCCCCAAGTCCCTGCCTGCCCAAGGCCGGTGCTC |
| 2155260 | TGAGTCTCCTACAGCCCCCTCCTCAGCCTCACTGGCCTCAGTCATCTTGGTTCAGGGAAG |
| 2155320 | GACTAAGGTCCCCTTTGGTCCCTGCCAATCTGCACCCCACCCCAGTGTGACCCTCAAGAG |
| 2155380 | CCTGACTCTGGCCTTTTACAGAATAAATCTGAACAAAATCAGGGTTCATTTTAATAGCAA |
| 2155440 | CAGGCTGCTGATGCAGACCTTATCAACTCCATCAAACTGTGTTCTTTCAAATGTTACGCT |
| 2155500 | CCCCTGGGGGTGTCCCACACCCTGACGTCACACATTCACTCAGTGAAGCCCATATTCATT |
| 2155560 | CGGGGAGCTCTTTCTTTCTCTCTTCTCTAACACACACTCTCCTTGGTTAGCTGGCTGCTG |
| 2155620 | ATCAACATTTCTGGATATACTGGTTTTCAGGAAAATATGATGGTTGGCTTCCAATCCCAG |
| 2155680 | ATTTTTCACTGATGGGTTCCATATTTACACCATCTTGGCCACAGTCTCTGGGTCACCATT |
| 2155740 | TCCACACATACCCACACACCATAAAGAGAGGCTTTTCTGAGTCTTCTGTTCATGCAGTC |
| 2155800 | TGGAATTGTATTTGCTTTTGTTTTGGGGCATCCTGGGCAGCTCATTCCACTAATAGGCAT |
| 2155860 | AACCATAACCATTGCAGTCTCCACTTACTGACATTTACAACTTTCCAGGCACATGCTAGG |
| 2155920 | GACCTTACATTCATTATTTCATTTTATTCTCACATCACAACCTTGTGAGGTGGAGGAGCA |
| 2155980 | TGATGGAAGGAGGAAGGAGCTAAAGCAAAGAATCTGGAGTCCGACTGCCTGGGTTCAAA |
| 2156040 | TCCTAGCTCTACCAATTTCCAGCTCTGTAACATCGAGCTAATTTCCTAACCTCTCTATGC |
| 2156100 | CATTTCCCTATCTCTAAAAGGAAGCTGACAATAGCATCTATCTCATAGGATTTGTACGAA |
| 2156160 | GATTAAATGAGTCAATATTTATAAAGTGTTCGGAATGATACCTGACATCTGGTAATGGTT |
| 2156220 | TGATAAATAAAATCCATTTTAATGATGAGGAAACAGGCTCAGAAGAGGGCGCTCATTTGC |

FIGURE 2 cont.

```
2156280   TCATGTGGTACAGATAGGTTCCAGACTCAAACTCAAGACCATCTGACTCTAAAACATCTA
2156340   AAACTGTTGCCCCGCATTCTCTTCATTTGACAGATAATAAAACTGAGGCTCAGAGAAGCT
2156400   AAGTGACTCGCCTGGGACTGCACAGCAAATCAAGACAAATAAGACCTAGGGTCTCCTGAC
2156460   TGCCAGAGTGGAGATGCTTCTATAGGCTTTTCTCACTGATGCTCTCTGGGCAGACAGGCT
2156520   CCTCAATATGAGAGTGACACACACTCCTTTCTTCATTTTCAGGTAAACCTCACACTGGTT
2156580   GGCAGAAGGAACTATACCAATAATTAGTGAACATGCGGTGAATTTGCAACAGACAAGAGG
2156640   AGCCTCATTATCCTATAGTTTCCAGGTTGCTTAGGGAGGCAGAAATCACAGCAAGGAAAA
2156700   CCTTCAATAATAAACAGACGTCTCATAAAATTAATTGCAACCCAACCTCTCTCTCTACTT
2156760   AAAATTAGCATCTATTTCCAGCTCTGCTTTCAATGCCCCATATGAATACATGTGAACTCC
2156820   CTCCCTCTCTTCCTCCCTGTCTCCTTCTCTCTCTCTGTCCCTCATTAAAAAATAAAAT
2156880   TTAAGAAAAAAATACAAGGTAGATTTACACAAATAGTGGGATCTCAGTCTTGAGTTAGCT
2156940   GTGTATGACTGAAAAGGATGCTGTGGTTAATAATTATCATAAAAACAATGACATGGCCGG
2157000   GCACAGTGGCTCACGCCTGTAATCCCAGAACTTTGGGAGGCCGAGGCAGGCAGATCACTT
2157060   GAGGCCAGGAGTTTGAGACCAGCCTGGCCAACATGGTGAAACTGCATCTCTACTAAAAAT
2157120   ACAAAAATTAGCCGGGCATCAATGGCCAGCCCCTGTAATCCCAGCTAATCAGGAGTCTGA
2157180   GGCAGGCGAATCACTTGAACCTGGGGGCTGGTGGTTGCAGTGAGCCGAGCTCACACCACT
2157240   GCACTCCAGCCTGGGCGACAGAGTGAGACTACATCTCAAAAAAACAAAAACAAACAAGCA
2157300   AAAAAAACCCCACAGTAACACAAAAGTAATAAAACTGCTGCTATTTACTCAGTGCTTATC
2157360   TGATGCCAGCCACTTTGCTAAGCCTATGAATGCATTATTTCCCCGTTGCTACAGATGAGA
2157420   GAATTGAGGTTCAGACAGGTTGAAATCATTGCTCCCAAAGTCACACAACTGGTGAGTGGC
2157480   AGAGCTGGGATGCAAACCCTAAACTGCCAGCCCTCAAAGCCTGTGCTCTTAATCTCCACC
2157540   CTGCTGTGCTTCCTTGTCCATTTAATTAAGCTCCACAGGCACACATTCCACGCCCTCCTT
2157600   TGCTGTACAATCCCAGGCAAGTCGCTCAGCTTCTCTGAGCCTCAGTTTCATAATCTGTCA
2157660   AATGGAGGTAACACAAATAATTCCTAGTTGTGACCAAGAATCATCATAGAAATCTGCCAT
2157720   TTCCAGCCTATTGTGCAATTCCTCAAGCACTGTGACTCCAAGTGGCATCAGCTCCTGGAA
2157780   GAACACACTGTCTTACTGTTGTTTCCTCCTTTGTCAACTGATCCCCCCTTGAACCTCACT
2157840   CTACCTCTGCTCTCAATGCCCCATCTACTGCCACCTGATTAAATAAAATCTTTTTTGAAA
2157900   ATCATAAGTGTCATGAGTAAGGTTTCTTGGTGTTGATGTAGAAGAACAAAACAGAATTGT
2157960   GAAATGAGAATCACTGCAGCTATCATGAAGTCCTGCCTAC
```

FIGURE 3

```
SEQ ID NO:20
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE
121 VQAPRWXNPR ALSFVLSSLQ LGEGVEFDVL PAFDALGQLT GXYKPNPQIY VKLIEECTDL
181 QKEGEFSTCF TELQRDFLKQ RPTKLKSLIR LVKHWYQN

SEQ ID NO:21
  1 SVSRRDKSKQ VWEAVLLPLS LLMMDLRNTP AKSLDKFIED YLLPDTCFRM QIXHAIDIIC
 61 GFLKERCFRG SSYPVCVSKV VKGGSSGKGT TLRGRSDADL VVFLSPLTTF QDQLNRRGEF
121 IQEIRRQLEA CQRERAXSVK FEVQAPRWGN PRALSFVLSS LQLGEGVEFD VLPAFDALGQ
181 LTGXYKPNPQ IYVKLIEECT DLQKEGEFST CFTELQRDFL KQRPTKLKSL IRLVKHWYQN

SEQ ID NO:22
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE
121 VQAPRWXNPR ALSFVLSSLQ LGEGVEFDVL PAFDALGQLT GXYKPNPQIY VKLIEECTDL
181 QKEGEFSTCF TELQRDFLKQ RPTKLKSLIR LVKHWYQNVW PSHQAWWVLS RLGAEEG

SEQ ID NO:23
  1 SVSRRDKSKQ VWEAVLLPLS LLMMDLRNTP AKSLDKFIED YLLPDTCFRM QIXHAIDIIC
 61 GFLKERCFRG SSYPVCVSKV VKGGSSGKGT TLRGRSDADL VVFLSPLTTF QDQLNRRGEF
121 IQEIRRQLEA CQRERAXSVK FEVQAPRWGN PRALSFVLSS LQLGEGVEFD VLPAFDALGQ
181 LTGXYKPNPQ IYVKLIEECT DLQKEGEFST CFTELQRDFL KQRPTKLKSL IRLVKHWYQN
241 VWPSHQAWWV LSRLGAEEG

SEQ ID NO:24
  1 SVSRRDKSKQ VWEAVLLPLS LLSMMDLRNT PAKSLDKFIE DYLLPDTCFR MQIXHAIDII
 61 CGFLKERCFR GSSYPVCVSK VVKGGSSGKG TTLRGRSDAD LVVFLSPLTT FQDQLNRRGE
121 FIQEIRRQLE ACQRERAXSV KFEVQAPRWG NPRALSFVLS SLQLGEGVEF DVLPAFDALG
181 QLTGXYKPNP QIYVKLIEEC TDLQKEGEFS TCFTELQRDF LKQRPTKLKS LIRLVKHWYQ
241 NVWPSHPACW YLYIFI

SEQ ID NO:25
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE
121 VQAPRWXNPR ALSFVLSSLQ LGEGVEFDVL PAFDALGQLT GXYKPNPQIY VKLIEECTDL
181 QKEGEFSTCF TELQRDFLKQ RPTKLKSLIR LVKHWYQNVW PSHPACWYLY IFI

SEQ ID NO:26
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE
121 VQAPRWXNPR ALSFVLSSLQ LGEGVEFDVL PAFDALGQLT GXYKPNPQIY VKLIEECTDL
181 QKEGEFSTCF TELQRDFLKQ RPTKLKSLIR LVKHWYQNCK KKLGKLPPQY ALELLTVYAW
241 ERGSMKTHFN TAQGFRTVLE LVINYQQLCI YWTKYYDFKX PIIEKYLRRQ LTKPRPVILD
301 PADPTGNLGG GDPKGWRQLA QEAEAWLNYX CFKNWDGSPV SSWILLMRQR LREVRSLAQG
361 HQLTSGGNGI QAQWTLKPVL MSLC
```

FIGURE 3 cont.

```
SEQ ID NO:27
   1 MMDLRNTPAK SLDKFIEDYL LPDTCFRMQI XHAIDIICGF LKERCFRGSS YPVCVSKVVK
  61 GGSSGKGTTL RGRSDADLVV FLSPLTTFQD QLNRRGEFIQ EIRRQLEACQ RERAXSVKFE
 121 VQAPRWXNPR ALSFVLSSLQ LGEGVEFDVL PAFDALGQLT GXYKPNPQIY VKLIEECTDL
 181 QKEGEFSTCF TELQRDFLKQ RPTKLKSLIR LVKHWYQNCK KKLGKLPPQY ALELLTVYAW
 241 ERGSMKTHFN TAQGFRTVLE LVINYQQLCI YWTKYYDFKX PIIEKYLRRQ LTKPRPVILD
 301 PADPTGNLGG GDPKGWRQLA QEAEAWLNYX CFKNWDGSPV SSWILLLKAT VQTMRPTIPG
 361 XIRNMVTLEH MSTLISLIDP AHSRQHPPHR QKRTGPAPSS ECQCILGERA PVLSGPVPSF
 421 SGGTLDPEXT KLLSELVYNP GQNPGLLTPG LLCPLSYHR

SEQ ID NO:28
   1 MMDLRNTPAK SLDKFIEDYL LPDTCFRMQI XHAIDIICGF LKERCFRGSS YPVCVSKVVK
  61 GGSSGKGTTL RGRSDADLVV FLSPLTTFQD QLNRRGEFIQ EIRRQLEACQ RERAXSVKFE
 121 VQAPRWXNPR ALSFVLSSLQ LGEGVEFDVL PAFDALGQLT GXYKPNPQIY VKLIEECTDL
 181 QKEGEFSTCF TELQRDFLKQ RPTKLKSLIR LVKHWYQNCK KKLGKLPPQY ALELLTVYAW
 241 ERGSMKTHFN TAQGFRTVLE LVINYQQLCI YWTKYYDFKX PIIEKYLRRQ LTKPRPVILD
 301 PADPTGNLGG GDPKGWRQLA QEAEAWLNYX CFKNWDGSPV SSWILLIKLR LREAK

SEQ ID NO:29
   1 MMDLRNTPAK SLDKFIEDYL LPDTCFRMQI XHAIDIICGF LKERCFRGSS YPVCVSKVVK
  61 GGSSGKGTTL RGRSDADLVV FLSPLTTFQD QLNRRGEFIQ EIRRQLEACQ RERAXSVKFE
 121 VQAPRWXNPR ALSFVLSSLQ LGEGVEFDVL PAFDALGQLT GXYKPNPQIY VKLIEECTDL
 181 QKEGEFSTCF TELQRDFLKQ RPTKLKSLIR LVKHWYQNCK KKLGKLPPQY ALELLTVYAW
 241 ERGSMKTHFN TAQGFRTVLE LVINYQQLCI YWTKYYDFKX PIIEKYLRRQ LTKPRPVILD
 301 PADPTGNLGG GDPKGWRQLA QEAEAWLNYX CFKNWDGSPV SSWILLVNLT LVGRRNYPII
 361 SEHAVNLQQT RXASLSYSFQ VA

SEQ ID NO:30
   1 AESNSXDDET DDPRXYQKYG YIGTHEYPHF SHRPSTLQAA STPQAEEDWT CTIL

SEQ ID NO:31
   1 GCTGAAAGCA ACAGTRCAGA CGATGAGACC GACGATCCCA GGASGTATCA GAAATATGGT
  61 TACATTGGAA CACATGAGTA CCCTCATTTC TCTCATAGAC CCAGCACACT CCAGGCAGCA
 121 TCCACCCCAC AGGCAGAAGA GGACTGGACC TGCACCATCC TCTGAATGCC AGTGCATCTT
 181 GGGGGAAAGG GCTCCAGTGT TATCTGGACC AGTTCCTTCA TTTTCAGGTG GGACTCTTGA
 241 TCCAGAGARG ACAAAGCTCC TCAGTGAGCT GGTGTATAAT CCAGGACAGA ACCCAGGTCT
 301 CCTGACTCCT GGCCTTCTAT GCCCTCTATC CTATCATAGA TAACATTCTC CACAGCCTCA
 361 CTTCATTCCA CCTATTCTCT GAAAATATTC CTGAGAGAG AACAGAGAGA TTTAGATAAG
 421 AGAATGAAAT TCCAGCCTTG ACTTTCTTCT GTGCACCTGA TGGGAGGGTA ATGTCTAATG
 481 TATTATCAAT AACAATAAAA ATAAAGCAAA TACCATTTA

SEQ ID NO:32
   1 MMDLRNTPAK SLDKFIEDYL LPDTCFRMQI XHAIDIICGF LKERCFRGSS YPVCVSKVVK
  61 GGSSGKGTTL RGRSDADLVV FLSPLTTFQD QLNRRGEFIQ EIRRQLEACQ RERAXSVKFE
 121 VQAPRWXNPR ALSFVLSSLQ LGEGVEFDVL PAFDALGQLT GXYKPNPQIY VKLIEECTDL
 181 QKEGEFSTCF TELQRDFLKQ RPTKLKSLIR LVKHWYQNCK KKLGKLPPQY ALELLTVYAW
 241 ERGSMKTHFN TAQGFRTVLE LVINYQQLCI YWTKYYDFKX PIIEKYLRRQ LTKPR
```

FIGURE 3 cont.

SEQ ID NO:33
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE
121 VQAPRWXNPR ALSFVLSSLQ LGEGVEFDVL PAFDALGQLT GXYKPNPQIY VKLIEECTDL
181 QKEGEFSTCF TELQRDFLKQ RPTKLKSLIR LVKHWYQNCK KKLGKLPPQY ALELLTVYAW
241 ERGSMKTHFN TAQGFRTVLE LVINYQQLCI YWTKYYDFKX PIIEKYLRRQ LTKPRPVILD
301 PADPTGNLGG GDPKGWRQLA QEAEAWLNYX CFKNWDGSPV SSWILLVRPP ASSLPFIPAP
361 LHEA

SEQ ID NO:34
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE
121 VQAPRWXNPR ALSFVLSSLQ LGEGVEFDVL PAFDALGQLT GXYKPNPQIY VKLIEECTDL
181 QKEGEFSTCF TELQRDFLKQ RPTKLKSLIR LVKHWYQNCK KKLGKLPPQY ALELLTVYAW
241 ERGSMKTHFN TAQGFRTVLE LVINYQQLCI YWTKYYDFKX PIIEKYLRRQ LTKPRPVILD
301 PADPTGNLGG GDPKGWRQLA QEAEAWLNYX CFKNWDGSPV SSWILLAESN SXDDETDDPR
361 XYQKYGYIGT HEYPHFSHRP STLQAASTPQ AEEDWTCTIL

SEQ ID NO:35
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE
121 VQAPRWXNPR ALSFVLSSLQ LGEGVEFDVL PAFDALGQLT GXYKPNPQIY VKLIEECTDL
181 QKEGEFSTCF TELQRDFLKQ RPTKLKSLIR LVKHWYQNCK KKLGKLPPQY ALELLTVYAW
241 ERGSMKTHFN TAQGFRTVLE LVINYQQLCI YWTKYYDFKX PIIEKYLRRQ LTKPRPVILD
301 PADPTGNLGG GDPKGWRQLA QEAEAWLNYX CFKNWDGSPV SSWILLTQHT PGSIHPTGRR
361 GLDLIHPLNA SASWGKGLQC YLDQFLHFQV GLLIQRXQSS SVSWCIIQDR TQVS

SEQ ID NO:36
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGAGAGCATTTTCCGTGA
AGTTTGAGGTCCAGGCTCCACGCTGGGGCAACCCCCGTGCGCTCAGCTTCGTACTGAGTTCGCTCCAGCTCGGGGAG
GGGGTGGAGTTCGATGTGCTGCCTGCCTTTGATGCCCTGGGTCAGTTGACTGGCRGCTATAAACCTAACCCCCAAAT
CTATGTCAAGCTCATCGAGGAGTGCACCGACCTGCAGAAAGAGGGCGAGTTCTCCACCTGCTTCACAGAACTACAGA
GAGACTTCCTGAAGCAGCGCCCCACCAAGCTCAAGAGCCTCATCCGCCTAGTCAAGCACTGGTACCAAAATTGTAAG
AAGAAGCTTGGGAAGCTGCCACCTCAGTATGCCCTGGAGCTCCTGACGGTCTATGCTTGGGAGCGAGGGAGCATGAA
AACACATTTCAACACAGCCCAGGGATTTCGGACGGTCTTGGAATTAGTCATAAACTACCAGCAACTCTGCATCTACT
GGACAAAGTATTATGACTTTAAAAACCCCATTATTGAAAAGTACCTGAGAAGGCAGCTCACGAAACCCAGGCCTGTG
ATCCTGGACCCGGCGGACCCTACAGGAAACTTGGGTGGTGGAGACCCAAAGGGTTGGAGGCAGCTGGCACAAGAGGC
TGAGGCCTGGCTGAATTACCCATGCTTTAAGAATTGGGATGGGTCCCCAGTGAGCTCCTGGATTCTGCTGGTGAGAC
CTCCTGCTTCCTCCCTGCCATTCATCCCTGCCCCTCTCCATGAAGCTTGAGACATATAGCTGGAGACCATTCTTTCC
AAAGAACTTACCTCTTGCCAAAGGCCATTTATATTCATATAGTGACAGGCTGTGCTCCATATTTTACAGTCATTTTG
GTCACAATCGAGGGTTTCTGGAATTTTCACATCCCTTGTCCAGAATTCATTCCCCTAAGAGTAATAATAAATAATCT
CTAACACCATTTATTGACTGTCTGCTTCGGGCTCAGGTTCTGTCCTAAGCCCTTTAATATGCACTCTCTCATTAAAT
A

SEQ ID NO:37
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGAGAGCATTTTCCGTGA
AGTTTGAGGTCCAGGCTCCACGCTGGGGCAACCCCCGTGCGCTCAGCTTCGTACTGAGTTCGCTCCAGCTCGGGGAG

FIGURE 3 cont.

GGGGTGGAGTTCGATGTGCTGCCTGCCTTTGATGCCCTGGGTCAGTTGACTGGCRGCTATAAACCTAACCCCCAAAT
CTATGTCAAGCTCATCGAGGAGTGCACCGACCTGCAGAAAGAGGGCGAGTTCTCCACCTGCTTCACAGAACTACAGA
GAGACTTCCTGAAGCAGCGCCCCACCAAGCTCAAGAGCCTCATCCGCCTAGTCAAGCACTGGTACCAAAATTGTAAG
AAGAAGCTTGGGAAGCTGCCACCTCAGTATGCCCTGGAGCTCCTGACGGTCTATGCTTGGGAGCGAGGGAGCATGAA
AACACATTTCAACACAGCCCAGGGATTTCGGACGGTCTTGGAATTAGTCATAAACTACCAGCAACTCTGCATCTACT
GGACAAAGTATTATGACTTTAAAAACCCCATTATTGAAAAGTACCTGAGAAGGCAGCTCACGAAACCCAGGCCTGTG
ATCCTGGACCCGGCGGACCCTACAGGAAACTTGGGTGGTGGAGACCCAAAGGGTTGGAGGCAGCTGGCACAAGAGGC
TGAGGCCTGGCTGAATTACCCATGCTTTAAGAATTGGGATGGGTCCCCAGTGAGCTCCTGGATTCTGCTGGCTGAAA
GCAACAGTRCAGACGATGAGACCGACGATCCCAGGASGTATCAGAAATATGGTTACATTGGAACACATGAGTACCCT
CATTTCTCTCATAGACCCAGCACACTCCAGGCAGCATCCACCCCACAGGCAGAAGAGGACTGGACCTGCACCATCCT
CTGAATGCCAGTGCATCTTGGGGGAAAGGGCTCCAGTGTTATCTGGACCAGTTCCTTCATTTTCAGGTGGGACTCTT
GATCCAGAGARGACAAAGCTCCTCAGTGAGCTGGTGTATAATCCAGGACAGAACCCAGGTCTCCTGACTCCTGGCCT
TCTATGCCCTCTATCCTATCATAGATAACATTCTCCACAGCCTCACTTCATTCCACCTATTCTCTGAAAATATTCCC
TGAGAGAGAACAGAGAGATTTAGATAAGAGAATGAAATTCCAGCCTTGACTTTCTTCTGTGCACCTGATGGGAGGGT
AATGTCTAATGTATTATCAATAACAATAAAAATAAAGCAAATACCATTTATTGGGTGTTTATTAACTTCAAGGCACA
GAGCCAAGAAGTACAGATGCATATCTAGGGGTATTGTGTGTGTATACATTGATTCAACAAGAAATATTTATTGAG
CACTT

SEQ ID NO:38
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGAGAGCATTTTCCGTGA
AGTTTGAGGTCCAGGCTCCACGCTGGGGCAACCCCCGTGCGCTCAGCTTCGTACTGAGTTCGCTCCAGCTCGGGGAG
GGGGTGGAGTTCGATGTGCTGCCTGCCTTTGATGCCCTGGGTCAGTTGACTGGCRGCTATAAACCTAACCCCCAAAT
CTATGTCAAGCTCATCGAGGAGTGCACCGACCTGCAGAAAGAGGGCGAGTTCTCCACCTGCTTCACAGAACTACAGA
GAGACTTCCTGAAGCAGCGCCCCACCAAGCTCAAGAGCCTCATCCGCCTAGTCAAGCACTGGTACCAAAATTGTAAG
AAGAAGCTTGGGAAGCTGCCACCTCAGTATGCCCTGGAGCTCCTGACGGTCTATGCTTGGGAGCGAGGGAGCATGAA
AACACATTTCAACACAGCCCAGGGATTTCGGACGGTCTTGGAATTAGTCATAAACTACCAGCAACTCTGCATCTACT
GGACAAAGTATTATGACTTTAAAAACCCCATTATTGAAAAGTACCTGAGAAGGCAGCTCACGAAACCCAGGCCTGTG
ATCCTGGACCCGGCGGACCCTACAGGAAACTTGGGTGGTGGAGACCCAAAGGGTTGGAGGCAGCTGGCACAAGAGGC
TGAGGCCTGGCTGAATTACCCATGCTTTAAGAATTGGGATGGGTCCCCAGTGAGCTCCTGGATTCTGCTGACCCAGC
ACACTCCAGGCAGCATCCACCCCACAGGCAGAAGAGGACTGGACCTGCACCATCCTCTGAATGCCAGTGCATCTTGG
GGGAAAGGGCTCCAGTGTTATCTGGACCAGTTCCTTCATTTTCAGGTGGGACTCTTGATCCAGAGARGACAAAGCTC
CTCAGTGAGCTGGTGTATAATCCAGGACAGAACCCAGGTCTCCTGACTCCTGGCCTTCTATGCCCTCTATCCTATCA
TAGATAACATTCTCCACAGCCTCACTTCATTCCACCTATTCTCTGAAAATATTCCCTGAGAGAGAACAGAGAGATTT
AGATAAGAGAATGAAATTCCAGCCTTGACTTTCTTCTGTGCACCTGATGGGAGGGTAATGTCTAATGTATTATCAAT
AACAATAAAAATAAAGCAAATACCATTTATTGGGTGTTTATTAACTTCAAGGCACAGAGCCAAGAAGTACAGATGCA
TATCTAGGGGTATTGTGTGTGTATACATTGATTCAACAAGAAATATTTATTGAGCACTT

SEQ ID NO:39
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGAGAGCATTTTCCGTGA
AGTTTGAGGTCCAGGCTCCACGCTGGGGCAACCCCCGTGCGCTCAGCTTCGTACTGAGTTCGCTCCAGCTCGGGGAG
GGGGTGGAGTTCGATGTGCTGCCTGCCTTTGATGCCCTGGGTCAGTTGACTGGCRGCTATAAACCTAACCCCCAAAT
CTATGTCAAGCTCATCGAGGAGTGCACCGACCTGCAGAAAGAGGGCGAGTTCTCCACCTGCTTCACAGAACTACAGA
GAGACTTCCTGAAGCAGCGCCCCACCAAGCTCAAGAGCCTCATCCGCCTAGTCAAGCACTGGTACCAAAATTGTAAG
AAGAAGCTTGGGAAGCTGCCACCTCAGTATGCCCTGGAGCTCCTGACGGTCTATGCTTGGGAGCGAGGGAGCATGAA
AACACATTTCAACACAGCCCAGGGATTTCGGACGGTCTTGGAATTAGTCATAAACTACCAGCAACTCTGCATCTACT
GGACAAAGTATTATGACTTTAAAAACCCCATTATTGAAAAGTACCTGAGAAGGCAGCTCACGAAACCCAGGCCTGTG
ATCCTGGACCCGGCGGACCCTACAGGAAACTTGGGTGGTGGAGACCCAAAGGGTTGGAGGCAGCTGGCACAAGAGGC

FIGURE 3 cont.

TGAGGCCTGGCTGAATTACCCATGCTTTAAGAATTGGGATGGGTCCCCAGTGAGCTCCTGGATTCTGCTGCTGAAAG
CAACAGTRCAGACGATGAGACCGACGATCCCAGGASGTATCAGAAATATGGTTACATTGGAACACATGAGTACCCTC
ATTTCTCTCATAGACCCAGCACACTCCAGGCAGCATCCACCCCACAGGCAGAAGAGGACTGGACCTGCACCATCCTC
TGAATGCCAGTGCATCTTGGGGGAAAGGGCTCCAGTGTTATCTGGACCAGTTCCTTCATTTTCAGGTGGGACTCTTG
ATCCAGAGARGACAAAGCTCCTCAGTGAGCTGGTGTATAATCCAGGACAGAACCCAGGTCTCCTGACTCCTGGCCTT
CTATGCCCTCTATCCTATCATAGATAACATTCTCCACAGCCTCACTTCATTCCACCTATTCTCTGAAAATATTCCCT
GAGAGAGAACAGAGAGATTTAGATAAGAGAATGAAATTCCAGCCTTGACTTTCTTCTGTGCACCTGATGGGAGGGTA
ATGTCTAATGTATTATCAATAACAATAAAAATAAAGCAAATACCATTTATTGGGTGTTTATTAACTTCAAGGCACAG
AGCCAAGAAGTACAGATGCATATCTAGGGGTATTGTGTGTGTATATACATTGATTCAACAAGAAATATTTATTGAGC
ACTT

SEQ ID NO:40
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGAGAGCATTTTCCGTGA
AGTTTGAGGTCCAGGCTCCACGCTGGGGCAACCCCCGTGCGCTCAGCTTCGTACTGAGTTCGCTCCAGCTCGGGGAG
GGGGTGGAGTTCGATGTGCTGCCTGCCTTTGATGCCCTGGGTCAGTTGACTGGCRGCTATAAACCTAACCCCCAAAT
CTATGTCAAGCTCATCGAGGAGTGCACCGACCTGCAGAAAGAGGGCGAGTTCTCCACCTGCTTCACAGAACTACAGA
GAGACTTCCTGAAGCAGCGCCCCACCAAGCTCAAGAGCCTCATCCGCCTAGTCAAGCACTGGTACCAAAATTGTAAG
AAGAAGCTTGGGAAGCTGCCACCTCAGTATGCCCTGGAGCTCCTGACGGTCTATGCTTGGGAGCGAGGGAGCATGAA
AACACATTTCAACACAGCCCAGGGATTTCGGACGGTCTTGGAATTAGTCATAAACTACCAGCAACTCTGCATCTACT
GGACAAAGTATTATGACTTTAAAAACCCCATTATTGAAAAGTACCTGAGAAGGCAGCTCACGAAACCCAGGCCTGTG
ATCCTGGACCCGGCGGACCCTACAGGAAACTTGGGTGGCAGACCCAAAGGGTTGGAGGCAGCTGGCACAAGAGGC
TGAGGCCTGGCTGAATTACCCATGCTTTAAGAATTGGGATGGGTCCCCAGTGAGCTCCTGGATTCTGCTGATGAGAC
AAAGGCTCAGAGAGGTGAGGTCACTTGCTCAAGGACATCAGCTAACAAGTGGTGGAAATGGAATTCAAGCTCAGTGG
ACTCTAAAGCCAGTGCTCATGTCACTGTGCTAAACAGCCTGCCTTGTCACATCCCCACCTCTCATCTGACCAATGGG
AGACTCTGAGCAGCTGAGTGACTTGGGTTGTCACACAGCTAAACAGGGGCAAAGGACCCAGTCTTGGATCTTTCCAC
CTCCAAGCAGGAATCTGTCTGATTCCAGGGGATTGATGATCTTGCAGATGGCTAGGAAGCAGACTCCAGGATGGAAT
TTAGTATGCAGGATGTTCTGGGGGAGAGCCACTGGAACCAGCACTCAGGGAAAGGGGGGAAGAAAGGATAGGAAGGA
AGCATGAAAGAGAATAGGGAGAAGTGAACAGGGATGCAGAGCGAATGCCAGTTTCAGCCAACTCCAAGGACAGCCCT
GGAGCTGGAATGGCCTTTAGAGCTGCCCCATGGTGACAGAGGTGGCCAGGCTTCTATACCCCTACGTGGATCACTCA
CTGTGCTTGGGCACCTTGGGAAAGGGCATGGCTTTGAGCAAAAGGCTCTCTGCAGCTGAGGCAACCCCTAAAAGGGC
TGACGGCTGAAGTCTGTCTGCTGACCACTGTCCCAGCAGCTGGGGCTTGTTAGTCCTTCCTCAAAGGGGGATCCAGA
TGGCATGTCACAGTGTCTACCGTAAATGCTCACTGAATCCAGCTGCAATGCAGGAAGACTCCCTGATGTGATCATGT
GTCTCACCCTTTCARGCTGAAAGCAACAGTRCAGACGATGAGACCGACGATCCCAGGASGTATCAGAAATATGGTTA
CATTGGAACACATGAGTACCCTCATTTCTCTCATAGACCCAGCACACTCCAGGCAGCATCCACCCCACAGGCAGAAG
AGGACTGGACCTGCACCATCCTCTGAATGCCAGTGCATCTTGGGGGAAAGGGCTCCAGTGTTATCTGGACCAGTTCC
TTCATTTTCAGGTGGGACTCTTGATCCAGAGARGACAAAGCTCCTCAGTGAGCTGGTGTATAATCCAGGACAGAACC
CAGGTCTCCTGACTCCTGGCCTTCTATGCCCTCTATCCTATCATAGATAACATTCTCCACAGCCTCACTTCATTCCA
CCTATTCTCTGAAAATATTCCCTGAGAGAGAACAGAGAGATTTAGATAAGAGAATGAAATTCCAGCCTTGACTTTCT
TCTGTGCACCTGATGGGAGGGTAATGTCTAATGTATTATCAATAACAATAAAAATAAAGCAAATACCATTTATTGGG
TGTTTATTAACTTCAAGGCACAGAGCCAAGAAGTACAGATGCATATCTAGGGGTATTGTGTGTGTATATACATTGAT
TCAACAAGAAATATTTATTGAGCACTT

SEQ ID NO:41
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGAGAGCATTTTCCGTGA
AGTTTGAGGTCCAGGCTCCACGCTGGGGCAACCCCCGTGCGCTCAGCTTCGTACTGAGTTCGCTCCAGCTCGGGGAG
GGGGTGGAGTTCGATGTGCTGCCTGCCTTTGATGCCCTGGGTCAGTTGACTGGCRGCTATAAACCTAACCCCCAAAT
CTATGTCAAGCTCATCGAGGAGTGCACCGACCTGCAGAAAGAGGGCGAGTTCTCCACCTGCTTCACAGAACTACAGA

FIGURE 3 cont.

GAGACTTCCTGAAGCAGCGCCCCACCAAGCTCAAGAGCCTCATCCGCCTAGTCAAGCACTGGTACCAAAATTGTAAG
AAGAAGCTTGGGAAGCTGCCACCTCAGTATGCCCTGGAGCTCCTGACGGTCTATGCTTGGGAGCGAGGGAGCATGAA
AACACATTTCAACACAGCCCAGGGATTTCGGACGGTCTTGGAATTAGTCATAAACTACCAGCAACTCTGCATCTACT
GGACAAAGTATTATGACTTTAAAAACCCCATTATTGAAAAGTACCTGAGAAGGCAGCTCACGAAACCCAGGCCTGTG
ATCCTGGACCCGGCGGACCCTACAGGAAACTTGGGTGGTGGAGACCCAAAGGGTTGGAGGCAGCTGGCACAAGAGGC
TGAGGCCTGGCTGAATTACCCATGCTTTAAGAATTGGGATGGGTCCCCAGTGAGCTCCTGGATTCTGCTGGTAAACC
TCACACTGGTTGGCAGAAGGAACTATACCAATAATTAGTGAACATGCGGTGAATTTGCAACAGACAAGASGAGCCTC
ATTATCCTATAGTTTCCAGGTTGCTTAGGGAGGCAGAAATCACAGCAAGGAAAACCTTCAATAATAAACAGACGTCT
CATAAAATTAATTGCAACCCAACCTCTCTCTCTACTTAAAATTAGCATCTATTTCCAGCTCTGCTTTCAATGCCCCA
TATGAATACATGTGAACTCCCTCCCTCTCTTCCTCCCTGTCTCCTTCTCTCTCTCTGTCCCTCATTAAAAAATAA
AATTTAAGAAAAAAATACAAGGTAGATTTACACAAATAGTGGGATCTCAGTCTTGAGTTAGCTGTGTATGACTGAAA
AGGATGCTGTGGTTAATAATTATCATAAAAACAATGACATGGCCGGG

SEQ ID NO:42
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGAGAGCATTTTCCGTGA
AGTTTGAGGTCCAGGCTCCACGCTGGGGCAACCCCCGTGCGCTCAGCTTCGTACTGAGTTCGCTCCAGCTCGGGGAG
GGGGTGGAGTTCGATGTGCTGCCTGCCTTTGATGCCCTGGGTCAGTTGACTGGCRGCTATAAACCTAACCCCCAAAT
CTATGTCAAGCTCATCGAGGAGTGCACCGACCTGCAGAAAGAGGGCGAGTTCTCCACCTGCTTCACAGAACTACAGA
GAGACTTCCTGAAGCAGCGCCCCACCAAGCTCAAGAGCCTCATCCGCCTAGTCAAGCACTGGTACCAAAATTGTAAG
AAGAAGCTTGGGAAGCTGCCACCTCAGTATGCCCTGGAGCTCCTGACGGTCTATGCTTGGGAGCGAGGGAGCATGAA
AACACATTTCAACACAGCCCAGGGATTTCGGACGGTCTTGGAATTAGTCATAAACTACCAGCAACTCTGCATCTACT
GGACAAAGTATTATGACTTTAAAAACCCCATTATTGAAAAGTACCTGAGAAGGCAGCTCACGAAACCCAGGCCTGTG
ATCCTGGACCCGGCGGACCCTACAGGAAACTTGGGTGGTGGAGACCCAAAGGGTTGGAGGCAGCTGGCACAAGAGGC
TGAGGCCTGGCTGAATTACCCATGCTTTAAGAATTGGGATGGGTCCCCAGTGAGCTCCTGGATTCTGCTGATAAAAC
TGAGGCTCAGAGAAGCTAAGTGACTCGCCTGGGACTGCACAGCAAATCAAGACAAATAAGACCTAGGGTCTCCTGAC
TGCCAGAGTGGAGATGCTTCTATAGGCTTTTCTCACTGATGCTCTGGGCAGACAGGCTCCTCAATATGAGAGTGA
CACACACTCCTTTCTTCATTTTCAGGTAAACCTCACACTGGTTGGCAGAAGGAACTATCCAATAATTAGTGAACATG
CGGTGAATTTGCAACAGACAAGASGAGCCTCATTATCCTATAGTTTCCAGGTTGCTTAGGGAGGCAGAAATCACAGC
AAGGAAAACCTTCAATAATAAACAGACGTCTCATAAAATTAATTGCAACCCAACCTCTCTCTCTACTTAAAATTAGC
ATCTATTTCCAGCTCTGCTTTCAATGCCCCATATGAATACATGTGAACTCCCTCCCTCTCTTCCTCCCTGTCTCCTT
CTCTCTCTCTGTCCCTCATTAAAAAATAAAATTTAAGAAAAAAATACAAGGTAGATTTACACAAATAGTGGGATC
TCAGTCTTGAGTTAGCTGTGTATGACTGAAAAGGATGCTGTGGTTAATAATTATCATAAAAACAATGACATGGCCGG
G

SEQ ID NO:43
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGAGAGCATTTTCCGTGA
AGTTTGAGGTCCAGGCTCCACGCTGGGGCAACCCCCGTGCGCTCAGCTTCGTACTGAGTTCGCTCCAGCTCGGGGAG
GGGGTGGAGTTCGATGTGCTGCCTGCCTTTGATGCCCTGGGTCAGTTGACTGGCRGCTATAAACCTAACCCCCAAAT
CTATGTCAAGCTCATCGAGGAGTGCACCGACCTGCAGAAAGAGGGCGAGTTCTCCACCTGCTTCACAGAACTACAGA
GAGACTTCCTGAAGCAGCGCCCCACCAAGCTCAAGAGCCTCATCCGCCTAGTCAAGCACTGGTACCAAAATTGTAAG
AAGAAGCTTGGGAAGCTGCCACCTCAGTATGCCCTGGAGCTCCTGACGGTCTATGCTTGGGAGCGAGGGAGCATGAA
AACACATTTCAACACAGCCCAGGGATTTCGGACGGTCTTGGAATTAGTCATAAACTACCAGCAACTCTGCATCTACT
GGACAAAGTATTATGACTTTAAAAACCCCATTATTGAAAAGTACCTGAGAAGGCAGCTCACGAAACCCAGGTAAACC
TCACACTGGTTGGCAGAAGGAACTATCCAATAATTAGTGAACATGCGGTGAATTTGCAACAGACAAGASGAGCCTCA
TTATCCTATAGTTTCCAGGTTGCTTAGGGAGGCAGAAATCACAGCAAGGAAAACCTTCAATAATAAACAGACGTCTC
ATAAAATTAATTGCAACCCAACCTCTCTCTCTACTTAAAATTAGCATCTATTTCCAGCTCTGCTTTCAATGCCCCAT
ATGAATACATGTGAACTCCCTCCCTCTCTTCCTCCCTGTCTCCTTCTCTCTCTCTGTCCCTCATTAAAAAATAAA

FIGURE 3 cont.

ATTTAAGAAAAAAATACAAGGTAGATTTACACAAATAGTGGGATCTCAGTCTTGAGTTAGCTGTGTATGACTGAAAA
GGATGCTGTGGTTAATAATTATCATAAAAACAATGACATGGCCGGG

SEQ ID NO:44
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTCCAAGGTGGTAAAGTGTAAGAAGAAGCTTGGG
AAGCTGCCACCTCAGTATGCCCTGGAGCTCCTGACGGTCTATGCTTGGGAGCGAGGGAGCATGAAAACACATTTCAA
CACAGCCCAGGGATTTCGGACGGTCTTGGAATTAGTCATAAACTACCAGCAACTCTGCATCTACTGGACAAAGTATT
ATGACTTTAAAAACCCCATTATTGAAAAGTACCTGAGAAGGCAGCTCACGAAACCCAGGCCTGTGATCCTGGACCCG
GCGGACCCTACAGGAAACTTGGGTGGTGGAGACCCAAAGGGTTGGAGGCAGCTGGCACAAGAGGCTGAGGCCTGGCT
GAATTACCCATGCTTTAAGAATTGGGATGGGTCCCCAGTGAGCTCCTGGATTCTGCTGGTAAACCTCACACTGGTTG
GCAGAAGGAACTATCCAATAATTAGTGAACATGCGGTGAATTTGCAACAGACAAGASGAGCCTCATTATCCTATAGT
TTCCAGGTTGCTTAGGGAGGCAGAAATCACAGCAAGGAAAACCTTCAATAATAAACAGACGTCTCATAAAATTAATT
GCAACCCAACCTCTCTCTCTACTTAAAATTAGCATCTATTTCCAGCTCTGCTTTCAATGCCCCATATGAATACATGT
GAACTCCCTCCCTCTCTTCCTCCCTGTCTCCTTCTCTCTCTCTGTCCCTCATTAAAAAATAAAATTTAAGAAAAA
AATACAAGGTAGATTTACACAAATAGTGGGATCTCAGTCTTGAGTTAGCTGTGTATGACTGAAAAGGATGCTGTGGT
TAATAATTATCATAAAAACAATGACATGGCCGGG

SEQ ID NO:45
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACACGTGTTTCCGCATGCAAATCAACCATGCCATTGACATCATCTGTGGGTTCC
TGAAGGAAAGGTGCTTCCGAGGTAGCTCCTACCCTGTGTGTGTCCAAGGTGGTAAAGTGTAAGAAGAAGCTTGGG
AAGCTGCCACCTCAGTATGCCCTGGAGCTCCTGACGGTCTATGCTTGGGAGCGAGGGAGCATGAAAACACATTTCAA
CACAGCCCAGGGATTTCGGACGGTCTTGGAATTAGTCATAAACTACCAGCAACTCTGCATCTACTGGACAAAGTATT
ATGACTTTAAAAACCCCATTATTGAAAAGTACCTGAGAAGGCAGCTCACGAAACCCAGGTAAACCTCACACTGGTTG
GCAGAAGGAACTATCCAATAATTAGTGAACATGCGGTGAATTTGCAACAGACAAGASGAGCCTCATTATCCTATAGT
TTCCAGGTTGCTTAGGGAGGCAGAAATCACAGCAAGGAAAACCTTCAATAATAAACAGACGTCTCATAAAATTAATT
GCAACCCAACCTCTCTCTCTACTTAAAATTAGCATCTATTTCCAGCTCTGCTTTCAATGCCCCATATGAATACATGT
GAACTCCCTCCCTCTCTTCCTCCCTGTCTCCTTCTCTCTCTCTGTCCCTCATTAAAAAATAAAATTTAAGAAAAA
AATACAAGGTAGATTTACACAAATAGTGGGATCTCAGTCTTGAGTTAGCTGTGTATGACTGAAAAGGATGCTGTGGT
TAATAATTATCATAAAAACAATGACATGGCCGGG

SEQ ID NO:46
  1 MMDLRNTPAK SLDKFIEDYL LPDTCFRMQI XHAIDIICGF LKERCFRGSS YPVCVSKVVK
 61 CKKKLGKLPP QYALELLTVY AWERGSMKTH FNTAQGFRTV LELVINYQQL CIYWTKYYDF
121 KXPIIEKYLR RQLTKPRPVI LDPADPTGNL GGGDPKGWRQ LAQEAEAWLN YXCFKNWDGS
181 PVSSWILLVN LTLVGRRNYP IISEHAVNLQ QTRXASLSYS FQVA

SEQ ID NO:47
  1 MMDLRNTPAK SLDKFIEDYL LPDTCFRMQI XHAIDIICGF LKERCFRGSS YPVCVSKVVK
 61 CKKKLGKLPP QYALELLTVY AWERGSMKTH FNTAQGFRTV LELVINYQQL CIYWTKYYDF
121 KXPIIEKYLR RQLTKPR

SEQ ID NO:48
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE
121 VQAPRWXNPR ALSPVLSSLQ LGEGVEFDVL PAFDALCQLT GXYKPNPQIY VKLIEECTDL
181 QKEGEFSTCF TELQRDFLKQ RPTKLKSLIR LVKHWYQNCK KKLGKLPPQY ALELLTVYAW
241 ERGSMKTHFN TAQGFRTVLE LVINYQQLCI YWTKYYDFKX PIIEKYLRRQ LTKPRPVILD
301 PADPTGNLGG GDPKGWRQLA QEAEAWLNYX CFKNWDGSPV SSWILL

SEQ ID NO:49
  1 MMDLRNTPAK SLDKFIEDYL LPDTCFRMQI XHAIDIICGF LKERCFRGSS YPVCVSKVVK
 61 GGSSGKGTTL RGRSDADLVV FLSPLTTFQD QLNRRGEFIQ EIRRQLEACQ RERAXSVKFE

FIGURE 3 cont.

```
121 VQAPRWXNPR  ALSFVLSSLQ  LGEGVEFDVL  PAFDALGQLT  GXYKPNPQIY  VKLIEECTDL
181 QKEGEFSTCF  TELQRDFLKQ  RPTKLKSLIR  LVKHWYQNCK  KKLGKLPPQY  ALELLTVYAW
241 ERGSMKTHFN  TAQGFRTVLE  LVINYQQLCI  YWTKYYDFKX  PIIEKYLRRQ  LTKPRPVILD
301 PADPTGNLGG  GDPKGWRQLA  QEAEAWLNYX  CFKN

SEQ ID NO:50
  1 MMDLRNTPAK  SLDKFIEDYL  LPDTCFRMQI  XHAIDIICGF  LKERCFRGSS  YPVCVSKVVK
 61 GGSSGKGTTL  RGRSDADLVV  FLSPLTTFQD  QLNRRGEFIQ  EIRRQLEACQ  RERAXSVKFE
121 VQAPRWXNPR  ALSFVLSSLQ  LGEGVEFDVL  PAFDALGQLT  GXYKPNPQIY  VKLIEECTDL
181 QKEGEFSTCF  TELQRDFLKQ  RPTKLKSLIR  LVKHWYQNCK  KKLGKLPPQY  ALELLTVYAW
241 ERGSMKTHFN  TAQGFRTVLE  LVINYQQLCI  YWTKYYDFKX  PIIEKYLRRQ  LTKPRPVILD
301 PADPTGNLGG  GDPKGWRQLA  QEAEAWLNYX  CFKNWDGSPV  SSWILLAESN  SXD

SEQ ID NO:51
  1 MMDLRNTPAK  SLDKFIEDYL  LPDKCFRKQI  NHAIDIICGF  LKERCFQGSS  YPVHVSKVVK
 61 GGSSGKGTTL  RGRSDADLVV  FLSPLTTFQD  QLNRRGEFIQ  EIRRQLEACQ  REERAFSVKF
121 EVQAPRWDNP  RALSFVLSSL  QLGEGVEFDV  LPAFDALGQL  TDGYKPDPQI  YVKLIEECTY
181 LQKEGEFSTC  FTELQRDFLK  QRPTKLKSLI  RLVKHWYQNC  KKKLGKLPPQ  YALELLTVYA
241 WEQGSMETDF  NTAQEFRTVL  ELVINYQQLC  IYWTKYYDFE  NPIIEKYLRR  QLTKPRPVIL
301 DPADPTGNLG  GGDPKGWRQL  AQEAEAWLNY  PCFKN

SEQ ID NO:52
  1 PVILDPADPT  GNLGGGDPKG  WRQLAQEAEA  WLNYPCFKNW  DGSPVSSWIL  LAESDSGR

SEQ ID NO:55
GAGGCAGTTCTGTTGCCACTCTCTCTCCTGTCAATGATGGATCTCAGAAATACCCCAGCCAAATCTCTGGACAAGTT
CATTGAAGACTATCTCTTGCCAGACAAGTGTTTCCGCAAGCAAATCAACCATGCCATTGACATCATCTGTGGGTTCC
TGAAGGAAAGGTGCTTCCAAGGTAGCTCCTACCCTGTGCATGTGTCCAAGGTGGTAAAGGGTGGCTCCTCAGGCAAG
GGCACCACCCTCAGAGGCCGATCTGACGCTGACCTGGTTGTCTTCCTCAGTCCTCTCACCACTTTTCAGGATCAGTT
AAATCGCCGGGGAGAGTTCATCCAGGAAATTAGGAGACAGCTGGAAGCCTGTCAAAGAGAGGAGAGAGCATTTTCCG
TGAAGTTTGAGGTCCAGGCTCCACGCTGGGACAACCCCCGTGCGCTCAGCTTCGTACTGAGTTCGCTCCAGCTCGGG
GAGGGGGTGGAGTTCGATGTGCTGCCTGCCTTTGATGCCCTGGGTCAGTTGACTGACGGCTATAAACCTGACCCCCA
AATCTATGTCAAGCTCATCGAGGAGTGCACCTACCTGCAGAAAGAGGGCGAGTTCTCCACCTGCTTCACAGAACTAC
AGAGAGACTTCCTGAAGCAGCGCCCCACCAAGCTCAAGAGCCTCATCCGCCTAGTCAAGCACTGTACCAAAATTGT
AAGAAGAAGCTTGGGAAGCTGCCACCTCAGTATGCCCTGGAGCTCCTGACGGTCTATGCTTGGGAGCAAGGGAGCAT
GGAAACAGATTTCAACACAGCCCAGGAATTTCGGACGGTCTTGGAATTAGTCATAAACTACCAGCAACTCTGCATCT
ACTGGACAAAGTATTATGACTTTGAAAACCCCATTATTGAAAAGTACCTGAGAAGGCAGCTCACGAAACCCAGGCCT
GTGATCCTGGACCCGGCGGACCCTACAGGAAACTTGGGTGGTGGAGACCCAAAGGGTTGGAGGCAGCTGGCACAAGA
GGCTGAGGCCTGGCTGAATTACCCATGCTTTAAGAATTGAGATGGGTCCCCAGTGAGCTCCTGGATTCTGCTGGTGA
GACCTCCTGCTTCCTCCCTGCCATTCATCCCTGCCCCTCTCCATGAAGCTTGAGACATATAGCTGGAGACCATTCTT
TCCAAAGAACTTACCTCTTGCCAAAGGCCATTTTATATTCATATAGTGACAGGCTGTGCTCCATATTTTACAGTTATT
TTGGTCACAATCGAGGGTTTCTGGAATTTTCACATCCCTTGTCCAGAATTCATTCCCCTAAGAGTAATAATAAATAA
TCTCTAACAC

SEQ ID NO:56
GCCTGTGATCCTGGACCCGGCAGACCCTACAGGAAACTTGGGTGGTGGAGACCCAAAGGGTTGGAGGCAGCTGGCAC
AAGAGGCTGAGGCCTGGCTGAATTACCCATGCTTTAAGAATTGGGATGGGTCCCCAGTGAGCTCCTGGATTCTGCTG
GCTGAAAGCGACAGTGGACGATGAGACCGACGATCCCAGGAGGTATCAGAAATATGGTTACATTGGAACACATGAGT
ACCCTCATTTCTCTCATAGACCCAGCACACTCCAGGCAGCATCCACCCCACAGGCAGAAGAGGACTGGACCTGCACC
ATCCTCTGAATGCYAGTGCATCTTGGGGGAAAGGGCTCCAGTGTTATCTGGACCAGTTCCTTCATTTTCAGGTGGGA
CTCTTGATCCAGAGAGGACAAAGCTCCTCAGTGAGCTGGTGTATAATCCAGGACAGAACCCAGGTCTCCTGACTCCT
GGCCTTCTATGCCCTCTATCCTATCATAGATAACATTCTCCACAGCCTCACTTCATTCCACCTATTCTCTGAAAATA
TTCCCTGAGAGAGAACAGAGAGATTTAGATAAGAGAATGAAATTCCAGCCTTGACTTTCTTCTGTGCACCTGATGGG
AGGGTTATGTCTAATGTATTATCAATAACAGTAAAAATAAAGCAAATGCC
```

FIGURE 3 cont.

FOR NUCLEOTIDE SEQUENCES ABOVE (SEQ ID NO:31, SEQ ID NO:36-45, and SEQ ID NO: 55-56):
R denotes A or G
S denotes G or C FOR AMINO ACID SEQUENCES ABOVE (SEQ ID NO:20-30, SEQ ID NO:32-35, and SEQ ID NO: 46-52):
X denotes amino acid variants according to the table below

| SEQ ID NO | Amino acid position | Amino acid |
|---|---|---|
| 20 | 31 | D or N |
|  | 115 | L or F |
|  | 127 | G or R |
|  | 162 | G or S |
| 21 | 53 | D or N |
|  | 137 | L or F |
|  | 184 | G or S |
| 22 | 31 | D or N |
|  | 115 | L or F |
|  | 127 | G or R |
|  | 162 | G or S |
| 23 | 53 | D or N |
|  | 137 | L or F |
|  | 184 | G or S |
| 24 | 64 | D or N |
|  | 138 | L or F |
|  | 185 | G or S |
| 25 | 31 | D or N |
|  | 115 | L or F |
|  | 127 | G or R |
|  | 162 | G or S |
| 26 | 31 | D or N |
|  | 115 | L or F |
|  | 127 | G or R |
|  | 162 | S or G |
|  | 280 | N or T |
|  | 330 | P or S |
| 27 | 31 | D or N |
|  | 115 | L or F |
|  | 127 | G or R |
|  | 162 | S or G |
|  | 280 | N or T |
|  | 330 | P or S |

FIGURE 3 cont.

| | 361 | G or R |
|---|---|---|
| | 429 | K or R |
| 28 | 31 | D or N |
| | 115 | L or F |
| | 127 | G or R |
| | 162 | S or G |
| | 280 | N or T |
| | 330 | P or S |
| 29 | 31 | D or N |
| | 115 | L or F |
| | 127 | G or R |
| | 162 | S or G |
| | 280 | N or T |
| | 330 | P or S |
| | 372 | R or G |
| 30 | 6 | A or T |
| | 15 | R or T |
| 32 | 31 | D or N |
| | 115 | L or F |
| | 127 | G or R |
| | 162 | S or G |
| | 280 | N or T |
| 33 | 31 | D or N |
| | 115 | L or F |
| | 127 | G or R |
| | 162 | S or G |
| | 280 | N or T |
| | 330 | P or S |
| 34 | 31 | D or N |
| | 115 | L or F |
| | 127 | G or R |
| | 162 | S or G |
| | 280 | N or T |
| | 330 | P or S |
| | 352 | A or T |
| | 361 | R or T |
| 35 | 31 | D or N |
| | 115 | L or F |
| | 127 | G or R |
| | 162 | S or G |
| | 280 | N or T |
| | 330 | P or S |
| | 397 | G or R |

FIGURE 3 cont.

| 46 | 31 | D or N |
|---|---|---|
|  | 122 | N or T |
|  | 172 | P or S |
|  | 214 | R or G |
| 47 | 31 | D or N |
|  | 122 | N or T |
| 48 | 31 | D or N |
|  | 115 | L or F |
|  | 127 | G or R |
|  | 162 | S or G |
|  | 280 | N or T |
|  | 330 | P or S |
| 49 | 31 | D or N |
|  | 115 | L or F |
|  | 127 | G or R |
|  | 162 | S or G |
|  | 280 | N or T |
|  | 330 | P or S |
| 50 | 31 | D or N |
|  | 115 | L or F |
|  | 127 | G or R |
|  | 162 | S or G |
|  | 280 | N or T |
|  | 330 | P or S |
|  | 352 | A or T |

FIGURE 4

Population haplotypes inferred from Case & Control subjects

| Inferred Haplotype | Approximate Population Frequency | SEQ ID NO:2 Allele | SEQ ID NO:3 Allele | SEQ ID NO:4 Allele | SEQ ID NO:5 Allele |
|---|---|---|---|---|---|
| HAP1 | 54% | A | G | A | A |
| HAP2 | 32% | G | G | G | G |
| HAP3 | 8% | G | A | A | A |
| HAP4 | 5% | G | G | G | A |
| HAP5 | <1% | A | G | G | G |
| HAP6 | <1% | G | G | A | A |

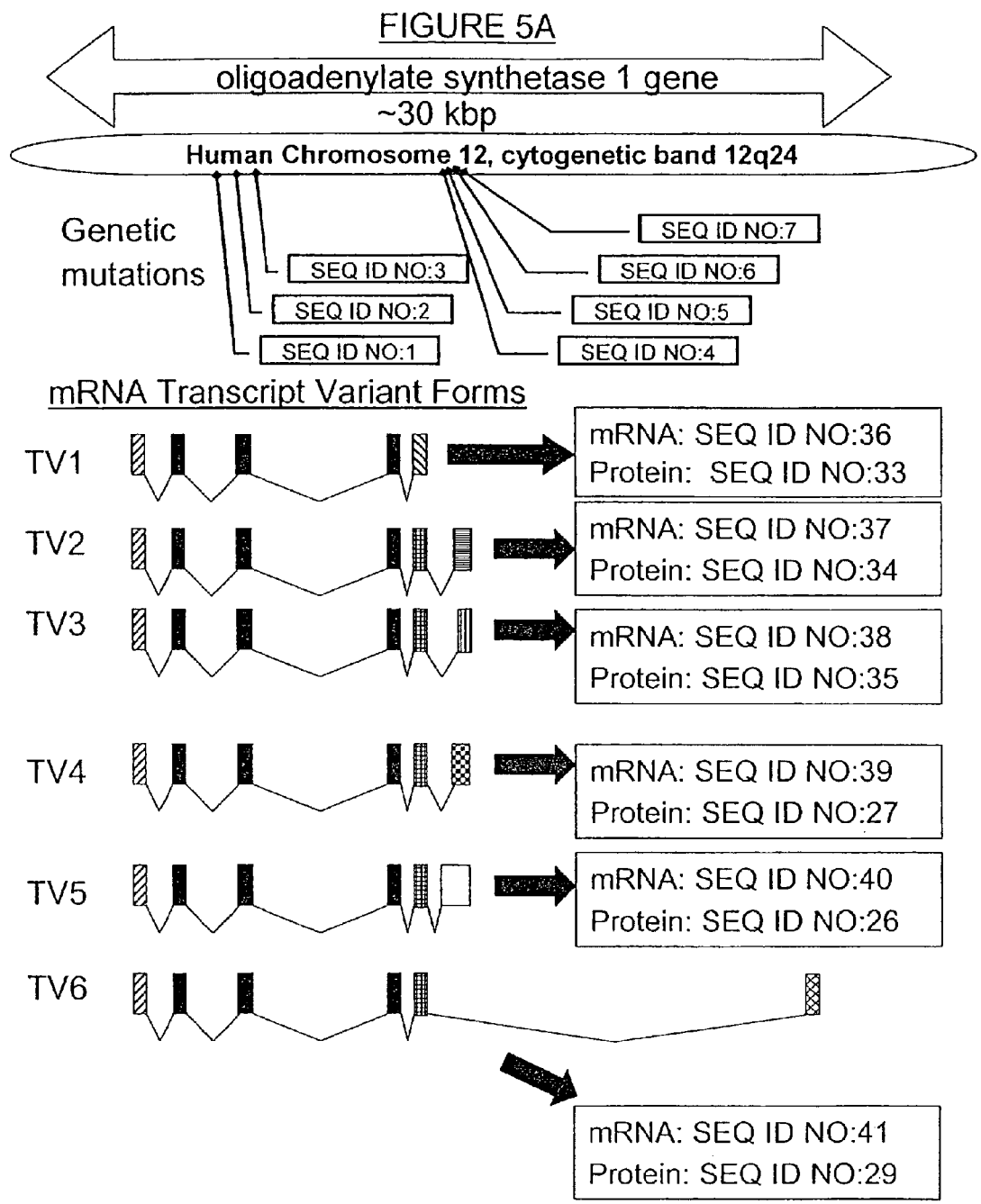

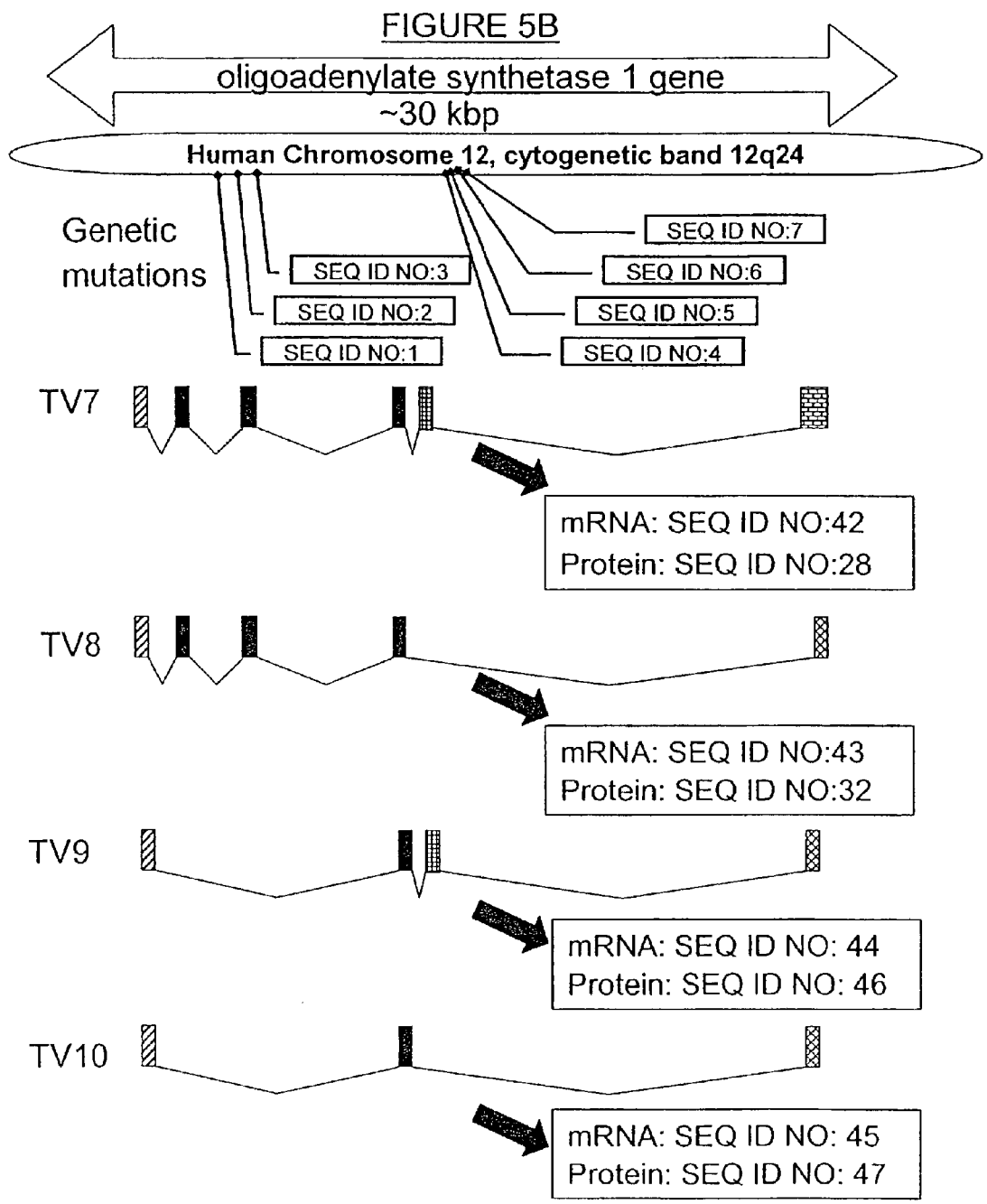

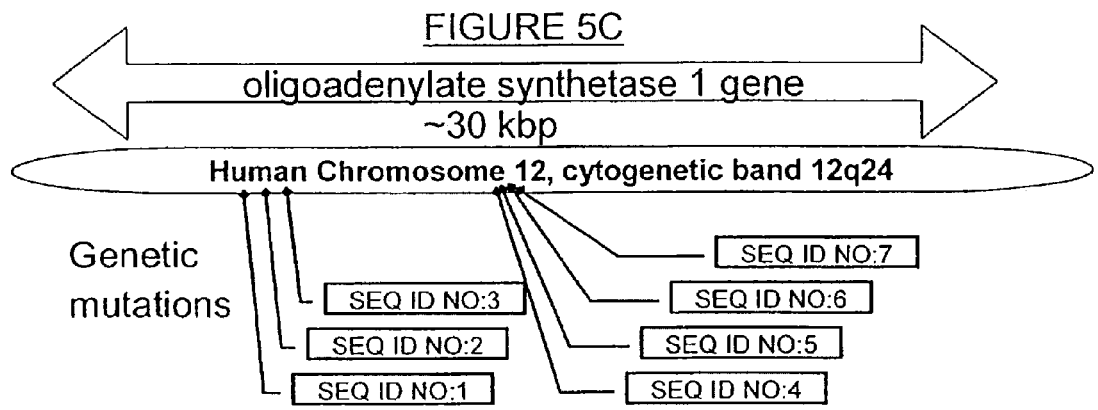
Inferred structure of Non-human OAS1 genes
Chimpanzee
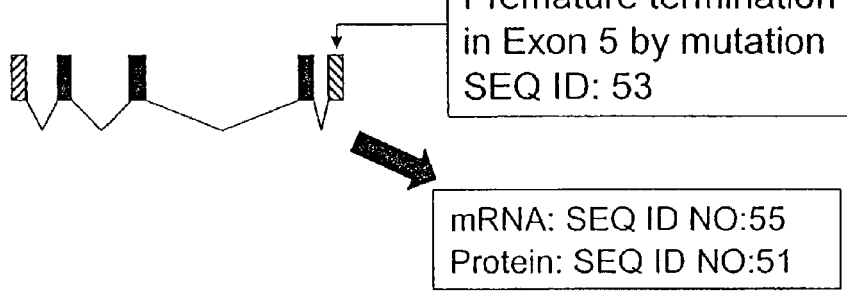
Gorilla
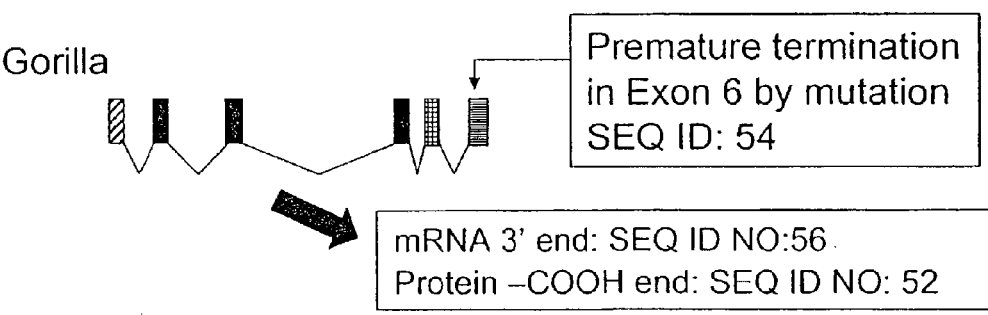

FIGURE 6
NON-HUMAN PRIMATE MUTATIONS

| |
|---|
| SEQ ID NO: 53<br>Organism: *Pan troglodytes*<br>Variant relative to human: A (A substitution for G)<br>Homologous human genomic sequence Genbank ID: NT_009775.13<br>Coordinates of mutation on human genomic sequence (start-stop): 2,142,351-2,142,351<br>Organism's local identifying genomic sequence context:<br>CTGGCACAAGAGGCTGAGGCCTGGCTGAATTACCCATGCTTTAAGAATTG<br><u>A</u><br>GATGGGTCCCCAGTGAGCTCCTGGATTCTGCTGGTGAGACCTCCTGCTTC |
| SEQ ID NO: 54<br>Organism: *Gorilla gorilla*<br>Variant relative to human: -- (two base pair deletion of CA)<br>Homologous human genomic sequence Genbank ID: NT_009775.13<br>Coordinates of mutation on human genomic sequence (start-stop): 2,144,089-2,144,090<br>Organism's local identifying genomic sequence context:<br>CTCCCTGATGTGATCATGTGTCTCACCCTTTCAGGCTGAAAGC<u>G</u>ACAGTG<br><u>- -</u><br>GACGATGAGACCGACGATCCCAGGAGGTATCAGAAATATGGTTACATTGG |

Bold, singly underlined bases represent the particular organism variant relative to human being identified by each SEQ ID NO.

Doubly underlined bases represent other co-localized variants between the human genomic sequence and the indicated organism.

Degenerate nucleic acid codes:
R=A/G
Y=C/T
S=C/G
K=G/T

Figure 8:
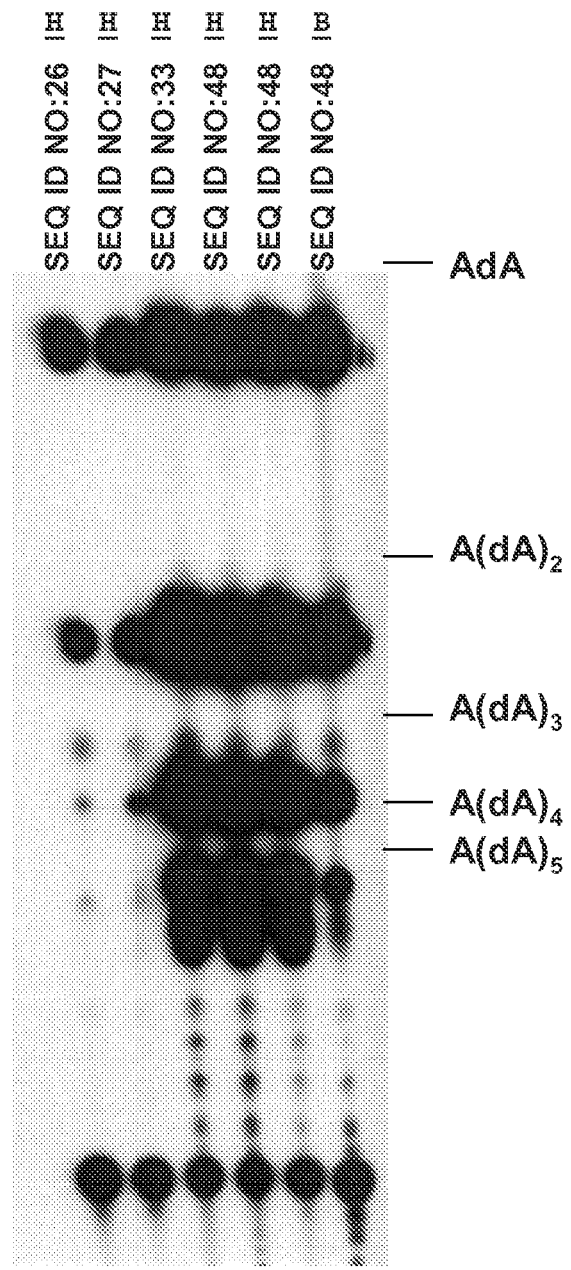

Figure 8: Activity of OAS1

FIGURE 9
DEVELOPMENT OF ANTIBODIES SPECIFIC TO NOVEL FORMS OF OAS1

| Antibody | | | | |
|---|---|---|---|---|
| A2801 | A2802 | A2803 | A2804 | |
| | | | | 181.8 KDa |
| | | | | 115.5 |
| | | | | 82.2 |
| | | | | 64.2 |
| | | | | 48.8 |
| | | | | 37.1 |
| SEQ ID NO:26 | SEQ ID NO:26 | SEQ ID NO:27 | SEQ ID NO:27 | |

FIGURE 10
EXEMPLARY PROTEIN TRANSDUCTION DOMAIN SYSTEMS

| Sequence ID Number | Polypeptide Sequence |
| --- | --- |
| SEQ ID NO:85 | YGRKKRRQRRR |
| SEQ ID NO:86 | RQIKIWFQNRRMKWKK |
| SEQ ID NO:87 | MTSRRSVKSGPREVPRDEYEDLYYIPSSGMASPDSPPD TSRRGALQTRSRQRGEVRFVQYDESDYALYGGSSSEDD EHPEVPRTRRPVSGAVLSGPGPARAPPPPAGSGGAGRTP TTAPRAPRTQRVATKAPAAPAAETTRGRKSAQPESAAL PDAPASTAPTRSKTPAQGLARKLHFSTAPPNPDAPWTPR VAGFNKRVFCAAVGRLAAMHARMAAVQLWDMSRPRT DEDLNELLGITTIRVTVCEGKNLLQRANELVNPDVVQDV DAATATRGRSAASRPTERPRAPARSASRPRRPVE |
| SEQ ID NO:88 | MSRKLFASILIGALLGIGAPPSAHAGADDVVDSSKSFVM ENFSSYHGTKPGYVDSIQKGIQKPKSGTQGN YDDDWKGFYSTDNKYDAAGYSVDNENPLSGKAGGVV KVTYPGLTKVLALKVDNAETIKKELGLSLTEPLM EQVGTEEFIKRFGDGASRVVLSLPFAEGSSSVEYINNWE QAKALSVELEINFETRGKRGQDAMYEYMAQA CAGNRVRRSVGSSLSCINLDWDVIRDKTKTKIESLKEHG PIKNKMSESPNKTVSEEKAKQYLEEFHQTAL EHPELSELKTVTGTNPVFAGANYAAWAVNVAQVIDSET ADNLEKTTAALSILPGIGSVMGIADGAVHHNT EEIVAQSIALSSLMVAQAIPLVGELVDIGFAAYNFVESIIN LFQVVHNSYNRPAYSPGHKTQPFLHDGYA VSWNTVEDSIIRTGFQGESGHDIKITAENTPLPIAGVLLP TIPGKLDVNKSKTHISVNGRKIRMRCRAID GDVTFCRPKSPVYVGNGVHANLHVAFHRSSSEKIHSNE ISSDSIGVLGYQKTVDHTKVNSKLSLFFEIKS |
| SEQ ID NO:89 | GDIMGEWGNEIFGAIAGFLG |
| SEQ ID NO:90 | RRRRRRR |
| SEQ ID NO:91 | RRQRRTSKLMKR |
| SEQ ID NO:92 | GWTLNSAGYLLGKINLKALAALAKKIL |
| SEQ ID NO:93 | WEAKLAKALAKALAKHLAKALAKALKACEA |
| SEQ ID NO:94 | KETWWETWWTEWSQPKKKRKV |

DETECTION OF MUTATIONS IN A GENE ASSOCIATED WITH RESISTANCE TO VIRAL INFECTION, OAS1

CROSS-REFERENCES TO RELATED APPLICATIONS

This application is a continuation of U.S. application Ser. No. 13/468,937 filed May 10, 2012, which is a continuation of U.S. application Ser. No. 11/592,711 filed Nov. 2, 2006 which is a divisional of U.S. application Ser. No. 10/972,135 filed Oct. 22, 2004, now abandoned, which claims priority from Provisional Application Nos. 60/605,243 filed Aug. 26, 2004, 60/578,323 filed Jun. 9, 2004, 60/560,524 filed Apr. 8, 2004, 60/554,758 filed Mar. 19, 2004, 60/542,373 filed Feb. 6, 2004, and 60/513,888 filed Oct. 23, 2003, which applications are incorporated by reference in their entirety herein.

TECHNICAL FIELD

The present invention relates to a method for detecting a mutation in a human oligoadenylate synthetase gene, wherein a mutation confers resistance to flavivirus infection, including infection by hepatitis C virus, and a mutation relates to other disease states including prostate cancer and diabetes, and uses of the encoded proteins and antibodies thereto.

BACKGROUND OF THE INVENTION

A number of diseases have been identified to date in which natural resistance to infection exists in the human population. Alter and Moyer, *J. Acquir. Immune Defic. Syndr. Hum Retrovirol.* 18 Suppl. 1:S6-10 (1998) report hepatitis C viral infection (HCV) rates as high as 90% in high-risk groups such as injecting drug users. However, the mechanism by which the remaining 10% are apparently resistant to infection has not been identified in the literature. Proteins that play a role in HCV infection include the 2-prime, 5-prime oligoadenylate synthetases. OASs are interferon-induced proteins characterized by their capacity to catalyze the synthesis of 2-prime,5-prime oligomers of adenosine (2-5As). Hovanessian et al., *EMBO* 6: 1273-1280 (1987) found that interferon-treated human cells contain several OASs corresponding to proteins of 40 (OAS1), 46 (OAS1), 69, and 100 kD. Marie et al., *Biochem. Biophys. Res. Commun.* 160:580-587 (1989) generated highly specific polyclonal antibodies against p69, the 69-kD OAS. By screening an interferon-treated human cell expression library with the anti-p69 antibodies, Marie and Hovanessian, *J. Biol. Chem.* 267: 9933-9939 (1992) isolated a partial OAS2 cDNA. They screened additional libraries with the partial cDNA and recovered cDNAs encoding two OAS2 isoforms. The smaller isoform is encoded by two mRNAs that differ in the length of the 3-prime untranslated region.

Northern blot analysis revealed that OAS2 is expressed as four interferon-induced mRNAs in human cells. The predicted OAS2 proteins have a common 683-amino acid sequence and different 3-prime termini. According to SDS-PAGE of in vitro transcription/translation products, two isoforms have molecular masses of 69 and 71 kD. Both isoforms exhibited OAS activity in vitro. Sequence analysis indicated that OAS2 contains two OAS1-homologous domains separated by a proline-rich putative linker region. The N- and C-terminal domains are 41% and 53% identical to OAS1, respectively.

By fluorescence in situ hybridization and by inclusion within mapped clones, Hovanian et al., *Genomics* 52: 267-277 (1998) determined that the OAS1, OAS2, and OAS3 genes are clustered with a 130-kb region on 12q24.2. 2-5As bind to and activate RNase I, which degrades viral and cellular RNAs, leading to inhibition of cellular protein synthesis and impairment of viral replication.

A fourth human OAS gene, referred to as OASL, differs from OAS1, OAS2 and OAS3 in that OASL lacks enzyme activity. The OASL gene encodes a two-domain protein composed of an OAS unit fused to a 164 amino acid C-terminal domain that is homologous to a tandem repeat of ubiquitin. (Eskildsen et al., Nuc. Acids Res. 31:3166-3173, 2003; Kakuta et al., J. Interferon & Cytokine Res. 22:981-993, 2002.)

Because of their role in inhibiting viral replication and viral infection, there is a need in the art for methods and compositions that suppress viral replication related to OAS1 activity, including a profound need for inhibitor-based therapies that suppress HCV replication.

BRIEF SUMMARY OF THE INVENTION

The present invention relates to detecting hepatitis C resistance-related mutations which are characterized as point mutations in the oligoadenylate synthetase 1 gene.

In one embodiment, a human genetic screening method is contemplated. The method comprises assaying a nucleic acid sample isolated from a human for the presence of an oligoadenylate synthetase 1 gene point mutation characterized as a base substitution at nucleotide position 2135728, 2135749, 2135978, 2144072, 2144088, 2144116, 2144321, 2131025, 2133961, 2139587, 2144294, 2144985, 2156523, or 2156638 or a base deletion at nucleotide position 2156595 for oligoadenylate synthetase 1 gene (OAS1) with reference to Genbank Sequence Accession No. NT_009775.13 (consecutive nucleotides 2,130,000-2,157,999 of which are shown in FIG. 2 as SEQ ID NO:19).

In a preferred embodiment, the method comprises treating, under amplification conditions, a sample of genomic DNA from a human with a polymerase chain reaction (PCR) primer pair for amplifying a region of human genomic DNA containing nucleotide position 2135728, 2135749, 2135978, 2144072, 2144088, 2144116, 2144321, 2131025, 2133961, 2139587, 2144294, 2144985, 2156523, 2156595, or 2156638 of oligoadenylate synthetase 1 gene NT_009775.13. The PCR treatment produces an amplification product containing the region, which is then assayed for the presence of a point mutation.

In a further embodiment, the invention provides a protein encoded by a gene having at least one mutation at position 2135728, 2135749, 2135978, 2144072, 2144088, 2144116, 2144321, 2131025, 2133961, 2139587, 2144294, 2144985, 2156523, 2156595, or 2156638 of NT_009775.13, and use of the protein to prepare a diagnostic for resistance to viral infection, preferably flaviviral infection, most preferably hepatitis C infection. In specific embodiments, the diagnostic is an antibody.

In a still further embodiment, the invention provides a therapeutic compound for preventing or inhibiting infection by a virus, preferably a flavivirus, most preferably hepatitis C virus, wherein the therapeutic compound is a protein encoded by an OAS1 gene having at least one mutation at position 2135728, 2135749, 2135978, 2144072, 2144088, 2144116, 2144321, 2131025, 2133961, 2139587, 2144294, 2144985, 2156523, 2156595, or 2156638 of NT_009775.13. In other embodiments the therapeutic compound is a polynucleotide, such as DNA or RNA, encoding the protein.

In a still further embodiment, the invention provides a therapeutic compound for preventing or inhibiting infection by a virus, preferably a flavivirus, most preferably a hepatitis C virus, wherein the therapeutic compound is a protein of the sequence: SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO:29, SEQ ID NO:32, SEQ ID NO:33, SEQ ID NO:34, SEQ ID NO:35, SEQ ID NO:46, SEQ ID NO:47 and/or SEQ ID NO:48.

In a still further embodiment, the invention provides a therapeutic compound for preventing or inhibiting infection by a virus, preferably a flavivirus, most preferably hepatitis C virus, wherein the therapeutic compound mimics the beneficial effects of at least one mutation at position 2135728, 2135749, 2135978, 2144072, 2144088, 2144116, 2144321, 2131025, 2133961, 2139587, 2144294, 2144985, 2156523, 2156595, or 2156638 of NT_009775.13. The therapeutic compound can be a small molecule, protein, peptide, DNA or RNA molecule, or antibody.

In a still further embodiment, the invention provides a therapeutic compound for preventing or treating cancer, preferably prostate cancer, wherein the therapeutic compound is a protein encoded by an OAS1 gene having at least one mutation at position 2135728, 2135749, 2135978, 2144072, 2144088, 2144116, 2144321, 2131025, 2133961, 2139587, 2144294, 2144985, 2156523, 2156595, or 2156638 of NT_009775.13. In other embodiments the therapeutic compound is a polynucleotide, such as DNA or RNA, encoding the protein.

In a still further embodiment, the invention provides a therapeutic compound for preventing or treating cancer, preferably prostate cancer, wherein the therapeutic compound is a protein of the sequence: SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO:29, SEQ ID NO:32, SEQ ID NO:33, SEQ ID NO:34, SEQ ID NO:35, SEQ ID NO:46, SEQ ID NO:47 and/or SEQ ID NO:48.

In a still further embodiment, the invention provides a therapeutic compound for preventing or treating cancer, preferably prostate cancer, wherein the therapeutic compound mimics the beneficial effects of at least one mutation at position 2135728, 2135749, 2135978, 2144072, 2144088, 2144116, 2144321, 2131025, 2133961, 2139587, 2144294, 2144985, 2156523, 2156595, or 2156638 of NT_009775.13. The therapeutic compound can be a small molecule, protein, peptide, DNA or RNA molecule, or antibody.

In further embodiments, the therapeutic compound is capable of inhibiting the activity of OAS1 or at least one sub-region or sub-function of the entire protein, and such compounds are represented by antisense molecules, ribozymes, and RNAi molecules capable of specifically binding to OAS1 polynucleotides, and by antibodies and fragments thereof capable of specifically binding to OAS1 proteins and polypeptides.

The present invention provides, in another embodiment, inhibitors of OAS1. Inventive inhibitors include, but are not limited to, antisense molecules, ribozymes, RNAi, antibodies or antibody fragments, proteins or polypeptides as well as small molecules. Exemplary antisense molecules comprise at least 10, 15 or 20 consecutive nucleotides of, or that hybridize under stringent conditions to the polynucleotide of SEQ ID NO:19. More preferred are antisense molecules that comprise at least 25 consecutive nucleotides of, or that hybridize under stringent conditions to the sequence of SEQ ID NO:19.

In a still further embodiment, inhibitors of OAS1 are envisioned that specifically bind to the region of the protein defined by the polypeptide of SEQ ID NO:30. Inventive inhibitors include but are not limited to antibodies, antibody fragments, small molecules, proteins, or polypeptides.

In a still further embodiment, inhibitors of OAS1 are envisioned that are comprised of antisense or RNAi molecules that specifically bind or hybridize to the polynucleotide of SEQ ID NO:31.

In further embodiments, compositions are provided that comprise one or more OAS1 inhibitors in a pharmaceutically acceptable carrier.

Additional embodiments provide methods of decreasing OAS1 gene expression or biological activity.

Additional embodiments provide for methods of specifically increasing or decreasing the expression of certain forms of the OAS1 gene having at least one mutation at position 2135728, 2135749, 2135978, 2144072, 2144088, 2144116, 2144321, 2131025, 2133961, 2139587, 2144294, 2144985, 2156523, 2156595, or 2156638 of NT_009775.13.

The invention provides an antisense oligonucleotide comprising at least one modified internucleoside linkage.

The invention further provides an antisense oligonucleotide having a phosphorothioate linkage.

The invention still further provides an antisense oligonucleotide comprising at least one modified sugar moiety.

The invention also provides an antisense oligonucleotide comprising at least one modified sugar moiety which is a 2'-O-methyl sugar moiety.

The invention further provides an antisense oligonucleotide comprising at least one modified nucleobase.

The invention still further provides an antisense oligonucleotide having a modified nucleobase wherein the modified nucleobase is 5-methylcytosine.

The invention also provides an antisense compound wherein the antisense compound is a chimeric oligonucleotide.

The invention provides a method of inhibiting the expression of human OAS1 in human cells or tissues comprising contacting the cells or tissues in vivo with an antisense compound or a ribozyme of 8 to 35 nucleotides in length targeted to a nucleic acid molecule encoding human OAS1 so that expression of human OAS1 is inhibited.

The invention further provides a method of decreasing or increasing expression of specific forms of OAS1 in vivo, such forms being defined by having at least one mutation at position 2135728, 2135749, 2135978, 2144072, 2144088, 2144116, 2144321, 2131025, 2133961, 2139587, 2144294, 2144985, 2156523, 2156595, or 2156638 of NT_009775.13, using antisense or RNAi compounds or ribozymes.

The invention further provides a method of modulating growth of cancer cells comprising contacting the cancer cells in vivo with an antisense compound or ribozyme of 8 to 35 nucleotides in length targeted to a nucleic acid molecule encoding human OAS1 so that expression of human OAS1 is inhibited.

The invention still further provides for identifying target regions of OAS1 polynucleotides. The invention also provides labeled probes for identifying OAS1 polynucleotides by in situ hybridization.

The invention provides for the use of an OAS1 inhibitor according to the invention to prepare a medicament for preventing or inhibiting HCV infection.

The invention further provides for directing an OAS1 inhibitor to specific regions of the OAS1 protein or at specific functions of the protein.

The invention also provides a pharmaceutical composition for inhibiting expression of OAS1, comprising an antisense oligonucleotide according to the invention in a mixture with a physiologically acceptable carrier or diluent.

The invention further provides a ribozyme capable of specifically cleaving OAS1 RNA, and a pharmaceutical composition comprising the ribozyme.

The invention also provides small molecule inhibitors of OAS1 wherein the inhibitors are capable of reducing the activity of OAS1 or of reducing or preventing the expression of OAS1 mRNA.

The invention further provides for inhibitors of OAS1 that modify specific functions of the protein other than the synthesis of 2'-5' oligoadenylates, such functions including interaction with other proteins such as Hepatitis C virus NS5A protein.

The invention further provides for compounds that alter post-translational modifications of OAS1 including but not limited to glycosylation and phosphorylation.

The invention further provides a human genetic screening method for identifying an oligoadenylate synthetase gene mutation comprising: (a) treating, under amplification conditions, a sample of genomic DNA from a human with a polymerase chain reaction (PCR) primer pair for amplifying a region of human genomic DNA containing nucleotide position 2135728, 2135749, 2135978, 2144072, 2144088, 2144116, 2144321, 2131025, 2133961, 2139587, 2144294, 2144985, 2156523, 2156595, or 2156638 of oligoadenylate synthetase gene, said treating producing an amplification product containing said region; and (b) detecting in the amplification product of step (a) the presence of an nucleotide point mutation at nucleotide position 2135728, 2135749, 2135978, 2144072, 2144088, 2144116, 2144321, 2131025, 2133961, 2139587, 2144294, 2144985, 2156523, 2156595, or 2156638, thereby identifying said mutation.

In certain embodiments of this method, the region comprises a nucleotide sequence represented by a sequence selected from the group consisting of SEQ ID NO:1-7 and SEQ ID NO:57-64. In other embodiments, the region consists essentially of a nucleotide sequence selected from the group consisting of SEQ ID NO:1-7 and SEQ ID NO:57-64. Also provided is a method of detecting, wherein the detecting comprises treating, under hybridization conditions, the amplification product of step (a) above with an oligonucleotide probe specific for the point mutation, and detecting the formation of a hybridization product. In certain embodiments of the method, the oligonucleotide probe comprises a nucleotide sequence selected from the group consisting of SEQ ID NO:12-18.

The invention also relates to a method for detecting in a human a hepatitis C infection resistance disease allele containing a point mutation comprising substitution of a non wild-type nucleotide for a wild-type nucleotide at nucleotide position 2135728, 2135749, 2135978, 2144072, 2144088, 2144116, 2144321, 2131025, 2133961, 2139587, 2144294, 2144985, 2156523, 2156595, or 2156638 of oligoadenylate synthetase gene (OAS1), which method comprises: (a) forming a polymerase chain reaction (PCR) admixture by combining, in a PCR buffer, a sample of genomic DNA from said human and an oligoadenylate synthetase gene-specific PCR primer pair selected from the group consisting of SEQ ID NO:8 and 9, and SEQ ID NO:10 and 11; (b) subjecting the PCR admixture to a plurality of PCR thermocycles to produce an oligoadenylate synthetase gene amplification product; and (c) treating, under hybridization conditions products produced in step (b), with a probe selected from the group consisting of SEQ ID NO:12-18, thereby detecting said mutation.

Also provided is an isolated OAS1 inhibitor selected from the group consisting of an antisense oligonucleotide, a ribozyme, a small inhibitory RNA (RNAi), a protein, a polypeptide, an antibody, and a small molecule. The isolated inhibitor may be an antisense molecule or the complement thereof comprising at least 15 consecutive nucleic acids of the sequence of SEQ ID NO:19. In other embodiments, the isolated OAS1 inhibitor (antisense molecule or the complement thereof) hybridizes under high stringency conditions to the sequence of SEQ ID NO:19.

The isolated OAS1 inhibitor may be selected from the group consisting of an antibody and an antibody fragment. Also provided is a composition comprising a therapeutically effective amount of at least one OAS1 inhibitor in a pharmaceutically acceptable carrier.

The invention also relates to a method of inhibiting the expression of OAS1 in a mammalian cell, comprising administering to the cell an OAS1 inhibitor selected from the group consisting of an antisense oligonucleotide, a ribozyme, a protein, an RNAi, a polypeptide, an antibody, and a small molecule.

The invention further relates to a method of inhibiting the expression of OAS1 gene expression in a subject, comprising administering to the subject, in a pharmaceutically effective vehicle, an amount of an antisense oligonucleotide which is effective to specifically hybridize to all or part of a selected target nucleic acid sequence derived from said OAS1 gene.

The invention still further relates to a method of preventing infection by a flavivirus in a human subject susceptible to the infection, comprising administering to the human subject an OAS1 inhibitor selected from group consisting of an antisense oligonucleotide, a ribozyme, an RNAi, a protein, a polypeptide, an antibody, and a small molecule, wherein said OAS1 inhibitor prevents infection by said flavivirus.

The invention still further relates to a method of preventing or curing infection by a flavivirus or other virus in a human subject susceptible to the infection, comprising administering to the human subject an OAS1 inhibitor selected from group consisting of an antisense oligonucleotide, a ribozyme, an RNAi, a protein, a polypeptide, an antibody, and a small molecule, wherein said OAS1 inhibitor prevents infection by said flavivirus or other virus and wherein said OAS1 inhibitor is directed at one or more specific forms of the protein defined by a mutation at position 2135728, 2135749, 2135978, 2144072, 2144088, 2144116, 2144321, 2131025, 2133961, 2139587, 2144294, 2144985, 2156523, 2156595, or 2156638 of NT_009775.13.

The invention still further relates to a method of preventing or curing infection by a flavivirus or any other virus in a human subject susceptible to the infection by administering one of the polypeptides of the sequence: SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO:29, SEQ ID NO:32, SEQ ID NO:33, SEQ ID NO:34, SEQ ID NO:35, SEQ ID NO:46, SEQ ID NO:47 and/or SEQ ID NO:48.

The invention embodies also treatments for infection with the human immunodeficiency virus (HIV).

The invention still further relates to a method of preventing insulin dependent diabetes mellitus (IDDM) in a human subject, comprising administering to the human subject an OAS1 inhibitor selected from group consisting of an antisense oligonucleotide, a ribozyme, an RNAi, a protein, a polypeptide, an antibody, and a small molecule, wherein said OAS1 inhibitor prevents IDDM.

The invention still further relates to a method of preventing IDDM in a human subject, comprising administering to the human subject an OAS1 inhibitor selected from group consisting of an antisense oligonucleotide, a ribozyme, an RNAi, a protein, a polypeptide, an antibody, and a small molecule, wherein said OAS1 inhibitor prevents IDDM and wherein said OAS1 inhibitor is directed at one or more specific forms of the protein defined by a mutation at position 2135728, 2135749, 2135978, 2144072, 2144088, 2144116, 2144321, 2131025, 2133961, 2139587, 2144294, 2144985, 2156523, 2156595, or 2156638 of NT_009775.13.

The invention still further relates to a method of treating cancer, such as prostate cancer by increasing expression of the OAS1 gene or by therapeutic administration of polypeptides disclosed herein.

Also provided is a method for inhibiting expression of a OAS1 target gene in a cell in vitro comprising introduction of a ribonucleic acid (RNA) into the cell in an amount sufficient to inhibit expression of the OAS1 target gene, wherein the RNA is a double-stranded molecule with a first strand consisting essentially of a ribonucleotide sequence which corresponds to a nucleotide sequence of the OAS1 target gene and a second strand consisting essentially of a ribonucleotide sequence which is complementary to the nucleotide sequence of the OAS1 target gene, wherein the first and the second ribonucleotide strands are separate complementary strands that hybridize to each other to form said double-stranded molecule, and the double-stranded molecule inhibits expression of the target gene.

In certain embodiments of the method, the first ribonucleotide sequence comprises at least 20 bases which correspond to the OAS1 target gene and the second ribonucleotide sequence comprises at least 20 bases which are complementary to the nucleotide sequence of the OAS1 target gene. In still further embodiments, the target gene expression is inhibited by at least 10%.

In still further embodiments of the method, the double-stranded ribonucleic acid structure is at least 20 bases in length and each of the ribonucleic acid strands is able to specifically hybridize to a deoxyribonucleic acid strand of the OAS1 target gene over the at least 20 bases.

The invention provides a polypeptide or protein capable of restoring function of OAS1 that may be diminished or lost due to gene mutation. In some embodiments the polypeptide or protein has the amino acid sequence of wild type OAS1 encoded by a gene comprising SEQ ID NO:19. In other embodiments, wherein a mutation in the OAS1 gene confers increased activity, stability, and/or half life on the OAS1 protein, or other change making the OAS1 protein more suitable for anti-viral activity, the protein or polypeptide encoded by the mutated OAS1 gene is preferred.

Any of the foregoing proteins and polypeptides can be provided as a component of a therapeutic composition.

Also provided is the use of any of the proteins consisting of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO:29, SEQ ID NO:32, SEQ ID NO:33, SEQ ID NO:34, SEQ ID NO:35, SEQ ID NO:46, SEQ ID NO:47 and/or SEQ ID NO:48 as a component of a therapeutic composition.

In a further embodiment, a nucleic acid encoding the OAS1 protein, OAS1 mutant protein, or OAS1 polypetitide can be administered in the form of gene therapy.

BRIEF DESCRIPTION OF THE FIGURES

FIG. 1 is a Table showing the locations of the mutations of the present invention in the OAS1 gene, the allelic variants (base substitutions), coordinates of the mutation on the genomic sequence, and NCBI dbSNP ID if any.

FIG. 2 (SEQ ID NO:19) is a polynucleotide sequence consisting of the consecutive nucleotide bases at positions 2,130,000-2,157,999 of NCBI Accession No. NT_009775.13, OAS1.

FIG. 3 shows SEQ ID NO: 20-64.

FIG. 4 shows approximate haplotype distributions within the OAS1 gene in a Caucasian population.

FIGS. 5A and B illustrates the variety of transcript variants disclosed by the invention and their relation to mutations disclosed by the invention. FIG. 5A shows transcript Variant (TV) forms 1-6, and FIG. 5B shows TV forms 7-10. FIG. 5C further illustrates the inferred structure of chimpanzee and gorilla variants relative to human.

FIG. 6 is a table describing non-human primate mutations in the OAS1 gene relative to human and the coordinates of the mutations on the corresponding human genomic sequence.

FIG. 7 demonstrates the enzymatic activity of exemplary polypeptides of the present invention when expressed and recovered from *E. coli.*

FIG. 8 demonstrates the enzymatic activity of exemplary polypeptides resulting from polynucleotides of the present invention when expressed in HeLa cells. OAS1 isoforms were expressed in HeLa cells by transient transfection, and crude cellular lysates were evaluated for enzyme activity by their ability to catalyze the formation of oligoadenylates using $\alpha^{32}$PdATP as a substrate. Oligoadenylates are separated by denaturing gel electrophoresis in 12% acrylamide/bis-acrylamide gels. Crude HeLa extracts (H) are compared against enzyme purified in, and purified from, bacteria (B).

FIG. 9 demonstrates development of antibodies to exemplary polypeptides of the present invention.

FIG. 10 is a table detailing exemplary protein transduction domain polypeptides.

DETAILED DESCRIPTION OF THE INVENTION

Introduction and Definitions

This invention relates to novel mutations in the oligoadenylate synthetase gene, use of these mutations for diagnosis of susceptibility or resistance to viral infection, to proteins encoded by a gene having a mutation according to the invention, and to prevention or inhibition of viral infection using the proteins, antibodies, and related nucleic acids. These mutations correlate with resistance of the carrier to infection with flavivirus, particularly hepatitis C virus.

Much of current medical research is focused on identifying mutations and defects that cause or contribute to disease. Such research is designed to lead to compounds and methods of treatment aimed at the disease state. Less attention has been paid to studying the genetic influences that allow people to remain healthy despite exposure to infectious agents and other risk factors. The present invention represents a successful application of a process developed by the inventors by which specific populations of human subjects are ascertained and analyzed in order to discover genetic variations or mutations that confer resistance to disease. The identification of a sub-population segment that has a natural resistance to a particular disease or biological condition further enables the identification of genes and proteins that are suitable targets for pharmaceutical intervention, diagnostic evaluation, or prevention, such as prophylactic vaccination.

The sub-population segment identified herein is comprised of individuals who, despite repeated exposure to hepatitis C virus (HCV) have nonetheless remained sero-negative, while cohorts have become infected (sero-positive). The populations studied included hemophiliac patients subjected to repeated blood transfusions, and intravenous drug users who become exposed through shared needles and other risk factors.

HCV infection involves a complex set of proteins and immune system components that work together to achieve a level of infection that, while it causes disease, can develop into low steady state of virus in infected cells, apparently allowing HCV to escape from the host immuno-surveillance system, while enabling persistent viral infection. (Dansako et al., Virus Research 97:17-30, 2003.) The present invention focuses on one component of this system, the interferon-inducible 2'-5'-oligoadenylate synthetase gene, specifically OAS1. The OAS1 gene plays a major role in the antiviral activity of host cells in the human, by activating ribonuclease L (RNase L) to cleave viral RNA. HCV RNA activates the 2'-5'-OAS/RNase L pathway. As pointed out by Dansako et al., it may appear contradictory for HCV RNA to activate a pathway that leads to cleavage of the viral RNA. However, such activity may serve to retain a balance between the host immune defense and a level of infection that would kill the host.

In view of this complex role of the OAS1 gene, it is of significant interest that the present invention has identified a strong correlation between mutations in the OAS1 gene, and resistance to HCV infection in carriers of these mutations. The presence of such individuals now permits the elucidation of how OAS1 contributes to resistance to HCV infection despite repeated exposure to infectious levels of the virus. This information will then lead to development of methods and compositions for replicating the resistance mechanism in individuals lacking natural resistance.

The present invention therefore provides that, regardless of the mechanism, the mutations identified herein are useful for identifying individuals who are resistant to HCV infection. The resistance may come about through a loss of function of the OAS1 protein, in which case it is predicted that HCV viral levels would be high enough to prevent the virus from escaping from the host immuno-surveillance system, hence facilitating destruction of the virus. The resistance may also come about through gain of function in that the OAS1 protein level is enhanced, the half life of the protein is increased, and/or the protein structure is affected in a way that enhances its ability to activate ribonuclease L to cleave viral RNA. The resistance may also come about through modifications to the OAS1 protein that prevent inhibition of normal OAS1 protein function by HCV viral proteins or nucleotides. The resistance may also come about through modifications to the OAS1 protein that prevent interaction of the protein with HCV viral proteins or nucleotides that are necessary for the normal HCV viral lifespan. The invention is not limited to one mechanism. Furthermore, although several different point mutations are disclosed herein, this is not intended to be indicative that each mutation has the same effect on OAS1 protein structure or function.

OAS1 plays a role in infection by other viruses of the flavivirus family, of which HCV is a member. The flavivirus family also includes viruses that cause yellow fever, dengue fever, St. Louis encephalitis, Japanese encephalitis, and other viral diseases disclosed herein. The host defense to these viruses includes virus-inducible interferon. The interferon induces 2'-5'-oligoadenylate synthetases, which as discussed above, are involved in the activation of RNaseL. RNaseL in turn cleaves viral RNA. Other viral infections may by amenable to prevention and/or inhibition by the methods disclosed herein, including RSV.

In reference to the detailed description and preferred embodiment, the following definitions are used:

A: adenine; C: cytosine; G: guanine; T: thymine (in DNA); and U: uracil (in RNA)

Allele: A variant of DNA sequence of a specific gene. In diploid cells a maximum of two alleles will be present, each in the same relative position or locus on homologous chromosomes of the chromosome set. When alleles at any one locus are identical the individual is said to be homozygous for that locus, and when they differ the individual is said to be heterozygous for that locus. Since different alleles of any one gene may vary by only a single base, the possible number of alleles for any one gene is very large. When alleles differ, one is often dominant to the other, which is said to be recessive. Dominance is a property of the phenotype and does not imply inactivation of the recessive allele by the dominant. In numerous examples the normally functioning (wild-type) allele is dominant to all mutant alleles of more or less defective function. In such cases the general explanation is that one functional allele out of two is sufficient to produce enough active gene product to support normal development of the organism (i.e., there is normally a two-fold safety margin in quantity of gene product).

Haplotype: One of many possible pluralities of Alleles, serially ordered by chromosomal localization and representing that set of Alleles carried by one particular homologous chromosome of the chromosome set.

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of operatively linked nucleotides is typically referred to herein as a "base sequence" or "nucleotide sequence", and their grammatical equivalents, and is represented herein by a formula whose left to right orientation is in the conventional direction of 5'-terminus to 3'-terminus.

Base Pair (bp): A partnership of adenine (A) with thymine (T), or of cytosine (C) with guanine (G) in a double stranded DNA molecule. In RNA, uracil (U) is substituted for thymine. When referring to RNA herein, the symbol T may be used interchangeably with U to represent uracil at a particular position in the RNA molecule.

Nucleic Acid: A polymer of nucleotides, either single or double stranded.

Polynucleotide: A polymer of single or double stranded nucleotides. As used herein "polynucleotide" and its grammatical equivalents will include the full range of nucleic acids. A polynucleotide will typically refer to a nucleic acid molecule comprised of a linear strand of two or more deoxyribonucleotides and/or ribonucleotides. The exact size will depend on many factors, which in turn depends on the ultimate conditions of use, as is well known in the art. The polynucleotides of the present invention include primers, probes, RNA/DNA segments, oligonucleotides or "oligos" (relatively short polynucleotides), genes, vectors, plasmids, and the like.

RNAi: RNA interference (RNAi) is a method whereby small interfering RNA (siRNA), a duplex typically about 21-23 nucleotides long, is introduced into a cell, leading ultimately to the degradation of messenger RNA of a targeted gene containing an identical or complementary sequence and effectively silencing it.

Gene: A nucleic acid whose nucleotide sequence codes for an RNA or polypeptide. A gene can be either RNA or DNA.

Duplex DNA: A double-stranded nucleic acid molecule comprising two strands of substantially complementary polynucleotides held together by one or more hydrogen bonds between each of the complementary bases present in a base pair of the duplex. Because the nucleotides that form a base pair can be either a ribonucleotide base or a deoxyribonucleotide base, the phrase "duplex DNA" refers to either a DNA-DNA duplex comprising two DNA strands (ds DNA), or an RNA-DNA duplex comprising one DNA and one RNA strand.

Complementary Bases: Nucleotides that normally pair up when DNA or RNA adopts a double stranded configuration.

Complementary Nucleotide Sequence: A sequence of nucleotides in a single-stranded molecule of DNA or RNA that is sufficiently complementary to that on another single strand to specifically hybridize to it with consequent hydrogen bonding.

Conserved: A nucleotide sequence is conserved with respect to a preselected (reference) sequence if it non-randomly hybridizes to an exact complement of the preselected sequence.

Hybridization: The pairing of substantially complementary nucleotide sequences (strands of nucleic acid) to form a duplex or heteroduplex by the establishment of hydrogen bonds between complementary base pairs. It is a specific, i.e. non-random, interaction between two complementary polynucleotides that can be competitively inhibited.

Nucleotide Analog: A purine or pyrimidine nucleotide that differs structurally from A, T, G, C, or U, but is sufficiently similar to substitute for the normal nucleotide in a nucleic acid molecule.

DNA Homolog: A nucleic acid having a preselected conserved nucleotide sequence and a sequence coding for a receptor capable of binding a preselected ligand.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Stop Codon: Any of three codons that do not code for an amino acid, but instead cause termination of protein synthesis. They are UAG, UAA and UGA and are also referred to as a nonsense or termination codon.

Reading Frame: Particular sequence of contiguous nucleotide triplets (codons) employed in translation. The reading frame depends on the location of the translation initiation codon.

Intron: Also referred to as an intervening sequence, a non-coding sequence of DNA that is initially copied into RNA but is cut out of the final RNA transcript.

Modes of Practicing the Invention

The present invention provides a novel method for screening humans for oligoadenylate synthetase alleles associated with resistance to infection by a flavivirus, particularly hepatitis C. The invention is based on the discovery that such resistance is associated with a point mutation (base substitution) in the oligoadenylate synthetase gene DNA sequence at nucleotide position 2135728, 2135749, 2135978, 2144072, 2144088, 2144116, 2144321, 2131025, 2133961, 2139587, 2144294, 2144985, 2156523, 2156595, or 2156638 of Genbank Accession No. NT_009775.13 (SEQ ID NO:19), which encodes the human OAS1 gene.

This invention discloses the results of a study that identified populations of subjects resistant or partially resistant to infection with the hepatitis C virus (HCV) and that further identified genetic mutations that confer this beneficial effect. Several genetic mutations in the 2'-5'-oligoadenylate synthetase genes are identified, that are significantly associated with resistance to HCV infection. The study design used was a case-control, allele association analysis. Cases assigned as subjects had serially documented or presumed exposure to HCV, but who did not develop infection as documented by the development of antibodies to the virus (i.e. HCV seronegative). Control subjects were serially exposed subjects who did seroconvert to HCV positive. Case and control subjects were recruited from three populations, hemophilia patients from Vancouver, British Columbia, Canada; hemophilia patients from Northwestern France; and injecting drug users from the Seattle metropolitan region.

Case and control definitions differed between the hemophilia and IDU groups and were based upon epidemiological models of infection risk published in the literature and other models developed by the inventors, as described herein. For the hemophilia population, control subjects were documented to be seropositive for antibodies to HCV using commercial diagnostics laboratory testing. Case subjects were documented as being HCV seronegative, having less than 5% of normal clotting factor, and having received concentrated clotting factors before January 1987. Control injecting drug users were defined as documented HCV seropositive. Case injecting drug users were defined as documented HCV seronegative, having injected drugs for more than ten years, and having reported engaging in one or more additional risk behaviors. Additional risk behaviors include the sharing of syringes, cookers, or cottons with another IDU. In one particular Caucasian population 20 cases and 42 controls were included in the study.

Selection of case and control subjects was performed essentially as described in U.S. patent application Ser. No. 09/707,576 using the population groups at-risk affected ("controls") and at-risk unaffected ("cases").

The present inventive approach to identifying gene mutations associated with resistance to HCV infection involved the selection of candidate genes. Approximately 50 candidate genes involved in viral binding to the cell surface, viral propagation within the cell, the interferon response, and aspects of the innate immune system and the antiviral response, were interrogated. Candidate genes were sequenced in cases and controls by using the polymerase chain reaction to amplify target sequences from the genomic DNA of each subject. PCR products from candidate genes were sequenced directly using automated, fluorescence-based DNA sequencing and an ABI3730 automated sequencer.

Genetic mutations were identified in an oligoadenylate synthetase gene (OAS1) that either alone, or in combination, were significantly associated ($p<0.05$) with resistance to HCV infection. The base substitutions and deletions that constitute these mutations are shown in FIG. 1. Variant forms of the OAS1 gene ("OAS1R") are produced by the presence of one or more of the mutations of the present invention (identified as SEQ ID NO:1-7 and SEQ ID NO:57-64). These variant OAS1R forms of the OAS1 gene are believed to confer resistance to viral infection.

Population and subject parental haplotypes, comprising pluralities of the OAS1 mutations (SEQ ID NO:1-7 and SEQ ID NO:57-64), are computationally inferred from the case-control genotyping data set by Expectation Maximation methods as known to those skilled in the art (Excoffier and Slatkin, Mol. Biol. Evol. 12:921-927, 1995). The invention embraces both the use of the full range of OAS1 mutations for haplotypic analysis as well as the use of subsets of OAS1 mutations for computational convenience. Comparative analysis of patterns of segregation of haplotypes and haplotype subsets with the case and control groups identify mutations of particular potency with regard to viral resistance or susceptibility.

In one illustrative example, haplotypes are computed comprising pluralities of the OAS1 mutations identified by SEQ ID NO: 2 through SEQ ID NO: 6. Several haplotypes are identified in a Caucasian case and control population by this analysis. The definition of these haplotypes is shown in FIG. 4. Two common haplotypes (identified as HAP1 and HAP2) are identified that account for approximately 85% of inferred haplotypes and are in Hardy-Weinberg equilibrium, particularly with regard to the occurrence of haplotype homozygotes in the population. Further analysis of OAS1 in various human populations and in primates indicates that HAP2 is the ancestral primate haplotype pre-dating the divergence of old world monkeys and hominids. One additional haplotype (identified as HAP3) is associated with the persistently HCV-resistant case group in this particular population. Therefore subjects carrying the HAP3 haplotype are at substantially lower risk of HCV infection. The HAP3 haplotype appears to have arisen through a complex series of recombination and mutation originating from the ancestral haplotype. The combined rarity of such events combined with the considerable occurrence of haplotype HAP3 suggests positive selection acted to develop and retain haplotype HAP3 in the population, possibly as a response to recurring viral challenge over time. In this example, haplotype HAP3 is the only haplotype occurring at an appreciable population frequency that combines the effects of a G nucleotide for mutation SEQ ID NO:2 together with an A nucleotide for mutation SEQ ID NO:4 in a single pre-cursor RNA.

The present invention is not limited by the foregoing illustrative example. Nor is the present invention limited by other illustrative examples that provide insight into the relevance and utility of particular OAS1 mutations. In another illustrative example, the substitution of a G nucleotide for an A nucleotide in SEQ ID NO:2 results in a predicted amino acid substitution of a Serine to Glycine. Computational prediction as known to those skilled in the art is highly suggestive that the Serine is a site of phosphorylation whereas the Glycine would not be phosphorylated.

In a further illustrative example, the substitution of an A nucleotide for a G nucleotide in mutation SEQ ID NO:4 occurs in the consensus splice acceptor site for the wild-type sixth exon in OAS1. This substitution replaces the requisite G in the splice acceptor recognition signal but in the process creates a new splice recognition site one base pair downstream. The mutated form thereby creates a frameshift in the translated protein. The mutated site also is a less effective splice signal and as a result encourages additional alternative splicing of pre-cursor RNAs in addition to the frameshifted exon 6 splicing. Preferred embodiments of these alternative splice forms are provided in FIGS. 5A and 5B. Further illustrative examples of genetic analysis are provided below.

Promiscuous splicing of OAS1 transcript variants was independently confirmed by reverse transcription of RNA derived from both lymphocyte cell lines and peripheral blood mononuclear cells (PBMCs) isolated from fresh human serum. PCR analysis of reverse transcribed RNA products from various haplotype carrying cell lines and PBMCs indicated RNA forms carrying A nucleotides for mutation SEQ ID NO:4 resulted in a multitude of transcript variant OAS1R forms. These OAS1R transcript variants are depicted graphically in FIGS. 5A and 5B and comprise SEQ ID NO:36 through SEQ ID NO:47 as provided in FIG. 3.

These variant OAS1R forms of the OAS1 gene and corresponding transcript variants are believed to encode one or more of the polypeptides consisting of SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO:29, SEQ ID NO:32, SEQ ID NO: 35, SEQ ID NO: 46, and/or SEQ ID NO: 47. The foregoing polypeptides, either singly or plurally, may be referred to herein as OAS1R polypeptides or OAS1 R proteins interchangeably. A common feature of many of the foregoing polypeptides is that they differ primarily in their carboxyl-terminus while conserving the amino-terminal portion.

In addition to the production of alternative transcripts themselves, the OAS1R forms of the gene may also contain or abolish specific sequence contexts (such as Exon Splice Enhancers) that modify the selective preference for specific transcript variants. This in turn would cause differing relative levels of abundance of the resulting proteins. These variant OAS1R forms of the OAS1 gene may also modify localization or post-translational modification of the resulting proteins. Those skilled in the art will appreciate that increased abundance or other modifications that improve the activity, stability, or availability of a specific OAS1 protein form may improve the overall anti-viral performance of the 2'-5'-OAS/RNase L pathway. Those skilled in the art can likewise appreciate that depressing the activity or availability of a specific OAS1 form may also improve the overall anti-viral performance of the 2'-5'-OAS/RNase L pathway in cases where said specific protein is not advantaged, or even disadvantaged, over other specific OAS1 forms. Without limitation, one embodiment of a disadvantaged OAS1 protein is one which is specifically targeted by viral protein(s) in such a manner as to preclude the enzymatic activity of said specific OAS1 protein. A further embodiment of a non-advantaged OAS1 protein is one with lower enzymatic activity polymerizing with other active forms thereby lowering, or abolishing, the overall enzymatic activity (and hence decreasing overall anti-viral effect) of the polymerized protein. One or more of the foregoing mechanisms may contribute to resistance to viral infection. The present invention is not limited, however, by the specific mechanism of action of the disclosed variant polynucleotides or polypeptides.

The invention therefore provides novel forms of the human 2'-5'-oligoadenylate synthetase gene, novel mRNA transcripts, and associated proteins. The invention also discloses utility for the novel mRNA transcripts and novel proteins. These novel forms are characterized by the presence in the gene of one or more of several rare genetic mutations or haplotypes not disclosed in the public databases. These novel forms of OAS1, OAS1R, confer on carriers a level of resistance to the hepatitis C virus and associated flaviviruses including but not limited to the West Nile virus, dengue viruses, yellow fever virus, tick-borne encephalitis virus, Japanese encephalitis virus, St. Louis encephalitis virus, Murray Valley virus, Powassan virus, Rocio virus, louping-ill virus, Banzi virus, Ilheus virus, Kokobera virus, Kunjin virus, Alfuy virus, bovine diarrhea virus, and the Kyasanur forest disease virus. The OAS proteins have also been shown to be important in attenuating infection in experimental respiratory syncitial virus and picornavirus cell culture infection systems. Failure of human immunodeficiency virus-1 (HIV-1) infected cells to release virus has been correlated with high concentrations of OAS and/or 2-5A. Furthermore, HIV-1 transactivator protein (tat) has been shown to block activation of OAS (Muller et al, J Biol Chem. 1990 Mar. 5; 265(7):3803-8) thus indicating that novel forms of OAS might evade HIV-1 defense mechanisms and provide an effective therapy. Thus, these OAS1R forms of OAS1 disclosed herein may confer resistance to these non-flavivirus infectious agents as well.

The present invention also provides novel description of the chimpanzee (*Pan troglodytes*) and gorilla (*Gorilla gorilla*) forms of OAS1, each of which leads to a novel mRNA and polypeptide with utility. While genes are typically very highly conserved in closely related primates, such as humans, chimpanzees and gorillas, important differences in OAS1 are observed between the three species. Chimpanzees, the closest human relative, possess a single base substitution within OAS1 exon 5 (at a site equivalent to 2,142,351 in NT_009775.13 in humans and defined by SEQ ID NO: 53) that causes a truncated protein product. The chimpanzee OAS1 polypeptide and mRNA sequences are provided by SEQ ID NO: 51 and SEQ ID NO: 55, respectively. Gorillas also possess a two base pair deletion (at the sites equivalent to 2,144,089-2,144,090 in NT_009775.13 in humans and defined by SEQ ID NO: 54) within exon 6 near the acceptor splice site that causes a premature stop of translation. The gorilla partial polypeptide and partial mRNA sequences are provided by SEQ ID NO: 52 and SEQ ID NO: 56, respectively. The inferred structure of the chimpanzee and gorilla transcripts relative to human is provided in FIG. 5C. Each of these cases, like the human OAS1R polypeptides, possess highly conserved polypeptide sequences that differ most notably in the structure and content of the carboxyl-terminal tail. The common amino-terminal portion of these polypeptides contains all of the elements previously demonstrated to be required for OAS1 enzymatic activity. As chimpanzees and gorillas have been subjected to viral challenges similar to that of humans in Africa, the prevalence of these distinct but functionally similar primate variants provides further evidence that the carboxy-terminal portions of longer OAS1 forms are unnecessary or even disadvantaging in surviving viral challenges. The fact that chimpanzees possess an outright truncation of the OAS1 polypeptide as opposed to the heterogeneity of transcript variants in humans is consistent with the observation that chimpanzees, while the only other primate known to be susceptible to HCV infection, do have an atypical infection relative to humans characterized by an increased frequency of viral clearance and the absence of resulting fibrosis or hepatocellular carcinoma.

Each novel OAS1R cDNA is cloned from human subjects who are carriers of these mutations. Cloning is carried out by standard cDNA cloning methods that involve the isolation of RNA from cells or tissue, the conversion of RNA to cDNA, and the conversion of cDNA to double-stranded DNA suitable for cloning. As one skilled in the art will recognize, all of these steps are routine molecular biological analyses. Other methods include the use of reverse transcriptase PCR, 5'RACE (Rapid Amplification of cDNA Ends), or traditional cDNA library construction and screening by Southern hybridization. All OAS1R alleles described herein are recovered from patient carriers. Each newly cloned OAS1R cDNA is sequenced to confirm its identity and to identify any additional sequence differences relative to wild-type.

Novel OAS1R gene mutations may affect resistance to viral infection by modifying the properties of the resulting OAS1 mRNA. Therefore, differences in mRNA stability between carriers of the OAS1R alleles and homozygous wild-type subjects are evaluated. RNA stability is evaluated and compared using known assays including Taqman® and simple Northern hybridization. These constitute routine methods in molecular biology.

OAS1R mutations may affect infection resistance by modifying the regulation of the OAS1 gene. It is known that expression of OAS genes is induced by interferon treatment and during viral infection. The OAS1R alleles may confer resistance to viral infection through constitutive expression, over-expression, or other disregulated expression. Several methods are used to evaluate gene expression with and without interferon or viral stimulation. These methods include expression microarray analysis, Northern hybridization, Taqman®, and others. Samples are collected from tissues known to express the OAS genes such as the peripheral blood mononuclear cells. Gene expression is compared between tissues from OAS1R carriers and non-carriers. In one embodiment, peripheral blood mononuclear cells are collected from carriers and non carriers, propagated in culture, and stimulated with interferon. The level of expression of OAS1R alleles during interferon induction is compared to wild-type alleles. In another embodiment, human subjects are treated with interferon and the level of induction of the OAS1 gene is evaluated in carriers of the OAS1R mutations versus non-carriers. As one skilled in the art can appreciate, numerous combinations of tissues, experimental designs, and methods of analysis are used to evaluate OAS1R gene regulation.

Once the novel cDNA for each OAS1R is cloned, it is used to manufacture recombinant OAS1R proteins using any of a number of different known expression cloning systems. In one embodiment of this approach, an OAS1R cDNA is cloned by standard molecular biological methods into an *Escherichia coli* expression vector adjacent to an epitope tag that contains a sequence of DNA coding for a polyhistidine polypeptide. The recombinant protein is then purified from *Escherichia coli* lysates using immobilized metal affinity chromatography or similar method. One skilled in the art will recognize that there are many different expression vectors and host cells that can be used to purify recombinant proteins, including but not limited to yeast expression systems, baculovirus expression systems, Chinese hamster ovary cells, and others.

Computational methods are used to identify short peptide sequences from OAS1R proteins that uniquely distinguish these proteins from wild-type OAS1 proteins. Various computational methods and commercially available software packages can be used for peptide selection. These computationally selected peptide sequences can be manufactured using the FMOC peptide synthesis chemistry or similar method. One skilled in the art will recognize that there are numerous chemical methods for synthesizing short polypeptides according to a supplied sequence.

Peptide fragments and the recombinant protein from the OAS1R gene can be used to develop antibodies specific to this gene product. As one skilled in the art will recognize, there are numerous methods for antibody development involving the use of multiple different host organisms, adjuvants, etc. In one classic embodiment, a small amount (150 micrograms) of purified recombinant protein is injected subcutaneously into the backs of New Zealand White Rabbits with subsequent similar quantities injected every several months as boosters. Rabbit serum is then collected by venipuncture and the serum, purified IgG, or affinity purified antibody specific to the immunizing protein can be collected. As one skilled in the art will recognize, similar methods can be used to develop antibodies in rat, mouse, goat, and other organisms. Peptide fragments as described above can also be used to develop antibodies specific to the OAS1R protein. The development of both monoclonal and polyclonal antibodies is suitable for practicing the invention. The generation of mouse hybridoma cell lines secreting specific monoclonal antibodies to the OAS1R proteins can be carried out by standard molecular techniques.

Antibodies prepared as described above can be used to develop diagnostic methods for evaluating the presence or absence of the OAS1R proteins in cells, tissues, and organisms. In one embodiment of this approach, enzyme-linked immunosorbent assays can be developed using purified recombinant OAS1R proteins and specific antibodies in order to detect these proteins in human serum. These diagnostic methods can be used to validate the presence or absence of OAS1R proteins in the tissues of carriers and non-carriers of the above-described genetic mutations.

Antibodies prepared as described above can also be used to purify native OAS1R proteins from those patients who carry these mutations. Numerous methods are available for using antibodies to purify native proteins from human cells and tissues. In one embodiment, antibodies can be used in immunoprecipitation experiments involving homogenized human tissues and antibody capture using protein A. This method enables the concentration and further evaluation of mutant OAS1R proteins. Numerous other methods for isolating the native forms of OAS1R are available including column chromatography, affinity chromatography, high pressure liquid chromatography, salting-out, dialysis, electrophoresis, isoelectric focusing, differential centrifugation, and others.

Proteomic methods are used to evaluate the effect of OAS1R mutations on secondary, tertiary, and quaternary protein structure. Proteomic methods are also used to evaluate the impact of OAS1R mutations on the post-translational modification of the OAS protein. There are many known possible post-translational modifications to a protein including protease cleavage, glycosylation, phosphorylation, sulfation, the addition of chemical groups or complex molecules, and the like. A common method for evaluating secondary and tertiary protein structure is nuclear magnetic resonance (NMR) spectroscopy. NMR is used to probe differences in secondary and tertiary structure between wild-type OAS1 proteins and OAS1R proteins. Modifications to traditional NMR are also suitable, including methods for evaluating the activity of functional sites including Transfer Nuclear Overhauser Spectroscopy (TrNOESY) and others. As one skilled in the art will recognize, numerous minor modifications to this approach and methods for data interpretation of results can be employed. All of these methods are intended to be included in practicing this invention. Other methods for determining protein structure by crystallization and X-ray diffraction are employed.

Mass spectroscopy can also be used to evaluate differences between mutant and wild-type OAS proteins. This method can be used to evaluate structural differences as well as differences in the post-translational modifications of proteins. In one typical embodiment of this approach, the wild-type OAS1 protein and mutant OAS1R proteins are purified from human peripheral blood mononuclear cells using one of the methods described above. These cells can be stimulated with interferon, as described above, in order to increase expression of the OAS proteins. Purified proteins are digested with specific proteases (e.g. trypsin) and evaluated using mass spectrometry. As one skilled in the art will recognize, many alternative methods can also be used. This invention contemplates these additional alternative methods. For instance, either matrix-assisted laser desorption/ionization (MALDI) or electrospray ionization (ESI) mass spectrometric methods can be used. Furthermore, mass spectroscopy can be coupled with the use of two-dimensional gel electrophoretic separation of cellular proteins as an alternative to comprehensive pre-purification. Mass spectrometry can also be coupled with the use of peptide fingerprint database and various searching algorithms. Differences in post-translational modification, such as phosphorylation or glycosylation, can also be probed by coupling mass spectrometry with the use of various pretreatments such as with glycosylases and phosphatases. All of these methods are to be considered as part of this application.

OAS1 is active as a tetramer, and mutations that interfere with self-association affect enzyme activity. Known methods are used to evaluate the effect of OAS1R mutations on tetramer formation. For instance, immunoprecipitation with OAS1 and OAS1R specific antibodies is performed in order to isolate OAS1/OAS1R complexes from patient cells, cell culture, or transfected cells over-expressing the OAS1 or OAS1R. These complexes can then be evaluated by gel electrophoresis or other chromatographic methods which are well known to those skilled in the art.

OAS1 may confer viral resistance by interaction with other proteins. The enzyme contains a region with structural homology to the BH3 domain of the bcl-2 family. This domain may be critical to the function of OAS1. According to the invention, OAS1-specific antibodies can be used to isolate protein complexes involving the OAS1 proteins from a variety of sources as discussed above. These complexes can then be evaluated by gel electrophoresis to separate members of the interacting complex. Gels can be probed using numerous methods including Western blotting, and novel interacting proteins can be isolated and identified using peptide sequencing. Differences in the content of OAS complexes in wild-type and OAS1R extracts will also be evaluated. As one skilled in the art will recognize, the described methods are only a few of numerous different approaches that can be used to purify, identify, and evaluate interacting proteins in the OAS complex. Additional methods include, but are not limited to, phage display and the use of yeast two-hybrid methods.

OAS1 is known to interact with hepatitis C virus NS5A protein (Taguchi, T. et al., J. Gen. Virol. 85:959-969, 2004). Without being bound by a mechanism, the invention therefore relates to OAS1 proteins that do not interact with the NS5A protein, wherein the proteins are polypeptides of the present invention, expressed by polynucleotides of the present invention, expressed by mRNA encoded by splice variants of OAS1, by OAS1 polynucleotides containing at least one mutation of the present invention, by OAS1 polynucleotides having at least one mutation in the coding region, and or by OAS1 polynucleotides having at least one base substitution, deletion or addition wherein binding to NS5A protein is altered or prevented.

NS5A protein may exert a biological activity by inhibiting the antiviral activity of interferon. This antiviral activity is in one model normally implemented when interferon stimulates OAS1 activity in the presence of a co-factor, such as double stranded RNA. OAS1 polymerizes ATP into 2'-5'-linked oligoadenylates, which activate RNase L to cleave single stranded RNA including mRNA. Binding of NS5A to OAS1 can inhibit its activity, thereby inhibiting or preventing the cascade of activities that would otherwise lead to destruction of the viral RNA.

Although the invention is not dependent on this model, the binding of NS5A to OAS1 is consistent with a model in which mutated forms of OAS1 avoid NS5A binding and inhibition and are thereby able to carry out the normal function of polymerizing ATP. In such cases, consistent with the clinical results described herein, a person carrying such a mutation is resistant to infection by hepatitis C virus. Similarly, the truncated form of OAS1 possessed by chimpanzees, as disclosed above, may elude binding by NS5A or other viral proteins and thereby allow the observed higher frequency of chimpanzee viral clearance. The mutation may in some cases directly affect the binding site of OAS1 for NS5A. In other cases the mutation may be at a site separate from the actual binding site, but causes a conformational change such that binding of OAS1 to NS5A is inhibited, slowed, or prevented.

The binding of OAS1 to NS5A in a physiologically and pathologically relevant manner therefore provides an objective test for assaying the effect of a base mutation, deletion or addition in an OAS1 polynucleotide on a biological function of the encoded OAS1 protein. Such binding is assayed in a manner known in the art. In one exemplary but not limiting method, such as described by Taguchi, T. et al. (J. Gen. Virol. 85:959-969, 2004), HeLa cells are transiently transfected with expression plasmids encoding GST-tagged NS5A and HA-tagged OAS1. By OAS1 in this example is meant OAS1 according to the invention, including OAS1 encoded by splice variants of OAS1, by OAS I polynucleotides having at least one mutation in the coding region, and/or by OAS1 polynucleotides having at least one base substitution, deletion or addition. After an appropriate incubation time such as 12-16 hours, the cells are washed, lysed, and centrifuged, and the resulting supernatant is mixed with glutathione-conjugated Sepharose beads, which aid in separating GST-tagged proteins. Complexes of GST-tagged NS5A and HA-tagged OAS1 protein are identified by using and imaging antibodies to NS5A and anti-HA antibody. Variations on this method include using other tags for the individual proteins, such as FLAG-tag. In the context of the present invention, the main variable is the OAS1 protein or polypeptide. The ability of the OAS1 protein or polypeptide to carry out one biologically relevant activity (i.e. the binding to a hepatitis C protein that is known to be protective for the ability of the virus to replicate in the host) is objectively tested using these assays. OAS1 proteins and polypeptides that do not bind to NS5A are suitable candidates as therapeutic proteins.

The OAS1 proteins are enzymes that catalyze the conversion of ATP into oligoadenylate molecules. Several methods are available to evaluate the activity of OAS1 enzymes. These methods are employed to determine the effects of OAS1R mutations on the activity of the mutant proteins relative to the wild type enzyme. For example, oligoadenylate synthesis activity can be measured by quantifying the incorporation of $^{32}$P-radiolabeled ATP into polyadenylates. The radiolabeled polyadenylates can be quantified and characterized in terms of length by a number of chromatographic methods including electrophoresis or ion exchange chromatography. These assays also enable characterization of substrate (ATP) binding and enzyme kinetics. OAS1 is activated by dsRNA. The kinetics of this activation is analyzed in OAS1 and compared to OAS1R using the activity assays described herein and synthetic dsRNAs as described in the art.

The polypeptides of the present invention are demonstrated by these and other methods known in the art to possess oligoadenylate synthesis activity. FIGS. 7 and 8 demonstrate the activities of several exemplary polypeptides of the present invention. Regardless of their quantitative level of activity, this capacity to produce 2'-5'-oligoadenylates is well understood by those skilled in the art to produce anti-viral effects through the activation of RNaseL. As such, the mere fact that the polypeptides of the present invention possess oligoadenylate synthesis activity indicates that said polypeptides have utility, particularly in consideration of therapeutic uses thereof which are disclosed below.

Biological studies are performed to evaluate the degree to which OAS1R mutant genes protect from viral infection. These biological studies generally take the form of introducing the mutant OAS1R genes or proteins into cells or whole organisms, and evaluating their biological and antiviral activities relative to wild-type controls. In one typical embodiment of this approach, the OAS1R genes are introduced into African Green monkey kidney (Vero) cells in culture by cloning the cDNAs isolated as described herein into a mammalian expression vector that drives expression of the cloned cDNA from an SV40 promoter sequence. This vector will also contain SV40 and cytomegalovirus enhancer elements that permit efficient expression of the OAS1R genes, and a neomycin resistance gene for selection in culture. The biological effects of OAS1R expression can then be evaluated in Vero cells infected with the dengue virus. In the event that OAS1R confers broad resistance to multiple flaviviruses, one would expect an attenuation of viral propagation in cell lines expressing these mutant forms of OAS1 relative to wild-type. As one skilled in the art will recognize, there are multiple different experimental approaches that can be used to evaluate the biological effects of OAS1R genes and proteins in cells and organisms and in response to different infectious agents. For instance, in the above example, different expression vectors, cell types, and viral species may be used to evaluate the OAS1R resistance effects. Primary human cells in culture may be evaluated as opposed to cell lines. Cells may be stimulated with double-stranded RNA or interferon before introduction of the virus. Expression vectors containing alternative promoter and enhancer sequences may be evaluated. Viruses other than the flaviviruses (e.g. respiratory syncytial virus and picornavirus) are evaluated.

Transgenic animal models are developed to assess the usefulness of mutant forms of OAS1 in protecting against whole-organism viral infection. In one embodiment, OAS1R genes are introduced into the genomes of mice susceptible to flavivirus infection (e.g. the C3H/He inbred laboratory strain). These OAS1R genes are evaluated for their ability to modify infection or confer resistance to infection in susceptible mice. As one skilled in the art will appreciate, numerous standard methods can be used to introduce transgenic human OAS1R genes into mice. These methods can be combined with other methods that affect tissue specific expression patterns or that permit regulation of the transgene through the introduction of endogenous chemicals, the use of inducible or tissue specific promoters, etc.

As a model for hepatitis C infection, cell lines expressing OAS1R genes can be evaluated for susceptibility, resistance, or modification of infection with the bovine diarrheal virus (BVDV). BVDV is a commonly used model for testing the efficacy of potential anti-HCV antiviral drugs (Buckwold et. al., Antiviral Research 60:1-15, 2003). In one embodiment, the OAS1R genes can be introduced into KL (calf lung) cells using expression vectors essentially as described above and tested for their ability to modify BVDV infection in this cell line. Furthermore, mouse models of HCV infection (e.g. the transplantation of human livers into mice, the infusion of human hepatocyte into mouse liver, etc.) may also be evaluated for modification of HCV infection in the transgenic setting of OAS1R genes. Experiments can be performed whereby the effects of expression of OAS1R genes are assessed in HCV viral culture systems.

Cell culture systems can also be used to assess the impact of the mutant OAS1R gene on promoting apoptosis under varying conditions. In one embodiment, cell culture mutant forms of OAS1R can be assessed relative to wild-type OAS1 sequences for their ability to promote apoptosis in cells infected with a number of viruses including BVDV, HCV, and other flaviviruses. As one skilled in the art will recognize, numerous methods for measuring apoptosis are available. The most common method involves the detection of the characteristic genomic "DNA laddering" effect in apoptosing cells using fluorescent conjugation methods coupled to agarose gel electrophoresis.

The ability of defective interfering viruses to potentiate the effects of OAS1R mutant forms can be tested in cell culture and in small animal models.

The degree to which the presence or absence of OAS1R genotypes affects other human phenotypes can also be examined. For instance, OAS1R mutations are evaluated for their association with viral titer and spontaneous viral clearance in HCV infected subjects. Similar methods of correlating host OAS1 genotype with the course of other flavivirus infections can also be undertaken. The impact of OAS1R mutations on promoting successful outcomes during interferon or interferon with ribavirin treatment in HCV infected patients is also examined. These mutations may not only confer a level of infection resistance, but also promote spontaneous viral clearance in infected subjects with or without interferon-ribavirin treatment. Furthermore, it has been reported that schizophrenia occurs at a higher frequency in geographic areas that are endemic for flavivirus infection, suggesting an association between flavivirus resistance alleles and predisposition to schizophrenia. This link is evaluated by performing additional genetic association studies involving the schizophrenia phenotype and the OAS1R mutations. The impact of OAS1R mutations on susceptibility to IDDM, prostate and other cancers, and schizophrenia will also be evaluated.

The invention discloses OAS1 variant mRNAs (identified as SEQ ID NO:36 through SEQ ID NO:43) that are novel and have utility. The invention is not limited by the mode of use of the disclosed variant mRNAs. In one preferred embodiment, these variant mRNAs are used in differentially screening human subjects for increased or decreased viral (including HCV) susceptibility. In other preferred embodiments, these variant mRNAs are useful in screening for susceptibility to IDDM, prostate and other cancers, and/or schizophrenia. Such differential screening is performed by expression analyses known to those skilled in the art to determine relative amounts of one or more variant OAS1R mRNAs present in samples derived from a given human subject. Increased or decreased amounts of one or more OAS1R mRNA variants in a human subject’s sample relative to a control sample is indicative of the subject’s degree of susceptibility to viral, IDDM, prostate and other cancers, and/or schizophrenia, as appropriate to the test under consideration.

As discussed herein, 2',5'-oligoadenylate synthetases (OAS) are a family of IFN-α-inducible, RNA dependent effector molecules enzymes that synthesize short 2' to 5' linked oligoadenylate (2-5A) molecules from ATP. OAS enzymes constitute an important part of the nonspecific immune defense against viral infections and have been used as a cellular marker for viral infection. In addition to the role in hepatitis C infection discussed herein, OAS activity is implicated in other disease states, particularly those in which a viral infection plays a role.

While specific pathogenic mechanisms are subjects of current analysis, viral infections are believed to play a role in the development of diseases such as diabetes. Lymphocytic OAS activity is significantly elevated in patients with type 1 diabetes, suggesting that OAS may be an important link between viral infections and disease development. In a study involving diabetic twins from monozygotic twin pairs, Bonnevie-Nielsen et al. (Clin Immunol. 2000 July; 96(1):11-8) showed that OAS is persistently activated in both recent-onset and long-standing type 1 diabetes. Continuously elevated OAS activity in type 1 diabetes is clearly different from a normal antiviral response and might indicate a chronic stimulation of the enzyme, a failure of down regulatory mechanisms, or an aberrant response to endogenous or exogenous viruses or their products.

A more direct link between a viral infection and the development of diabetes is exemplified by a number of studies showing that between 13 and 33% of patients with chronic hepatitis C have diabetes mellitus (type 2 diabetes), a level that is significantly increased compared with that in matched healthy controls or patients with chronic hepatitis B (Knobler et al. Am J Gastroenterol. 2003 December; 98(12):2751-6). While OAS has not to date been reported to play a role in the development of diabetes mellitus following hepatitis C infection, it may be a useful marker for the antiviral response system. Furthermore, the results reported according to the present invention illustrate that if hepatitis C infection is causally related to diabetes mellitus, inhibition or abolition of hepatitis C infection using the compositions and methods disclosed herein may be advantageous in preventing or alleviating development of diabetes mellitus.

A further published study has shown that OAS plays an essential role in wound healing and its pathological disorders, particularly in the case of venous ulcers and diabetes-associated poorly-healing wounds (WO 02/090552). In the case of poor wound healing, OAS mRNA levels in the affected tissues were reduced, rather than elevated as in lymphocytes derived from patients suffering from type 1 diabetes. These findings point to OAS as an etiologically important marker of immune reactions in diabetes and diabetes-related wound healing.

OAS may also play an intermediary role in cell processes involved in prostate cancer. A primary biochemical function of OAS is to promote the activity of RNaseL, a uniquely-regulated endoribonuclease that is enzymatically stimulated by 2-5A molecules. RNaseL has a well-established role in mediating the antiviral effects of IFN, and is a strong candidate for the hereditary prostate cancer 1 allele (HPC1). Mutations in RNaseL have been shown to predispose men to an increased incidence of prostate cancer, which in some cases reflect more aggressive disease and/or decreased age of onset compared with non RNase L-linked cases. Xiang et al. (Cancer Res. 2003 Oct. 15;63(20):6795-801) demonstrated that biostable phosphorothiolate analogs of 2-5A induced RNaseL activity and caused apoptosis in cultures of late-stage metastatic human prostate cancer cell lines. Their findings suggest that the elevation of OAS activity with a concurrent increase in 2-5A levels may facilitate the destruction of cancer cells through a potent apoptotic pathway. Thus, use of compositions and methods disclosed herein may find utility in the detection, treatment and/or prevention of prostate cancer.

OAS may further play a role in normal cell growth regulation, either through its regulation of RNaseL or through another as yet undiscovered pathway. There is considerable evidence to support the importance of OAS in negatively regulating cell growth. Rysiecki et al. (J. Interferon Res. 1989 December; 9(6):649-57) demonstrated that stable transfection of human OAS into a glioblastoma cell line results in reduced cellular proliferation. OAS levels have also been shown to be measurable in several studies comparing quiescent versus proliferating cell lines (e.g. Hassel and Ts’O, Mol Carcinog. 1992; 5(1):41-51 and Kimchi et al., Eur J Biochem. 1981; 114(1):5-10) and in each case the OAS levels were greatest in quiescent cells. Other studies have shown a correlation between OAS level and cell cycle phase, with OAS levels rising sharply during late S phase and then dropping abruptly in G2 (Wells and Mallucci, Exp Cell Res. 1985 July;

159(1):27-36). Several studies have shown a correlation between the induction of OAS and the onset of antiproliferative effects following stimulation with various forms of interferon (see Player and Torrence, Pharmacol Ther. 1998 May; 78(2):55-113). Induction of OAS has also been shown during cell differentiation (e.g. Salzberg et al., J Cell Sci. 1996 June; 109(Pt 6):1517-26 and Schwartz and Nilson, Mol Cell Biol. 1989 September; 9(9):3897-903). Other reports of induction of OAS by platelet derived growth factor (PDGF) (Zullo et al. Cell. 1985 December; 43(3 Pt 2):793-800) and under conditions of heat-shock induced growth (Chousterman et al., J Biol Chem. 1987 Apr. 5; 262(10):4806-11) lead to the hypothesis that induction of OAS is a normal cell growth control mechanism. Thus, use of compositions and methods disclosed herein may find broad utility in the detection, treatment and/or prevention of cancer.

Polynucleotide Analysis

An oligoadenylate synthetase gene is a nucleic acid whose nucleotide sequence codes for oligoadenylate synthetase, mutant oligoadenylate synthetase, or oligoadenylate synthetase pseudogene. It can be in the form of genomic DNA, an mRNA or cDNA, and in single or double stranded form. Preferably, genomic DNA is used because of its relative stability in biological samples compared to mRNA. The sequence of a polynucleotide consisting of consecutive nucleotides 2,130,000-2,157,999 of the complete genomic sequence of the reference oligoadenylate synthetase gene is provided in the Sequence Listing as SEQ ID NO:19, and corresponds to Genbank Accession No. NT_009775.13.

The nucleic acid sample is obtained from cells, typically peripheral blood leukocytes. Where mRNA is used, the cells are lysed under RNase inhibiting conditions. In one embodiment, the first step is to isolate the total cellular mRNA. Poly A+ mRNA can then be selected by hybridization to an oligo-dT cellulose column.

In preferred embodiments, the nucleic acid sample is enriched for a presence of oligoadenylate synthetase allelic material. Enrichment is typically accomplished by subjecting the genomic DNA or mRNA to a primer extension reaction employing a polynucleotide synthesis primer as described herein. Particularly preferred methods for producing a sample to be assayed use preselected polynucleotides as primers in a polymerase chain reaction (PCR) to form an amplified (PCR) product.

Preparation of Polynucleotide Primers

The term "polynucleotide" as used herein in reference to primers, probes and nucleic acid fragments or segments to be synthesized by primer extension is defined as a molecule comprised of two or more deoxyribonucleotides or ribonucleotides, preferably more than three. Its exact size will depend on many factors, which in turn depends on the ultimate conditions of use.

The term "primer" as used herein refers to a polynucleotide whether purified from a nucleic acid restriction digest or produced synthetically, which is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase and the like, and at a suitable temperature and pH. The primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer. For example, depending on the complexity of the target sequence, a polynucleotide primer typically contains 15 to 25 or more nucleotides, although it can contain fewer nucleotides. Short primer molecules generally require cooler temperatures to form sufficiently stable hybrid complexes with template.

The primers used herein are selected to be "substantially" complementary to the different strands of each specific sequence to be synthesized or amplified. This means that the primer must be sufficiently complementary to non-randomly hybridize with its respective template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically code for an endonuclease restriction site. Alternatively, non-complementary bases or longer sequences can be interspersed into the primer, provided the primer sequence has sufficient complementarity with the sequence of the strand to be synthesized or amplified to non-randomly hybridize therewith and thereby form an extension product under polynucleotide synthesizing conditions.

Primers of the present invention may also contain a DNA-dependent RNA polymerase promoter sequence or its complement. See for example, Krieg, et al., Nucl. Acids Res., 12:7057-70 (1984); Studier, et al., J. Mol. Biol., 189:113-130 (1986); and Molecular Cloning: A Laboratory Manual, Second Edition, Maniatis, et al., eds., Cold Spring Harbor, N.Y. (1989).

When a primer containing a DNA-dependent RNA polymerase promoter is used, the primer is hybridized to the polynucleotide strand to be amplified and the second polynucleotide strand of the DNA-dependent RNA polymerase promoter is completed using an inducing agent such as *E. coli* DNA polymerase I, or the Klenow fragment of *E. coli* DNA polymerase. The starting polynucleotide is amplified by alternating between the production of an RNA polynucleotide and DNA polynucleotide.

Primers may also contain a template sequence or replication initiation site for a RNA-directed RNA polymerase. Typical RNA-directed RNA polymerase include the QB replicase described by Lizardi, et al., Biotechnology, 6:1197-1202 1988). RNA-directed polymerases produce large numbers of RNA strands from a small number of template RNA strands that contain a template sequence or replication initiation site. These polymerases typically give a one million-fold amplification of the template strand as has been described by Kramer, et al., J. Mol. Biol., 89:719-736 (1974).

The polynucleotide primers can be prepared using any suitable method, such as, for example, the phosphotriester or phosphodiester methods see Narang, et al., Meth. Enzymol., 68:90, (1979); U.S. Pat. Nos. 4,356,270, 4,458,066, 4,416, 988, 4,293,652; and Brown, et al., Meth. Enzymol., 68:109 (1979).

The choice of a primer's nucleotide sequence depends on factors such as the distance on the nucleic acid from the hybridization point to the region coding for the mutation to be detected, its hybridization site on the nucleic acid relative to any second primer to be used, and the like.

If the nucleic acid sample is to be enriched for oligoadenylate synthetase gene material by PCR amplification, two primers, i.e., a PCR primer pair, must be used for each coding strand of nucleic acid to be amplified. The first primer becomes part of the non-coding (anti-sense or minus or complementary) strand and hybridizes to a nucleotide sequence on the plus or coding strand. Second primers become part of the coding (sense or plus) strand and hybridize to a nucleotide sequence on the minus or non-coding strand. One or both of the first and second primers can contain a nucleotide sequence defining an endonuclease recognition site. The site can be heterologous to the oligoadenylate synthetase gene being amplified.

In one embodiment, the present invention utilizes a set of polynucleotides that form primers having a priming region located at the 3'-terminus of the primer. The priming region is typically the 3'- most (3'-terminal) 15 to 30 nucleotide bases. The 3'-terminal priming portion of each primer is capable of acting as a primer to catalyze nucleic acid synthesis, i.e., initiate a primer extension reaction off its 3' terminus. One or both of the primers can additionally contain a 5'-terminal (5'-most) non-priming portion, i.e., a region that does not participate in hybridization to the preferred template.

In PCR, each primer works in combination with a second primer to amplify a target nucleic acid sequence. The choice of PCR primer pairs for use in PCR is governed by considerations as discussed herein for producing oligoadenylate synthetase gene regions. When a primer sequence is chosen to hybridize (anneal) to a target sequence within an oligoadenylate synthetase gene allele intron, the target sequence should be conserved among the alleles in order to insure generation of target sequence to be assayed.

Polymerase Chain Reaction

Oligoadenylate synthetase genes are comprised of polynucleotide coding strands, such as mRNA and/or the sense strand of genomic DNA. If the genetic material to be assayed is in the form of double stranded genomic DNA, it is usually first denatured, typically by melting, into single strands. The nucleic acid is subjected to a PCR reaction by treating (contacting) the sample with a PCR primer pair, each member of the pair having a preselected nucleotide sequence. The PCR primer pair is capable of initiating primer extension reactions by hybridizing to nucleotide sequences, preferably at least about 10 nucleotides in length, more preferably at least about 20 nucleotides in length, conserved within the oligoadenylate synthetase alleles. The first primer of a PCR primer pair is sometimes referred to herein as the "anti-sense primer" because it hybridizes to a non-coding or anti-sense strand of a nucleic acid, i.e., a strand complementary to a coding strand. The second primer of a PCR primer pair is sometimes referred to herein as the "sense primer" because it hybridizes to the coding or sense strand of a nucleic acid.

The PCR reaction is performed by mixing the PCR primer pair, preferably a predetermined amount thereof, with the nucleic acids of the sample, preferably a predetermined amount thereof, in a PCR buffer to form a PCR reaction admixture. The admixture is thermocycled for a number of cycles, which is typically predetermined, sufficient for the formation of a PCR reaction product, thereby enriching the sample to be assayed for oligoadenylate synthetase genetic material.

PCR is typically carried out by thermocycling i.e., repeatedly increasing and decreasing the temperature of a PCR reaction admixture within a temperature range whose lower limit is about 30 degrees Celsius (30° C.) to about 55° C. and whose upper limit is about 90° C. to about 100° C. The increasing and decreasing can be continuous, but is preferably phasic with time periods of relative temperature stability at each of temperatures favoring polynucleotide synthesis, denaturation and hybridization.

A plurality of first primer and/or a plurality of second primers can be used in each amplification, e.g., one species of first primer can be paired with a number of different second primers to form several different primer pairs. Alternatively, an individual pair of first and second primers can be used. In any case, the amplification products of amplifications using the same or different combinations of first and second primers can be combined for assaying for mutations.

The PCR reaction is performed using any suitable method. Generally it occurs in a buffered aqueous solution, i.e., a PCR buffer, preferably at a pH of 7-9, most preferably about 8. Preferably, a molar excess (for genomic nucleic acid, usually about $10^6$:1 primer:template) of the primer is admixed to the buffer containing the template strand. A large molar excess is preferred to improve the efficiency of the process.

The PCR buffer also contains the deoxyribonucleotide triphosphates (polynucleotide synthesis substrates) dATP, dCTP, dGTP, and dTTP and a polymerase, typically thermostable, all in adequate amounts for primer extension (polynucleotide synthesis) reaction. The resulting solution (PCR admixture) is heated to about 90° C.-100° C. for about 1 to 10 minutes, preferably from 1 to 4 minutes. After this heating period the solution is allowed to cool to 54° C., which is preferable for primer hybridization. The synthesis reaction may occur at from room temperature up to a temperature above which the polymerase (inducing agent) no longer functions efficiently. The thermocycling is repeated until the desired amount of PCR product is produced. An exemplary PCR buffer comprises the following: 50 mM KCl; 10 mM Tris-HCl at pH 8.3; 1.5 mM $MgCl_2$; 0.001% (wt/vol) gelatin, 200 μM dATP; 200 μM dTTP; 200 μM dCTP; $200^2$ μM dGTP; and 2.5 units Thermus aquaticus (Taq) DNA polymerase I (U.S. Pat. No. 4,889,818) per 100 microliters of buffer.

The inducing agent may be any compound or system which will function to accomplish the synthesis of primer extension products, including enzymes. Suitable enzymes for this purpose include, for example, E. coli DNA polymerase I, Klenow fragment of E. coli DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above.

The inducing agent also may be a compound or system which will function to accomplish the synthesis of RNA primer extension products, including enzymes. In preferred embodiments, the inducing agent may be a DNA-dependent RNA polymerase such as T7 RNA polymerase, T3 RNA polymerase or SP6 RNA polymerase. These polymerases produce a complementary RNA polynucleotide. The high turn-over rate of the RNA polymerase amplifies the starting polynucleotide as has been described by Chamberlin, et al., The Enzymes, ed. P. Boyer, pp. 87-108, Academic Press, New York (1982). Amplification systems based on transcription have been described by Gingeras, et al., in PCR Protocols, A Guide to Methods and Applications, pp. 245-252, Innis, et al., eds, Academic Press, Inc., San Diego, Calif. (1990).

If the inducing agent is a DNA-dependent RNA polymerase and, therefore incorporates ribonucleotide triphosphates, sufficient amounts of ATP, CTP, GTP and UTP are admixed to the primer extension reaction admixture and the resulting solution is treated as described above.

The newly synthesized strand and its complementary nucleic acid strand form a double-stranded molecule which can be used in the succeeding steps of the process.

The PCR reaction can advantageously be used to incorporate into the product a preselected restriction site useful in detecting a mutation in the oligoadenylate synthetase gene.

PCR amplification methods are described in detail in U.S. Pat. Nos. 4,683,192, 4,683,202, 4,800,159, and 4,965,188, and at least in several texts including PCR Technology: Principles and Applications for DNA Amplification, H. Erlich, ed., Stockton Press, New York (1989); and PCR Protocols: A Guide to Methods and Applications, Innis, et al., eds., Academic Press, San Diego, Calif. (1990).

In some embodiments, two pairs of first and second primers are used per amplification reaction. The amplification reaction products obtained from a plurality of different amplifications, each using a plurality of different primer pairs, can be combined or assayed separately.

However, the present invention contemplates amplification using only one pair of first and second primers. Exemplary primers for amplifying the sections of DNA containing the mutations disclosed herein are shown below in Table 1. AmpliconA corresponds to the polynucleotide sequence that contains the mutations referred to in SEQ ID NO:1-3. AmpliconB corresponds to the polynucleotide sequence containing the mutations referred to in SEQ ID NO:4-7 and SEQ ID NO:60. AmpliconC corresponds to the polynucleotide sequence containing the mutation referred to in SEQ ID NO:57. AmpliconD corresponds to the polynucleotide sequence containing the mutation referred to in SEQ ID NO:58. AmpliconE corresponds to the polynucleotide sequence containing the mutation referred to in SEQ ID NO: 59. AmpliconF corresponds to the polynucleotide sequence containing the mutation referred to in SEQ ID NO:61. AmpliconG corresponds to the polynucleotide sequences containing the mutation referred to in SEQ ID NO: 62-64.

Table 2 discloses the position in the above Amplicons of the mutations of the invention.

TABLE 2

Position of Mutations of the Invention in Amplicons

| Mutation | Amplicon | Position in Amplicon (relative to 5' end of PrimerA side of Amplicon) |
|---|---|---|
| 1 (SEQ ID-NO: 1) | AmpliconA | 134 |
| 2 (SEQ ID NO: 2) | AmpliconA | 155 |
| 3 (SEQ ID NO: 3) | AmpliconA | 384 |
| 4 (SEQ ID NO: 4) | AmpliconB | 98 |
| 5 (SEQ ID NO: 5) | AmpliconB | 114 |
| 6 (SEQ ID NO: 6) | AmpliconB | 142 |
| 7 (SEQ ID NO: 7) | AmpliconB | 347 |
| 8 (SEQ ID NO: 57) | AmpliconC | 319 |
| 9 (SEQ ID NO: 58) | AmpliconD | 404 |
| 10 (SEQ ID NO: 59) | AmpliconE | 133 |
| 11 (SEQ ID NO: 60) | AmpliconB | 320 |
| 12 (SEQ ID NO: 61) | AmpliconF | 367 |
| 13 (SEQ ID NO: 62) | AmpliconG | 138 |
| 14 (SEQ ID NO: 63) | AmpliconG | 210 |
| 15 (SEQ ID NO: 64) | AmpliconG | 253 |

Nucleic Acid Sequence Analysis

Nucleic acid sequence analysis is approached by a combination of (a) physiochemical techniques, based on the hybridization or denaturation of a probe strand plus its complementary target, and (b) enzymatic reactions with endonucleases, ligases, and polymerases. Nucleic acid can be assayed at the DNA or RNA level. The former analyzes the genetic potential of individual humans and the latter the expressed information of particular cells.

In assays using nucleic acid hybridization, detecting the presence of a DNA duplex in a process of the present invention can be accomplished by a variety of means.

TABLE 1

Amplicons Containing Mutations of the Present Invention

| Amplicon | PrimerA | PrimerB | Product size (bp) |
|---|---|---|---|
| AmpliconA | 5'-AATGGACCTCAAGACTTCCC-3' (SEQ ID NO: 8) | 5'-ATTCTCCCTTCTGTTGCAGG-3' (SEQ ID NO: 9) | 509 |
| AmpliconB | 5'-TCCAGATGGCATGTCACAGT-3' (SEQ ID NO: 10) | 5'-GAGCTATGCTTGGCACATAG-3' (SEQ ID NO: 11) | 747 |
| AmpliconC | 5'-CACAAGAGTGAACCTTAATGT-3' (SEQ ID NO: 65) | 5'-CCAGGAAGTGGAAAGATCAT-3' (SEQ ID NO: 66) | 603 |
| AmpliconD | 5'-ATCTCCCACAGTTTGAGAGC-3' (SEQ ID NO: 67) | 5'-TCAGCCTCCAAAAGTGTTGG-3' (SEQ ID NO: 68) | 553 |
| AmpliconE | 5'-GGGTACATGTGCACAATGTG-3' (SEQ ID NO: 69) | 5'-CCCTTATACAAAATTCAACTC-3' (SEQ ID NO: 70) | 532 |
| AmpliconF | 5'-GAGCCAAGAAGTACAGATGC-3' (SEQ ID NO: 71) | 5'-AGGACAGAGCTGTCCAATAG-3' (SEQ ID NO: 72) | 648 |
| AmpliconG | 5'-GGCTCAGAGAAGCTAAGTGA-3' (SEQ ID NO: 73) | 5'-CCACAGCATCCTTTTCAGTC-3' (SEQ ID NO: 74) | 581 |

In one approach for detecting the presence of a DNA duplex, an oligonucleotide that is hybridized in the DNA duplex includes a label or indicating group that will render the duplex detectable. Typically such labels include radioactive atoms, chemically modified nucleotide bases, and the like.

The oligonucleotide can be labeled, i.e., operatively linked to an indicating means or group, and used to detect the presence of a specific nucleotide sequence in a target template.

Radioactive elements operatively linked to or present as part of an oligonucleotide probe (labeled oligonucleotide) provide a useful means to facilitate the detection of a DNA duplex. A typical radioactive element is one that produces beta ray emissions. Elements that emit beta rays, such as $^3$H, $^{12}$C, $^{32}$P and $^{35}$S represent a class of beta ray emission-producing radioactive element labels. A radioactive polynucleotide probe is typically prepared by enzymatic incorporation of radioactively labeled nucleotides into a nucleic acid using DNA kinase.

Alternatives to radioactively labeled oligonucleotides are oligonucleotides that are chemically modified to contain metal complexing agents, biotin-containing groups, fluorescent compounds, and the like.

One useful metal complexing agent is a lanthanide chelate formed by a lanthanide and an aromatic beta-diketone, the lanthanide being bound to the nucleic acid or oligonucleotide via a chelate-forming compound such as an EDTA-analogue so that a fluorescent lanthanide complex is formed. See U.S. Pat. Nos. 4,374,120, 4,569,790 and published Patent Application EP0139675 and W087/02708.

Biotin or acridine ester-labeled oligonucleotides and their use to label polynucleotides have been described. See U.S. Pat. No. 4,707,404, published Patent Application EP0212951 and European Patent No. 0087636. Useful fluorescent marker compounds include fluorescein, rhodamine, Texas Red, NBD and the like.

A labeled oligonucleotide present in a DNA duplex renders the duplex itself labeled and therefore distinguishable over other nucleic acids present in a sample to be assayed. Detecting the presence of the label in the duplex and thereby the presence of the duplex, typically involves separating the DNA duplex from any labeled oligonucleotide probe that is not hybridized to a DNA duplex.

Techniques for the separation of single stranded oligonucleotide, such as non-hybridized labeled oligonucleotide probe, from DNA duplex are well known, and typically involve the separation of single stranded from double stranded nucleic acids on the basis of their chemical properties. More often separation techniques involve the use of a heterogeneous hybridization format in which the non-hybridized probe is separated, typically by washing, from the DNA duplex that is bound to an insoluble matrix. Exemplary is the Southern blot technique, in which the matrix is a nitrocellulose sheet and the label is $^{32}$P. Southern, J. Mol. Biol., 98:503 (1975).

The oligonucleotides can also be advantageously linked, typically at or near their 5'-terminus, to a solid matrix, i.e., aqueous insoluble solid support. Useful solid matrices are well known in the art and include cross-linked dextran such as that available under the tradename SEPHADEX from Pharmacia Fine Chemicals (Piscataway, N.J.); agarose, polystyrene or latex beads about 1 micron to about 5 millimeters in diameter, polyvinyl chloride, polystyrene, cross-linked polyacrylamide, nitrocellulose or nylon-based webs such as sheets, strips, paddles, plates microtiter plate wells and the like.

It is also possible to add "linking" nucleotides to the 5' or 3' end of the member oligonucleotide, and use the linking oligonucleotide to operatively link the member to the solid support.

In nucleotide hybridizing assays, the hybridization reaction mixture is maintained in the contemplated method under hybridizing conditions for a time period sufficient for the oligonucleotides having complementarity to the predetermined sequence on the template to hybridize to complementary nucleic acid sequences present in the template to form a hybridization product, i.e., a complex containing oligonucleotide and target nucleic acid.

The phrase "hybridizing conditions" and its grammatical equivalents, when used with a maintenance time period, indicates subjecting the hybridization reaction admixture, in the context of the concentrations of reactants and accompanying reagents in the admixture, to time, temperature and pH conditions sufficient to allow one or more oligonucleotides to anneal with the target sequence, to form a nucleic acid duplex. Such time, temperature and pH conditions required to accomplish hybridization depend, as is well known in the art, on the length of the oligonucleotide to be hybridized, the degree of complementarity between the oligonucleotide and the target, the guanine and cytosine content of the oligonucleotide, the stringency of hybridization desired, and the presence of salts or additional reagents in the hybridization reaction admixture as may affect the kinetics of hybridization. Methods for optimizing hybridization conditions for a given hybridization reaction admixture are well known in the art.

Typical hybridizing conditions include the use of solutions buffered to pH values between 4 and 9, and are carried out at temperatures from 4° C. to 37° C., preferably about 12° C. to about 30° C., more preferably about 22° C., and for time periods from 0.5 seconds to 24 hours, preferably 2 minutes (min) to 1 hour.

Hybridization can be carried out in a homogeneous or heterogeneous format as is well known. The homogeneous hybridization reaction occurs entirely in solution, in which both the oligonucleotide and the nucleic acid sequences to be hybridized (target) are present in soluble forms in solution. A heterogeneous reaction involves the use of a matrix that is insoluble in the reaction medium to which either the oligonucleotide, polynucleotide probe or target nucleic acid is bound.

Where the nucleic acid containing a target sequence is in a double stranded (ds) form, it is preferred to first denature the dsDNA, as by heating or alkali treatment, prior to conducting the hybridization reaction. The denaturation of the dsDNA can be carried out prior to admixture with an oligonucleotide to be hybridized, or can be carried out after the admixture of the dsDNA with the oligonucleotide.

Predetermined complementarity between the oligonucleotide and the template is achieved in two alternative manners. A sequence in the template DNA may be known, such as where the primer to be formed can hybridize to known oligoadenylate synthetase sequences and can initiate primer extension into a region of DNA for sequencing purposes, as well as subsequent assaying purposes as described herein, or where previous sequencing has determined a region of nucleotide sequence and the primer is designed to extend from the recently sequenced region into a region of unknown sequence. This latter process has been referred to a "directed sequencing" because each round of sequencing is directed by a primer designed based on the previously determined sequence.

Effective amounts of the oligonucleotide present in the hybridization reaction admixture are generally well known and are typically expressed in terms of molar ratios between the oligonucleotide to be hybridized and the template. Preferred ratios are hybridization reaction mixtures containing equimolar amounts of the target sequence and the oligonucleotide. As is well known, deviations from equal molarity will produce hybridization reaction products, although at lower efficiency. Thus, although ratios where one component can be in as much as 100 fold molar excess relative to the other component, excesses of less than 50 fold, preferably less than 10 fold, and more preferably less than two fold are desirable in practicing the invention.

Detection of Membrane-Immobilized Target Sequences

In the DNA (Southern) blot technique, DNA is prepared by PCR amplification as previously discussed. The PCR products (DNA fragments) are separated according to size in an agarose gel and transferred (blotted) onto a nitrocellulose or nylon membrane. Conventional electrophoresis separates fragments ranging from 100 to 30,000 base pairs while pulsed field gel electrophoresis resolves fragments up to 20 million base pairs in length. The location on the membrane a containing particular PCR product is determined by hybridization with a specific, labeled nucleic acid probe.

In preferred embodiments, PCR products are directly immobilized onto a solid-matrix (nitrocellulose membrane) using a dot-blot (slot-blot) apparatus, and analyzed by probe-hybridization. See U.S. Pat. Nos. 4,582,789 and 4,617,261.

Immobilized DNA sequences may be analyzed by probing with allele-specific oligonucleotide (ASO) probes, which are synthetic DNAn oligomers of approximately 15, 17, 20, 25 or up to about 30 nucleotides in length. These probes are long enough to represent unique sequences in the genome, but sufficiently short to be destabilized by an internal mismatch in their hybridization to a target molecule. Thus, any sequences differing at single nucleotides may be distinguished by the different denaturation behaviors of hybrids between the ASO probe and normal or mutant targets under carefully controlled hybridization conditions. Exemplary probes are disclosed herein as SEQ ID NO:1-7 and SEQ ID NO:57-64 (Table 3), but any probes are suitable as long as they hybridize specifically to the region of the OAS1 gene carrying the point mutation of choice, and are capable of specifically distinguishing between polynucleotide carrying the point mutation and a wild type polynucleotide.

Detection of Target Sequences in Solution

Several rapid techniques that do not require nucleic acid purification or immobilization have been developed. For example, probe/target hybrids may be selectively isolated on a solid matrix, such as hydroxylapatite, which preferentially binds double-stranded nucleic acids. Alternatively, probe nucleic acids may be immobilized on a solid support and used to capture target sequences from solution. Detection of the target sequences can be accomplished with the aid of a second, labeled probe that is either displaced from the support by the target sequence in a competition-type assay or joined to the support via the bridging action of the target sequence in a sandwich-type format.

In the oligonucleotide ligation assay (OLA), the enzyme DNA ligase is used to covalently join two synthetic oligonucleotide sequences selected so that they can base pair with a target sequence in exact head-to-tail juxtaposition. Ligation of the two oligomers is prevented by the presence of mismatched nucleotides at the junction region. This procedure allows for the distinction between known sequence variants in samples of cells without the need for DNA purification. The joining of the two oligonucleotides may be monitored by immobilizing one of the two oligonucleotides and observing whether the second, labeled oligonucleotide is also captured.

Scanning Techniques for Detection of Base Substitutions

Three techniques permit the analysis of probe/target duplexes several hundred base pairs in length for unknown single-nucleotide substitutions or other sequence differences. In the ribonuclease (RNase) A technique, the enzyme cleaves a labeled RNA probe at positions where it is mismatched to a target RNA or DNA sequence. The fragments may be separated according to size allowing for the determination of the approximate position of the mutation. See U.S. Pat. No. 4,946,773.

In the denaturing gradient gel technique, a probe-target DNA duplex is analyzed by electrophoresis in a denaturing gradient of increasing strength. Denaturation is accompanied by a decrease in migration rate. A duplex with a mismatched base pair denatures more rapidly than a perfectly matched duplex.

A third method relies on chemical cleavage of mismatched base pairs. A mismatch between T and C, G, or T, as well as mismatches between C and T, A, or C, can be detected in heteroduplexes. Reaction with osmium tetroxide (T and C mismatches) or hydroxylamine (C mismatches) followed by treatment with piperidine cleaves the probe at the appropriate mismatch.

Therapeutic Agents for Restoring and/or Enhancing OAS1 Function

Where a mutation in the OAS1 gene leads to defective OAS1 function and this defective function is associated with increased susceptibility of a patient to pathogenic infection, whether through lower levels of OAS1 protein, mutation in the protein affecting its function, or other mechanisms, it may be advantageous to treat the patient with wild type OAS1 protein. Furthermore, if the mutation gives rise in infection-resistant carriers to a form of the protein that differs from the wild-type protein, and that has an advantage in terms of inhibiting HCV infection, it may be advantageous to administer a protein encoded by the mutated gene. As described previously, administration of either native or mutant forms of OAS1 proteins or polypeptides may also be advantageous in the treatment of other indications including but not limited to cancer, diabetes mellitus, and wound healing. The discussion below pertains to administration of any of the foregoing proteins or polypeptides.

The polypeptides of the present invention, including those encoded by OAS I R, may be a naturally purified product, or a product of chemical synthetic procedures, or produced by recombinant techniques from a prokaryotic or eukaryotic host (for example, by bacterial, yeast, higher plant, insect and mammalian cells in culture) of a polynucleotide sequence of the present invention. Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue (at position minus 1).

The polypeptides of the present invention also include the protein sequences defined in SEQ ID NO: 20, SEQ ID NO: 21, SEQ ID NO: 22, SEQ ID NO: 23, SEQ ID NO: 24 and SEQ ID NO: 25, SEQ ID NO: 26, SEQ ID NO: 27, SEQ ID NO: 28, SEQ ID NO: 29, SEQ ID NO: 32, SEQ ID NO: 33, SEQ ID NO: 34, SEQ ID NO: 35, SEQ ID NO: 46, and SEQ ID NO: 47 and derivatives thereof. In addition to naturally occurring allelic forms of the polypeptide(s) the present invention also embraces analogs and fragments thereof, which function similarly to the naturally occurring allelic forms. Thus, for example, one or more of the amino acid residues of the polypeptide may be replaced by conserved amino acid residues, as long as the function of the OAS1R protein is maintained. Examples 8-10, below, provide representative illustrations of suitable amino acid replacements with regard to the polypeptides of the present invention. As another example, the polypeptides of the present invention specifically include the truncated or analog forms of OAS defined in SEQ ID NO: 48, SEQ ID NO: 49, SEQ ID NO: 50, SEQ ID NO: 51 and SEQ ID NO:52. As discussed previously, SEQ ID NO: 51 represents the shortened form of OAS1 possessed by chimpanzees and SEQ ID NO: 52 represents a carboxyl-terminus fragment of the longer but still truncated form possessed by gorillas. SEQ ID NO: 49 and SEQ ID NO: 50 represent synthetic human OAS1R constructs truncated to the corresponding chimpanzee and gorilla sites of truncation, respectively. SEQ ID NO: 48 represents a synthetic human OAS1R polypeptide truncated to a length intermediate to the chimpanzee and gorilla forms. SEQ ID NO: 48 has further been demonstrated to be enzymatically active by methods known in the art as disclosed elsewhere herein. Correspondingly, the remaining highly similar truncated forms may also be demonstrated to be enzymatically active. As those skilled in the art will appreciate, therapeutic use of truncated but functional forms of OAS1R polypeptides can preclude the development of antibody response which would otherwise hinder the therapeutic efficacy of the polypeptide. The foregoing truncated polypeptides, and others that can be envisioned by one skilled in the art, maintain function but remove non-ubiquitous portions of the polypeptide that could induce antibody response in individuals not possessing the full length OAS1R polypeptide endogenously. Those skilled in the art will also appreciate that smaller polypeptides, in general, are more amenable to the complexities of manufacturing, delivery, and clearance typically encountered in therapeutic development. Additionally, those skilled in the art will appreciate that the occurrence of distinct homozygous truncating variants in chimpanzee and gorilla are also highly suggestive for the broad anti-viral potency of the presently disclosed truncated OAS1 forms. Although the truncated polypeptide forms specifically disclosed above represent truncations to the carboxyl-terminus of the polypeptide, the invention is not limited by the form of the fragment and specifically includes amino-terminus truncations and internal amino acid deletions that retain enzymatic function.

Also included in the scope of the invention are polypeptides that retain at least one activity of a specific disclosed polypeptide, but differ from the disclosed amino acid sequence. Such polypeptides preferably have at least 80% sequence homology, preferably 85% sequence homology, more preferably 90% sequence homology, most preferably 95% more sequence homology to the corresponding disclosed SEQ ID NO: as calculated using standard methods of alignment.

The polypeptides may also be employed in accordance with the present invention by expression of such polypeptides in vivo, which is often referred to as gene therapy. Thus, for example, cells may be transduced with a polynucleotide (DNA or RNA) encoding the polypeptides ex vivo with those transduced cells then being provided to a patient to be treated with the polypeptide. Such methods are well known in the art. For example, cells may be transduced by procedures known in the art by use of a retroviral particle containing RNA encoding the polypeptide of the present invention.

Similarly, transduction of cells may be accomplished in vivo for expression of the polypeptide in vivo, for example, by procedures known in the art. As known in the art, a producer cell for producing a retroviral particle containing RNA encoding the polypeptides of the present invention may be administered to a patient for transduction in vivo and expression of the polypeptides in vivo.

These and other methods for administering the polypeptides of the present invention by such methods should be apparent to those skilled in the art from the teachings of the present invention. For example, the expression vehicle for transducing cells may be other than a retrovirus, for example, an adenovirus which may be used to transduce cells in vivo after combination with a suitable delivery vehicle.

In the case where the polypeptides are prepared as a liquid formulation and administered by injection, preferably the solution is an isotonic salt solution containing 140 millimolar sodium chloride and 10 millimolar calcium at pH 7.4. The injection may be administered, for example, in a therapeutically effective amount, preferably in a dose of about 1 µg/kg body weight to about 5 mg/kg body weight daily, taking into account the routes of administration, health of the patient, etc.

The polypeptide(s) of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The polypeptide(s) of the present invention can also be modified by chemically linking the polypeptide to one or more moieties or conjugates to enhance the activity, cellular distribution, or cellular uptake of the polypeptide(s). Such moieties or conjugates include lipids such as cholesterol, cholic acid, thioether, aliphatic chains, phospholipids and their derivatives, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

The polypeptide(s) of the present invention may also be modified to target specific cell types for a particular disease indication, including but not limited to liver cells in the case of hepatitis C infection. As can be appreciated by those skilled in the art, suitable methods have been described that achieve the described targeting goals and include, without limitation, liposomal targeting, receptor-mediated endocytosis, and antibody-antigen binding. In one embodiment, the asiaglycoprotein receptor may be used to target liver cells by the addition of a galactose moiety to the polypeptide(s). In another embodiment, mannose moieties may be conjugated to the polypeptide(s) in order to target the mannose receptor found on macrophages and liver cells. The polypeptide(s) of the present invention may also be modified for cytosolic delivery by methods known to those skilled in the art, including, but not limited to, endosome escape mechanisms or protein transduction domain (PTD) systems. PTD systems are disclosed in, for example, Vives E, et al. (1997) J. Biol. Chem. 272: 16010-16017, Derossi, et al. (1994) J. Biol. Chem. 269: 10444-10450, Elliott, G et al. (1997) Cell 88:223-233, Wadia, J S et al. (2004) Nat. Med. 10:310-315, and Kabouridis, P S. (2003) Trends Biotech., 21: 498-503. Known endosome escape systems include the use of ph-responsive polymeric carriers such as poly(propylacrylic acid). Known PTD systems range from natural peptides such as HIV-1 TAT, HSV-1 VP22, *Drosophila* Antennapedia, or diphtheria toxin to synthetic peptide carriers (Wadia and Dowdy, Cur. Opin. Biotech. 13:52-56, 2002; Becker-Hapak et. al., Methods 24:247-256, 2001). FIG. 10 provides detailed description of several of these exemplary PTDs. As one skilled in the art will recognize, multiple delivery and targeting methods, may be combined. For example, the polypeptide(s) of the present invention may be targeted to liver cells by encapsulation within liposomes, such liposomes being conjugated to galactose for targeting to the asialoglycoprotein receptor.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

When the OAS1 variants of the present invention are used as a pharmaceutical, they can be given to mammals, in a suitable vehicle. When the polypeptides of the present invention are used as a pharmaceutical as described above, they are given, for example, in therapeutically effective doses of about 10 µg/kg body weight to about 4 mg/kg body weight daily, taking into account the routes of administration, health of the patient, etc. The amount given is preferably adequate to achieve prevention or inhibition of infection by a virus, preferably a flavivirus, most preferably HCV, thus replicating the natural resistance found in humans carrying an OAS1R allele as disclosed herein.

Inhibitor-based drug therapies that mimic the beneficial effects of at least one mutation at position 2135728, 2135749, 2135978, 2144072, 2144088, 2144116, 2144321, 2131025, 2133961, 2139587, 2144294, 2144985, 2156523, 2156595, or 2156638 of NT_009775.13 are also envisioned, as discussed in detail below. As discussed previously, one exemplary rationale for developing such inhibitors is the case where the beneficial mutation diminishes or eradicates expression, translation, or function of one or more particular isoforms of OAS1. The present invention is not limited by the precise form or effect of the beneficial mutation nor the biological activity of the particular isoforms thereby affected. In such case, one skilled in the art will appreciate the utility of therapeutically inhibiting said particular isoform(s) of OAS1. These inhibitor-based therapies can take the form of chemical entities, peptides or proteins, antisense oligonucleotides, small interference RNAs, and antibodies.

The proteins, their fragments or other derivatives, or analogs thereof, or cells expressing them can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies.

Antibodies generated against the polypeptide encoded by OAS1R of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Moreover, a panel of such antibodies, specific to a large number of polypeptides, can be used to identify and differentiate such tissue. As an example, FIG. 9 demonstrates development of antibodies specific to particular exemplary polypeptides of the present invention.

For preparation of monoclonal antibodies, any technique which provides antibodies produced by continuous cell line cultures can be used. Examples include the hybridoma technique (Kohler and Milstein, 1975, *Nature,* 256:495-597), the trioma technique, the human B-cell hybridoma technique (Kozbor, et al., 1983, *Immunology Today* 4:72), and the EBV-hybridoma technique to produce human monoclonal antibodies (Coe, et al., 1985, *Monoclonal Antibodies and Cancer Therapy*, Alan R. Liss, Inc. pp. 77-96).

Techniques described for the production of single chain antibodies (U.S. Pat. No. 4,946,778) can be adapted to produce single chain antibodies to immunogenic polypeptide products of this invention.

The antibodies can be used in methods relating to the localization and activity of the protein sequences of the invention, e.g., for imaging these proteins, measuring levels thereof in appropriate physiological samples, and the like.

The present invention provides detectably labeled oligonucleotides for imaging OAS1 polynucleotides within a cell. Such oligonucleotides are useful for determining if gene amplification has occurred, and for assaying the expression levels in a cell or tissue using, for example, in situ hybridization as is known in the art.

Therapeutic Agents for Inhibition of OAS1 Function

The present invention also relates to antisense oligonucleotides designed to interfere with the normal function of OAS1 polynucleotides. Any modifications or variations of the antisense molecule which are known in the art to be broadly applicable to antisense technology are included within the scope of the invention. Such modifications include preparation of phosphorus-containing linkages as disclosed in U.S. Pat. Nos. 5,536,821; 5,541,306; 5,550,111; 5,563,253; 5,571,799; 5,587,361, 5,625,050 and 5,958,773.

The antisense compounds of the invention can include modified bases as disclosed in U.S. Pat. No. 5,958,773 and patents disclosed therein. The antisense oligonucleotides of the invention can also be modified by chemically linking the oligonucleotide to one or more moieties or conjugates to enhance the activity, cellular distribution, or cellular uptake of the antisense oligonucleotide. Such moieties or conjugates include lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585,481, 5,587,371, 5,597,696 and 5,958,773.

Chimeric antisense oligonucleotides are also within the scope of the invention, and can be prepared from the present inventive oligonucleotides using the methods described in, for example, U.S. Pat. Nos. 5,013,830, 5,149,797, 5,403,711, 5,491,133, 5,565,350, 5,652,355, 5,700,922 and 5,958,773.

Preferred antisense oligonucleotides can be selected by routine experimentation using, for example, assays described in the Examples. Although the inventors are not bound by a particular mechanism of action, it is believed that the antisense oligonucleotides achieve an inhibitory effect by binding to a complementary region of the target polynucleotide within the cell using Watson-Crick base pairing. Where the target polynucleotide is RNA, experimental evidence indicates that the RNA component of the hybrid is cleaved by RNase H (Giles et al., *Nuc. Acids Res.* 23:954-61, 1995; U.S. Pat. No. 6,001,653). Generally, a hybrid containing 10 base pairs is of sufficient length to serve as a substrate for RNase H. However, to achieve specificity of binding, it is preferable to use an antisense molecule of at least 17 nucleotides, as a sequence of this length is likely to be unique among human genes.

As disclosed in U.S. Pat. No. 5,998,383, incorporated herein by reference, the oligonucleotide is selected such that the sequence exhibits suitable energy related characteristics important for oligonucleotide duplex formation with their complementary templates, and shows a low potential for self-dimerization or self-complementation (Anazodo et al., *Biochem. Biophys. Res. Commun.* 229:305-09, 1996). The computer program OLIGO (Primer Analysis Software, Version 3.4), is used to determined antisense sequence melting temperature, free energy properties, and to estimate potential self-dimer formation and self-complimentarity properties. The program allows the determination of a qualitative estimation of these two parameters (potential self-dimer formation and self-complimentary) and provides an indication of "no potential" or "some potential" or "essentially complete potential." Segments of OAS1 polynucleotides are generally selected that have estimates of no potential in these parameters. However, segments can be used that have "some potential" in one of the categories. A balance of the parameters is used in the selection.

In the antisense art a certain degree of routine experimentation is required to select optimal antisense molecules for particular targets. To be effective, the antisense molecule preferably is targeted to an accessible, or exposed, portion of the target RNA molecule. Although in some cases information is available about the structure of target mRNA molecules, the current approach to inhibition using antisense is via experimentation. According to the invention, this experimentation can be performed routinely by transfecting cells with an antisense oligonucleotide using methods described in the Examples. mRNA levels in the cell can be measured routinely in treated and control cells by reverse transcription of the mRNA and assaying the cDNA levels. The biological effect can be determined routinely by measuring cell growth or viability as is known in the art.

Measuring the specificity of antisense activity by assaying and analyzing cDNA levels is an art-recognized method of validating antisense results. It has been suggested that RNA from treated and control cells should be reverse-transcribed and the resulting cDNA populations analyzed. (Branch, A. D., *T.I.B.S* 23:45-50, 1998.) According to the present invention, cultures of cells are transfected with two different antisense oligonucleotides designed to target OAS1. The levels of mRNA corresponding to OAS1 are measured in treated and control cells.

Additional inhibitors include ribozymes, proteins or polypeptides, antibodies or fragments thereof as well as small molecules. Each of these OAS1 inhibitors share the common feature in that they reduce the expression and/or biological activity of OAS1. In addition to the exemplary OAS1 inhibitors disclosed herein, alternative inhibitors may be obtained through routine experimentation utilizing methodology either specifically disclosed herein or as otherwise readily available to and within the expertise of the skilled artisan.

Ribozymes

OAS1 inhibitors may be ribozymes. A ribozyme is an RNA molecule that specifically cleaves RNA substrates, such as mRNA, resulting in specific inhibition or interference with cellular gene expression. As used herein, the term ribozymes includes RNA molecules that contain antisense sequences for specific recognition, and an RNA-cleaving enzymatic activity. The catalytic strand cleaves a specific site in a target RNA at greater than stoichiometric concentration.

A wide variety of ribozymes may be utilized within the context of the present invention, including for example, the hammerhead ribozyme (for example, as described by Forster and Symons, *Cell* 48:211-20, 1987; Haseloff and Gerlach, *Nature* 328:596-600, 1988; Walbot and Bruening, *Nature* 334:196, 1988; Haseloff and Gerlach, *Nature* 334:585, 1988); the hairpin ribozyme (for example, as described by Haseloff et al., U.S. Pat. No. 5,254,678, issued Oct. 19, 1993 and Hempel et al., European Patent Publication No. 0 360 257, published Mar. 26, 1990); and Tetrahymena ribosomal RNA-based ribozymes (see Cech et al., U.S. Pat. No. 4,987,071). Ribozymes of the present invention typically consist of RNA, but may also be composed of DNA, nucleic acid analogs (e.g., phosphorothioates), or chimerics thereof (e.g., DNA/RNA/RNA).

Ribozymes can be targeted to any RNA transcript and can catalytically cleave such transcripts (see, e.g., U.S. Pat. Nos. 5,272,262; 5,144,019; and 5,168,053, 5,180,818, 5,116,742 and 5,093,246 to Cech et al.). According to certain embodiments of the invention, any such OAS1 mRNA-specific ribozyme, or a nucleic acid encoding such a ribozyme, may be delivered to a host cell to effect inhibition of OAS1 gene expression. Ribozymes and the like may therefore be delivered to the host cells by DNA encoding the ribozyme linked to a eukaryotic promoter, such as a eukaryotic viral promoter, such that upon introduction into the nucleus, the ribozyme will be directly transcribed.

RNAi

The invention also provides for the introduction of RNA with partial or fully double-stranded character into the cell or into the extracellular environment. Inhibition is specific to the OAS1 expression in that a nucleotide sequence from a portion of the target OAS1 gene is chosen to produce inhibitory RNA. This process is (1) effective in producing inhibition of gene expression, and (2) specific to the targeted OAS1 gene. The procedure may provide partial or complete loss of function for the target OAS1 gene. A reduction or loss of gene expression in at least 99% of targeted cells has been shown using comparable techniques with other target genes. Lower doses of injected material and longer times after administration of dsRNA may result in inhibition in a smaller fraction of cells. Quantitation of gene expression in a cell may show similar amounts of inhibition at the level of accumulation of target mRNA or translation of target protein. Methods of preparing and using RNAi are generally disclosed in U.S. Pat. No. 6,506,559, incorporated herein by reference.

The RNA may comprise one or more strands of polymerized ribonucleotide; it may include modifications to either the phosphate-sugar backbone or the nucleoside. The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses of double-stranded material may yield more effective inhibition. Inhibition is sequence-specific in that nucleotide sequences corresponding to the duplex region of the RNA are targeted for genetic inhibition. RNA containing a nucleotide sequence identical to a portion of the OAS1 target gene is preferred for inhibition. RNA sequences with insertions, deletions, and single point mutations relative to the target sequence have also been found to be effective for inhibition. Thus, sequence identity may optimized by alignment algorithms known in the art and calculating the percent difference between the nucleotide sequences. Alternatively, the duplex region of the RNA may be defined functionally as a nucleotide sequence that is capable of hybridizing with a portion of the target gene transcript.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region may be used to transcribe the RNA strand (or strands).

For RNAi, the RNA may be directly introduced into the cell (i.e., intracellularly), or introduced extracellularly into a cavity, interstitial space, into the circulation of an organism, introduced orally, or may be introduced by bathing an organism in a solution containing RNA. Methods for oral introduction include direct mixing of RNA with food of the organism, as well as engineered approaches in which a species that is used as food is engineered to express an RNA, then fed to the organism to be affected. Physical methods of introducing nucleic acids include injection directly into the cell or extracellular injection into the organism of an RNA solution.

The advantages of the method include the ease of introducing double-stranded RNA into cells, the low concentration of RNA which can be used, the stability of double-stranded RNA, and the effectiveness of the inhibition.

Inhibition of gene expression refers to the absence (or observable decrease) in the level of protein and/or mRNA product from a OAS1 target gene. Specificity refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin.

Depending on the assay, quantitation of the amount of gene expression allows one to determine a degree of inhibition which is greater than 10%, 33%, 50%, 90%, 95% or 99% as compared to a cell not treated according to the present invention. Lower doses of injected material and longer times after administration of dsRNA may result in inhibition in a smaller fraction of cells (e.g., at least 10%, 20%, 50%, 75%, 90%, or 95% of targeted cells). Quantitation of OAS1 gene expression in a cell may show similar amounts of inhibition at the level of accumulation of OAS1 target mRNA or translation of OAS1 target protein. As an example, the efficiency of inhibition may be determined by assessing the amount of gene product in the cell: mRNA may be detected with a hybridization probe having a nucleotide sequence outside the region used for the inhibitory double-stranded RNA, or translated polypeptide may be detected with an antibody raised against the polypeptide sequence of that region.

The RNA may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. RNA may be produced enzymatically or by partial/total organic synthesis, any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition.

RNA containing a nucleotide sequences identical to a portion of the OAS1 target gene are preferred for inhibition. RNA sequences with insertions, deletions, and single point mutations relative to the target sequence may be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the OAS1 target gene is preferred. Alternatively, the duplex region of the RNA may be defined functionally as a nucleotide sequence that is capable of hybridizing with a portion of the OAS1 target gene transcript (e.g., 400 mM NaCl, 40 mM PIPES pH 6.4, 1 mM EDTA, 50° C. or 70° C. hybridization for 12-16 hours; followed by washing). The length of the identical nucleotide sequences may be at least 25, 50, 100, 200, 300 or 400 bases.

100% sequence identity between the RNA and the OAS1 target gene is not required to practice the present invention. Thus the methods have the advantage of being able to tolerate sequence variations that might be expected due to genetic mutation, strain polymorphism, or evolutionary divergence.

OAS1RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). The use and production of an expression construct are known in (see WO 97/32016; U.S. Pat. Nos. 5,593,874, 5,698,425, 5,712, 135, 5,789,214, and 5,804,693; and the references cited therein). If synthesized chemically or by in vitro enzymatic synthesis, the RNA may be purified prior to introduction into the cell. For example, RNA can be purified from a mixture by extraction with a solvent or resin, precipitation, electrophoresis, chromatography, or a combination thereof. Alternatively, the RNA may be used with no or a minimum of purification to avoid losses due to sample processing. The RNA may be dried for storage or dissolved in an aqueous solution. The solution may contain buffers or salts to promote annealing, and/or stabilization of the duplex strands.

RNA may be directly introduced into the cell (i.e., intracellularly); or introduced extracellularly into a cavity, interstitial space, into the circulation of an organism, introduced orally, or may be introduced by bathing an organism in a solution containing the RNA. Methods for oral introduction include direct mixing of the RNA with food of the organism, as well as engineered approaches in which a species that is used as food is engineered to express the RNA, then fed to the organism to be affected. For example, the RNA may be sprayed onto a plant or a plant may be genetically engineered to express the RNA in an amount sufficient to kill some or all of a pathogen known to infect the plant. Physical methods of introducing nucleic acids, for example, injection directly into the cell or extracellular injection into the organism, may also be used. Vascular or extravascular circulation, the blood or lymph system, and the cerebrospinal fluid are sites where the RNA may be introduced. A transgenic organism that expresses RNA from a recombinant construct may be produced by introducing the construct into a zygote, an embryonic stem cell, or another multipotent cell derived from the appropriate organism.

Physical methods of introducing nucleic acids include injection of a solution containing the RNA, bombardment by particles covered by the RNA, soaking the cell or organism in a solution of the RNA, or electroporation of cell membranes in the presence of the RNA. A viral construct packaged into a viral particle would accomplish both efficient introduction of an expression construct into the cell and transcription of RNA encoded by the expression construct. Other methods known in the art for introducing nucleic acids to cells may be used, such as lipid-mediated carrier transport, chemical-mediated transport, such as calcium phosphate, and the like. Thus the RNA may be introduced along with components that perform one or more of the following activities: enhance RNA uptake by the cell, promote annealing of the duplex strands, stabilize the annealed strands, or other-wise increase inhibition of the target gene.

The present invention may be used alone or as a component of a kit having at least one of the reagents necessary to carry out the in vitro or in vivo introduction of RNA to test samples or subjects. Preferred components are the dsRNA and a vehicle that promotes introduction of the dsRNA. Such a kit may also include instructions to allow a user of the kit to practice the invention.

Suitable injection mixes are constructed so animals receive an average of $0.5 \times 10^6$ to $1.0 \times 10^6$ molecules of RNA. For comparisons of sense, antisense, and dsRNA activities, injections are compared with equal masses of RNA (i.e., dsRNA at half the molar concentration of the single strands). Numbers of molecules injected per adult are given as rough approximations based on concentration of RNA in the injected material (estimated from ethidium bromide staining) and injection volume (estimated from visible displacement at the site of injection). A variability of several-fold in injection volume between individual animals is possible.

Proteins and Polypeptides

In addition to the antisense molecules and ribozymes disclosed herein, OAS1 inhibitors of the present invention also include proteins or polypeptides that are effective in either reducing OAS1 gene expression or in decreasing one or more of OAS1's biological activities, including but not limited to enzymatic activity; interaction with single stranded RNA, configurations; and binding to other proteins such as Hepatitis C virus NS5A or a fragment thereof. A variety of methods are readily available in the art by which the skilled artisan may, through routine experimentation, rapidly identify such OAS1 inhibitors. The present invention is not limited by the following exemplary methodologies.

Literature is available to the skilled artisan that describes methods for detecting and analyzing protein-protein interactions. Reviewed in Phizicky et al., *Microbiological Reviews* 59:94-123, 1995, incorporated herein by reference. Such methods include, but are not limited to physical methods such as, e.g., protein affinity chromatography, affinity blotting, immunoprecipitation and cross-linking as well as library-based methods such as, e.g., protein probing, phage display and two-hybrid screening. Other methods that may be employed to identify protein-protein interactions include genetic methods such as use of extragenic suppressors, synthetic lethal effects and unlinked noncomplementation. Exemplary methods are described in further detail below.

Inventive OAS1 inhibitors may be identified through biological screening assays that rely on the direct interaction between the OAS1 protein and a panel or library of potential inhibitor proteins. Biological screening methodologies, including the various "n-hybrid technologies," are described in, for example, Vidal et al., *Nucl. Acids Res.* 27(4):919-29, 1999; Frederickson, R. M., *Curr. Opin. Biotechnol.* 9(1):90-96, 1998; Brachmann et al., *Curr. Opin. Biotechnol.* 8(5):561-68, 1997; and White, M. A., *Proc. Natl. Acad. Sci. U.S.A.* 93:10001-03, 1996, each of which is incorporated herein by reference.

The two-hybrid screening methodology may be employed to search new or existing target cDNA libraries for OAS1 binding proteins that have inhibitory properties. The two-hybrid system is a genetic method that detects protein-protein interactions by virtue of increases in transcription of reporter genes. The system relies on the fact that site-specific transcriptional activators have a DNA-binding domain and a transcriptional activation domain. The DNA-binding domain targets the activation domain to the specific genes to be expressed. Because of the modular nature of transcriptional activators, the DNA-binding domain may be severed covalently from the transcriptional activation domain without loss of activity of either domain. Furthermore, these two domains may be brought into juxtaposition by protein-protein contacts between two proteins unrelated to the transcriptional machinery. Thus, two hybrids are constructed to create a functional system. The first hybrid, i.e., the bait, consists of a transcriptional activator DNA-binding domain fused to a protein of interest. The second hybrid, the target, is created by the fusion of a transcriptional activation domain with a library of proteins or polypeptides. Interaction between the bait protein and a member of the target library results in the juxtaposition of the DNA-binding domain and the transcriptional activation domain and the consequent up-regulation of reporter gene expression.

A variety of two-hybrid based systems are available to the skilled artisan that most commonly employ either the yeast Gal4 or *E. coli* LexA DNA-binding domain (BD) and the yeast Gal4 or herpes simplex virus VP16 transcriptional activation domain. Chien et al., *Proc. Natl. Acad. Sci. U.S.A.* 88:9578-82, 1991; Dalton et al., *Cell* 68:597-612, 1992; Durfee et al., *Genes Dev.* 7:555-69, 1993; Vojtek et al., *Cell* 74:205-14, 1993; and Zervos et al., *Cell* 72:223-32, 1993. Commonly used reporter genes include the *E. coli* lacZ gene as well as selectable yeast genes such as HIS3 and LEU2. Fields et al., *Nature* (London) 340:245-46, 1989; Durfee, T. K., supra; and Zervos, A. S., supra. A wide variety of activation domain libraries is readily available in the art such that the screening for interacting proteins may be performed through routine experimentation.

Suitable bait proteins for the identification of OAS1 interacting proteins may be designed based on the OAS1 DNA sequence presented herein as SEQ ID NO:19. Such bait proteins include either the full-length OAS1 protein or fragments thereof.

Plasmid vectors, such as, e.g., pBTM116 and pAS2-1, for preparing OAS1 bait constructs and target libraries are readily available to the artisan and may be obtained from such commercial sources as, e.g., Clontech (Palo Alto, Calif.), Invitrogen (Carlsbad, Calif.) and Stratagene (La Jolla, Calif.). These plasmid vectors permit the in-frame fusion of cDNAs with the DNA-binding domains as LexA or Gal4BD, respectively.

OAS1 inhibitors of the present invention may alternatively be identified through one of the physical or biochemical methods available in the art for detecting protein-protein interactions.

Through the protein affinity chromatography methodology, lead compounds to be tested as potential OAS1 inhibitors may be identified by virtue of their specific retention to OAS1 when either covalently or non-covalently coupled to a solid matrix such as, e.g., Sepharose beads. The preparation of protein affinity columns is described in, for example, Beeckmans et al., *Eur. J. Biochem.* 117:527-35, 1981, and Formosa et al., *Methods Enzymol.* 208:24-45, 1991. Cell lysates containing the full complement of cellular proteins may be passed through the OAS1 affinity column. Proteins having a high affinity for OAS1 will be specifically retained under low-salt conditions while the majority of cellular proteins will pass through the column. Such high affinity proteins may be eluted from the immobilized OAS1 under conditions of high-salt, with chaotropic solvents or with sodium dodecyl sulfate (SDS). In some embodiments, it may be preferred to radiolabel the cells prior to preparing the lysate as an aid in identifying the OAS1 specific binding proteins. Methods for radiolabeling mammalian cells are well known in the art and are provided, e.g., in Sopta et al., *J. Biol. Chem.* 260:10353-60, 1985.

Suitable OAS1 proteins for affinity chromatography may be fused to a protein or polypeptide to permit rapid purification on an appropriate affinity resin. For example, the OAS1 cDNA may be fused to the coding region for glutathione S-transferase (GST) which facilitates the adsorption of fusion proteins to glutathione-agarose columns. Smith et al., *Gene* 67:31-40, 1988. Alternatively, fusion proteins may include protein A, which can be purified on columns bearing immunoglobulin G; oligohistidine-containing peptides, which can be purified on columns bearing $Ni^{2+}$; the maltose-binding protein, which can be purified on resins containing amylose; and dihydrofolate reductase, which can be purified on methotrexate columns. One exemplary tag suitable for the preparation of OAS1 fusion proteins that is presented herein is the epitope for the influenza virus hemagglutinin (HA) against which monoclonal antibodies are readily available and from which antibodies an affinity column may be prepared.

Proteins that are specifically retained on a OAS1 affinity column may be identified after subjecting to SDS polyacrylamide gel electrophoresis (SDS-PAGE). Thus, where cells are radiolabeled prior to the preparation of cell lysates and passage through the OAS1 affinity column, proteins having high affinity for OAS1 may be detected by autoradiography. The identity of OAS1 specific binding proteins may be determined by protein sequencing techniques that are readily available to the skilled artisan, such as Mathews, C. K. et al., *Biochemistry*, The Benjamin/Cummings Publishing Company, Inc., 1990, pp.166-70.

Small Molecules

The present invention also provides small molecule OAS1 inhibitors that may be readily identified through routine application of high-throughput screening (HTS) methodologies. Reviewed by Persidis, A., *Nature Biotechnology* 16:488-89, 1998. HTS methods generally refer to those technologies that permit the rapid assaying of lead compounds, such as small molecules, for therapeutic potential. HTS methodology employs robotic handling of test materials, detection of positive signals and interpretation of data. Such methodologies include, e.g., robotic screening technology using soluble molecules as well as cell-based systems such as the two-hybrid system described in detail above.

A variety of cell line-based HTS methods are available that benefit from their ease of manipulation and clinical relevance of interactions that occur within a cellular context as opposed to in solution. Lead compounds may be identified via incorporation of radioactivity or through optical assays that rely on absorbance, fluorescence or luminescence as read-outs. See, e.g., Gonzalez et al., *Curr. Opin. Biotechnol.* 9(6):624-31, 1998, incorporated herein by reference.

HTS methodology may be employed, e.g., to screen for lead compounds that block one of. OAS1's biological activities. By this method, OAS1 protein may be immunoprecipitated from cells expressing the protein and applied to wells on an assay plate suitable for robotic screening. Individual test compounds may then be contacted with the immunoprecipitated protein and the effect of each test compound on OAS1.

Methods for Assessing the Efficacy of OAS1 Inhibitors

Lead molecules or compounds, whether antisense molecules or ribozymes, proteins and/or peptides, antibodies and/or antibody fragments or small molecules, that are identified either by one of the methods described herein or via techniques that are otherwise available in the art, may be further characterized in a variety of in vitro, ex vivo and in vivo animal model assay systems for their ability to inhibit OAS1 gene expression or biological activity. As discussed in further detail in the Examples provided below, OAS1 inhibitors of the present invention are effective in reducing OAS1 expression levels. Thus, the present invention further discloses methods that permit the skilled artisan to assess the effect of candidate inhibitors.

Candidate OAS1 inhibitors may be tested by administration to cells that either express endogenous OAS1 or that are made to express OAS1 by transfection of a mammalian cell with a recombinant OAS1 plasmid construct.

Effective OAS1 inhibitory molecules will be effective in reducing the enzymatic activity of OAS1 or ability of OAS1 to respond to IFN induction. Methods of measuring OAS1 enzymatic activity and IFN induction are known in the art, for example, as described in Eskildsen et al., *Nuc. Acids Res.* 31:3166-3173, 2003; and Justesen et al., *Nuc. Acids Res.* 8:3073-3085, 1980, incorporated herein by reference. The effectiveness of a given candidate antisense molecule may be assessed by comparison with a control "antisense" molecule known to have no substantial effect on OAS1 expression when administered to a mammalian cell.

OAS1 inhibitors effective in reducing OAS1 gene expression by one or more of the methods discussed above may be further characterized in vitro for efficacy in one of the readily available established cell culture or primary cell culture model systems as described herein, in reference to use of Vero cells challenged by infection with a flavivirus, such as dengue virus.

Pharmaceutical Compositions

The antisense oligonucleotides and ribozymes of the present invention can be synthesized by any method known in the art for ribonucleic or deoxyribonucleic nucleotides. For example, the oligonucleotides can be prepared using solid-phase synthesis such as in an Applied Biosystems 380B DNA synthesizer. Final purity of the oligonucleotides is determined as is known in the art.

The antisense oligonucleotides identified using the methods of the invention modulate tumor cell proliferation. Therefore, pharmaceutical compositions and methods are provided for interfering with virus infection, preferably flavivirus, most preferably HCV infection, comprising contacting tissues or cells with one or more of antisense oligonucleotides identified using the methods of the invention.

The invention provides pharmaceutical compositions of antisense oligonucleotides and ribozymes complementary to the OAS1 mRNA gene sequence as active ingredients for therapeutic application. These compositions can also be used in the method of the present invention. When required, the compounds are nuclease resistant. In general the pharmaceutical composition for inhibiting virus infection in a mammal includes an effective amount of at least one antisense oligonucleotide as described above needed for the practice of the invention, or a fragment thereof shown to have the same effect, and a pharmaceutically physiologically acceptable carrier or diluent.

The compositions can be administered orally, subcutaneously, or parenterally including intravenous, intraarterial, intramuscular, intraperitoneally, and intranasal administration, as well as intrathecal and infusion techniques as required. The pharmaceutically acceptable carriers, diluents, adjuvants and vehicles as well as implant carriers generally refer to inert, non-toxic solid or liquid fillers, diluents or encapsulating material not reacting with the active ingredients of the invention. Cationic lipids may also be included in the composition to facilitate oligonucleotide uptake. Implants of the compounds are also useful. In general, the pharmaceutical compositions are sterile.

By bioactive (expressible) is meant that the oligonucleotide is biologically active in the cell when delivered directly to the cell and/or is expressed by an appropriate promotor and active when delivered to the cell in a vector as described below. Nuclease resistance is provided by any method known in the art that does not substantially interfere with biological activity as described herein.

"Contacting the cell" refers to methods of exposing or delivering to a cell antisense oligonucleotides whether directly or by viral or non-viral vectors and where the antisense oligonucleotide is bioactive upon delivery.

The nucleotide sequences of the present invention can be delivered either directly or with viral or non-viral vectors. When delivered directly the sequences are generally rendered nuclease resistant. Alternatively, the sequences can be incorporated into expression cassettes or constructs such that the sequence is expressed in the cell. Generally, the construct contains the proper regulatory sequence or promotor to allow the sequence to be expressed in the targeted cell.

Once the oligonucleotide sequences are ready for delivery they can be introduced into cells as is known in the art. Transfection, electroporation, fusion, liposomes, colloidal polymeric particles, and viral vectors as well as other means known in the art may be used to deliver the oligonucleotide sequences to the cell. The method selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like.

The present invention provides vectors comprising an expression control sequence operatively linked to the oligonucleotide sequences of the invention. The present invention further provides host cells, selected from suitable eukaryotic and prokaryotic cells, which are transformed with these vectors as necessary.

Vectors are known or can be constructed by those skilled in the art and should contain all expression elements necessary to achieve the desired transcription of the sequences. Other beneficial characteristics can also be contained within the vectors such as mechanisms for recovery of the oligonucleotides in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual*, Cold Springs Harbor Laboratory, New York, 1989, 1992; in Ausubel et al., *Current Protocols in Molecular Biology*, John Wiley and Sons, Baltimore, Md., 1989; Chang et al., *Somatic Gene Therapy*, CRC Press, Ann Arbor, Mich., 1995; Vega et al., *Gene Targeting*, CRC Press, Ann Arbor, Mich., 1995; *Vectors: A Survey of Molecular Cloning Vectors and Their Uses*, Butterworths, Boston, Mass., 1988; and Gilboa et al., *BioTechniques* 4:504-12, 1986, and include, for example, stable or transient transfection, lipofection, electroporation and infection with recombinant viral vectors.

Recombinant methods known in the art can also be used to achieve the antisense inhibition of a target nucleic acid. For example, vectors containing antisense nucleic acids can be employed to express an antisense message to reduce the expression of the target nucleic acid and therefore its activity.

The present invention also provides a method of evaluating if a compound inhibits transcription or translation of an OAS1 gene and thereby modulates (i.e., reduces) the ability of the cell to activate RNaseL, comprising transfecting a cell with an expression vector comprising a nucleic acid sequence encoding OAS1, the necessary elements for the transcription or translation of the nucleic acid; administering a test compound; and comparing the level of expression of the OAS1 with the level obtained with a control in the absence of the test compound.

Preferred Embodiments

Utilizing methods described above and others known in the art, the present invention contemplates a screening method comprising treating, under amplification conditions, a sample of genomic DNA, isolated from a human, with a PCR primer pair for amplifying a region of human genomic DNA containing any of nucleotide (nt) positions 2135728, 2135749, 2135978, 2144072, 2144088, 2144116, 2144321, 2131025, 2133961, 2139587, 2144294, 2144985, 2156523, 2156595, or 2156638 of oligoadenylate synthetase (OAS1, SEQ ID NO:19). Amplification conditions include, in an amount effective for DNA synthesis, the presence of PCR buffer and a thermocycling temperature. The PCR product thus produced is assayed for the presence of a point mutation at the relevant nucleotide position. In one embodiment, the PCR product contains a continuous nucleotide sequence comprising about 358 base pairs (bp) written from 5' to 3' direction and including position 2135728 (mutation 1), 2135749 (mutation 2), 2135978 (mutation 3), 2144072 (mutation 4), 2144088 (mutation 5), 2144116 (mutation 6), or 2144321 (mutation 7) and the approximately 175 bases flanking the position at each side. In another embodiment, the amplicons as described above in Tables 1 and 2 are exemplary of the PCR products and corresponding primers.

In one preferred embodiment, the PCR product is assayed for the corresponding mutation by treating the amplification product, under hybridization conditions, with an oligonucleotide probe specific for the corresponding mutation, and detecting the formation of any hybridization product. Preferred oligonucleotide probes comprise a nucleotide sequence indicated in Table 3 below. Oligonucleotide hybridization to target nucleic acid is described in U.S. Pat. No. 4,530,901.

TABLE 3

| Mutation SEQ ID NO | Probe sequence |
|---|---|
| SEQ ID NO: 1 | GTAGATTTTGCC<u>Y</u>GAACAGGTCAGT (SEQ ID NO: 12) |
| SEQ ID NO: 2 | CAGTTGACTGGC<u>R</u>GCTATAAACCTA (SEQ ID NO: 13) |
| SEQ ID NO: 3 | CAGAGGAGGGGT<u>R</u>GGGGGAGGAGA (SEQ ID NO: 14) |
| SEQ ID NO: 4 | TCTCACCCTTTCA<u>R</u>GCTGAAAGCAAC (SEQ ID NO: 15) |
| SEQ ID NO: 5 | GAAAGCAACAGT<u>R</u>CAGACGATGAGA (SEQ ID NO: 16) |
| SEQ ID NO: 6 | ACGATCCCAGGA<u>S</u>GTATCAGAAATAT (SEQ ID NO: 17) |
| SEQ ID NO: 7 | TTGATCCAGAGA<u>R</u>GACAAAGCTCCTC (SEQ ID NO: 18) |

Wherein R = A/G, S = C/G, and Y = C/T.

The PCR admixture thus formed is subjected to a plurality of PCR thermocycles to produce OAS1 and OAS1R gene amplification products. The amplification products are then treated, under hybridization conditions, with an oligonucleotide probe specific for each mutation. Any hybridization products are then detected.

The following examples are intended to illustrate but are not to be construed as limiting of the specification and claims in any way.

EXAMPLES

Example 1

Preparation and Preliminary Screening of Genomic DNA

This example relates to screening of DNA from two specific populations of patients, but is equally applicable to other patient groups in which repeated exposure to HCV is documented, wherein the exposure does not result in infection. The example also relates to screening patients who have been exposed to other flaviviruses as discussed above, wherein the exposure did not result in infection.

Here, two populations are studied: (1) a hemophiliac population, chosen with the criteria of moderate to severe hemophilia, and receipt of concentrated clotting factor before January, 1987; and (2) an intravenous drug user population, with a history of injection for over 10 years, and evidence of other risk behaviors such as sharing needles. The study involves exposed but HCV negative patients, and exposed and HCV positive patients.

High molecular weight DNA is extracted from the white blood cells from IV drug users, hemophiliac patients, and other populations at risk of hepatitis C infection, or infection by other flaviviruses. For the initial screening of genomic DNA, blood is collected after informed consent from the patients of the groups described above and anticoagulated with a mixture of 0.14M citric acid, 0.2M trisodium citrate, and 0.22M dextrose. The anticoagulated blood is centrifuged at 800×g for 15 minutes at room temperature and the platelet-rich plasma supernatant is discarded. The pelleted erythrocytes, mononuclear and polynuclear cells are resuspended and diluted with a volume equal to the starting blood volume with chilled 0.14M phosphate buffered saline (PBS), pH 7.4. The peripheral blood white blood cells are recovered from the diluted cell suspension by centrifugation on low endotoxin Ficoll-Hypaque (Sigma Chem. Corp. St. Louis, Mo.) at 400×g for 10 minutes at 18° C. (18° C.). The pelleted white blood cells are then resuspended and used for the source of high molecular weight DNA.

The high molecular weight DNA is purified from the isolated white blood cells using methods well known to one skilled in the art and described by Maniatis, et al., Molecular Cloning: A Laboratory Manual, 2nd ed. Cold Spring Harbor Laboratory, Sections 9.16-9.23, (1989) and U.S. Pat. No. 4,683,195.

Each sample of DNA is then examined for a point mutation of any one of the nucleotides at position 2135728, 2135749, 2135978, 2144072, 2144088, 2144116, 2144321, 2131025, 2133961, 2139587, 2144294, 2144985, 2156523, 2156595, or 2156638 with reference to the nucleotides positions of Genbank Accession No. NT_009775.13, corresponding to the oligoadenylate synthetase 1 gene (OAS1).

Example 2

Mutations in OAS1 Gene Associated with Resistance to HCV Infection

Using methods described in Example 1, a population of unrelated hemophiliac patients and intravenous drug users was studied, and the presence or absence of a mutation in OAS1 as disclosed in SEQ ID NO:1-SEQ ID NO:7 and SEQ ID NO:57-64 was determined.

In a study of 20 cases and 42 controls in a Caucasian population, these mutations were found in the context of resistance to hepatitis C infection. There was a statistically significant correlation between resistance to HCV infection and presence of a point mutation in OAS1.

Example 3

Preparation and Sequencing of CDNA

Total cellular RNA is purified from cultured lymphoblasts or fibroblasts from the patients having the hepatitis C resistance phenotype. The purification procedure is performed as described by Chomczynski, et al., Anal. Biochem., 162:156-159 (1987). Briefly, the cells are prepared as described in Example 1. The cells are then homogenized in 10 milliliters (ml) of a denaturing solution containing 4.0M guanidine thiocyanate, 0.1M Tris-HCl at pH 7.5, and 0.1M beta-mercaptoethanol to form a cell lysate. Sodium lauryl sarcosinate is then admixed to a final concentration of 0.5% to the cell lysate after which the admixture was centrifuged at 5000×g for 10 minutes at room temperature. The resultant supernatant containing the total RNA is layered onto a cushion of 5.7M cesium chloride and 0.01M EDTA at pH 7.5 and is pelleted by centrifugation. The resultant RNA pellet is dissolved in a solution of 10 mM Tris-HCl at pH 7.6 and 1 mM EDTA (TE) containing 0.1% sodium docecyl sulfate (SDS). After phenolchloroform extraction and ethanol precipitation, the purified total cellular RNA concentration is estimated by measuring the optical density at 260 nm.

Total RNA prepared above is used as a template for cDNA synthesis using reverse transcriptase for first strand synthesis and PCR with oligonucleotide primers designed so as to amplify the cDNA in two overlapping fragments designated the 5' and the 3' fragment. The oligonucleotides used in practicing this invention are synthesized on an Applied Biosystems 381A DNA Synthesizer following the manufacturer's instructions. PCR is conducted using methods known in the art. PCR amplification methods are described in detail in U.S. Pat. Nos. 4,683,192, 4,683,202, 4,800,159, and 4,965,188, and at least in several texts including PCR Technology: Principles and Applications for DNA Amplification, H. Erlich, ed., Stockton Press, New York (1989); and PCR Protocols: A Guide to Methods and Applications, Innis, et al., eds., Academic Press, San Diego, Calif. (1990) and primers as described in Table 1 herein.

The sequences determined directly from the PCR-amplified DNAs from the patients with and without HCV infection, are analyzed. The presence of a mutation upstream from the coding region of the OAS gene can be detected in patients who are seronegative for HCV despite repeated exposures to the virus.

Example 4

Preparation of PCR Amplified Genomic DNA Containing a Point Mutation and Detection by Allele Specific Oligonucleotide Hybridization The point mutation in an oligoadenylate synthetase (OAS1) gene at one of nucleotide positions 2135728, 2135749, 2135978, 2144072, 2144088, 2144116, 2144321, 2131025, 2133961, 2139587, 2144294, 2144985, 2156523, 2156595, or 2156638 can be determined by an approach in which PCR amplified genomic DNA containing the mutation is detected by hybridization with oligonucleotide probes that hybridized to that region. To amplify the region having the point mutation for hybridization with oligonucleotide specific probes, PCR amplifications are performed as essentially described in Example 3 with, for example, 180 ng of each of the primers shown in Table 1.

Following the PCR amplification, 2 µl of the amplified oligoadenylate synthetase DNA products are spotted onto separate sheets of nitrocellulose. After the spotted amplified DNA has dried, the nitrocellulose is treated with 0.5N NaOH for 2 minutes, 1M Tris-HCl at pH 7.5 for 2 minutes, followed by 0.5M Tris-HCl at pH 7.5 containing 1.5M NaCl for 2 minutes to denature and then neutralize the DNA. The resultant filters are baked under a vacuum for 1 hour at 80° C., are prehybridized for at least 20 minutes at 42° C. with a prehybridization solution consisting of 6×SSC (1×=0.15M NaCl, 0.15M sodium citrate), 5× Denhardt's solution (5×=0.1% polyvinylpyrrolidone, 0.1% ficoll, and 0.1% bovine serum albumin), 5 mM sodium phosphate buffer at pH 7.0, 0.5 mg/ml salmon testis DNA and 1% SDS.

After the prehybridization step, the nitrocellulose filters are separately exposed to $^{32}$P-labeled oligonucleotide probes diluted in prehybridization buffer. Labeling of the probes with $^{32}$P is performed by admixing 2.5 µl of 10× concentrate of kinase buffer (10×=0.5M Tris[hydroxymethyl] aminomethane hydrochloride (Tris-HCl) at pH 7.6, 0.1M MgCl$_2$, 50 mM dithiothreitol (DTT), 1 mM spermidine-HCl, and 1 mM ethylenediaminetetraacetic acid (EDTA)), 1.1 µl of 60 µg/µl of a selected oligonucleotide, 18.4 µl water, 2 µl of 6000 Ci/mM of gamma $^{32}$P ATP at a concentration of 150 mCi/µl, and 1 µl of 10 U/µl polynucleotide kinase. The labeling admixture is maintained for 20 minutes at 37° C. followed by 2 minutes at 68° C. The maintained admixture is then applied to a Sephadex G50 (Pharmacia, Inc., Piscataway, N.J.) spin column to remove unincorporated $^{32}$P-labeled ATP.

The oligonucleotide probes used to hybridize to the region containing the mutation are shown in Table 3 above. The underlined nucleotide corresponds to the mutation nucleotide. In probes for detecting wild type (normal), the underlined nucleotide is replaced with the wild-type nucleotide.

Ten×10$^6$ cpm of the normal and mutant labeled probes are separately admixed with each filter. The nitrocellulose filters are then maintained overnight at 42° C. to allow for the formation of hybridization products. The nitrocellulose filters exposed to the normal probe are washed with 6×SSC containing 0.1% SDS at 46° C. whereas the filters exposed to the mutant probe are washed with the same solution at a more stringent temperature of 52° C. The nitrocellulose filters are then dried and subjected to radioautography.

Only those products having the point mutation hybridize with the mutant probe. Positive and negative controls are included in each assay to determine whether the PCR amplification is successful. Thus, the patients' genomic DNA prepared in Example 1 are determined by this approach to have the unique point mutation of a non-wild type nucleotide substituted for a wild type nucleotide at the indicated position.

Example 5

Antisense Inhibition of Target RNA

A. Preparation of Oligonucleotides for Transfection

A carrier molecule, comprising either a lipitoid or chlesteroid, is prepared for transfection by diluting to 0.5 mM in water, followed by sonication to produce a uniform solution, and filtration through a 0.45 µm PVDF membrane. The lipitoid or cholesteroid is then diluted into an appropriate volume of OptiMEM™ (Gibco/BRL) such that the final concentration would be approximately 1.5-2 nmol lipitoid per µg oligonucleotide.

Antisense and control oligonucleotides are prepared by first diluting to a working concentration of 100 µM in sterile Millipore water, then diluting to 2 µM (approximately 20 mg/mL) in OptiMEM™. The diluted oligonucleotides are then immediately added to the diluted lipitoid and mixed by pipetting up and down.

B. Transfection

Human PH5CH8 hepatocytes, which are susceptible to HCV infection and supportive of HCV replication, are used (Dansako et al., Virus Res. 97:17-30, 2003; Ikeda et al., Virus Res. 56:157-167, 1998; Noguchi and Hirohashi, In Vitro Cell Dev. Biol Anim. 32:135-137, 1996.) The cells are transfected by adding the oligonucleotide/lipitoid mixture, immediately after mixing, to a final concentration of 300 nM oligonucleotide. The cells are then incubated with the transfection mixture overnight at 37° C., 5% CO$_2$ and the transfection mixture remains on the cells for 3-4 days.

C. Total RNA Extraction and Reverse Transcription

Total RNA is extracted from the transfected cells using the RNeasy™ kit (Qiagen Corporation, Chatsworth, Calif.), following protocols provided by the manufacturer. Following extraction, the RNA is reverse-transcribed for use as a PCR template. Generally 0.2-1 µg of total extracted RNA is placed into a sterile microfuge tube, and water is added to bring the total volume to 3 µL. 7 µL of a buffer/enzyme mixture is added to each tube. The buffer/enzyme mixture is prepared by mixing, in the order listed:
- 4 µL 25 mM MgCl$_2$
- 2 µL 10× reaction buffer
- 8 µL 2.5 mM dNTPs
- 1 µL MuLV reverse transcriptase (50 u) (Applied Biosystems)
- 1 µL RNase inhibitor (20 u)
- 1 µL oligo dT (50 pmol)

The contents of the microfuge tube are mixed by pipetting up and down, and the reaction is incubated for 1 hour at 42° C.

D. PCR Amplification and Quantification of Target Sequences

Following reverse transcription, target genes are amplified using the Roche Light Cycler™ real-time PCR machine. 20 µL aliquots of PCR amplification mixture are prepared by mixing the following components in the order listed: 2 µL 10× PCR buffer II (containing 10 mM Tris pH 8.3 and 50 mM KCl, Perkin-Elmer, Norwalk, Conn.) 3 mM MgCl$_2$, 140 µM each dNTP, 0.175 pmol of each OAS1 oligo, 1:50,000 dilution of SYBR® Green, 0.25 mg/mL BSA, 1 unit Taq polymerase, and H$_2$O to 20 µL. SYBR® Green (Molecular Probes, Eugene, Oreg.) is a dye that fluoresces when bound to double-stranded DNA, allowing the amount of PCR product produced in each reaction to be measured directly. 2 µL of completed reverse transcription reaction is added to each 20 µL aliquot of PCR amplification mixture, and amplification is carried out according to standard protocols.

Example 6

Treatment of Cells with OAS1 RNAi

Using the methods of Example 5, for antisense treatment, cells are treated with an oligonucleotide based on the OAS1 sequence (SEQ ID NO:19). Two complementary ribonucleotide monomers with deoxy-TT extensions at the 3' end are synthesized and annealed. Cells of the PH3CH8 hepatocyte cell line are treated with 50-200 nM RNAi with 1:3 L2 lipitoid. Cells are harvested on day 1, 2, 3 and 4, and analyzed for OAS1 protein by Western analysis, as described by Dansako et al., Virus Res. 97:17-30, 2003.

Example 7

OAS1 Interaction with Hepatitis C Virus NS5A Protein

The ability of an OAS1 protein or polypeptide of the invention to interact with hepatitis C virus NS5A protein is assayed using a method described in Taguchi, T. et al., J. Gen. Virol. 85:959-969, 2004. Polynucleotides encoding OAS1 proteins and polypeptides are prepared as described above, and plasmids are constructed using routine methods, such as described in Taguchi, T. et al One plasmid contains a polynucleotide encoding an OAS1 protein or polypeptide, and a second plasmid contains polynucleotide encoding NS5A. The plasmids also encode appropriate tags for the respective proteins, such as FLAG-tag, HA, or GST. Suitable cells, such as HeLa cells, are transiently transfected with a plasmid encoding a tag and NS5A protein, and a plasmid encoding a different tag and an OAS1 protein or polypeptide. After incubation and preparation of supernatant as described (Taguchi, T. et al.), a variety of analytic techniques can be used to detect and quantify the binding of NS5A with the OAS1 protein or polypeptide. Such techniques are known in the art and include co-precipitation analysis, immunofluorescence analysis, and immunoblot analysis. OAS1 proteins and polynucleotides that do not exhibit binding to NS5A are appropriate for further analysis as inhibitors of hepatitis C infection.

Example 8

Chemically and Sterically Conserved Regions of OAS1

As one skilled in the art will recognize, when modifying the structure of OAS1 to improve enzymatic activity or therapeutic potential, certain residues or regions of residues must be chemically and structurally conserved. By example, several conserved domains are described below. As one skilled in the art will recognize, chemically conservative changes to some amino acids that preserve the structure and function of the protein may be tolerated. For example, Asp75 and Asp77 both coordinate catalytic divalent metal ions that are essential to OAS1 function. While modifications to these bases may be tolerated (e.g. to asparagine or glutamic acid), the essentially polar and acid nature of these residues must be preserved.

As examples, with regard to SEQ ID NO: 26-29, SEQ ID NO:33, SEQ ID NO:34, and SEQ ID NO:50, the following polypeptide fragments represent conserved domains:

```
Amino Acids 40-47:
  FLKERCFR                           (SEQ ID NO: 75)

Amino acids 55-82:
  VSKVVKGGSSGKGTTLRGRSDADLVVFL       (SEQ ID NO: 76)

Amino Acids 94-112:
  RRGEFIQEIRRQLEACQRE                (SEQ ID NO: 77)

Amino Acids 128-138:
  NPRALSFVLSS                        (SEQ ID NO: 78)

Amino Acids 145-158:
  VEFDVLPAFDALGQ                     (SEQ ID NO: 79)

Amino Acids 182-198:
  KEGEFSTCFTELQRDFL                  (SEQ ID NO: 80)

Amino Acids 201-217:
  RPTKLKSLIRLVKHWYQ                  (SEQ ID NO: 81)

Amino Acids 225-241:
  KLPPQYALELLTVYAWE                  (SEQ ID NO: 82)

Amino Acids 296-307:
  PVILDPADPTGN                       (SEQ ID NO: 83)

Amino Acids 337-343:
  GSPVSSW                            (SEQ ID NO: 84)
```

Example 9

Amino Acids Changes that Improve Enzyme Active Site

Changes in OAS amino acids sequences can be envisioned that improve the enzymatic activity of the protein. In one preferred embodiment, amino acids within the active site of the enzyme can be modified to improve ATP or metal ion binding, enzyme efficiency, and enzyme processivity. An example of such an alteration would be the substitution of a tyrosine for a glycine at amino acid position 61 of SEQ ID NO:26, SEQ ID NO:27, SEQ ID NO:33, SEQ ID NO:34, SEQ ID NO:35, or SEQ ID NO:48. Substitution of the chemically innocuous glycine for the polar tyrosine should facilitate hydrogen bonding between the N3 atom of ATP and this amino acid position, thereby improving the dissociation constant and energetics of this interaction. A tyrosine is found at this position in, for example, the more processive poly-A polymerase. As one skilled in the art will recognize, other modifications can be envisioned.

Example 10

Amino Acid Changes that Improve Double-Stranded RNA Binding

A second example of amino acid modifications to OAS that improve enzymatic activity would be those that stabilize the interaction between this protein and double-stranded viral RNA. The table below lists those amino acids in the RNA binding groove of the protein and several proposed changes designed to stabilize the interaction between the basic, positively charged amino acid side chains and the negatively charged ribonucleic acid. Changes are envisioned that increase the positive charge density in the RNA binding groove of the protein. As one skilled in the art will recognize, similar types of modifications to the RNA binding groove can be envisioned.

TABLE 4

Proposed changes to amino acids in RNA binding groove

| Amino Acid | Position | Proposed Modification |
|---|---|---|
| Glycine | 39 | Arginine or Lysine |
| Lysine | 42 | Arginine |
| Lysine | 60 | Arginine |

TABLE 4-continued

Proposed changes to amino acids in RNA binding groove

| Amino Acid | Position | Proposed Modification |
|---|---|---|
| Arginine | 195 | Lysine |
| Lysine | 199 | Arginine |
| Lysine | 204 | Arginine |

Example 11

Analysis of Genetic Mutations

Those skilled in the art will recognize that numerous other analytical methods exist for assessing the evolutionary importance of particular mutations in a genetic analysis. One example is the well-known calculation of a linkage disequilibrium estimate, commonly referred to as D' (Lewontin, Genetics 49:49-67, 1964). Other particularly relevant methods attempt to estimate selective pressures and/or recent evolutionary events within a genetic locus (for example, selective sweeps) by comparing the relative abundance of high-, moderate-, or low-frequency mutations in the locus. Most familiar of these tests is the Tajima D statistic (Tajima, Genetics 123: 585-595, 1989). Fu and Li, Genetics 133:693-709 (1993) have also developed a variant to the Tajima and other statistics that also makes use of knowledge regarding the ancestral allele for each mutation. These and other methods are applied to the mutations of the present invention to assess relative contribution to the observed effects.

The foregoing specification, including the specific embodiments and examples, is intended to be illustrative of the present invention and is not to be taken as limiting. Numerous other variations and modifications can be effected without departing from the true spirit and scope of the invention. All patents, patent publications, and non-patent publications cited are incorporated by reference herein.

What is claimed is:

1. An isolated polypeptide consisting of the amino acid sequence of SEQ ID NO:49 covalently attached to a protein transduction domain.

2. The protein of claim 1 wherein the protein transduction domain consists of the amino acid sequence of SEQ ID NO:85.

3. The protein of claim 1 wherein the protein transduction domain has at least 80% sequence similarity to the amino acid sequence of SEQ ID NO:85.

4. An isolated polypeptide consisting of the amino acid sequence of SEQ ID NO:49 wherein (a) the polypeptide is covalently attached to polyethylene glycol, (b) the polypeptide is encapsulated in a liposome; (c) the polypeptide is covalently attached to an endosome disrupting agent; or (b) the polypeptide is noncovalently attached to an endosome disrupting agent.

5. The isolated polypeptide of claim 4 wherein the endosome disrupting agent is pH sensitive.

6. An isolated polypeptide consisting of the amino acid sequence of SEQ ID NO:49 covalently conjugated to a sugar moiety.

7. The isolated polypeptide of claim 6 wherein the sugar moiety is comprised of galactose or mannose.

* * * * *

SEQUENCE LISTING

```
<160> NUMBER OF SEQ ID NOS: 94

<210> SEQ ID NO 1
<211> LENGTH: 121
<212> TYPE: DNA
<213> ORGANISM: Artificial Sequence
<220> FEATURE:
<223> OTHER INFORMATION: Amplicon A

<400> SEQUENCE: 1
ccctcagagt gactgaagga aattcagaga agagctgaca cctaagttgt agattttgcc      60
ygaacaggtc agttgactgg crgctataaa cctaacccccc aaatctatgt caagctcatc    120
g                                                                     121

<210> SEQ ID NO 2
<211> LENGTH: 121
<212> TYPE: DNA
<213> ORGANISM: Artificial Sequence
<220> FEATURE:
<223> OTHER INFORMATION: Amplicon A

<400> SEQUENCE: 2
attcagagaa gagctgacac ctaagttgta gattttgccy gaacaggtca gttgactggc      60
```
rgctataaac ctaaccccca aatctatgtc aagctcatcg aggagtgcac cgacctgcag    120
a                                                                    121

<210> SEQ ID NO 3
<211> LENGTH: 121
<212> TYPE: DNA
<213> ORGANISM: Artificial Sequence
<220> FEATURE:
<223> OTHER INFORMATION: Amplicon A

<400> SEQUENCE: 3
atgtatggcc ctcccaccag gcctggtggg tcctgtctcg actgggagca gaggaggggt    60 rggggagga gagaaagaag ggagtgaagg gaagaggagg gggagtggtg gagggaaata    120
g                                                                    121

<210> SEQ ID NO 4
<211> LENGTH: 121
<212> TYPE: DNA
<213> ORGANISM: Artificial Sequence
<220> FEATURE:
<223> OTHER INFORMATION: Amplicon B

<400> SEQUENCE: 4
actgaatcca gctgcaatgc aggaagactc cctgatgtga tcatgtgtct cacccttca    60 rgctgaaagc aacagtrcag acgatgagac cgacgatccc aggasgtatc agaaatatgg    120
t                                                                    121

<210> SEQ ID NO 5
<211> LENGTH: 121
<212> TYPE: DNA
<213> ORGANISM: Artificial Sequence
<220> FEATURE:
<223> OTHER INFORMATION: Amplicon B

<400> SEQUENCE: 5
atgcaggaag actccctgat gtgatcatgt gtctcaccct ttcargctga aagcaacagt    60
rcagacgatg agaccgacga tcccaggasg tatcagaaat atggttacat tggaacacat    120
g                                                                    121

<210> SEQ ID NO 6
<211> LENGTH: 121
<212> TYPE: DNA
<213> ORGANISM: Artificial Sequence
<220> FEATURE:
<223> OTHER INFORMATION: Amplicon B

<400> SEQUENCE: 6
gtgtctcacc ctttcargct gaaagcaaca gtrcagacga tgagaccgac gatcccagga    60
sgtatcagaa atatggttac attggaacac atgagtaccc tcatttctct catagaccca    120
g                                                                    121

<210> SEQ ID NO 7
<211> LENGTH: 121
<212> TYPE: DNA
<213> ORGANISM: Artificial Sequence
<220> FEATURE:
<223> OTHER INFORMATION: Amplicon B

<400> SEQUENCE: 7

```
gggctccagt gttatctgga ccagttcctt catkttcagg tgggactctt gatccagaga      60
rgacaaagct cctcagtgag ctggtgtata atccaggaca gaacccaggt ctcctgactc     120
c                                                                     121
```

<210> SEQ ID NO 8
<211> LENGTH: 20
<212> TYPE: DNA
<213> ORGANISM: Artificial Sequence
<220> FEATURE:
<223> OTHER INFORMATION: Amplicon A primer

<400> SEQUENCE: 8

```
aatggacctc aagacttccc                                                  20
```

<210> SEQ ID NO 9
<211> LENGTH: 20
<212> TYPE: DNA
<213> ORGANISM: Artificial Sequence
<220> FEATURE:
<223> OTHER INFORMATION: Amplicon A primer

<400> SEQUENCE: 9

```
attctccctt ctgttgcagg                                                  20
```

<210> SEQ ID NO 10
<211> LENGTH: 20
<212> TYPE: DNA
<213> ORGANISM: Artificial Sequence
<220> FEATURE:
<223> OTHER INFORMATION: Amplicon B primer

<400> SEQUENCE: 10

```
tccagatggc atgtcacagt                                                  20
```

<210> SEQ ID NO 11
<211> LENGTH: 20
<212> TYPE: DNA
<213> ORGANISM: Artificial Sequence
<220> FEATURE:
<223> OTHER INFORMATION: Amplicon B primer

<400> SEQUENCE: 11

```
gagctatgct tggcacatag                                                  20
```

<210> SEQ ID NO 12
<211> LENGTH: 25
<212> TYPE: DNA
<213> ORGANISM: Artificial Sequence
<220> FEATURE:
<223> OTHER INFORMATION: Probe sequence

<400> SEQUENCE: 12

```
gtagattttg ccygaacagg tcagt                                            25
```

<210> SEQ ID NO 13
<211> LENGTH: 25
<212> TYPE: DNA
<213> ORGANISM: Artificial Sequence
<220> FEATURE:
<223> OTHER INFORMATION: Probe sequence

<400> SEQUENCE: 13

```
cagttgactg gcrgctataa accta                                            25
```

```
<210> SEQ ID NO 14
<211> LENGTH: 24
<212> TYPE: DNA
<213> ORGANISM: Artificial Sequence
<220> FEATURE:
<223> OTHER INFORMATION: Probe sequence

<400> SEQUENCE: 14
cagaggaggg gtrgggggag gaga                                              24

<210> SEQ ID NO 15
<211> LENGTH: 26
<212> TYPE: DNA
<213> ORGANISM: Artificial Sequence
<220> FEATURE:
<223> OTHER INFORMATION: Probe sequence

<400> SEQUENCE: 15 tctcacccctt tcargctgaa agcaac                                           26

<210> SEQ ID NO 16
<211> LENGTH: 25
<212> TYPE: DNA
<213> ORGANISM: Artificial Sequence
<220> FEATURE:
<223> OTHER INFORMATION: Probe sequence

<400> SEQUENCE: 16
gaaagcaaca gtrcagacga tgaga                                             25

<210> SEQ ID NO 17
<211> LENGTH: 25
<212> TYPE: DNA
<213> ORGANISM: Artificial Sequence
<220> FEATURE:
<223> OTHER INFORMATION: Probe sequence

<400> SEQUENCE: 17
gaaagcaaca gtrcagacga tgaga                                             25

<210> SEQ ID NO 18
<211> LENGTH: 26
<212> TYPE: DNA
<213> ORGANISM: Artificial Sequence
<220> FEATURE:
<223> OTHER INFORMATION: Probe sequence

<400> SEQUENCE: 18
ttgatccaga gargacaaag ctcctc                                            26

<210> SEQ ID NO 19
<211> LENGTH: 28000
<212> TYPE: DNA
<213> ORGANISM: Homo sapiens

<400> SEQUENCE: 19
ggctgcagtg agctaagatt gtgccactgc accccagcct gggcaacaga gtgagaccct       60
gtctcaacaa aataaataaa tatattttga attaaattaa aatgaaaaaa cagcctatca      120
aaaagtgtgg gatgtagtga aagtagtgtt tagagggaaa gttatagcat tgaatgcata      180
tattaggaga agaaagatct aactcagaga gggatgaaca ggtgaggcat agggggatttt     240 aaggtagtga aactcttgca gggcagggga gccccaaaac tgggacaccg tccgggaagg      300
ctcttggctt cgtccaggaa ggaattcaag ggtgagctag aggaggaaga aaaaggttta      360
```

```
ttgaggcagc agggttacag ttctgtgact gtccctgcag agcagggcca ccccataggc    420
agtgcctgga gagcagcagc tcagggcact tctatagtca cattcatacc cactttaaa    480
tacgtgcaaa ttaagggcag gttattcaga aatttctaga agaagggtgg taactgggtc    540
attgccaggg aatgagtaaa ctgttcatgg tgctggtgct catgccagcc agtcttcaat    600
ctggccctga gtcaagcccc acctcctatc tcaaaactat tctgcatggt gctgtaatgg    660
tggatacatg acatgttatg tttggcaaaa tccatagaac tgtaggacac aagagtgaac    720
cttaatgtaa accttaatgt aaatggactt tgttaattaa tgatgtatta atatcaattc    780
atcaattgta acaaatgtat cacagtactg ttaataatag aggaacttat tggcaggaga    840
gagagcttat ggaactctct gcacattcag ctcaatattt ctgtaagcct aaaactgctg    900
tgagaaataa aatccaacct gggcaacata gcaagacctt gtctctacaa aaataaaaaa    960
atgagctggg tgcagtaacg catgcctgta gtcccaggta ttcaggaggc tggggcagga   1020
ggatcccttg aacccaggaa gttgaggttg cacgagtcat gatcatgccc ctgcactcca   1080
gcctggataa caaagcaaga tcctgtctcc aaaaataat aaaataaaat aaaaatctac   1140
taattgaaag ggaaaaaagc atagtataat accattctta acaaaaagaa aagagacctg   1200
tgtttgtgtg tgtgttaaca tttgaaaaaa atctggaaag ctctatatca aaacgtttat   1260
agaggcaatt ttgtagtgtt agaatcatag atgatctttc cacttcctgg ttttctgac   1320
tttttttctt tttgcagtgg gcatgtattg ctggaaaata ccacagacaa ctgtgaaagg   1380
atttcatcaa caacaaaaaa aagataaaga aggaaacaca aaatctgtta aataagattt   1440
atgttggctg gaggttaaaa tgcatttcca gagcagagtt cagagaaagg ctgggctgct   1500
tgttgctggc taaaggacaa agggtaagtt tcaggaagca gaagagtgag cagatgaaat   1560
tcagcactgg gatcagggga gtgtctgatt tgcaaaagga agtgcaaag acagctcctc   1620
ccttctgagg aaacgaaacc aacagcagtc caagctcagt cagcagaaga gataaaagca   1680
aacaggtctg ggaggcagtt ctgttgccac tctctctcct gtcaatgatg gatctcagaa   1740
atacccagc caaatctctg gacaagttca ttgaagacta tctcttgcca gacacgtgtt   1800
tccgcatgca aatcaaccat gccattgaca tcatctgtgg gttcctgaag gaaaggtgct   1860
tccgaggtag ctcctaccct gtgtgtgtgt ccaaggtggt aaaggtgagt ccaggcctgc   1920
ctggccaggg gaggggtggc tgaatgtgca agagttgaga ttgagaatga gagagagaga   1980
gagagagaag caaaaaccta gaacccaggg tgcaaatgtg agtacagaga gctgagatct   2040
tctgggatgt ggttctta tttatccaca cagcatgtta aaatagattc tggggtgaaa   2100
tcctacatcc ctattattaa caagtgaccc tccccctac ttcccgctga gtttatgaa   2160
ccactgtcct gggcgatgcc catttcagaa atagggaact gaatcccagc tctggtaaac   2220
agtttgctaa ttcgtggcca ggctaggggc tcaccatttc tgcagtgaag aatcatatgt   2280
tttgaaagca aatagcacct gctggctgca agaccttgag caagtcactt aactactctg   2340
tgttccaatt tcctcagcca taatccccaa tactgttgca gtcttgccag tgcaccttaa   2400
tgtagcagct tctcactgaa ttagtaccca aggttctttg tcctgcatcc aagaaaatta   2460
aggaacatgg acacaaacgt gagcttggag caaaagttca gtaagcaaaa gaagaaagct   2520
gtctccactg tggagaggga agtctgagtg gattgccaga ttgcagctga atgcaaaaaa   2580
cttttataag aaaccactct cctccctgta actgtttgag aaacttttta tcagtaaagc   2640
tgtgcaactt cccttacctt atgcagctgt gggtatatct ctaggcaagc ataaagcgct   2700
gcttctcttg tatgtataac tgtggatttg ttttaggtaa gtcccactcc ctgcgccagt   2760
```

```
ttcaggcagg ccgctcctcc agggcccagc cttgaccatt tacctaactg attttccctc    2820
tactttccct caatacctca tagggccgtg tagattaagt aaaatagtaa gtgtgaacca    2880
cccagcataa gctagtcctg ggcatcgtaa aggacaatgg gaaaagaaca cagatcctgg    2940
aagaaggccc ccaggtttga attgtatttg ccacctacta gctgggtgat ggggctgata    3000
tattatctca ctgagcatcc attttcccat ctgtaaaatg ggaactaatg ataatggcat    3060
ccaaatcata gcatcattgt gagcattata ggagtttaag acatgcaatg ccttcagaac    3120
agtggctagt gctccataat gttagtgatt gctcctgtca ttttatttag ggaggtttgc    3180
ctcactaagc atcaattatt attttgtcg tcttttcag ggtggctcct caggcaaggg    3240 caccacccte agaggccgat ctgacgctga cctggttgtc ttcctcagtc ctctcaccac    3300
ttttcaggat cagttaaatc gccggggaga gttcatccag gaaattagga cacagctgga    3360
agcctgtcaa agagagagag cattttccgt gaagtttgag gtccaggctc cacgctgggg    3420 caaccccgt gcgctcagct tcgtactgag ttcgctccag ctcggggagg gggtggagtt    3480
cgatgtgctg cctgcctttg atgccctggg tgagagctcc cagcttcttt ttctccctct    3540
tcccatttct gagcagaaat ctcccacagt ttgagagctt tttgccccaa cagggcatct    3600
ctctaaagca gggtgggagg agatcttagg atctgtcccg gggcaagaat gaatacggtc    3660
atgatctatc acaggagaga cattaaacag caaattggca taatgtgggg acaaagacat    3720
ttcttacaga acatctgcaa ggcttactgg ttctgtttaa ggcaaaatgt gtgaatttta    3780
tctttctaaa atcaggcagc aaagatgtgg cttaaagttc atgttactct catctttgtc    3840
ccaacatgag atctcatcaa acgtatgcag cacgttggga gatagatatt tataatttgc    3900
aggaacattt ggacaggaag tgtaacctct cagaggctcc cttgccacat caggagaatt    3960
ggtaaaacca cactacctgt atcatatcat tattttaagt gataaatgat catctacatt    4020
cagctctgat gagtaatagg tgttcaaaaa taggaacttc cagccaagtg tggtggctca    4080
tgcttgtaat tccaacactt tggaggctg aggcaggagg gtcgcttgag cccaggagtt    4140
caagaccagc ctgggcagca agtgaaacc tcatctctac taaaaatttt aaaacattag    4200
ccaagtgtgg tggtacatgc ctgtggtcgc agttattcag gacgctgaga ctgaacgatc    4260
acatgaggcc agccaaggat tcgaggtgtc agtgagccac gaatgtacca ctgcactcca    4320
tcctaggcac agagcaagag caagaccctg tctcaatcaa tcagtcaatc agtcaaaact    4380
atgaatttcc cagctgtata tgaaggcacc tcaaaacacc acagtgaact cacagaggga    4440
cacggaatag tttagatttt aattttttga gggaaatgcg atgacatctg tcacacaccg    4500
cacaaacggc tactattaaa ctgaacttac tgattagtgg ctactaatta atagttggtc    4560
attaagcagt aattagtgat taattatcaa gtaattagga cttaattaaa ggaactgtca    4620
cagtttcctt tagtcctagg gcagccatga aaaaaaaat gctgactctc caaagacacc    4680
agggtatgag aaagttttgg attctctcct ttgtgccatc tcctgtgttg ggggctgaag    4740
tacaatggtt gtaaaagaca agagggagaa ggctggtcac agtggctcac gcctgtaatc    4800
tcagcacttt gggaggccaa agtgggggga tcacttgaag tcaggaattc aagaccagcc    4860
tggccaacat ggtgaaatct cacatctact aaaaatacaa aaattagctg ggcgtggtgg    4920
tgtgtgcctg taatcacagc tactcggag gctgaggcag gagaattgct tgaacccagg    4980
agatggaggt tgcaatgagc caagatcatg ccattgcact ccagcctggg caacagagtg    5040
agactccatc tcgaaaaaaa gaaaaaagaa aagaatataa ggagtgatta aaaagaaaa    5100
```

```
gaaaagaaaa ctaagtaggg tgaaacaata gatagccatg ggggttaggg agcttttta    5160 gacagggtcg tgagggaggg tccctgagcc tgagtggcga gaaggagtga gccttgggga    5220
gatctggagg ttctgggaag aggaatggca agtgcagagg ccctgaagca gcaatgacca    5280
tggcacattt gaggaagaga gaaaaagtca gagaagtaga aagtgggcaa aggaagcaag    5340
acaggaggtg aggtgggaga ggttccagag accagatcac accagacatc attggccacc    5400
ataagatctt tgggttttaa aattccagat gttatgggat gcaggaagca gcatgatcag    5460
cagcattctc taggtgccag gttgagaaca ggctgtgggg gaacctgtaa agaggttgct    5520
gccatagttc cggcgagtga cggtggtggc ttggatgggg tgatggcagt ggagagggca    5580
ggagggagga tcaggaatgg acctcaagac ttcccagccc tgggtctgct gcacttttca    5640
atcaaacccc atggccaggg agattgtccc ctcagagtga ctgaaggaaa ttcagagaag    5700
agctgacacc taagttgtag attttgcccg aacaggtcag ttgactggcg gctataaacc    5760 taaccccaa atctatgtca agctcatcga ggagtgcacc gacctgcaga aagagggcga    5820
gttctccacc tgcttcacag aactacagag agacttcctg aagcagcgcc ccaccaagct    5880
caagagcctc atccgcctag tcaagcactg gtaccaaaat gtatggccct cccaccaggc    5940
ctggtgggtc ctgtctcgac tgggagcaga ggaggggtgg ggggaggaga gaaagaaggg    6000
agtgaaggga agaggagggg gagtggtgga gggaaataga gggatggaaa aggagagaa    6060 aggaaaaaga ggtggagaga ggagcctgca acagaaggga gaatgaaagg gaaggaagag    6120
agaaaggaag ggattttggt gttctgttca ctgctgtatc cccagaactt aaaacagagc    6180
ctggtgcata ataggtgtaa ataactgttg aataaatgaa tcaatgctac atacacacac    6240
gcacgcacac acacacagag agagagtcaa ccacactctt cagaaggtgg ataagttaaa    6300
acaagagttt caaacaaata tatgttcaga tgcccttttcc tcccacttac tggctggctg    6360
gccttaagta agcaacttaa ccttttctgtt ctttctgctt tcttatctgc aacgagtagc    6420
atgccatagc tagagtaaca cggcatatag ttggtcctga taaatgtagc atattttagc    6480
caccatagga gtacacataa taaaagctaa catgtagtat gtgcttagct tatctatgtt    6540
ttgtggatgt gatacaattt tctgttcact tttaaatgcc ctgcatctta gtcaatttta    6600
acagtgattc tgtaagttag ataaggttag gcattattat taaatccatt ttacaccaag    6660
agaaacttgg gtcaaaaaga gaaactcctg ggtcacatgg ctcattcggc caataagtag    6720
cagaagtaaa atttgaattt ggctgggcgc ggtagctcac accagtaatc ccagcacttt    6780
gggaagccaa ggcaggtaga ttgcttgagc ccaggagttc aagactagcc tgagcaacat    6840
ggcaaaacct cgtctctaca aaataaacta aaaatttagc caggtgtgat ggtgagcacc    6900
tgtagcccca gctactgggt aggctgaggt gggaggatcg cttgagcctg ggaggaggag    6960
gttgcagtaa gtcaggattg cactactgcc ctccagcctg tgagacagag caagatcttc    7020
tctcaaacaa acaaacaaac aaacaaacaa aaactcgaat ttgggtctat tgacttaaga    7080
gtttgcctga taataatagg cattcaatgt atatttcttg aatgaacgaa tgaatgaaaa    7140
taatcaggaa taaactttcc aatttaaaag taacacctct aggtaaaaaa aagacaatca    7200
tttagttgcc agacttctaa gtgtttgctg ttctatgaat tgtaatcatg agcctgagc    7260 attgtagaat ttacaaaagc agttcctgac aaaagcagca ctgcccccag ggacatattg    7320
aaaattaatg agggtgtttt tggtaaccat ggtgatggga ggacatgggt gctacttata    7380
tttagtggaa agaagacaag aatgctagtt attgtacaat gatcaagaga gtcctgcaca    7440
gccaagaatt gtcttttttct ttctttcttg atgctgttct cctttaaaac aagacaagat    7500
```

```
taacaataat ttaactccac taaccaccat catcaccacc tccaacttat atgctacatt    7560
tcttgtatat ttcaagtctg tttatatttt caagtgcctc gaagtattat tgttttatag    7620
ccaaatgttt agttaatctg ctcacagatt taccactttc ttcactattc attctgtctt    7680
acacctctaa cattccatct ggggtaattt tcctaaatga tcatgcatcc tttgggattt    7740
cttttgatga tggtctattg gtagtaaact ctctcagtta ttgtttgtct gaaaatgtca    7800
tgcttttgcc ttcattgttg aagggtgctt ttgctgggtg gtcatttcag tatattgaat    7860
atatcattcc atcttccagt gtcatcatta aaaagtcagt tgccagtcta actgcagctc    7920
ttttataagt aacctgtctt attcttctgg ctgcatgtaa aagttttctc tttgtctttg    7980
attttgttta gcttcaatct gctgtgtctt aatgatgggt tcctattgtt tgtcctgatt    8040
gggattccgt taagattcct gaatctgtgg gtagatatct ttaatcagtt ttgaaacttc    8100
tcagccattc ttctaaaata ttgattctcc ttcattctct cctcaccttc tagaattcca    8160
attaaatgta tgttagaccc tgctctatct ttcatatctc tatactctct tctgtgtttt    8220 tcatccttt gtctattttt ccatgcttta ttctgaatag ttccttctaa tctaccttcc     8280
aattaactaa ttttctcttt agctatatct aatttgctgt aattaattac agttgccatt    8340
tttatcctaa aatttctatt tcatattttt gtatctgcca tggtacttct tatggctttt    8400
aattccctgc taactattta aagttcttat tttatcctgt gaatatgata ttcctagtta    8460 ttttatttt aattttttatt atttgttaat cttatgtttt atttacactt cttttctgtg     8520
acatgagcac acacagattc atgtgtatac atatatggct ctgataccte tcctttcctg    8580 tcctcattca aaccactgat cacagagaga ggactatttt tttttatttt taattttct    8640 atttcaatag gttttttgggg gaacaggtgg tgtttggtta catgaataag ttctttagtg    8700
gtgattttgg tgcacccatc acccaaacag tgtacattgt acccaatgtg taatctttta    8760
acccttgcca caccccaccc tttccccgca gtccgcaaag tcccatgtat cattcttatg    8820
cctttgcttc ctcatagctt agctcccaca tatgagtgag aacatacaat gtttggtttt    8880
ccattcctga gttatttaat taaaataata gtatccaatt ccatccaggt tgctgtgaat    8940
gccattattt tgttcctttt tatggttgag tagtattcca tggtgtgttt gtgtgtgtat    9000 aacattttc tttatccact cattgattga tgggcatttg ggctggttcc atattttgc     9060 aattgcaaat tgtgctgtta taaacatgtg tgtgcaagta tcttttttgt ataatgactt    9120
cttttcctct gggtagatac ctagtagtgg gattgctgga tcaaatggta gatctacttt    9180
tagttctata aggaatctcc acactgtttt ccatagtggt tgtatgagtt tacattccca    9240
ccaatggtgt aaaagtgttc ccttttcacc acatccacac caacatctat tattgtttga    9300 tttttatta tgaccattct tgcaggagtg aggtggtatc acattgtggt tttgatttgc    9360
atttccctga taattaggga tgttgagcat ttttccatat gcttgttggt atttgttttt    9420 tttttttt tttcattatt atactttaag ttttaggta catgtgcaca atgtgcaggt       9480
tagttacata tgtatacatg tgccatgctg gtgtgctgca cccattaacc cgtcatttag    9540
cattaggtat atctcctaat gctatccctc cccaattccc cccacccgc ttgttggtat     9600 ttgtatatct tcatttgaga attctctgtt catgtcctta gcccactttt tgatgagatt    9660 tttttttct tgctgattcg tttgagttct ttgtagattc tggatattag ttggatgtat    9720
agattgtgaa gattttctcc cattctgtgg gttgtctgtt aactctgcta attatttctt    9780
ttgctttgca gaagcttttt agtttaatta agtcccatct atttatcttt gttttgtttg    9840
```

```
catttgcttt tgggttcttg gtcatgaagt ctttgcctaa gccaatgtgt aggagggttt    9900
ttccaatatt atcttctaga atctttatgg tttcaggtct tagatttaag tatttgatcg    9960
attttgagtt gaattttgta taaggggaga gagaaggatt cagtttcatt cttctacatg   10020
caacttgcca attatcctag gaccatttgt tgaatagggt gtcctttccc cattttatgt   10080
ttttgtttgg tttgtcaaag atcagttggc tgtaagtgtt tggctttatt tctgggttat   10140
ctattctgtt ccatttgtct acgtgactat tttatacca gtaccatgtt gttttggtga   10200
ctatggcctt acagtatagt ttgaagtctg ataatgtaat gcctccagat ttgttctttt   10260
tacttagtct tgctttggct atgtgagctc ttttttggtg ccatatgaat tttaggattg   10320
tttttttctag ttctgtgaag aatgatggtg gtattttgat gggaattgca ttgaatttgt   10380
agattgtttt tgggagtatg gtcattttca caatattgat tctacccatt catgagcatg   10440
ggatgtgttt ccatttgttt gtgtcatcta tgattttctt tcagcaatgt tttgtagttt   10500
tccttgtaga gttcctagtt attttaaagt ctgtgttcgg tctttcagca tttaaagttt   10560
gtaggtttat tactatttct cttctttctg ttggtcataa ctcttagtgt tttgtttcct   10620
tgtgtgcctg gttacatatg tgctggtcat tgtatttgaa aattatgtgt gaaataattt   10680
gaggttttgg attatgtata ttcctccaga aagaatttca tttgcttctg tgcatttctt   10740
aggaacatta caagtccttc ttctcagtta attttcgtag tatctttatc agataggtgc   10800
tattacaacc actcacttag cagatgaaaa tcatgaggct ctgagagtct aagtcatcta   10860
cttagaattg gacaatggtg aagccaggat tcaaacccac atcaataaga atccagcgct   10920
cttaacaagg ggccagtaca cttttttaaa aaataaaagg ctagatagta aatattttag   10980
actttgtgga ctgcacagcc tctgttgcaa ctactcaacc ctgcctttgt agcatgaatg   11040
cagtcataaa ctatacataa atgaatgagc ctggattcgt tccaaggaaa ctttataaaa   11100
acaggtggca ggctggattt ggcccatgag aagtgtagtt tacacaaaag ttgagcaaac   11160
caattttttt ctgattgttt ttcctcttct cagtgtaaga agaagcttgg gaagctgcca   11220
cctcagtatg ccctggagct cctgacggtc tatgcttggg agcgagggag catgaaaaca   11280
catttcaaca cagcccaggg atttcggacg gtcttggaat tagtcataaa ctaccagcaa   11340
ctctgcatct actggacaaa gtattatgac tttaaaaacc ccattattga aaagtacctg   11400
agaaggcagc tcacgaaacc caggtatgct atccccacat ggcttagctc ccctatgtaa   11460
atgaacacct ggatacaggt acagtgcctt ggaaatggag gaggtgggag ggctccccac   11520
ttagtgagaa tctcctgttg cccatcattg tactgggcat tttactactg ccatctgttt   11580
taaacaccta cctccaaccc tgtgaggcag gcactatgcc aattattta caggtgagta   11640
aactgaggtt ctgagaggta aggagcttgt ccaacccctta acagaaaatg agtaaaatag   11700
ctgcagtttg aactgaaata agaacagcag caacaacaat gatagtaatt gctcccaggt   11760
attgaaagct tgttgtaaga ctaacacatg ctaatataat agtaaaaatt attagcaata   11820
ttactgatat gtatgttatg ttctagtcgc tgtgctgagc atttcatata actgggcttt   11880
ttctatcctc acagcatagc ctttgagata ggtatgtgga actattccca ttttacagat   11940
aagaatcctg aggcttagag agttcaagtg acctacccaa gggcacatca ctgataaagg   12000
gcagaggtgg gattcaaacc cacatctgtc aggtgcaagt gcaaggctcc ttctcctcat   12060
gctcactgcc tgctggggaa tagggcactg gggacatacc ccaggagcc cttcctcatg   12120
ttctgagtcc cagttcatcc catgctgcta ttttgctctc ccaggagcat ctggactccc   12180
tagacagagc cccagcttct cacctgtccc tctctaaatg ctgctctgca ggcctgtgat   12240
```

-continued

```
cctggacccg gcggaccta caggaaactt gggtggtgga gacccaaagg gttggaggca    12300
gctggcacaa gaggctgagg cctggctgaa ttacccatgc tttaagaatt gggatgggtc    12360
cccagtgagc tcctggattc tgctggtgag acctcctgct tcctccctgc cattcatccc    12420 tgccctctc catgaagctt gagacatata gctggagacc attctttcca aagaacttac    12480
ctcttgccaa aggccattta tattcatata gtgacaggct gtgctccata ttttacagtc    12540
attttggtca caatcgaggg tttctggaat tttcacatcc cttgtccaga attcattccc    12600
ctaagagtaa taataaataa tctctaacac catttattga ctgtctgctt cgggctcagg    12660
ttctgtccta agccctttaa tatgcactct ctcattaaat agtcacaaca atcccatgag    12720
gcatttttaa aaattttta ttattttaga ttcagagggc acatgtgcca tttgttacac    12780
agctatattg tgtaatggtg gggtttgggc ctctattgat cctgtcgccc aaatagtgaa    12840
cagagtaccc aaaagaatt ttttcaacct ttgcctttct ccttcctcc tccctgttgg    12900 agtccctagt gtctattgtt cccatcttta gcagatgtta agtatttgat tttctgtttc    12960
tgggttaatt cacttcggat aatggcctcc agctgcaacc atgatttcat tctttcttat    13020
ggctgcataa tactccatgg tgtagatata ccacactttc tttatccagt tcacactgat    13080
gggcacttaa gttgattcca tgactttgct attgtgaatc gtactgcgat aaacatacga    13140
gtgccggtgt cttttgatag aatgatttct ttacctttgg gtagataccg agtagtggga    13200
ttgctgggtt gaatggacat tctacttta gttatttgaa aagtcccatg aggcatgttt    13260
tctatcattc ccatcttaca gatgagacaa aggctcagag aggtgaggtc acttgctcaa    13320
ggacatcagc taacaagtgg tggaaatgga attcaagctc agtggactct aaagccagtg    13380
ctcatgtcac tgtgctaaac agcctgcctt gtcacatccc cacctctcat ctgaccaatg    13440
ggagactctg agcagctgag tgacttgggt tgtcacacag ctaaacaggg gcaaaggacc    13500
cagtcttgga tctttccacc tccaagcagg aatctgtctg attccagggg attgatgatg    13560
ttgcagatgg ctaggaagca gactccagga tggaatttag tatgcaggat gttctggggg    13620
agagccactg gaaccagcac tcagggaaag gggggaagaa aggataggaa ggaagcatga    13680
aagagaatag ggagaagtga acagggatgc agagcgaatg ccagtttcag ccaactccaa    13740
ggacagccct ggagctggaa tggcctttag agctgcccca tggtgacaga ggtggccagg    13800
cttctatacc cctacgtgga tcactcactg tgcttgggca ccttgggaaa gggcatggct    13860
ttgagcaaaa ggctctctgc agctgaggca acccctaaaa gggctgacgg ctgaagtctg    13920
tctgctgacc actgtcccag cagctggggc ttgttagtcc ttcctcaaag ggggatccag    13980
atggcatgtc acagtgtcta ccgtaaatgc tcactgaatc cagctgcaat gcaggaagac    14040
tccctgatgt gatcatgtgt ctcaccctt caggctgaaa gcaacagtgc agacgatgag    14100
accgacgatc ccaggaggta tcagaaatat ggttacattg aacacatga gtaccctcat    14160 ttctctcata gacccagcac actccaggca gcatccaccc cacaggcaga agaggactgg    14220
acctgcacca tcctctgaat gccagtgcat cttgggggaa agggctccag tgttatctgg    14280
accagttcct tcattttcag gtgggactct tgatccagag aggacaaagc tcctcagtga    14340
gctggtgtat aatccaggac agaacccagg tctcctgact cctggccttc tatgccctct    14400
atcctatcat agataacatt ctccacagcc tcacttcatt ccacctattc tctgaaaata    14460
ttccctgaga gagaacagag agatttagat aagagaatga aattccagcc ttgactttct    14520
tctgtgcacc tgatgggagg gtaatgtcta atgtattatc aataacaata aaaataaagc    14580
```

```
aaataccatt tattgggtgt ttattaactt caaggcacag agccaagaag tacagatgca   14640
tatctagggg tattgtgtgt gtatatacat tgattcaaca agaaatattt attgagcact   14700
tactatgtgc caagcatagc tctgggcact gggaatatag caatgcacaa aagcagacag   14760
aaatccctgt cctcatgacc ctgcagagcc aagacttcca gaattttta aataaaaaaa   14820 tccctgtcct catggagttg acatttgtgc aaaacatctt aatgttagat ggttttccta   14880
ttactaataa ttctgaaata agcatccttg atttatcctt tctccatatc tctgagaaaa   14940
attatagaac ctccctgtgt gacacagcag ccactagcca catgtatcaa atgcttaaaa   15000
tgtagctagt ctaaatctac atgtgctgtg agtgcaaggt atatacttgg tttcaaagac   15060
ttagtacaaa tgaaaagaat gccaagttct tgccaactga taattttttt aattgtgtgc   15120
tgaaatgaca atttttaaat atatttgagt taaatcaaat gaacttcatc tctttctttt   15180
ccctttttaa ttgtggctac tagaaaatgt gaaatcatac atgtggcttg tgttatatta   15240
tgtatttcta ttggacagct ctgtcctcca aggtaaatca ctggattaaa gattcgacta   15300
tactgactta cattgccaca ttgtcacact gtccttggga ccaagaatca acatatcatt   15360
cataagactc taaatataaa aactctcata aatactcaca aaagaaccta gcatgctctg   15420
atcacctgag ttgctggtca cttttggtgg ctggtaagca gcctttggtc cgtccagatt   15480
atattcttcc atttagtccc cccacatccc tgtgagatgg gttttgttgt tattctcata   15540
atattaagtg gaataacttg aggttctaag aggttacagt gcttgcccag ggtcacccag   15600
ctggtcaggg gcagagtctg aacttgaacc ctaatccttc tctctctaaa gctcatgttc   15660
ttaatcactg tagcatggtc ttaatgtgtc ctcattcatt gaaagcttat gttttcctac   15720
tctggcgcca tgagaaccag aagcatcaat gtccaggggc agggaaagat gaatgtccca   15780
gctcaacctg agcacagatt caccccttcct cggtcttttt gtcctatttg tagactggat   15840
tagatgatgc cagtctactg attcaaatgt gaatctcttt cagaaaaacc ctcacagata   15900
cacctagaaa tgatgtttca ccagctatct tggcacccct agcccagtca acttgtcaca   15960
taaaatcaat catcacacac tccatgctga taggcaagtg tggacatccc aatgtaatgg   16020
cttcattgta ttttactgtg tggaaaatgc acttgtgttg cctttgaga gtgtttcatt   16080 ttatagcaat gccacaacca acagtagatt aatggaatca gtaattagtt gcttgatcga   16140
agagccacat ggccacgtga tcagccttcc atctacaaca ggacccagga gtataccggg   16200
attgtttttc aaagggcata gacattttg ctgcaaatga catgggctta ctccagagtc   16260
ctggaggggt ctgtgttata attctctaaa tagatattgc cataatctct gaatgacacc   16320
ttttcccatg actaacactt tgaacaccat ggggtctgcc aggctggtgt gggccaagta   16380 gagggcgac ttgcaccaca gcctatacca gctgcagagc cctttaggac ttaataaaag   16440
ggtgctaatt tctgtacttc cctggctctg agatgtaata gtggttttaa tttactatcc   16500
tggccaggga ggtggcagtt tcaaaggtat ccccatgacc ttcctcactg tgatagccct   16560
cacttaaccc tcaggccaat gtcgggtagt gtcttttacc aagcatgtcc ttttgaata   16620 tacattcagg ggacagggaa atgatcacca ggtcggtcca tagacacagt gggcaaatga   16680
caagcctgac ttgccaggg ctccattttt cactcttggc tcctatatgc ccctactctg   16740
atggggacag aatctgatga cgcttttcgt tatcagtgtt gatcctctgc ccaacagtct   16800
tagaaatgtt gagtgactcc ccttttccag tgtatcatcc tctgaataaa tggccatagg   16860
tcctttgggg gaaaccatta ctatatatgc tatggtgtca cagcatcctt tcccaagggg   16920
actctgcctc ctctttgtta atggggtcta gtctgaaaac tgggttggtc agttccaaaa   16980
```

```
atcaggaagg gatgatgact ttttattgga atggctcccc ttaacccct ggtcgtccgg    17040 ccttgatttc ttctaatggt ataaattgag tagtgcccct tcaagatact catccactaa    17100
gtcactaaga ggccacattg tgttaaccag gtccctaacc ctgtatcagt cacgacccct    17160
ggctgcccct ccaacctcac cattcattat agtcattgca cccacctggc ttctattgct    17220
ctgggagtcc tgcctgccct attgcccttt tcaatccaag ctctgtaaca gcccctcttc    17280
ccaggaggcc accaccagaa cacctcatga tgcaggtgtc cctctctcca cacattcctt    17340
atggcctcgg ggaatgtttt gtccctggg actctatttc cagacttaca tagtaaacat    17400
atccactcct cttcactgtg cccatttccc ttggcctctt aataccttct tccatcagct    17460
ccacagcaat tctggaattt catacttttc tgcatttcta ggagccatcc taggagtcag    17520
ggaaaacctc ggcttcacaa gtaaatggga cttcagttgt gtgccaacat gcctggctaa    17580 ttttttaaatt tttttgtaga gatggggtct tgctgtgttg tccaggctgg tcttgaactc    17640
ctggcctcaa acaatctttc ctccttggcc actcaaagtg ctgggatcac agctaccatt    17700
cccacacaca ttttcttatt tttaaaggct gtatgtgcac tgtatacatt aaatgtgtgc    17760
actgtataca ttaactgtgt gcactgtata cattaatttt ctttaacgaa tttatccatt    17820
tatagttgct ttggttgttt ccacttgatt attgtgaata gtgctgcagt aaacatggga    17880
atgcagttat ctctttgata tcctgatttc aattcttttg gatactcaga agtgggattg    17940
ctggaacata tcgtagttcc attttaatt tttttgaggaa cctccatact gttttcaca    18000 gtggctcacc aacagtgtgc aagagttccc atccctccac atcctcacac ttgttatctt    18060
ttgttcattc tttaaaaaat gatagccatc ctaccaggag taaggtgata ttgcatcgtg    18120
attttgattt gcacttctct gataattagt gatattgagt atatttcat agacctgtta    18180 tccatttgtg tgtcttcttt ggagaaagat ctattcctat ccttagccca ttttaaaatc    18240
aagttattaa ttttttttgct agtgagtggt aggagttcct tacatattgt ggagattaac    18300
ccttattaga tgtatggttt gtgaatgttt tcttcattcc atagattgtc ttttcagccc    18360
gttgattgtt tccttttgcta tgcagaagct ttttagtctg atgtagtcca agttgcctat    18420
ttttgctttt gttgcctgtg ctttgcatac gtggccacct gatctttgac aagattgcca    18480
agaatacaca atggggaaag gacagtgtct tcaacaaatg gtgtttggaa agctgaatgt    18540
ccacatgcaa aagaataaaa ttggacccct accttacagc atacacaaaa atcaactcaa    18600
aatggattaa agacttaaac gtaagacctg aaactgaaac tactagaaga aaacttaggg    18660
gaaaacttca tgacattggt cttttccagtg atttcaggga tgtgacacca aaagcacaga    18720
caacaaaagg catttatttt tatatggcat gtgaggaagg ggttcagttc cagttcttcc    18780
aatgtggatg ctcaattatc ccagcagcat ttattgaacg gatcatgttc tctccacttc    18840
tttgcaaagc cacctcttaa atattcccag agcccatcta tgtgggagtc tgtttctgga    18900
ctctgctctt ttccattggt ctattttttg tgtccttgag ttaacacaac cttgtcttaa    18960
ttactataac cttataattc ttagtatctt tgggagaact ctgttctctt tttatcaagt    19020
cattggttcc tcttggccct ttttatttct acattaattt tatactcaat ttgtgaagct    19080
cctcccaaaa tatggggagg catttgatta gaattacaca tattagcttg ggaagaataa    19140
catctatatt ttatatatat atctatatag aatttgatga ttctgatcca tgaacttgga    19200
gtttcttttc attaattttt gtcctctttta gtgacagtga caatgtttta tcatttttccc    19260 tgcagaggtc tttcatggtt tttgtcatat gtattcccaa gtatttgttt cagtactatc    19320
```

```
gtacttggca tgctttcttt aatttcattt tgcaatggtt gcttcatggg agacttaaac   19380
attttcagtg gtgatatttg gctatagcat tataggtgat ctttatactt ttctaaattt   19440
tctgtggcca cggaaataa taaagacact tttcttgcac agaaaaaaaa aactttggg    19500 aagtatttct cacagctaag atctgatagt ttacgcaaag ttggcaggca caggctacag   19560
aaagctctgg ggtgctgttg tttggagctg ctggttcaag gacaaattca caagatttgg   19620
aaacagagga ccaagtgtgt aaggacgagg gaaactatgg tataacattg aagcacctga   19680
gctggaaatt tctgagccct cagagataaa tttcctcagc tcctccctgc cgagaaaaca   19740
aaactaaaaa gagttaatgt ttagccaaca gaaatgagag tgaagttcac agaagaaatt   19800
agggcacagc tggaagtgtt caaaatgagg aaacgttcaa tgtcaagttt gagatccagg   19860
gttgatgggt gaactctgca cgctcagctt catgttaggt ctcccagctc aacgagggg    19920 tgaattttgg tgtactgctg tctttgaggc cctgcgtgaa ctctcccaca ccctccccct   19980
tttcctcata caaatcccct ccttgcacac ccctcacgcc tgtctgtgag gtgccagggc   20040
ccctctccca gccaaccgca ggccagtatt gcccctcccc aaacttccct tcaggcagat   20100
caaacccagg gctctggagt cacactgcct gggctcaaat cctgcttctg aatcttatga   20160
gacatcaagt cacttaccta actccttggt gaaacaggct ctcctctgtc aaataggtgt   20220
gcatgctttg ggaggccaag gcaggaggat tgcttgagcc caggagttca agaccagcct   20280
gggtaacata gtgagaccct gtctctataa aaataaaaaa attagccagg tgtggtggct   20340
catgcctgta gtcccagcta ctcaggaggc tgaggaggaa gaattccttg agcccacgaa   20400
gtcaaggctg cagtgagcca tgatcaagcc gctgcactcc agcctgggca acagaatgcg   20460
accctgtctc agaaataagt aaataaataa atacataaat aaatttgggt gcaattgtgg   20520
ctcttagtgt tacagagagg actgaaggag ctaatggatg atggatttat ggcagtacct   20580
cacatatagc ttatcctaaa ggaagttaga gcttattatg atgattattc aaaaatattt   20640
atcaaaggtc tgccctgggc catgttctga gctaagtgct ggggatgcaa agatgagcaa   20700
gagactcctc agggacaatt gtctgatgag ataacaggca ctatttatga gaggtccaat   20760
caatacagtt ctatttatct tataattatc caataaatga tataataatt tattagaggg   20820
ccaataaatc tgatggcagg agcctgtggg gggtaatggc caggtctcac tattgtgccc   20880
aggctggtct tgaactcctg gcctcaagca ttccttctgc ctccacctcc cagcatgctg   20940
caattacaga ggcatgaaca actgcacctg gcctaaaatt ttatgttaat aaaaaaatgc   21000
atgtatttga ggagtacgac atgatgcttg aatatcatac tgtatcgggg gaaaccagcc   21060
cccgatattt caatgtaggt tcttttctat ttttccccaag tgtcggctgg tctgagaaat   21120
aaagggaaag agtacaaaag agataaattt taaagctggg tgtccagggc agacatcaca   21180
tgtcggcagg ttctgtggtg ccccctgagc cataaaacca gcaagttttt attagcaatc   21240
ttcaaaggga ggaatgtac atataggtg tgggtcacag agaacacatg attcaagggc    21300
gacaaaagat cacaaggcag aaggtcaggg tgagatcaca aggtcagggc aaaactagaa   21360
ttactaagga agtttcatgt tccactgtgc atgcattgtc attgataaac atcttaacag   21420
tgttcaagag cagagaacca gtctgactag aattcgccag gctggaattt cctaatccta   21480
gcaagcctgg gggtgctgca ggagaccagg gcgtgtttca tcccttatct gcaactggat   21540
aaggcagaca cccccagagc ggccatttta gaggccccc gggaatgcat tcttttccca    21600
gggctgttaa ttattaatat tccttactgg ggaaagaatt cagggatatt tctcttacct   21660 gttttttggta ataagagaaa tatggctctg tcttgcctgg ctcccaggca gtcagaccta   21720
```

```
atggttatct cccttgttcc ctgaacatcg ctattatcct gttcttcttt caaggtgccc   21780
agatttcata ttgttcaaac acacatgctt tacgaacaat ttgtgcagtt aacgcaatca   21840
tcacagggtc ctgaggcaac atacatcctc agcttatgaa gatgacagga ttaagagatt   21900
aaagacagac ataggaaatt atgagagtat tgattgagga agtgataaat gtccatgaaa   21960
tcttcacaat ttatgttctt ctgtcatggc ttcagtaggt ccctccgttc ggggtccctg   22020
acttcccaca acatcactgt atacctgaaa ttagcattga ttctaattct ctggtcacac   22080
gtcattcaga gcataggatc ttcggtggat ttaagaagtg cctccctccc tattctcagc   22140
catgtgactc ccagaatcct atgaaattaa agatcttgtg tttggccata ggagacttct   22200 attccaccatc tttgttctct cccacaaatg gcgaggcctc cagtctccca catgacagct   22260
ttgtactaaa atcaaccttta ctctatagaa catgcatgat tgcagcagga ctactatgat   22320
cttggtttga tgaattagtt aggataacat tagctgctgt aacaaacaga cccccaagct   22380
gcagcatgac tcagatgcaa tataagtgtc tttttcactt atatcaagca agaatgacca   22440
gattttctga ttttttttttc cgctgtgcta atgtagggag aagttgttgg aggtcacgtc   22500
acagttcaca gcaaccatct atgtttggga gcaaggatgc tggaaataga atccagcata   22560
cttgtagctt gtccataatt acagacacct ttgcatttac tgaactgaat cctatgactt   22620
gaagaccaaa gactgtagca tgcctgaagg gacagcctca gaactgtgga tgcctgtccc   22680
tctcctggtt tgggtttgtg ctgaccacag gcaaacccac tgaactcagg atcactgcat   22740
aaagtgacgt attaagccta gtgccaggat ctttagtgtt tgcaggaagg tctcatgatt   22800
tttctgctaa ctcagctaat aggtagtcct ctgtcccttc aagttacaaa cacatccttc   22860
attcaggaat ttgaatgttc agtccttgat atttttatcaa cccttcattc tgtggtcaaa   22920
gggcagacgt ctctcccagt taagactgga agttagcagc ctgcctccag ggatggggtt   22980
gtggttgcct tctgctctct ctgttcctct gggaagcagc agaatcattc catgggagga   23040
ctagagcagt tctttcttga gagaagagat ttactccttc caagtgtatt ggttagtgat   23100
tgctacataa caaactaccc caaaactctc agtagcttaa aacaactgtg aagtgattga   23160
tgctcatgtg agcatgggtt ggttgatcca ggctgggctc agctgggcac ctctgtatat   23220
gctgtgggtt ctcctgagct caactccttc ctgccagttg catttaaggc tgttctgtgc   23280
gtgtcttctg gagcccaggc tgaatgggct ttggagatgg cagaagcaca agcgagtaaa   23340
cagagacaca tgaagccatt taaggcctca gcccagcact gacgtgccgt cacttctcac   23400
attccactgg ccatgcaagt cacatggctg agcaaaactca aggacttggg aagtaaccat   23460
cgtctttagt gggaggaact acaacatccc atggcaaagc atggatccag gaagcagtga   23520
aatgggggcc agtgactcag tttaccacac tgaggtctgg cagatggcta gaagtggcgc   23580
tttctcttga ggattggggg agagggtgtg tttatggatt ctacagcaat cccaggcctg   23640
ggaacctctg taagtccctt tcccagggcc tctacatctc tcctctacat ggtcccgtct   23700
aactcctgcc tcatctagat ttctgtacca cacccagctt cttgtgagca tctctttgct   23760
gccagagggc cctgtgagac aagcccccaa gatgacccca tgccagaatt gtcacccatg   23820
tgattcacat ctggaccaga ggaaatgcct cccaaatgaa gccatcctg cccccatcag   23880 gcaactacag gccacttcag ctttcttggg tgtaaggcag acctcagaat ctctgtgtct   23940
cccagctaga tggaaagctt tccaggggct ccttgggaag ccagctggat tgaggcaagg   24000
aatatcacac ccccatccat ctcccaaagg gaagcaacac atcacctgac aacagttctc   24060
```

```
tccagggcaa tctctttgcc aaacattgct cctctccaca ctccaacccc tttatgtatt   24120
cttaacatga ctgaggagcc cctttataaa ttctgcattt gggagtttgt tgcatattct   24180
gtttggttcc tggagttacc tacacaagag cctcaggcaa tgagatttta tttatcaaac   24240
cattaccaga tgtcaggtgc tgtcccaaac actttgtaaa tgttaaccca tttaatcctc   24300
atataaatcc tatgaggtag gtgctattaa catctttatt ttagagatag ggaagctgag   24360
gcacagagag gttaagtaat tagcccaaag tcacacagaa ggcaactgtc ttctcaccca   24420
ggcaagaaga gtcctttttt atgataataa ggtggaagaa ggcaaggggg agataagcaa   24480
gaagatgata atgatgatgg tggccttccc tgagttactg tgcttagcac ttagtgtgcg   24540
tggccttgcc ttgcctgtcc tttgagacag gtatgtcaga ctctccccat ttcgcagatg   24600
aataaactga ggctgatata gtttgaatgt atgtctccac ccaaatctca tgttgaaatg   24660
taatccccag tgttggaggt ggggcctgtt gggaggtgat tggatcatgg gggtggattt   24720
ctcatgggta gtttaacacc atcgccttgg tgctatcctt atgatagtga gtacattctc   24780
atgagacctg gttgtttaaa actgggtggc acctcctccc cactttctct cactcctgct   24840
ttcgccacat gatatgcctg ctccccctt gccttctgct atgattgtaa gcctcctgag   24900 gcctcccag aagccaagca gacgtcagta ccatgcttcc tgtaaagcct gcagaaccat   24960
gagccgatta aacctctttt tctttataaa ttacccagtc tcagatatcc cttaatagca   25020
atgcaagaat ggcctgatac agaggctttg agaggtcaag tgacctgccc aagggcacac   25080
cactgataaa ggacagatgt gggatttgaa cccacctttg ttaggcccca gtgcaaggcc   25140
ccttctcctc atgctcactg cccactgcgg agctgggcac ttgggacaca ccctagggag   25200
ctgtgctctg ctggggcctt cctcatgccc caagtccctg cctgcccaag gccggtgctc   25260
tgagtctcct acagccccct cctcagcctc actggcctca gtcatcttgg ttcagggaag   25320
gactaaggtc cccctttggtc cctgccaatc tgcacccccac cccagtgtga ccctcaagag   25380
cctgactctg gccttttaca gaataaatct gaacaaaatc agggttcatt ttaatagcaa   25440
caggctgctg atgcagacct tatcaactcc atcaaactgt gttctttcaa atgttacgct   25500
cccctggggg tgtcccacac cctgacgtca cacattcact cagtgaagcc catattcatt   25560
cggggagctc tttctttctc tcttctctaa cacacactct ccttggttag ctggctgctg   25620
atcaacattt ctggatatac tggttttcag gaaaatatga tggttggctt ccaatcccag   25680 attttttcact gatgggttcc atatttacac catcttggcc acagtctctg ggtcaccatt   25740
tccacacata cccacacacc ataaagagag cttttttctg agtcttctgt tcatgcagtc   25800
tggaattgta tttgcttttg ttttggggca tcctgggcag ctcattccac taataggcat   25860
aaccataacc attgcagtct ccacttactg acatttacaa cttttccaggc acatgctagg   25920 gaccttacat tcattatttc attttattct cacatcacaa cctttgtgagg tggaggagca   25980 tgatggaagg aggaaggagc taaaagcaaa gaatctggag tccgactgcc tgggttcaaa   26040
tcctagctct accaatttcc agctctgtaa catcgagcta atttcctaac ctctctatgc   26100
catttcccta tctctaaaag gaagctgaca atagcatcta tctcatagga tttgtacgaa   26160
gattaaatga gtcaatattt ataaagtgtt cggaatgata cctgacatct ggtaatggtt   26220
tgataaataa aatccatttt aatgatgagg aaacaggctc agaagagggc gctcatttgc   26280
tcatgtggta cagataggtt ccagactcaa actcaagacc atctgactct aaaacatcta   26340
aaactgttgc cccgcattct cttcatttga cagataataa aactgaggct cagagaagct   26400
aagtgactcg cctgggactg cacagcaaat caagacaaat aagacctagg gtctcctgac   26460
```

```
tgccagagtg gagatgcttc tataggcttt tctcactgat gctctctggg cagacaggct    26520
cctcaatatg agagtgacac acactccttt cttcattttc aggtaaacct cacactggtt    26580
ggcagaagga actataccaa taattagtga acatgcggtg aatttgcaac agacaagagg    26640
agcctcatta tcctatagtt tccaggttgc ttagggaggc agaaatcaca gcaaggaaaa    26700
ccttcaataa taaacagacg tctcataaaa ttaattgcaa cccaacctct ctctctactt    26760
aaaattagca tctatttcca gctctgcttt caatgcccca tatgaataca tgtgaactcc    26820
ctccctctct tcctccctgt tccttctct ctctctctgt ccctcattaa aaataaaat     26880 ttaagaaaaa aatacaaggt agatttacac aaatagtggg atctcagtct tgagttagct    26940
gtgtatgact gaaaggatg ctgtggttaa taattatcat aaaaacaatg acatggccgg    27000
gcacagtggc tcacgcctgt aatcccagaa ctttgggagg ccgaggcagg cagatcactt    27060
gaggccagga gtttgagacc agcctggcca acatggtgaa actgcatctc tactaaaaat    27120
acaaaaatta gccgggcatc aatggccagc ccctgtaatc ccagctaatc aggagtctga    27180
ggcaggcgaa tcacttgaac ctgggggctg gtggttgcag tgagccgagc tcacaccact    27240
gcactccagc ctgggcgaca gagtgagact acatctcaaa aaaacaaaaa caaacaagca    27300
aaaaaaaccc cacagtaaca caaaagtaat aaaactgctg ctatttactc agtgcttatc    27360
tgatgccagc cactttgcta agcctatgaa tgcattattt ccccgttgct acagatgaga    27420
gaattgaggt tcagacaggt tgaaatcatt gctcccaaag tcacacaact ggtgagtggc    27480
agagctggga tgcaaaccct aaactgccag ccctcaaagc ctgtgctctt aatctccacc    27540
ctgctgtgct tccttgtcca tttaattaag ctccacaggc acacattcca cgccctcctt    27600
tgctgtacaa tcccaggcaa gtcgctcagc ttctctgagc ctcagtttca taatctgtca    27660
aatggaggta acacaaataa ttcctagttg tgaccaagaa tcatcataga aatctgccat    27720
ttccagccta ttgtgcaatt cctcaagcac tgtgactcca agtggcatca gctcctggaa    27780
gaacacactg tcttactgtt gtttcctcct ttgtcaactg atccccctt gaacctcact     27840 ctacctctgc tctcaatgcc ccatctactg ccacctgatt aaataaaatc ttttttgaaa    27900
atcataagtg tcatgagtaa ggtttcttgg tgttgatgta gaagaacaaa acagaattgt    27960
gaaatgagaa tcactgcagc tatcatgaag tcctgcctac                        28000
```

<210> SEQ ID NO 20
<211> LENGTH: 218
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Gly or Ser

<400> SEQUENCE: 20

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
            165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn
210                 215

<210> SEQ ID NO 21
<211> LENGTH: 240
<212> TYPE: PRT
<213> ORGANISM: Homo sapiens
<220> FEATURE:
<221> NAME/KEY: VARIANT
<222> LOCATION: 53
<220> FEATURE:
<223> OTHER INFORMATION: Xaa is Asp or Asn
<220> FEATURE:
<221> NAME/KEY: VARIANT
<222> LOCATION: 137
<220> FEATURE:
<223> OTHER INFORMATION: Xaa is Leu or Phe
<220> FEATURE:
<221> NAME/KEY: VARIANT
<222> LOCATION: 184
<220> FEATURE:
<223> OTHER INFORMATION: Xaa is Gly or Ser

<400> SEQUENCE: 21

Ser Val Ser Arg Arg Asp Lys Ser Lys Gln Val Trp Glu Ala Val Leu
1               5                   10                  15

Leu Pro Leu Ser Leu Leu Met Met Asp Leu Arg Asn Thr Pro Ala Lys
            20                  25                  30

Ser Leu Asp Lys Phe Ile Glu Asp Tyr Leu Leu Pro Asp Thr Cys Phe
        35                  40                  45

Arg Met Gln Ile Xaa His Ala Ile Asp Ile Ile Cys Gly Phe Leu Lys
50                  55                  60

-continued

```
Glu Arg Cys Phe Arg Gly Ser Ser Tyr Pro Val Cys Val Ser Lys Val
 65                  70                  75                  80

Val Lys Gly Gly Ser Ser Gly Lys Gly Thr Thr Leu Arg Gly Arg Ser
             85                  90                  95

Asp Ala Asp Leu Val Val Phe Leu Ser Pro Leu Thr Thr Phe Gln Asp
             100                 105                 110

Gln Leu Asn Arg Arg Gly Glu Phe Ile Gln Glu Ile Arg Arg Gln Leu
             115                 120                 125

Glu Ala Cys Gln Arg Glu Arg Ala Xaa Ser Val Lys Phe Glu Val Gln
         130                 135                 140

Ala Pro Arg Trp Gly Asn Pro Arg Ala Leu Ser Phe Val Leu Ser Ser
145                 150                 155                 160

Leu Gln Leu Gly Glu Gly Val Glu Phe Asp Val Leu Pro Ala Phe Asp
             165                 170                 175

Ala Leu Gly Gln Leu Thr Gly Xaa Tyr Lys Pro Asn Pro Gln Ile Tyr
             180                 185                 190

Val Lys Leu Ile Glu Glu Cys Thr Asp Leu Gln Lys Glu Gly Glu Phe
             195                 200                 205

Ser Thr Cys Phe Thr Glu Leu Gln Arg Asp Phe Leu Lys Gln Arg Pro
         210                 215                 220

Thr Lys Leu Lys Ser Leu Ile Arg Leu Val Lys His Trp Tyr Gln Asn
225                 230                 235                 240

<210> SEQ ID NO 22
<211> LENGTH: 237
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Gly or Ser

<400> SEQUENCE: 22

Met Met Asp Leu Arg Asn Thr Pro Ala Lys Ser Leu Asp Lys Phe Ile
 1               5                  10                  15

Glu Asp Tyr Leu Leu Pro Asp Thr Cys Phe Arg Met Gln Ile Xaa His
             20                  25                  30

Ala Ile Asp Ile Ile Cys Gly Phe Leu Lys Glu Arg Cys Phe Arg Gly
         35                  40                  45

Ser Ser Tyr Pro Val Cys Val Ser Lys Val Val Lys Gly Gly Ser Ser
 50                  55                  60

Gly Lys Gly Thr Thr Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
             85                  90                  95
```

```
Glu Phe Ile Gln Glu Ile Arg Arg Gln Leu Ala Cys Gln Arg Glu
                100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
                180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Val Trp Pro Ser His Gln
210                 215                 220

Ala Trp Trp Val Leu Ser Arg Leu Gly Ala Glu Glu Gly
225                 230                 235

<210> SEQ ID NO 23
<211> LENGTH: 259
<212> TYPE: PRT
<213> ORGANISM: Homo sapiens
<220> FEATURE:
<221> NAME/KEY: VARIANT
<222> LOCATION: 53
<220> FEATURE:
<223> OTHER INFORMATION: Xaa is Asp or Asn
<220> FEATURE:
<221> NAME/KEY: VARIANT
<222> LOCATION: 137
<220> FEATURE:
<223> OTHER INFORMATION: Xaa is Leu or Phe
<220> FEATURE:
<221> NAME/KEY: VARIANT
<222> LOCATION: 184
<220> FEATURE:
<223> OTHER INFORMATION: Xaa is Gly or Ser

<400> SEQUENCE: 23

Ser Val Ser Arg Arg Asp Lys Ser Lys Gln Val Trp Glu Ala Val Leu
1               5                   10                  15

Leu Pro Leu Ser Leu Leu Met Met Asp Leu Arg Asn Thr Pro Ala Lys
                20                  25                  30

Ser Leu Asp Lys Phe Ile Glu Asp Tyr Leu Leu Pro Asp Thr Cys Phe
            35                  40                  45

Arg Met Gln Ile Xaa His Ala Ile Asp Ile Ile Cys Gly Phe Leu Lys
50                  55                  60

Glu Arg Cys Phe Arg Gly Ser Ser Tyr Pro Val Cys Val Ser Lys Val
65                  70                  75                  80

Val Lys Gly Gly Ser Ser Gly Lys Gly Thr Thr Leu Arg Gly Arg Ser
                85                  90                  95

Asp Ala Asp Leu Val Val Phe Leu Ser Pro Leu Thr Thr Phe Gln Asp
                100                 105                 110

Gln Leu Asn Arg Arg Gly Glu Phe Ile Gln Glu Ile Arg Arg Gln Leu
            115                 120                 125

Glu Ala Cys Gln Arg Glu Arg Ala Xaa Ser Val Lys Phe Glu Val Gln
130                 135                 140

Ala Pro Arg Trp Gly Asn Pro Arg Ala Leu Ser Phe Val Leu Ser Ser
145                 150                 155                 160
```

```
Leu Gln Leu Gly Glu Gly Val Glu Phe Asp Val Leu Pro Ala Phe Asp
            165                 170                 175

Ala Leu Gly Gln Leu Thr Gly Xaa Tyr Lys Pro Asn Pro Gln Ile Tyr
            180                 185                 190

Val Lys Leu Ile Glu Glu Cys Thr Asp Leu Gln Lys Glu Gly Glu Phe
            195                 200                 205

Ser Thr Cys Phe Thr Glu Leu Gln Arg Asp Phe Leu Lys Gln Arg Pro
210                 215                 220

Thr Lys Leu Lys Ser Leu Ile Arg Leu Val Lys His Trp Tyr Gln Asn
225                 230                 235                 240

Val Trp Pro Ser His Gln Ala Trp Trp Val Leu Ser Arg Leu Gly Ala
            245                 250                 255

Glu Glu Gly

<210> SEQ ID NO 24
<211> LENGTH: 256
<212> TYPE: PRT
<213> ORGANISM: Homo sapiens
<220> FEATURE:
<221> NAME/KEY: VARIANT
<222> LOCATION: 64
<220> FEATURE:
<223> OTHER INFORMATION: Xaa is Asp or Asn
<220> FEATURE:
<221> NAME/KEY: VARIANT
<222> LOCATION: 138
<220> FEATURE:
<223> OTHER INFORMATION: Xaa is Leu or Phe
<220> FEATURE:
<221> NAME/KEY: VARIANT
<222> LOCATION: 185
<220> FEATURE:
<223> OTHER INFORMATION: Xaa is Gly or Ser

<400> SEQUENCE: 24

Ser Val Ser Arg Arg Asp Lys Ser Lys Gln Val Trp Glu Ala Val Leu
 1               5                  10                  15

Leu Pro Leu Ser Leu Leu Ser Met Met Asp Leu Arg Asn Thr Pro Ala
            20                  25                  30

Lys Ser Leu Asp Lys Phe Ile Glu Asp Tyr Leu Leu Pro Asp Thr Cys
            35                  40                  45

Phe Arg Met Gln Ile Xaa His Ala Ile Asp Ile Cys Gly Phe Leu
            50                  55                  60

Lys Glu Arg Cys Phe Arg Gly Ser Ser Tyr Pro Val Cys Val Ser Lys
65                  70                  75                  80

Val Val Lys Gly Gly Ser Ser Gly Lys Gly Thr Thr Leu Arg Gly Arg
            85                  90                  95

Ser Asp Ala Asp Leu Val Val Phe Leu Ser Pro Leu Thr Thr Phe Gln
            100                 105                 110

Asp Gln Leu Asn Arg Arg Gly Glu Phe Ile Gln Glu Ile Arg Arg Gln
            115                 120                 125

Leu Glu Ala Cys Gln Arg Glu Arg Ala Xaa Ser Val Lys Phe Glu Val
            130                 135                 140

Gln Ala Pro Arg Trp Gly Asn Pro Arg Ala Leu Ser Phe Val Leu Ser
145                 150                 155                 160

Ser Leu Gln Leu Gly Glu Gly Val Glu Phe Asp Val Leu Pro Ala Phe
            165                 170                 175

Asp Ala Leu Gly Gln Leu Thr Gly Xaa Tyr Lys Pro Asn Pro Gln Ile
            180                 185                 190
```

```
Tyr Val Lys Leu Ile Glu Glu Cys Thr Asp Leu Gln Lys Glu Gly Glu
        195                 200                 205

Phe Ser Thr Cys Phe Thr Glu Leu Gln Arg Asp Phe Leu Lys Gln Arg
        210                 215                 220

Pro Thr Lys Leu Lys Ser Leu Ile Arg Leu Val Lys His Trp Tyr Gln
225                 230                 235                 240

Asn Val Trp Pro Ser His Pro Ala Cys Trp Tyr Leu Tyr Ile Phe Ile
                245                 250                 255
```

<210> SEQ ID NO 25
<211> LENGTH: 233
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Gly or Ser

<400> SEQUENCE: 25

```
Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205
```

```
Ile Arg Leu Val Lys His Trp Tyr Gln Asn Val Trp Pro Ser His Pro
    210                 215                 220
Ala Cys Trp Tyr Leu Tyr Ile Phe Ile
225                 230
```

<210> SEQ ID NO 26
<211> LENGTH: 384
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr
<220> FEATURE:
<221> NAME/KEY: VARIANT
<222> LOCATION: 330
<220> FEATURE:
<223> OTHER INFORMATION: Xaa is Pro or Ser

<400> SEQUENCE: 26

```
Met Met Asp Leu Arg Asn Thr Pro Ala Lys Ser Leu Asp Lys Phe Ile
  1               5                  10                  15

Glu Asp Tyr Leu Leu Pro Asp Thr Cys Phe Arg Met Gln Ile Xaa His
             20                  25                  30

Ala Ile Asp Ile Ile Cys Gly Phe Leu Lys Glu Arg Cys Phe Arg Gly
         35                  40                  45

Ser Ser Tyr Pro Val Cys Val Ser Lys Val Val Lys Gly Gly Ser Ser
     50                  55                  60

Gly Lys Gly Thr Thr Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
                 85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Trp Xaa Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
```

```
                180             185             190
Leu Gln Arg Asp Phe Leu Lys Gln Arg Pro Thr Lys Leu Lys Ser Leu
            195                 200                 205
Ile Arg Leu Val Lys His Trp Tyr Gln Asn Cys Lys Lys Leu Gly
            210                 215                 220
Lys Leu Pro Pro Gln Tyr Ala Leu Glu Leu Thr Val Tyr Ala Trp
225                 230                 235                 240
Glu Arg Gly Ser Met Lys Thr His Phe Asn Thr Ala Gln Gly Phe Arg
                245                 250                 255
Thr Val Leu Glu Leu Val Ile Asn Tyr Gln Gln Leu Cys Ile Tyr Trp
                260                 265                 270
Thr Lys Tyr Tyr Asp Phe Lys Xaa Pro Ile Ile Glu Lys Tyr Leu Arg
                275                 280                 285
Arg Gln Leu Thr Lys Pro Arg Pro Val Ile Leu Asp Pro Ala Asp Pro
                290                 295                 300
Thr Gly Asn Leu Gly Gly Gly Asp Pro Lys Gly Trp Arg Gln Leu Ala
305                 310                 315                 320
Gln Glu Ala Glu Ala Trp Leu Asn Tyr Xaa Cys Phe Lys Asn Trp Asp
                325                 330                 335
Gly Ser Pro Val Ser Ser Trp Ile Leu Leu Met Arg Gln Arg Leu Arg
                340                 345                 350
Glu Val Arg Ser Leu Ala Gln Gly His Gln Leu Thr Ser Gly Gly Asn
                355                 360                 365
Gly Ile Gln Ala Gln Trp Thr Leu Lys Pro Val Leu Met Ser Leu Cys
370                 375                 380

<210> SEQ ID NO 27
<211> LENGTH: 459
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asp or Thr
<220> FEATURE:
<221> NAME/KEY: VARIANT
<222> LOCATION: 330
<220> FEATURE:
<223> OTHER INFORMATION: Xaa is Pro or Ser
<220> FEATURE:
<221> NAME/KEY: VARIANT
<222> LOCATION: (361)...(0)
<220> FEATURE:
<223> OTHER INFORMATION: Xaa is Gly or Arg
<220> FEATURE:
```

```
<221> NAME/KEY: VARIANT
<222> LOCATION: (429)...(0)
<220> FEATURE:
<223> OTHER INFORMATION: Xaa is Lys or Arg

<400> SEQUENCE: 27

Met Met Asp Leu Arg Asn Thr Pro Ala Lys Ser Leu Asp Lys Phe Ile
 1               5                  10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
50                      55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
            165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Lys Leu Gly
        210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Xaa Pro Ile Ile Glu Lys Tyr Leu Arg
        275                 280                 285

Arg Gln Leu Thr Lys Pro Arg Pro Val Ile Leu Asp Pro Ala Asp Pro
290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Xaa Cys Phe Lys Asn Trp Asp
                325                 330                 335

Gly Ser Pro Val Ser Ser Trp Ile Leu Leu Lys Ala Thr Val Gln
            340                 345                 350

Thr Met Arg Pro Thr Ile Pro Gly Xaa Ile Arg Asn Met Val Thr Leu
        355                 360                 365

Glu His Met Ser Thr Leu Ile Ser Leu Ile Asp Pro Ala His Ser Arg
        370                 375                 380
```

-continued

```
Gln His Pro Pro His Arg Gln Lys Arg Thr Gly Ala Pro Ser Ser
385                 390                 395                 400

Glu Cys Gln Cys Ile Leu Gly Glu Arg Ala Pro Val Leu Ser Gly Pro
            405                 410                 415

Val Pro Ser Phe Ser Gly Gly Thr Leu Asp Pro Glu Xaa Thr Lys Leu
            420                 425                 430

Leu Ser Glu Leu Val Tyr Asn Pro Gly Gln Asn Pro Gly Leu Leu Thr
            435                 440                 445

Pro Gly Leu Leu Cys Pro Leu Ser Tyr His Arg
        450                 455

<210> SEQ ID NO 28
<211> LENGTH: 355
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asp or Thr
<220> FEATURE:
<221> NAME/KEY: VARIANT
<222> LOCATION: 330
<220> FEATURE:
<223> OTHER INFORMATION: Xaa is Pro or Ser

<400> SEQUENCE: 28

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
    130                 135                 140
```

```
Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
            165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Lys Leu Gly
        210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Xaa Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Xaa Cys Phe Lys Asn Trp Asp
                325                 330                 335

Gly Ser Pro Val Ser Ser Trp Ile Leu Leu Ile Lys Leu Arg Leu Arg
                340                 345                 350

Glu Ala Lys
        355

<210> SEQ ID NO 29
<211> LENGTH: 382
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr
<220> FEATURE:
<221> NAME/KEY: VARIANT
<222> LOCATION: 330
<220> FEATURE:
<223> OTHER INFORMATION: Xaa is Pro or Ser
<220> FEATURE:
```

```
<221> NAME/KEY: VARIANT
<222> LOCATION: (372)...(0)
<220> FEATURE:
<223> OTHER INFORMATION: Xaa is Arg or Gly

<400> SEQUENCE: 29
```

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
            165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Lys Leu Gly
        210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
            245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Xaa Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Xaa Cys Phe Lys Asn Trp Asp
            325                 330                 335

Gly Ser Pro Val Ser Ser Trp Ile Leu Leu Val Asn Leu Thr Leu Val
            340                 345                 350

Gly Arg Arg Asn Tyr Pro Ile Ile Ser Glu His Ala Val Asn Leu Gln
        355                 360                 365

Gln Thr Arg Xaa Ala Ser Leu Ser Tyr Ser Phe Gln Val Ala
    370                 375                 380

```
<210> SEQ ID NO 30
<211> LENGTH: 54
<212> TYPE: PRT
<213> ORGANISM: Homo sapiens
<220> FEATURE:
<221> NAME/KEY: VARIANT
<222> LOCATION: 6
<220> FEATURE:
<223> OTHER INFORMATION: Xaa is Ala or Thr
<220> FEATURE:
<221> NAME/KEY: VARIANT
<222> LOCATION: 15
<220> FEATURE:
<223> OTHER INFORMATION: Xaa is Arg or Thr

<400> SEQUENCE: 30

Ala Glu Ser Asn Ser Xaa Asp Asp Glu Thr Asp Asp Pro Arg Xaa Tyr
 1               5                  10                  15

Gln Lys Tyr Gly Tyr Ile Gly Thr His Glu Tyr Pro His Phe Ser His
            20                  25                  30

Arg Pro Ser Thr Leu Gln Ala Ala Ser Thr Pro Gln Ala Glu Glu Asp
        35                  40                  45

Trp Thr Cys Thr Ile Leu
    50

<210> SEQ ID NO 31
<211> LENGTH: 519
<212> TYPE: PRT
<213> ORGANISM: Homo sapiens

<400> SEQUENCE: 31

Gly Cys Thr Gly Ala Ala Ala Gly Cys Ala Ala Cys Ala Gly Thr Arg
 1               5                  10                  15

Cys Ala Gly Ala Cys Gly Ala Thr Gly Ala Gly Ala Cys Cys Gly Ala
            20                  25                  30

Cys Gly Ala Thr Cys Cys Cys Ala Gly Gly Ala Ser Gly Thr Ala Thr
        35                  40                  45

Cys Ala Gly Ala Ala Thr Ala Thr Gly Gly Thr Thr Ala Cys Ala
    50                  55                  60

Thr Thr Gly Gly Ala Ala Cys Ala Cys Ala Thr Gly Ala Gly Thr Ala
65                  70                  75                  80

Cys Cys Cys Thr Cys Ala Thr Thr Thr Cys Thr Cys Thr Cys Ala Thr
            85                  90                  95

Ala Gly Ala Cys Cys Cys Ala Gly Cys Ala Cys Ala Cys Thr Cys Cys
        100                 105                 110

Ala Gly Gly Cys Ala Gly Cys Ala Thr Cys Cys Ala Cys Cys Cys Cys
    115                 120                 125

Ala Cys Ala Gly Gly Cys Gly Ala Ala Gly Ala Gly Gly Ala Cys
        130                 135                 140

Thr Gly Gly Ala Cys Cys Thr Gly Cys Ala Cys Cys Ala Thr Cys Cys
145                 150                 155                 160

Thr Cys Thr Gly Ala Ala Thr Gly Cys Ala Gly Thr Gly Cys Ala
            165                 170                 175

Thr Cys Thr Thr Gly Gly Gly Gly Gly Ala Ala Ala Gly Gly Gly Cys
        180                 185                 190

Thr Cys Cys Ala Gly Thr Gly Thr Thr Ala Thr Cys Thr Gly Gly Ala
    195                 200                 205

Cys Cys Ala Gly Thr Thr Cys Cys Thr Thr Cys Ala Thr Thr Thr
        210                 215                 220
```

```
Cys Ala Gly Gly Thr Gly Gly Ala Cys Thr Cys Thr Thr Gly Ala
225                 230                 235                 240

Thr Cys Cys Ala Gly Ala Gly Ala Arg Gly Ala Cys Ala Ala Gly
                245                 250                 255

Cys Thr Cys Cys Thr Cys Ala Gly Thr Gly Ala Gly Cys Thr Gly
                260                 265                 270

Thr Gly Thr Ala Thr Ala Ala Thr Cys Cys Ala Gly Gly Ala Cys Ala
                275                 280                 285

Gly Ala Ala Cys Cys Cys Ala Gly Gly Thr Cys Thr Cys Cys Thr Gly
                290                 295                 300

Ala Cys Thr Cys Cys Thr Gly Gly Cys Cys Thr Thr Cys Thr Ala Thr
305                 310                 315                 320

Gly Cys Cys Cys Thr Cys Thr Ala Thr Cys Cys Thr Ala Thr Cys Ala
                325                 330                 335

Thr Ala Gly Ala Thr Ala Ala Cys Ala Thr Thr Cys Thr Cys Cys Ala
                340                 345                 350

Cys Ala Gly Cys Cys Thr Cys Ala Cys Thr Thr Cys Ala Thr Thr Cys
                355                 360                 365

Cys Ala Cys Cys Thr Ala Thr Thr Cys Thr Cys Thr Gly Ala Ala Ala
                370                 375                 380

Ala Thr Ala Thr Thr Cys Cys Thr Gly Ala Gly Ala Gly Ala Gly
385                 390                 395                 400

Ala Ala Cys Ala Gly Ala Gly Ala Gly Ala Thr Thr Ala Gly Ala
                405                 410                 415

Thr Ala Ala Gly Ala Gly Ala Ala Thr Gly Ala Ala Ala Thr Thr Cys
                420                 425                 430

Cys Ala Gly Cys Cys Thr Thr Gly Ala Cys Thr Thr Cys Thr Thr
                435                 440                 445

Cys Thr Gly Thr Gly Cys Ala Cys Cys Thr Gly Ala Thr Gly Gly Gly
                450                 455                 460

Ala Gly Gly Gly Thr Ala Ala Thr Gly Thr Cys Thr Ala Ala Thr Gly
465                 470                 475                 480

Thr Ala Thr Thr Ala Thr Cys Ala Ala Thr Ala Ala Cys Ala Ala Thr
                485                 490                 495

Ala Ala Ala Ala Ala Thr Ala Ala Ala Gly Cys Ala Ala Ala Thr Ala
                500                 505                 510

Cys Cys Ala Thr Thr Thr Ala
        515
```

<210> SEQ ID NO 32
<211> LENGTH: 295
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:

```
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr

<400> SEQUENCE: 32

Met Met Asp Leu Arg Asn Thr Pro Ala Lys Ser Leu Asp Lys Phe Ile
 1               5                  10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Xaa Pro Ile Ile Glu Lys Tyr Leu Arg
        275                 280                 285

Arg Gln Leu Thr Lys Pro Arg
    290                 295

<210> SEQ ID NO 33
<211> LENGTH: 364
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
```

```
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr
<220> FEATURE:
<221> NAME/KEY: VARIANT
<222> LOCATION: 330
<220> FEATURE:
<223> OTHER INFORMATION: Xaa is Pro or Ser

<400> SEQUENCE: 33

Met Met Asp Leu Arg Asn Thr Pro Ala Lys Ser Leu Asp Lys Phe Ile
 1               5                  10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270
```

-continued

```
Thr Lys Tyr Tyr Asp Phe Lys Xaa Pro Ile Ile Glu Lys Tyr Leu Arg
            275                 280                 285

Arg Gln Leu Thr Lys Pro Arg Pro Val Ile Leu Asp Pro Ala Asp Pro
        290                 295                 300

Thr Gly Asn Leu Gly Gly Asp Pro Lys Gly Trp Arg Gln Leu Ala
305                 310                 315                 320

Gln Glu Ala Glu Ala Trp Leu Asn Tyr Xaa Cys Phe Lys Asn Trp Asp
                325                 330                 335

Gly Ser Pro Val Ser Ser Trp Ile Leu Leu Val Arg Pro Pro Ala Ser
            340                 345                 350

Ser Leu Pro Phe Ile Pro Ala Pro Leu His Glu Ala
            355                 360
```

<210> SEQ ID NO 34
<211> LENGTH: 400
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr
<220> FEATURE:
<221> NAME/KEY: VARIANT
<222> LOCATION: 330
<220> FEATURE:
<223> OTHER INFORMATION: Xaa is Pro or Ser
<220> FEATURE:
<221> NAME/KEY: VARIANT
<222> LOCATION: (352)...(0)
<220> FEATURE:
<223> OTHER INFORMATION: Xaa is Ala or Thr
<220> FEATURE:
<221> NAME/KEY: VARIANT
<222> LOCATION: (361)...(0)
<220> FEATURE:
<223> OTHER INFORMATION: Xaa is Arg or Thr

<400> SEQUENCE: 34

```
Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Lys Gly Gly Ser Ser
    50                  55                  60

Gly Lys Gly Thr Thr Leu Arg Gly Arg Ser Asp Ala Asp Leu Val Val
```

```
              65                  70                  75                  80
        Phe Leu Ser Pro Leu Thr Thr Phe Gln Asp Gln Leu Asn Arg Arg Gly
                         85                  90                  95

Glu Phe Ile Gln Glu Ile Arg Arg Gln Leu Glu Ala Cys Gln Arg Glu
                        100                 105                 110

Arg Ala Xaa Ser Val Lys Phe Glu Val Gln Ala Pro Arg Trp Xaa Asn
                        115                 120                 125

Pro Arg Ala Leu Ser Phe Val Leu Ser Ser Leu Gln Leu Gly Glu Gly
                        130                 135                 140

Val Glu Phe Asp Val Leu Pro Ala Phe Asp Ala Leu Gly Gln Leu Thr
        145                 150                 155                 160

Gly Xaa Tyr Lys Pro Asn Pro Gln Ile Tyr Val Lys Leu Ile Glu Glu
                        165                 170                 175

Cys Thr Asp Leu Gln Lys Glu Gly Glu Phe Ser Thr Cys Phe Thr Glu
                        180                 185                 190

Leu Gln Arg Asp Phe Leu Lys Gln Arg Pro Thr Lys Leu Lys Ser Leu
                        195                 200                 205

Ile Arg Leu Val Lys His Trp Tyr Gln Asn Cys Lys Lys Lys Leu Gly
                210                 215                 220

Lys Leu Pro Pro Gln Tyr Ala Leu Glu Leu Leu Thr Val Tyr Ala Trp
        225                 230                 235                 240

Glu Arg Gly Ser Met Lys Thr His Phe Asn Thr Ala Gln Gly Phe Arg
                        245                 250                 255

Thr Val Leu Glu Leu Val Ile Asn Tyr Gln Gln Leu Cys Ile Tyr Trp
                        260                 265                 270

Thr Lys Tyr Tyr Asp Phe Lys Xaa Pro Ile Ile Glu Lys Tyr Leu Arg
                        275                 280                 285

Arg Gln Leu Thr Lys Pro Arg Pro Val Ile Leu Asp Pro Ala Asp Pro
                        290                 295                 300

Thr Gly Asn Leu Gly Gly Gly Asp Pro Lys Gly Trp Arg Gln Leu Ala
        305                 310                 315                 320

Gln Glu Ala Glu Ala Trp Leu Asn Tyr Xaa Cys Phe Lys Asn Trp Asp
                        325                 330                 335

Gly Ser Pro Val Ser Ser Trp Ile Leu Leu Ala Glu Ser Asn Ser Xaa
                        340                 345                 350

Asp Asp Glu Thr Asp Asp Pro Arg Xaa Tyr Gln Lys Tyr Gly Tyr Ile
                        355                 360                 365

Gly Thr His Glu Tyr Pro His Phe Ser His Arg Pro Ser Thr Leu Gln
                        370                 375                 380

Ala Ala Ser Thr Pro Gln Ala Glu Glu Asp Trp Thr Cys Thr Ile Leu
        385                 390                 395                 400

<210> SEQ ID NO 35
<211> LENGTH: 414
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
```

```
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr
<220> FEATURE:
<221> NAME/KEY: VARIANT
<222> LOCATION: 330
<220> FEATURE:
<223> OTHER INFORMATION: Xaa is Pro or Ser
<220> FEATURE:
<221> NAME/KEY: VARIANT
<222> LOCATION: (397)...(0)
<220> FEATURE:
<223> OTHER INFORMATION: Xaa is Gly or Arg

<400> SEQUENCE: 35

Met Met Asp Leu Arg Asn Thr Pro Ala Lys Ser Leu Asp Lys Phe Ile
 1               5                  10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Xaa Pro Ile Ile Glu Lys Tyr Leu Arg
        275                 280                 285
```

```
Arg Gln Leu Thr Lys Pro Arg Pro Val Ile Leu Asp Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Xaa Cys Phe Lys Asn Trp Asp
                325                 330                 335

Gly Ser Pro Val Ser Ser Trp Ile Leu Leu Thr Gln His Thr Pro Gly
                340                 345                 350

Ser Ile His Pro Thr Gly Arg Arg Gly Leu Asp Leu His His Pro Leu
        355                 360                 365

Asn Ala Ser Ala Ser Trp Gly Lys Gly Leu Gln Cys Tyr Leu Asp Gln
    370                 375                 380

Phe Leu His Phe Gln Val Gly Leu Leu Ile Gln Arg Xaa Gln Ser Ser
385                 390                 395                 400

Ser Val Ser Trp Cys Ile Ile Gln Asp Arg Thr Gln Val Ser
                    405                 410

<210> SEQ ID NO 36
<211> LENGTH: 1387
<212> TYPE: DNA
<213> ORGANISM: Homo sapiens

<400> SEQUENCE: 36
gaggcagttc tgttgccact ctctctcctg tcaatgatgg atctcagaaa taccccagcc      60
aaatctctgg acaagttcat tgaagactat ctcttgccag acacgtgttt ccgcatgcaa     120
atcaaccatg ccattgacat catctgtggg ttcctgaagg aaaggtgctt ccgaggtagc     180
tcctaccctg tgtgtgtgtc caaggtggta aagggtggct cctcaggcaa gggcaccacc     240
ctcagaggcc gatctgacgc tgacctggtt gtcttcctca gtcctctcac cacttttcag     300
gatcagttaa atcgccgggg agagttcatc caggaaatta ggagacagct ggaagcctgt     360
caaagagaga gagcattttc cgtgaagttt gaggtccagg ctccacgctg gggcaacccc     420
cgtgcgctca gcttcgtact gagttcgctc cagctcgggg aggggtggga gttcgatgtg     480
ctgcctgcct ttgatgccct gggtcagttg actggcrgct ataaacctaa cccccaaatc     540
tatgtcaagc tcatcgagga gtgcaccgac ctgcagaaag agggcgagtt ctccacctgc     600
ttcacagaac tacagagaga cttcctgaag cagcgcccca ccaagctcaa gagcctcatc     660
cgcctagtca agcactggta ccaaaattgt aagaagaagc ttgggaagct gccacctcag     720
tatgccctgg agtcctgac ggtctatgct gggagcgag ggagcatgaa acacatttc       780
aacacagccc agggatttcg gacggtcttg gaattagtca taaactacca gcaactctgc     840
atctactgga caagtatta tgactttaaa accccatta ttgaaaagta cctgagaagg       900
cagctcacga aacccaggcc tgtgatcctg acccggcgg accctacagg aaacttgggt      960
ggtggagacc caaagggttg gaggcagctg gcacaagagg ctgaggcctg ctgaattac     1020
ccatgcttta agaattggga tgggtcccca gtgagctcct ggattctgct ggtgagacct    1080
cctgcttcct ccctgccatt catccctgcc cctctccatg aagcttgaga catatagctg    1140
gagaccattc tttccaaaga acttacctct tgccaaaggc catttatatt catatagtga    1200
caggctgtgc tccatatttt acagtcattt tggtcacaat cgagggtttc tggaattttc    1260
acatcccttg tccagaattc attccctaa gagtaataat aaataatctc taacaccatt    1320
tattgactgt ctgcttcggg ctcaggttct gtcctaagcc ctttaatatg cactctctca   1380
``` ttaaata                                                             1387

<210> SEQ ID NO 37
<211> LENGTH: 1699
<212> TYPE: DNA
<213> ORGANISM: Homo sapiens

<400> SEQUENCE: 37
gaggcagttc tgttgccact ctctctcctg tcaatgatgg atctcagaaa taccccagcc    60
aaatctctgg acaagttcat tgaagactat ctcttgccag acacgtgttt ccgcatgcaa   120
atcaaccatg ccattgacat catctgtggg ttcctgaagg aaaggtgctt ccgaggtagc   180
tcctaccctg tgtgtgtgtc caaggtggta aagggtggct cctcaggcaa gggcaccacc   240
ctcagaggcc gatctgacgc tgacctggtt gtcttcctca gtcctctcac cacttttcag   300
gatcagttaa atcgccgggg agagttcatc caggaaatta ggagacagct ggaagcctgt   360
caaagagaga gagcattttc cgtgaagttt gaggtccagg ctccacgctg ggcaaccccc   420
cgtgcgctca gcttcgtact gagttcgctc cagctcgggg aggggtgga gttcgatgtg    480
ctgcctgcct ttgatgccct gggtcagttg actggcrgct ataaacctaa cccccaaatc   540
tatgtcaagc tcatcgagga gtgcaccgac ctgcagaaag agggcgagtt ctccacctgc   600
ttcacagaac tacagagaga cttcctgaag cagcgcccca ccaagctcaa gagcctcatc   660
cgcctagtca agcactggta ccaaaattgt aagaagaagc ttgggaagct gccacctcag   720
tatgccctgg agctcctgac ggtctatgct gggagcgag ggagcatgaa aacacatttc    780
aacacagccc agggatttcg dacggtcttg gaattagtca taaactacca gcaactctgc   840
atctactgga caaagtatta tgactttaaa accccatta ttgaaaagta cctgagaagg     900
cagctcacga aacccaggcc tgtgatcctg gaccggcgg accctacagg aaacttgggt    960
ggtggagacc caaagggttg gaggcagctg gcacaagagg ctgaggcctg gctgaattac  1020
ccatgcttta agaattggga tgggtcccca gtgagctcct ggattctgct ggctgaaagc  1080
aacagtrcag acgatgagac cgacgatccc aggasgtatc agaaatatgg ttacattgga  1140
acacatgagt accctcatt ctctcataga cccagcacac tccaggcagc atccaccca    1200
caggcagaag aggactggac ctgcaccatc ctctgaatgc cagtgcatct tgggggaaag  1260
ggctccagtg ttatctggac cagttccttc attttcaggt gggactcttg atccagagar  1320
gacaaagctc ctcagtgagc tggtgtataa tccaggacag aacccaggtc tcctgactcc  1380
tggccttcta tgccctctat cctatcatag ataacattct ccacagcctc acttcattcc  1440
acctattctc tgaaaatatt ccctgagaga gaacagagag atttagataa gagaatgaaa  1500
ttccagcctt gactttcttc tgtgcacctg atgggagggt aatgtctaat gtattatcaa  1560
taacaataaa aataaagcaa ataccattta ttgggtgttt attaacttca aggcacagag  1620
ccaagaagta cagatgcata tctagggta ttgtgtgtgt atatacattg attcaacaag   1680
aaatatttat tgagcactt                                               1699

<210> SEQ ID NO 38
<211> LENGTH: 1601
<212> TYPE: DNA
<213> ORGANISM: Homo sapiens

<400> SEQUENCE: 38
gaggcagttc tgttgccact ctctctcctg tcaatgatgg atctcagaaa taccccagcc    60
aaatctctgg acaagttcat tgaagactat ctcttgccag acacgtgttt ccgcatgcaa   120

```
atcaaccatg ccattgacat catctgtggg ttcctgaagg aaaggtgctt ccgaggtagc      180
tcctaccctg tgtgtgtgtc caaggtggta aagggtggct cctcaggcaa ggcaccacc      240 ctcagaggcc gatctgacgc tgacctggtt gtcttcctca gtcctctcac cacttttcag      300
gatcagttaa atcgccgggg agagttcatc caggaaatta ggagacagct ggaagcctgt      360
caaagagaga gagcattttc cgtgaagttt gaggtccagg ctccacgctg gggcaacccc      420
cgtgcgctca gcttcgtact gagttcgctc cagctcgggg aggggtgga gttcgatgtg       480 ctgcctgcct ttgatgccct gggtcagttg actggcrgct ataaacctaa ccccccaaatc    540 tatgtcaagc tcatcgagga gtgcaccgac ctgcagaaag agggcgagtt ctccacctgc      600
ttcacagaac tacagagaga cttcctgaag cagcgcccca ccaagctcaa gagcctcatc      660
cgcctagtca agcactggta ccaaaattgt aagaagaagc ttgggaagct gccacctcag      720
tatgccctgg agctcctgac ggtctatgct tgggagcgag ggagcatgaa acacatttc      780 aacacagccc agggatttcg gacggtcttg gaattagtca taaactacca gcaactctgc      840
atctactgga caaagtatta tgactttaaa accccatta ttgaaaagta cctgagaagg        900
cagctcacga aacccaggcc tgtgatcctg gacccggcgg accctacagg aaacttgggt      960
ggtggagacc caaagggttg gaggcagctg gcacaagagg ctgaggcctg gctgaattac      1020
ccatgcttta agaattggga tgggtcccca gtgagctcct ggattctgct gacccagcac     1080
actccaggca gcatccaccc cacaggcaga agaggactgg acctgcacca tcctctgaat      1140
gccagtgcat cttgggggaa agggctccag tgttatctgg accagttcct tcatttcag      1200 gtgggactct tgatccagag argacaaagc tcctcagtga gctggtgtat aatccaggac      1260
agaacccagg tctcctgact cctggccttc tatgccctct atcctatcat agataacatt      1320
ctccacagcc tcacttcatt ccacctattc tctgaaaata ttccctgaga gagaacagag      1380
agatttagat aagagaatga aattccagcc ttgactttct tctgtgcacc tgatgggagg      1440
gtaatgtcta atgtattatc aataacaata aaaataaagc aaataccatt tattgggtgt      1500
ttattaactt caaggcacag agccaagaag tacagatgca tatctagggg tattgtgtgt      1560
gtatatacat tgattcaaca agaaatattt attgagcact t                          1601
```

<210> SEQ ID NO 39
<211> LENGTH: 1698
<212> TYPE: DNA
<213> ORGANISM: Homo sapiens

<400> SEQUENCE: 39

```
gaggcagttc tgttgccact ctctctcctg tcaatgatgg atctcagaaa taccccagcc      60
aaatctctgg acaagttcat tgaagactat ctcttgccag acacgtgttt ccgcatgcaa      120
atcaaccatg ccattgacat catctgtggg ttcctgaagg aaaggtgctt ccgaggtagc      180
tcctaccctg tgtgtgtgtc caaggtggta aagggtggct cctcaggcaa ggcaccacc      240 ctcagaggcc gatctgacgc tgacctggtt gtcttcctca gtcctctcac cacttttcag      300
gatcagttaa atcgccgggg agagttcatc caggaaatta ggagacagct ggaagcctgt      360
caaagagaga gagcattttc cgtgaagttt gaggtccagg ctccacgctg gggcaacccc      420
cgtgcgctca gcttcgtact gagttcgctc cagctcgggg aggggtgga gttcgatgtg       480 ctgcctgcct ttgatgccct gggtcagttg actggcrgct ataaacctaa ccccccaaatc    540 tatgtcaagc tcatcgagga gtgcaccgac ctgcagaaag agggcgagtt ctccacctgc      600
```

```
ttcacagaac tacagagaga cttcctgaag cagcgcccca ccaagctcaa gagcctcatc    660
cgcctagtca agcactggta ccaaaattgt aagaagaagc ttgggaagct gccacctcag    720
tatgccctgg agctcctgac ggtctatgct tgggagcgag ggagcatgaa aacacatttc    780
aacacagccc agggatttcg gacggtcttg gaattagtca taaactacca gcaactctgc    840
atctactgga caaagtatta tgactttaaa aacccccatta ttgaaaagta cctgagaagg    900
cagctcacga aacccaggcc tgtgatcctg gaccggcgg accctacagg aaacttgggt    960
ggtggagacc caaaggggttg gaggcagctg gcacaagagg ctgaggcctg gctgaattac   1020
ccatgcttta agaattggga tgggtcccca gtgagctcct ggattctgct gctgaaagca   1080
acagtrcaga cgatgagacc gacgatccca ggasgtatca gaaatatggt tacattggaa   1140
cacatgagta ccctcatttc tctcatagac ccagcacact ccaggcagca tccaccccac   1200
aggcagaaga ggactggacc tgcaccatcc tctgaatgcc agtgcatctt ggggggaaagg   1260 gctccagtgt tatctggacc agttccttca ttttcaggtg ggactcttga tccagagarg   1320
acaaagctcc tcagtgagct ggtgtataat ccaggacaga acccaggtct cctgactcct   1380
ggccttctat gccctctatc ctatcataga taacattctc cacagcctca cttcattcca   1440
cctattctct gaaaatattc cctgagagag aacagagaga tttagataag agaatgaaat   1500
tccagccttg actttcttct gtgcacctga tgggagggta atgtctaatg tattatcaat   1560
aacaataaaa ataaagcaaa taccatttat tgggtgttta ttaacttcaa ggcacagagc   1620
caagaagtac agatgcatat ctaggggtat tgtgtgtgta tatacattga ttcaacaaga   1680
aatatttatt gagcactt                                                 1698

<210> SEQ ID NO 40
<211> LENGTH: 2491
<212> TYPE: DNA
<213> ORGANISM: Homo sapiens

<400> SEQUENCE: 40
gaggcagttc tgttgccact ctctctcctg tcaatgatgg atctcagaaa taccccagcc     60
aaatctctgg acaagttcat tgaagactat ctcttgccag acacgtgttt ccgcatgcaa    120
atcaaccatg ccattgacat catctgtggg ttcctgaagg aaaggtgctt ccgaggtagc    180
tcctaccctg tgtgtgtgtc caaggtggta aagggtggct cctcaggcaa gggcaccacc    240
ctcagaggcc gatctgacgc tgacctggtt gtcttcctca gtcctctcac cactttcag    300 gatcagttaa atcgccgggg agagttcatc caggaaatta ggagacagct ggaagcctgt    360
caaagagaga gagcattttc cgtgaagttt gaggtccagg ctccacgctg gggcaacccc    420
cgtgcgctca gcttcgtact gagttcgctc cagctcgggg aggggtgga gttcgatgtg    480 ctgcctgcct ttgatgccct gggtcagttg actggcrgct ataaacctaa cccccaaatc    540
tatgtcaagc tcatcgagga gtgcaccgac ctgcagaaag agggcgagtt ctccaccctg    600
ttcacagaac tacagagaga cttcctgaag cagcgcccca ccaagctcaa gagcctcatc    660
cgcctagtca agcactggta ccaaaattgt aagaagaagc ttgggaagct gccacctcag    720
tatgccctgg agctcctgac ggtctatgct tgggagcgag ggagcatgaa aacacatttc    780
aacacagccc agggatttcg gacggtcttg gaattagtca taaactacca gcaactctgc    840
atctactgga caaagtatta tgactttaaa aacccccatta ttgaaaagta cctgagaagg    900
cagctcacga aacccaggcc tgtgatcctg gaccggcgg accctacagg aaacttgggt    960
ggtggagacc caaaggggttg gaggcagctg gcacaagagg ctgaggcctg gctgaattac   1020
```

```
ccatgcttta agaattggga tgggtcccca gtgagctcct ggattctgct gatgagacaa    1080
aggctcagag aggtgaggtc acttgctcaa ggacatcagc taacaagtgg tggaaatgga    1140
attcaagctc agtggactct aaagccagtg ctcatgtcac tgtgctaaac agcctgcctt    1200
gtcacatccc cacctctcat ctgaccaatg ggagactctg agcagctgag tgacttgggt    1260
tgtcacacag ctaaacaggg gcaaaggacc cagtcttgga tctttccacc tccaagcagg    1320
aatctgtctg attccagggg attgatgatg ttgcagatgg ctaggaagca gactccagga    1380
tggaatttag tatgcaggat gttctggggg agagccactg gaaccagcac tcagggaaag    1440
gggggaagaa aggataggaa ggaagcatga aagagaatag ggagaagtga acagggatgc    1500
agagcgaatg ccagtttcag ccaactccaa ggacagccct ggagctggaa tggcctttag    1560
agctgcccca tggtgacaga ggtggccagg cttctatacc cctacgtgga tcactcactg    1620
tgcttgggca ccttgggaaa gggcatggct ttgagcaaaa ggctctctgc agctgaggca    1680
acccctaaaa gggctgacgg ctgaagtctg tctgctgacc actgtcccag cagctggggc    1740
ttgttagtcc ttcctcaaag ggggatccag atggcatgtc acagtgtcta ccgtaaatgc    1800
tcactgaatc cagctgcaat gcaggaagac tccctgatgt gatcatgtgt ctcacccttt    1860
cargctgaaa gcaacagtrc agacgatgag accgacgatc ccaggasgta tcagaaatat    1920
ggttacattg aaacacatga gtaccctcat ttctctcata gacccagcac actccaggca    1980
gcatccaccc cacaggcaga agaggactgg acctgcacca tcctctgaat gccagtgcat    2040
cttgggggaa agggctccag tgttatctgg accagttcct tcattttcag gtgggactct    2100
tgatccagag argacaaagc tcctcagtga gctggtgtat aatccaggac agaacccagg    2160
tctcctgact cctggccttc tatgccctct atcctatcat agataacatt ctccacagcc    2220
tcacttcatt ccacctattc tctgaaaata ttccctgaga gagaacagag agatttagat    2280
aagagaatga aattccagcc ttgactttct tctgtgcacc tgatgggagg gtaatgtcta    2340
atgtattatc aataacaata aaaataaagc aaataccatt tattgggtgt ttattaactt    2400
caaggcacag agccaagaag tacagatgca tatctagggg tattgtgtgt gtatatacat    2460
tgattcaaca agaaatattt attgagcact t                                   2491
```

<210> SEQ ID NO 41
<211> LENGTH: 1510
<212> TYPE: DNA
<213> ORGANISM: Homo sapiens

<400> SEQUENCE: 41

```
gaggcagttc tgttgccact ctctctcctg tcaatgatgg atctcagaaa tacccagcc      60 aaatctctgg acaagttcat tgaagactat ctcttgccag acacgtgttt ccgcatgcaa    120
atcaaccatg ccattgacat catctgtggg ttcctgaagg aaaggtgctt ccgaggtagc    180
tcctaccctg tgtgtgtgtc caaggtggta aaggtggct cctcaggcaa ggcaccacc      240 ctcagaggcc gatctgacgc tgacctggtt gtcttcctca gtcctctcac cacttttcag    300
gatcagttaa atcgccgggg agagttcatc caggaaatta ggagacagct ggaagcctgt    360
caaagagaga gagcattttc cgtgaagttt gaggtccagg ctccacgctg ggcaacccc     420 cgtgcgctca gcttcgtact gagttcgctc cagctcgggg aggggtggaa gttcgatgtg    480
ctgcctgcct ttgatgccct gggtcagttg actggcrgct ataaacctaa cccccaaatc    540
tatgtcaagc tcatcgagga gtgcaccgac ctgcagaaag agggcgagtt ctccacctgc    600
```

```
ttcacagaac tacagagaga cttcctgaag cagcgcccca ccaagctcaa gagcctcatc    660
cgcctagtca agcactggta ccaaaattgt aagaagaagc ttgggaagct gccacctcag    720
tatgccctgg agctcctgac ggtctatgct tgggagcgag ggagcatgaa acacatttc    780
aacacagccc agggatttcg gacggtcttg gaattagtca taaactacca gcaactctgc    840
atctactgga caaagtatta tgactttaaa accccatta ttgaaaagta cctgagaagg     900
cagctcacga aacccaggcc tgtgatcctg gaccggcgg acccctacagg aaacttgggt    960
ggtggagacc caaagggttg gaggcagctg gcacaagagg ctgaggcctg gctgaattac   1020
ccatgcttta agaattggga tgggtcccca gtgagctcct ggattctgct ggtaaacctc   1080
acactggttg gcagaaggaa ctataccaat aattagtgaa catgcggtga atttgcaaca   1140
gacaagasga gcctcattat cctatagttt ccaggttgct tagggaggca gaaatcacag   1200
caaggaaaac cttcaataat aaacagacgt ctcataaaat taattgcaac ccaacctctc   1260
tctctactta aaattagcat ctatttccag ctctgctttc aatgcccat atgaatacat    1320
gtgaactccc tccctctctt cctccctgtc tccttctctc tctctctgtc cctcattaaa   1380
aaataaaatt taagaaaaaa atacaaggta gatttacaca aatagtggga tctcagtctt   1440
gagttagctg tgtatgactg aaaaggatgc tgtggttaat aattatcata aaaacaatga   1500
catggccggg                                                          1510

<210> SEQ ID NO 42
<211> LENGTH: 1695
<212> TYPE: DNA
<213> ORGANISM: Homo sapiens
<400> SEQUENCE: 42
gaggcagttc tgttgccact ctctctcctg tcaatgatgg atctcagaaa taccccagcc     60
aaatctctgg acaagttcat tgaagactat ctcttgccag acacgtgttt ccgcatgcaa    120
atcaaccatg ccattgacat catctgtggg ttcctgaagg aaaggtgctt ccgaggtagc    180
tcctaccctg tgtgtgtgtc caaggtggta aagggtggct cctcaggcaa gggcaccacc    240
ctcagaggcc gatctgacgc tgacctggtt gtcttcctca gtcctctcac cacttttcag    300
gatcagttaa atcgccgggg agagttcatc caggaaatta ggagacagct ggaagcctgt    360
caaagagaga gagcatttc cgtgaagttt gaggtccagg ctccacgctg ggcaaccc     420
cgtgcgctca gcttcgtact gagttcgctc cagctcgggg aggggtgga gttcgatgtg    480
ctgcctgcct ttgatgccct gggtcagttg actggcrgct ataaacctaa ccccaaatc    540
tatgtcaagc tcatcgagga gtgcaccgac ctgcagaaag agggcgagtt ctccacctgc    600
ttcacagaac tacagagaga cttcctgaag cagcgcccca ccaagctcaa gagcctcatc    660
cgcctagtca agcactggta ccaaaattgt aagaagaagc ttgggaagct gccacctcag    720
tatgccctgg agctcctgac ggtctatgct tgggagcgag ggagcatgaa acacatttc    780
aacacagccc agggatttcg gacggtcttg gaattagtca taaactacca gcaactctgc    840
atctactgga caaagtatta tgactttaaa accccatta ttgaaaagta cctgagaagg     900
cagctcacga aacccaggcc tgtgatcctg gaccggcgg acccctacagg aaacttgggt    960
ggtggagacc caaagggttg gaggcagctg gcacaagagg ctgaggcctg gctgaattac   1020
ccatgcttta agaattggga tgggtcccca gtgagctcct ggattctgct gataaaactg   1080
aggctcagag aagctaagtg actcgcctgg gactgcacag caaatcaaga caaataagac   1140
ctagggtctc ctgactgcca gagtggagat gcttctatag gcttttctca ctgatgctct   1200
```

```
ctgggcagac aggctcctca atatgagagt gacacacact cctttcttca ttttcaggta    1260
aacctcacac tggttggcag aaggaactat ccaataatta gtgaacatgc ggtgaatttg    1320
caacagacaa gasgagcctc attatcctat agtttccagg ttgcttaggg aggcagaaat    1380
cacagcaagg aaaaccttca ataataaaca gacgtctcat aaaattaatt gcaacccaac    1440
ctctctctct acttaaaatt agcatctatt ccagctctg ctttcaatgc cccatatgaa     1500
tacatgtgaa ctccctccct ctcttcctcc ctgtctcctt ctctctctct ctgtccctca    1560
ttaaaaaata aaatttaaga aaaaaataca aggtagattt acacaaatag tgggatctca    1620
gtcttgagtt agctgtgtat gactgaaaag gatgctgtgg ttaataatta tcataaaaac    1680
aatgacatgg ccggg                                                     1695

<210> SEQ ID NO 43
<211> LENGTH: 1355
<212> TYPE: DNA
<213> ORGANISM: Homo sapiens

<400> SEQUENCE: 43
gaggcagttc tgttgccact ctctctcctg tcaatgatgg atctcagaaa taccccagcc      60
aaatctctgg acaagttcat tgaagactat ctcttgccag acacgtgttt ccgcatgcaa    120
atcaaccatg ccattgacat catctgtggg ttcctgaagg aaaggtgctt ccgaggtagc    180
tcctaccctg tgtgtgtgtc caaggtggta aagggtggct cctcaggcaa gggcaccacc    240
ctcagaggcc gatctgacgc tgacctggtt gtcttcctca gtcctctcac cacttttcag    300
gatcagttaa atcgccgggg agagttcatc caggaaatta ggagacagct ggaagcctgt    360
caaagagaga gagcatttc cgtgaagttt gaggtccagg ctccacgctg ggcaaccccc    420
cgtgcgctca gcttcgtact gagttcgctc cagctcgggg aggggtgga gttcgatgtg    480 ctgcctgcct ttgatgccct gggtcagttg actggcrgct ataaacctaa cccccaaatc    540
tatgtcaagc tcatcgagga gtgcaccgac ctgcagaaag agggcgagtt ctccacctgc    600
ttcacagaac tacagagaga cttcctgaag cagcgcccca ccaagctcaa gagcctcatc    660
cgcctagtca agcactggta ccaaaattgt aagaagaagc ttgggaagct gccacctcag    720
tatgccctgg agctcctgac ggtctatgct tgggagcgag ggagcatgaa aacacatttc    780
aacacagccc agggatttcg gacggtcttg gaattagtca taaactacca gcaactctgc    840
atctactgga caaagtatta tgactttaaa accccatta ttgaaaagta cctgagaagg    900
cagctcacga aacccaggta aacctcacac tggttggcag aaggaactat ccaataatta    960
gtgaacatgc ggtgaatttg caacagacaa gasgagcctc attatcctat agtttccagg   1020
ttgcttaggg aggcagaaat cacagcaagg aaaaccttca ataataaaca gacgtctcat   1080
aaaattaatt gcaacccaac ctctctctct acttaaaatt agcatctatt ccagctctg   1140 ctttcaatgc cccatatgaa tacatgtgaa ctccctccct ctcttcctcc ctgtctcctt   1200
ctctctctct ctgtccctca ttaaaaaata aaatttaaga aaaaaataca aggtagattt   1260
acacaaatag tgggatctca gtcttgagtt agctgtgtat gactgaaaag gatgctgtgg   1320
ttaataatta tcataaaaac aatgacatgg ccggg                              1355

<210> SEQ ID NO 44
<211> LENGTH: 1035
<212> TYPE: DNA
<213> ORGANISM: Homo sapiens
```

<400> SEQUENCE: 44

```
gaggcagttc tgttgccact ctctctcctg tcaatgatgg atctcagaaa taccccagcc      60
aaatctctgg acaagttcat tgaagactat ctcttgccag acacgtgttt ccgcatgcaa     120
atcaaccatg ccattgacat catctgtggg ttcctgaagg aaaggtgctt ccgaggtagc     180
tcctaccctg tgtgtgtgtc caaggtggta aagtgtaaga agaagcttgg gaagctgcca     240
cctcagtatg ccctggagct cctgacggtc tatgcttggg agcgagggag catgaaaaca     300
catttcaaca cagcccaggg atttcggacg gtcttggaat tagtcataaa ctaccagcaa     360
ctctgcatct actggacaaa gtattatgac tttaaaaacc ccattattga aaagtacctg     420
agaaggcagc tcacgaaacc caggcctgtg atcctggacc cggcggaccc tacaggaaac     480
ttgggtggtg gagacccaaa gggttggagg cagctggcac aagaggctga ggcctggctg     540
aattacccat gctttaagaa ttgggatggg tccccagtga gctcctggat tctgctggta     600
aacctcacac tggttggcag aaggaactat ccaataatta gtgaacatgc ggtgaatttg     660
caacagacaa gasgagcctc attatcctat agtttccagg ttgcttaggg aggcagaaat     720
cacagcaagg aaaaccttca ataataaaca gacgtctcat aaaattaatt gcaacccaac     780
ctctctctct acttaaaatt agcatctatt tccagctctg ctttcaatgc ccatatgaa     840
tacatgtgaa ctccctccct tcttcctcc ctgtctcctt ctctctctct ctgtccctca     900
ttaaaaaata aaatttaaga aaaaaataca aggtagattt acacaaatag tgggatctca     960
gtcttgagtt agctgtgtat gactgaaaag gatgctgtgg ttaataatta tcataaaaac    1020
aatgacatgg ccggg                                                     1035
```

<210> SEQ ID NO 45
<211> LENGTH: 881
<212> TYPE: DNA
<213> ORGANISM: Homo sapiens

<400> SEQUENCE: 45

```
gaggcagttc tgttgccact ctctctcctg tcaatgatgg atctcagaaa taccccagcc      60
aaatctctgg acaagttcat tgaagactat ctcttgccag acacgtgttt ccgcatgcaa     120
atcaaccatg ccattgacat catctgtggg ttcctgaagg aaaggtgctt ccgaggtagc     180
tcctaccctg tgtgtgtgtc caaggtggta aagtgtaaga agaagcttgg gaagctgcca     240
cctcagtatg ccctggagct cctgacggtc tatgcttggg agcgagggag catgaaaaca     300
catttcaaca cagcccaggg atttcggacg gtcttggaat tagtcataaa ctaccagcaa     360
ctctgcatct actggacaaa gtattatgac tttaaaaacc ccattattga aaagtacctg     420
agaaggcagc tcacgaaacc caggtaaacc tcacactggt tggcagaagg aactatccaa     480
taattagtga acatgcggtg aatttgcaac agacaagasg agcctcatta tcctatagtt     540
tccaggttgc ttagggaggc agaaatcaca gcaggaaaa ccttcaataa taaacagacg     600
tctcataaaa ttaattgcaa cccaacctct ctctctactt aaaattagca tctatttcca     660
gctctgcttt caatgcccca tatgaataca tgtgaactcc ctccctctct tcctccctgt     720
ctccttctct ctctctctgt ccctcattaa aaataaaatt ttaagaaaaa aatacaaggt     780
agatttacac aaatagtggg atctcagtct tgagttagct gtgtatgact gaaaaggatg     840
ctgtggttaa taattatcat aaaaacaatg acatggccgg g                        881
```

<210> SEQ ID NO 46
<211> LENGTH: 224

```
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 122
<220> FEATURE:
<223> OTHER INFORMATION: Xaa is Asn or Thr
<220> FEATURE:
<221> NAME/KEY: VARIANT
<222> LOCATION: 172
<220> FEATURE:
<223> OTHER INFORMATION: Xaa is Pro or Ser
<220> FEATURE:
<221> NAME/KEY: VARIANT
<222> LOCATION: 214
<220> FEATURE:
<223> OTHER INFORMATION: Xaa is Arg or Gly

<400> SEQUENCE: 46

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Cys Lys Lys Lys
    50                  55                  60

Leu Gly Lys Leu Pro Pro Gln Tyr Ala Leu Glu Leu Thr Val Tyr
65                  70                  75                  80

Ala Trp Glu Arg Gly Ser Met Lys Thr His Phe Asn Thr Ala Gln Gly
                85                  90                  95

Phe Arg Thr Val Leu Glu Leu Val Ile Asn Tyr Gln Gln Leu Cys Ile
            100                 105                 110

Tyr Trp Thr Lys Tyr Tyr Asp Phe Lys Xaa Pro Ile Ile Glu Lys Tyr
        115                 120                 125

Leu Arg Arg Gln Leu Thr Lys Pro Arg Pro Val Ile Leu Asp Pro Ala
    130                 135                 140

Asp Pro Thr Gly Asn Leu Gly Gly Asp Pro Lys Gly Trp Arg Gln
145                 150                 155                 160

Leu Ala Gln Glu Ala Glu Ala Trp Leu Asn Tyr Xaa Cys Phe Lys Asn
                165                 170                 175

Trp Asp Gly Ser Pro Val Ser Ser Trp Ile Leu Leu Val Asn Leu Thr
            180                 185                 190

Leu Val Gly Arg Arg Asn Tyr Pro Ile Ile Ser Glu His Ala Val Asn
        195                 200                 205

Leu Gln Gln Thr Arg Xaa Ala Ser Leu Ser Tyr Ser Phe Gln Val Ala
    210                 215                 220

<210> SEQ ID NO 47
<211> LENGTH: 137
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
```

```
<222> LOCATION: 122
<220> FEATURE:
<223> OTHER INFORMATION: Xaa is Asn or Thr

<400> SEQUENCE: 47

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Lys Glu Arg Cys Phe Arg Gly
        35                  40                  45

Ser Ser Tyr Pro Val Cys Val Ser Lys Val Val Lys Cys Lys Lys Lys
    50                  55                  60

Leu Gly Lys Leu Pro Pro Gln Tyr Ala Leu Glu Leu Leu Thr Val Tyr
65              70                  75                  80

Ala Trp Glu Arg Gly Ser Met Lys Thr His Phe Asn Thr Ala Gln Gly
                85                  90                  95

Phe Arg Thr Val Leu Glu Leu Val Ile Asn Tyr Gln Gln Leu Cys Ile
            100                 105                 110

Tyr Trp Thr Lys Tyr Tyr Asp Phe Lys Xaa Pro Ile Ile Glu Lys Tyr
            115                 120                 125

Leu Arg Arg Gln Leu Thr Lys Pro Arg
            130                 135

<210> SEQ ID NO 48
<211> LENGTH: 346
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr
<220> FEATURE:
<221> NAME/KEY: VARIANT
<222> LOCATION: 330
<220> FEATURE:
<223> OTHER INFORMATION: Xaa is Pro or Ser

<400> SEQUENCE: 48

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Lys Glu Arg Cys Phe Arg Gly
        35                  40                  45
```

```
Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
            115                 120                 125

Pro Arg Ala Leu Ser Phe Val Leu Ser Ser Leu Gln Leu Gly Glu Gly
        130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Xaa Pro Ile Ile Glu Lys Tyr Leu Arg
        275                 280                 285

Arg Gln Leu Thr Lys Pro Arg Pro Val Ile Leu Asp Pro Ala Asp Pro
    290                 295                 300

Thr Gly Asn Leu Gly Gly Asp Pro Lys Gly Trp Arg Gln Leu Ala
305                 310                 315                 320

Gln Glu Ala Glu Ala Trp Leu Asn Tyr Xaa Cys Phe Lys Asn Trp Asp
                325                 330                 335

Gly Ser Pro Val Ser Ser Trp Ile Leu Leu
                340                 345

<210> SEQ ID NO 49
<211> LENGTH: 334
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
```

```
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr
<220> FEATURE:
<221> NAME/KEY: VARIANT
<222> LOCATION: 330
<220> FEATURE:
<223> OTHER INFORMATION: Xaa is Pro or Ser

<400> SEQUENCE: 49

Met Met Asp Leu Arg Asn Thr Pro Ala Lys Ser Leu Asp Lys Phe Ile
1               5                   10                  15

Glu Asp Tyr Leu Leu Pro Asp Thr Cys Phe Arg Met Gln Ile Xaa His
            20                  25                  30

Ala Ile Asp Ile Ile Cys Gly Phe Leu Lys Glu Arg Cys Phe Arg Gly
        35                  40                  45

Ser Ser Tyr Pro Val Cys Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Tyr Gln Asn Cys Lys Lys Lys Leu Gly
210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Thr Lys Tyr Tyr Asp Phe Lys Xaa Pro Ile Ile Glu Lys Tyr Leu Arg
        275                 280                 285

Arg Gln Leu Thr Lys Pro Arg Pro Val Ile Leu Asp Pro Ala Asp Pro
290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Xaa Cys Phe Lys Asn
                325                 330
```

<210> SEQ ID NO 50
<211> LENGTH: 353
<212> TYPE: PRT
<213> ORGANISM: Homo sapiens
<220> FEATURE:
<221> NAME/KEY: VARIANT
<222> LOCATION: 31
<220> FEATURE:
<223> OTHER INFORMATION: Xaa is Asp or Asn
<220> FEATURE:
<221> NAME/KEY: VARIANT
<222> LOCATION: 115
<220> FEATURE:
<223> OTHER INFORMATION: Xaa is Leu or Phe
<220> FEATURE:
<221> NAME/KEY: VARIANT
<222> LOCATION: 127
<220> FEATURE:
<223> OTHER INFORMATION: Xaa is Gly or Arg
<220> FEATURE:
<221> NAME/KEY: VARIANT
<222> LOCATION: 162
<220> FEATURE:
<223> OTHER INFORMATION: Xaa is Ser or Gly
<220> FEATURE:
<221> NAME/KEY: VARIANT
<222> LOCATION: 280
<220> FEATURE:
<223> OTHER INFORMATION: Xaa is Asn or Thr
<220> FEATURE:
<221> NAME/KEY: VARIANT
<222> LOCATION: 330
<220> FEATURE:
<223> OTHER INFORMATION: Xaa is Pro or Ser
<220> FEATURE:
<221> NAME/KEY: VARIANT
<222> LOCATION: (352)...(0)
<220> FEATURE:
<223> OTHER INFORMATION: Xaa is Ala or Thr

<400> SEQUENCE: 50

```
Met Met Asp Leu Arg Asn Thr Pro Ala Lys Ser Leu Asp Lys Phe Ile
  1               5                  10                  15

Glu Asp Tyr Leu Leu Pro Asp Thr Cys Phe Arg Met Gln Ile Xaa His
             20                  25                  30

Ala Ile Asp Ile Ile Cys Gly Phe Leu Lys Glu Arg Cys Phe Arg Gly
         35                  40                  45

Ser Ser Tyr Pro Val Cys Val Ser Lys Val Val Lys Gly Gly Ser Ser
     50                  55                  60

Gly Lys Gly Thr Thr Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
                 85                  90                  95

Glu Phe Ile Gln Glu Ile Arg Arg Gln Leu Glu Ala Cys Gln Arg Glu
            100                 105                 110

Arg Ala Xaa Ser Val Lys Phe Glu Val Gln Ala Pro Arg Trp Xaa Asn
        115                 120                 125

Pro Arg Ala Leu Ser Phe Val Leu Ser Ser Leu Gln Leu Gly Glu Gly
    130                 135                 140

Val Glu Phe Asp Val Leu Pro Ala Phe Asp Ala Leu Gly Gln Leu Thr
145                 150                 155                 160

Gly Xaa Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Phe Thr Glu
            180                 185                 190
```

```
Leu Gln Arg Asp Phe Leu Lys Gln Arg Pro Thr Lys Leu Lys Ser Leu
            195                 200                 205

Ile Arg Leu Val Lys His Trp Tyr Gln Asn Cys Lys Lys Leu Gly
210                 215                 220

Lys Leu Pro Pro Gln Tyr Ala Leu Glu Leu Thr Val Tyr Ala Trp
225                 230                 235                 240

Glu Arg Gly Ser Met Lys Thr His Phe Asn Thr Ala Gln Gly Phe Arg
            245                 250                 255

Thr Val Leu Glu Leu Val Ile Asn Tyr Gln Gln Leu Cys Ile Tyr Trp
                260                 265                 270

Thr Lys Tyr Tyr Asp Phe Lys Xaa Pro Ile Ile Glu Lys Tyr Leu Arg
            275                 280                 285

Arg Gln Leu Thr Lys Pro Arg Pro Val Ile Leu Asp Pro Ala Asp Pro
        290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Xaa Cys Phe Lys Asn Trp Asp
                325                 330                 335

Gly Ser Pro Val Ser Ser Trp Ile Leu Leu Ala Glu Ser Asn Ser Xaa
            340                 345                 350

Asp

<210> SEQ ID NO 51
<211> LENGTH: 335
<212> TYPE: PRT
<213> ORGANISM: Pan troglodytes

<400> SEQUENCE: 51

Met Met Asp Leu Arg Asn Thr Pro Ala Lys Ser Leu Asp Lys Phe Ile
1               5                   10                  15

Glu Asp Tyr Leu Leu Pro Asp Lys Cys Phe Arg Lys Gln Ile Asn His
                20                  25                  30

Ala Ile Asp Ile Ile Cys Gly Phe Leu Lys Glu Arg Cys Phe Gln Gly
            35                  40                  45

Ser Ser Tyr Pro Val His Val Ser Lys Val Val Lys Gly Gly Ser Ser
    50                  55                  60

Gly Lys Gly Thr Thr Leu Arg Gly Arg Ser Asp Ala Asp Leu Val Val
65                  70                  75                  80

Phe Leu Ser Pro Leu Thr Thr Phe Gln Asp Gln Leu Asn Arg Arg Gly
                85                  90                  95

Glu Phe Ile Gln Glu Ile Arg Arg Gln Leu Glu Ala Cys Gln Arg Glu
            100                 105                 110

Glu Arg Ala Phe Ser Val Lys Phe Glu Val Gln Ala Pro Arg Trp Asp
        115                 120                 125

Asn Pro Arg Ala Leu Ser Phe Val Leu Ser Ser Leu Gln Leu Gly Glu
    130                 135                 140

Gly Val Glu Phe Asp Val Leu Pro Ala Phe Asp Ala Leu Gly Gln Leu
145                 150                 155                 160

Thr Asp Gly Tyr Lys Pro Asp Pro Gln Ile Tyr Val Lys Leu Ile Glu
                165                 170                 175

Glu Cys Thr Tyr Leu Gln Lys Glu Gly Glu Phe Ser Thr Cys Phe Thr
            180                 185                 190

Glu Leu Gln Arg Asp Phe Leu Lys Gln Arg Pro Thr Lys Leu Lys Ser
        195                 200                 205
```

```
Leu Ile Arg Leu Val Lys His Trp Tyr Gln Asn Cys Lys Lys Leu
            210                 215                 220

Gly Lys Leu Pro Pro Gln Tyr Ala Leu Glu Leu Thr Val Tyr Ala
225                 230                 235                 240

Trp Glu Gln Gly Ser Met Glu Thr Asp Phe Asn Thr Ala Gln Glu Phe
                245                 250                 255

Arg Thr Val Leu Glu Leu Val Ile Asn Tyr Gln Gln Leu Cys Ile Tyr
                260                 265                 270

Trp Thr Lys Tyr Tyr Asp Phe Glu Asn Pro Ile Ile Glu Lys Tyr Leu
            275                 280                 285

Arg Arg Gln Leu Thr Lys Pro Arg Pro Val Ile Leu Asp Pro Ala Asp
            290                 295                 300

Pro Thr Gly Asn Leu Gly Gly Gly Asp Pro Lys Gly Trp Arg Gln Leu
305                 310                 315                 320

Ala Gln Glu Ala Glu Ala Trp Leu Asn Tyr Pro Cys Phe Lys Asn
                325                 330                 335
```

<210> SEQ ID NO 52
<211> LENGTH: 58
<212> TYPE: PRT
<213> ORGANISM: Gorilla gorilla

<400> SEQUENCE: 52

```
Pro Val Ile Leu Asp Pro Ala Asp Pro Thr Gly Asn Leu Gly Gly Gly
1               5                   10                  15

Asp Pro Lys Gly Trp Arg Gln Leu Ala Gln Glu Ala Glu Ala Trp Leu
                20                  25                  30

Asn Tyr Pro Cys Phe Lys Asn Trp Asp Gly Ser Pro Val Ser Ser Trp
                35                  40                  45

Ile Leu Leu Ala Glu Ser Asp Ser Gly Arg
            50                  55
```

<210> SEQ ID NO 53
<211> LENGTH: 101
<212> TYPE: DNA
<213> ORGANISM: Pan troglodytes

<400> SEQUENCE: 53
ctggcacaag aggctgaggc ctggctgaat tacccatgct ttaagaattg agatgggtcc    60
ccagtgagct cctggattct gctggtgaga cctcctgctt c                       101

<210> SEQ ID NO 54
<211> LENGTH: 100
<212> TYPE: DNA
<213> ORGANISM: Gorilla gorilla

<400> SEQUENCE: 54
ctccctgatg tgatcatgtg tctcacccctt tcaggctgaa agcgacagtg gacgatgaga    60
ccgacgatcc caggaggtat cagaaatatg gttacattgg                         100

<210> SEQ ID NO 55
<211> LENGTH: 1319
<212> TYPE: RNA
<213> ORGANISM: Pan troglodytes

<400> SEQUENCE: 55
gaggcaguuc uguugccacu cucucuccug ucaaugaugg aucucagaaa uaccccagcc    60

| | |
|---|---:|
| aaaucucugg acaaguucau ugaagacuau cucuugccag acaaguguuu ccgcaagcaa | 120 |
| aucaaccaug ccauugacau caucuguggg uuccugaagg aaaggugcuu ccaagguagc | 180 |
| uccuacccug ugcaugoguc caaggugua aaggguggcu ccucaggcaa gggcaccacc | 240 |
| cucagaggcc gaucugacgc ugaccugguu gucuucccuca guccucucac cacuuuucag | 300 |
| gaucaguuaa aucgccgggg agaguucauc caggaaauua ggagacagcu ggaagccugu | 360 |
| caaagagagg agagagcauu uccgugaag uuugaggucc aggcuccacg cuggacaac | 420 |
| ccccgugcgc ucagcuucgu acugaguucg cuccagcucg ggaggggu ggaguucgau | 480 |
| gugcugccug ccuuugaugc ccugggucag uugacugacg gcuauaaacc ugaccccaa | 540 |
| aucuauguca agcucaucga ggagugcacc uaccugcaga agagggcga uucuccacc | 600 |
| ugcuucacag aacuacagag agacuuccug aagcagcgcc ccaccaagcu caagagccuc | 660 |
| auccgccuag ucaagcacug guaccaaaau uguaagaaga agcuugggaa gcugccaccu | 720 |
| caguaugccc uggagcuccu gacgucuau gcugggagc aagggagcau ggaaacagau | 780 |
| uucaacacag cccaggaauu ucggacgguc uuggaauuag ucauaaacua ccagcaacuc | 840 |
| ugcaucuacu ggacaaagua uuaugacuuu gaaaacccca uuauugaaaa guaccugaga | 900 |
| aggcagcuca cgaaacccag gccugugauc cuggacccgg cggacccuac aggaaacuug | 960 |
| ggugguggag acccaaaggg uuggaggcag cuggcacaag aggcugaggc cuggcugaau | 1020 |
| uacccaugcu uuaagaauug agaugggucc ccagugagcu ccuggauucu gcuggugaga | 1080 |
| ccuccugcuu cccuccugcc auucaucccu gccccucucc augaagcuug agacauauag | 1140 |
| cuggagacca uucuuuccaa agaacuuacc ucuugccaaa ggccauuuau auucauauag | 1200 |
| ugacaggcug ugcuccauau uuuacaguua uuuggucac aaucgagggu uucuggaauu | 1260 |
| uucacauccc uugauccagaa uucauucccc uaagaguaau aauaaauaau cucuaacac | 1319 |

<210> SEQ ID NO 56
<211> LENGTH: 666
<212> TYPE: RNA
<213> ORGANISM: Gorilla gorilla

<400> SEQUENCE: 56

| | |
|---|---:|
| gccugugauc cuggacccgg cagacccuac aggaaacuug gguggggag acccaaaggg | 60 |
| uuggaggcag cuggcacaag aggcugaggc cuggcugaau uacccaugcu uuaagaauug | 120 |
| ggaugggucc ccagugagcu ccuggauucu gcuggcugaa agcgacagug gacgaugaga | 180 |
| ccgacgaucc caggagguau cagaaauaug guuacauugg aacacaugag uacccucauu | 240 |
| ucucucauag acccagcaca cuccaggcag cauccaccccc acaggcagaa gaggacugga | 300 |
| ccugcaccau ccucugaaug cyagugcauc uggggggaaa gggcuccagu guuaucgga | 360 |
| ccaguuccuu cauuuucagg uggacucuuu gauccagaga ggacaaagcu ccucagugag | 420 |
| cugguguaua auccaggaca gaacccaggu cuccugacuc cuggccuucu augcccucua | 480 |
| uccuaucaua gauaacauuc uccacagccu cacuucauuc caccuauucu cugaaaauau | 540 |
| ucccugagag agaacagaga gauuuagaua agagaaugaa auuccagccu ugacuuucuu | 600 |
| cugugcaccu gaugggaggg uuaugucuaa uguauuauca auaacaguaa aaauaaagca | 660 |
| aaugcc | 666 |

<210> SEQ ID NO 57
<211> LENGTH: 101
<212> TYPE: DNA
<213> ORGANISM: Artificial Sequence

```
<220> FEATURE:
<223> OTHER INFORMATION: Amplicon C

<400> SEQUENCE: 57
taacgcatgc ctgtagtccc aggtattcag gaggctgggg caggaggatc scttgaaccc    60
aggaagttga ggttgcacga gtcatgatca tgcccctgca c                       101

<210> SEQ ID NO 58
<211> LENGTH: 101
<212> TYPE: DNA
<213> ORGANISM: Artificial Sequence
<220> FEATURE:
<223> OTHER INFORMATION: Amplicon D

<400> SEQUENCE: 58
gacaggaagt gtaacctctc agaggctccc ttgccacatc aggagaattg rtaaaccac    60 actacctgta tcatatcatt attttaagtg ataaatgatc a                       101

<210> SEQ ID NO 59
<211> LENGTH: 101
<212> TYPE: DNA
<213> ORGANISM: Artificial Sequence
<220> FEATURE:
<223> OTHER INFORMATION: Amplicon E

<400> SEQUENCE: 59
tagcattagg tatatctcct aatgctatcc ctccccaatt cccccaccc mgcttgttgg    60 tatttgtata tcttcatttg agaattctct gttcatgtcc t                       101

<210> SEQ ID NO 60
<211> LENGTH: 101
<212> TYPE: DNA
<213> ORGANISM: Artificial Sequence
<220> FEATURE:
<223> OTHER INFORMATION: Amplicon B

<400> SEQUENCE: 60
gtgcatcttg ggggaaaggg ctccagtgtt atctggacca gttccttcat kttcaggtgg   60
gactcttgat ccagagarga caaagctcct cagtgagctg g                       101

<210> SEQ ID NO 61
<211> LENGTH: 101
<212> TYPE: DNA
<213> ORGANISM: Artificial Sequence
<220> FEATURE:
<223> OTHER INFORMATION: Amplicon F

<400> SEQUENCE: 61
gaaaaattat agaacctccc tgtgtgacac agcagccact agccacatgt rtcaaatgct   60
taaaatgtag ctagtctaaa tctacatgtg ctgtgagtgc a                       101

<210> SEQ ID NO 62
<211> LENGTH: 101
<212> TYPE: DNA
<213> ORGANISM: Artificial Sequence
<220> FEATURE:
<223> OTHER INFORMATION: Amplicon G

<400> SEQUENCE: 62
atgcttctat aggcttttct cactgatgct ctctgggcag acaggctcct yaatatgaga   60
gtgacacaca ctcctttctt cattttcagg taaacctcac a                       101
```

<210> SEQ ID NO 63
<211> LENGTH: 101
<212> TYPE: DNA
<213> ORGANISM: Artificial Sequence
<220> FEATURE:
<223> OTHER INFORMATION: Amplicon G

<400> SEQUENCE: 63
cctttcttca ttttcaggta aacctcacac tggttggcag aaggaactat accaataatt    60
agtgaacatg cggtgaattt gcaacagaca agasgagcct c                       101

<210> SEQ ID NO 64
<211> LENGTH: 101
<212> TYPE: DNA
<213> ORGANISM: Artificial Sequence
<220> FEATURE:
<223> OTHER INFORMATION: Amplicon G

<400> SEQUENCE: 64
gaactatacc aataattagt gaacatgcgg tgaatttgca acagacaaga sgagcctcat    60
tatcctatag tttccaggtt gcttagggag gcagaaatca c                       101

<210> SEQ ID NO 65
<211> LENGTH: 21
<212> TYPE: DNA
<213> ORGANISM: Artificial Sequence
<220> FEATURE:
<223> OTHER INFORMATION: Amplicon C primer

<400> SEQUENCE: 65
cacaagagtg aaccttaatg t                                              21

<210> SEQ ID NO 66
<211> LENGTH: 20
<212> TYPE: DNA
<213> ORGANISM: Artificial Sequence
<220> FEATURE:
<223> OTHER INFORMATION: Amplicon C primer

<400> SEQUENCE: 66
ccaggaagtg gaaagatcat                                                20

<210> SEQ ID NO 67
<211> LENGTH: 20
<212> TYPE: DNA
<213> ORGANISM: Artificial Sequence
<220> FEATURE:
<223> OTHER INFORMATION: Amplicon D primer

<400> SEQUENCE: 67
atctcccaca gtttgagagc                                                20

<210> SEQ ID NO 68
<211> LENGTH: 20
<212> TYPE: DNA
<213> ORGANISM: Artificial Sequence
<220> FEATURE:
<223> OTHER INFORMATION: Amplicon D primer

<400> SEQUENCE: 68
tcagcctcca aaagtgttgg                                                20

<210> SEQ ID NO 69
<211> LENGTH: 20

```
<212> TYPE: DNA
<213> ORGANISM: Artificial Sequence
<220> FEATURE:
<223> OTHER INFORMATION: Amplicon E primer

<400> SEQUENCE: 69
gggtacatgt gcacaatgtg                                              20

<210> SEQ ID NO 70
<211> LENGTH: 21
<212> TYPE: DNA
<213> ORGANISM: Artificial Sequence
<220> FEATURE:
<223> OTHER INFORMATION: Amplicon E primer

<400> SEQUENCE: 70
cccttataca aaattcaact c                                            21

<210> SEQ ID NO 71
<211> LENGTH: 20
<212> TYPE: DNA
<213> ORGANISM: Artificial Sequence
<220> FEATURE:
<223> OTHER INFORMATION: Amplicon F primer

<400> SEQUENCE: 71
gagccaagaa gtacagatgc                                              20

<210> SEQ ID NO 72
<211> LENGTH: 20
<212> TYPE: DNA
<213> ORGANISM: Artificial Sequence
<220> FEATURE:
<223> OTHER INFORMATION: Amplicon F primer

<400> SEQUENCE: 72
aggacagagc tgtccaatag                                              20

<210> SEQ ID NO 73
<211> LENGTH: 20
<212> TYPE: DNA
<213> ORGANISM: Artificial Sequence
<220> FEATURE:
<223> OTHER INFORMATION: Amplicon G primer

<400> SEQUENCE: 73
ggctcagaga agctaagtga                                              20

<210> SEQ ID NO 74
<211> LENGTH: 20
<212> TYPE: DNA
<213> ORGANISM: Artificial Sequence
<220> FEATURE:
<223> OTHER INFORMATION: Amplicon G primer

<400> SEQUENCE: 74
ccacagcatc cttttcagtc                                              20

<210> SEQ ID NO 75
<211> LENGTH: 8
<212> TYPE: PRT
<213> ORGANISM: Artificial Sequence
<220> FEATURE:
<223> OTHER INFORMATION: Conserved domain

<400> SEQUENCE: 75
```

Phe Leu Lys Glu Arg Cys Phe Arg
1               5

<210> SEQ ID NO 76
<211> LENGTH: 28
<212> TYPE: PRT
<213> ORGANISM: Artificial Sequence
<220> FEATURE:
<223> OTHER INFORMATION: Conserved domain

<400> SEQUENCE: 76

Val Ser Lys Val Val Lys Gly Gly Ser Ser Gly Lys Gly Thr Thr Leu
1               5                   10                  15

Arg Gly Arg Ser Asp Ala Asp Leu Val Val Phe Leu
            20                  25

<210> SEQ ID NO 77
<211> LENGTH: 19
<212> TYPE: PRT
<213> ORGANISM: Artificial Sequence
<220> FEATURE:
<223> OTHER INFORMATION: Conserved domain

<400> SEQUENCE: 77

Arg Arg Gly Glu Phe Ile Gln Glu Ile Arg Arg Gln Leu Glu Ala Cys
1               5                   10                  15

Gln Arg Glu

<210> SEQ ID NO 78
<211> LENGTH: 11
<212> TYPE: PRT
<213> ORGANISM: Artificial Sequence
<220> FEATURE:
<223> OTHER INFORMATION: Conserved domain

<400> SEQUENCE: 78

Asn Pro Arg Ala Leu Ser Phe Val Leu Ser Ser
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Conserved domain

<400> SEQUENCE: 79

Val Glu Phe Asp Val Leu Pro Ala Phe Asp Ala Leu Gly Gln
1               5                   10

<210> SEQ ID NO 80
<211> LENGTH: 17
<212> TYPE: PRT
<213> ORGANISM: Artificial Sequence
<220> FEATURE:
<223> OTHER INFORMATION: Conserved domain

<400> SEQUENCE: 80

Lys Glu Gly Glu Phe Ser Thr Cys Phe Thr Glu Leu Gln Arg Asp Phe
1               5                   10                  15

Leu

<210> SEQ ID NO 81
<211> LENGTH: 17
<212> TYPE: PRT

```
<213> ORGANISM: Artificial Sequence
<220> FEATURE:
<223> OTHER INFORMATION: Conserved domain

<400> SEQUENCE: 81

Arg Pro Thr Lys Leu Lys Ser Leu Ile Arg Leu Val Lys His Trp Tyr
1               5                   10                  15

Gln

<210> SEQ ID NO 82
<211> LENGTH: 17
<212> TYPE: PRT
<213> ORGANISM: Artificial Sequence
<220> FEATURE:
<223> OTHER INFORMATION: Conserved domain

<400> SEQUENCE: 82

Lys Leu Pro Pro Gln Tyr Ala Leu Glu Leu Leu Thr Val Tyr Ala Trp
1               5                   10                  15

Glu

<210> SEQ ID NO 83
<211> LENGTH: 12
<212> TYPE: PRT
<213> ORGANISM: Artificial Sequence
<220> FEATURE:
<223> OTHER INFORMATION: Conserved domain

<400> SEQUENCE: 83

Pro Val Ile Leu Asp Pro Ala Asp Pro Thr Gly Asn
1               5                   10

<210> SEQ ID NO 84
<211> LENGTH: 7
<212> TYPE: PRT
<213> ORGANISM: Artificial Sequence
<220> FEATURE:
<223> OTHER INFORMATION: Conserved domain

<400> SEQUENCE: 84

Gly Ser Pro Val Ser Ser Trp
1               5

<210> SEQ ID NO 85
<211> LENGTH: 11
<212> TYPE: PRT
<213> ORGANISM: Artificial Sequence
<220> FEATURE:
<223> OTHER INFORMATION: Protein transduction domain

<400> SEQUENCE: 85

Tyr Gly Arg Lys Lys Arg Arg Gln Arg Arg Arg
1               5                   10

<210> SEQ ID NO 86
<211> LENGTH: 16
<212> TYPE: PRT
<213> ORGANISM: Artificial Sequence
<220> FEATURE:
<223> OTHER INFORMATION: Protein transduction domain

<400> SEQUENCE: 86

Arg Gln Ile Lys Ile Trp Phe Gln Asn Arg Arg Met Lys Trp Lys Lys
1               5                   10                  15
```

```
<210> SEQ ID NO 87
<211> LENGTH: 301
<212> TYPE: PRT
<213> ORGANISM: Artificial Sequence
<220> FEATURE:
<223> OTHER INFORMATION: Protein transduction domain

<400> SEQUENCE: 87
```

Met Thr Ser Arg Arg Ser Val Lys Ser Gly Pro Arg Glu Val Pro Arg
1               5                   10                  15

Asp Glu Tyr Glu Asp Leu Tyr Tyr Ile Pro Ser Ser Gly Met Ala Ser
            20                  25                  30

Pro Asp Ser Pro Pro Asp Thr Ser Arg Arg Gly Ala Leu Gln Thr Arg
        35                  40                  45

Ser Arg Gln Arg Gly Glu Val Arg Phe Val Gln Tyr Asp Glu Ser Asp
    50                  55                  60

Tyr Ala Leu Tyr Gly Gly Ser Ser Ser Glu Asp Asp Glu His Pro Glu
65                  70                  75                  80

Val Pro Arg Thr Arg Arg Pro Val Ser Gly Ala Val Leu Ser Gly Pro
                85                  90                  95

Gly Pro Ala Arg Ala Pro Pro Pro Ala Gly Ser Gly Gly Ala Gly
            100                 105                 110

Arg Thr Pro Thr Thr Ala Pro Arg Ala Pro Arg Thr Gln Arg Val Ala
        115                 120                 125

Thr Lys Ala Pro Ala Ala Pro Ala Ala Glu Thr Thr Arg Gly Arg Lys
    130                 135                 140

Ser Ala Gln Pro Glu Ser Ala Ala Leu Pro Asp Ala Pro Ala Ser Thr
145                 150                 155                 160

Ala Pro Thr Arg Ser Lys Thr Pro Ala Gln Gly Leu Ala Arg Lys Leu
                165                 170                 175

His Phe Ser Thr Ala Pro Pro Asn Pro Asp Ala Pro Trp Thr Pro Arg
            180                 185                 190

Val Ala Gly Phe Asn Lys Arg Val Phe Cys Ala Ala Val Gly Arg Leu
        195                 200                 205

Ala Ala Met His Ala Arg Met Ala Ala Val Gln Leu Trp Asp Met Ser
    210                 215                 220

Arg Pro Arg Thr Asp Glu Asp Leu Asn Glu Leu Leu Gly Ile Thr Thr
225                 230                 235                 240

Ile Arg Val Thr Val Cys Glu Gly Lys Asn Leu Leu Gln Arg Ala Asn
                245                 250                 255

Glu Leu Val Asn Pro Asp Val Val Gln Asp Val Asp Ala Ala Thr Ala
            260                 265                 270

Thr Arg Gly Arg Ser Ala Ala Ser Arg Pro Thr Glu Arg Pro Arg Ala
        275                 280                 285

Pro Ala Arg Ser Ala Ser Arg Pro Arg Arg Pro Val Glu
    290                 295                 300

```
<210> SEQ ID NO 88
<211> LENGTH: 560
<212> TYPE: PRT
<213> ORGANISM: Artificial Sequence
<220> FEATURE:
<223> OTHER INFORMATION: Protein transduction domain

<400> SEQUENCE: 88
```

Met Ser Arg Lys Leu Phe Ala Ser Ile Leu Ile Gly Ala Leu Leu Gly
1               5                   10                  15

```
Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Val Val Lys Val Thr Tyr Pro Gly
            100                 105                 110

Leu Thr Lys Val Leu Ala Leu Lys Val Asp Asn Ala Glu Thr Ile Lys
        115                 120                 125

Lys Glu Leu Gly Leu Ser Leu Thr Glu Pro Leu Met Glu Gln Val Gly
    130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
            180                 185                 190

Glu Thr Arg Gly Lys Arg Gly Gln Asp Ala Met Tyr Glu Tyr Met Ala
        195                 200                 205

Gln Ala Cys Ala Gly Asn Arg Val Arg Arg Ser Val Gly Ser Ser Leu
    210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
            260                 265                 270

Glu Glu Phe His Gln Thr Ala Leu Glu His Pro Glu Leu Ser Glu Leu
        275                 280                 285

Lys Thr Val Thr Gly Thr Asn Pro Val Phe Ala Gly Ala Asn Tyr Ala
    290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
            340                 345                 350

Ile Val Ala Gln Ser Ile Ala Leu Ser Ser Leu Met Val Ala Gln Ala
        355                 360                 365

Ile Pro Leu Val Gly Glu Leu Val Asp Ile Gly Phe Ala Ala Tyr Asn
    370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430
```

```
Thr Gly Phe Gln Gly Glu Ser Gly His Asp Ile Lys Ile Thr Ala Glu
            435                 440                 445

Asn Thr Pro Leu Pro Ile Ala Gly Val Leu Leu Pro Thr Ile Pro Gly
        450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
            500                 505                 510

His Val Ala Phe His Arg Ser Ser Glu Lys Ile His Ser Asn Glu
        515                 520                 525

Ile Ser Ser Asp Ser Ile Gly Val Leu Gly Tyr Gln Lys Thr Val Asp
530                 535                 540

His Thr Lys Val Asn Ser Lys Leu Ser Leu Phe Phe Glu Ile Lys Ser
545                 550                 555                 560

<210> SEQ ID NO 89
<211> LENGTH: 20
<212> TYPE: PRT
<213> ORGANISM: Artificial Sequence
<220> FEATURE:
<223> OTHER INFORMATION: Protein transduction domain

<400> SEQUENCE: 89

Gly Asp Ile Met Gly Glu Trp Gly Asn Glu Ile Phe Gly Ala Ile Ala
1               5                   10                  15

Gly Phe Leu Gly
            20

<210> SEQ ID NO 90
<211> LENGTH: 7
<212> TYPE: PRT
<213> ORGANISM: Artificial Sequence
<220> FEATURE:
<223> OTHER INFORMATION: Protein transduction domain

<400> SEQUENCE: 90

Arg Arg Arg Arg Arg Arg Arg
1               5

<210> SEQ ID NO 91
<211> LENGTH: 12
<212> TYPE: PRT
<213> ORGANISM: Artificial Sequence
<220> FEATURE:
<223> OTHER INFORMATION: Protein transduction domain

<400> SEQUENCE: 91

Arg Arg Gln Arg Arg Thr Ser Lys Leu Met Lys Arg
1               5                   10

<210> SEQ ID NO 92
<211> LENGTH: 27
<212> TYPE: PRT
<213> ORGANISM: Artificial Sequence
<220> FEATURE:
<223> OTHER INFORMATION: Protein transduction domain

<400> SEQUENCE: 92

Gly Trp Thr Leu Asn Ser Ala Gly Tyr Leu Leu Gly Lys Ile Asn Leu
1               5                   10                  15
```

```
Lys Ala Leu Ala Ala Leu Ala Lys Lys Ile Leu
            20                  25

<210> SEQ ID NO 93
<211> LENGTH: 31
<212> TYPE: PRT
<213> ORGANISM: Artificial Sequence
<220> FEATURE:
<223> OTHER INFORMATION: Protein transduction domain

<400> SEQUENCE: 93

Trp Glu Ala Lys Leu Ala Lys Ala Leu Ala Lys Ala Leu Ala Lys Ala
 1               5                  10                  15

His Leu Ala Lys Ala Leu Ala Lys Ala Leu Lys Ala Cys Glu Ala
            20                  25                  30

<210> SEQ ID NO 94
<211> LENGTH: 21
<212> TYPE: PRT
<213> ORGANISM: Artificial Sequence
<220> FEATURE:
<223> OTHER INFORMATION: Protein transduction domain

<400> SEQUENCE: 94

Lys Glu Thr Trp Trp Glu Thr Trp Trp Thr Glu Trp Ser Gln Pro Lys
 1               5                  10                  15

Lys Lys Arg Lys Val
            20
```